(12) United States Patent
Wildt et al.

(10) Patent No.: US 8,932,825 B2
(45) Date of Patent: *Jan. 13, 2015

(54) METHOD TO ENGINEER MAMMALIAN-TYPE CARBOHYDRATE STRUCTURES

(75) Inventors: Stefan Wildt, Lebanon, NH (US); Robert Gordon Miele, So. Bend, IN (US); Juergen Hermann Nett, Grantham, NH (US); Robert C. Davidson, Enfield, NH (US)

(73) Assignee: GlycoFi Inc., Lebanon, NH (US)

( * ) Notice: Subject to any disclaimer, the term of this patent is extended or adjusted under 35 U.S.C. 154(b) by 1108 days.

This patent is subject to a terminal disclaimer.

(21) Appl. No.: 10/500,240

(22) PCT Filed: Dec. 24, 2002

(86) PCT No.: PCT/US02/41510
§ 371 (c)(1),
(2), (4) Date: Mar. 23, 2005

(87) PCT Pub. No.: WO03/056914
PCT Pub. Date: Jul. 17, 2003

(65) Prior Publication Data
US 2005/0170452 A1 Aug. 4, 2005

Related U.S. Application Data

(60) Provisional application No. 60/344,169, filed on Dec. 27, 2001.

(51) Int. Cl.
| | | |
|---|---|---|
| G01N 33/569 | (2006.01) | |
| C12P 1/02 | (2006.01) | |
| C12N 1/00 | (2006.01) | |
| A61K 51/00 | (2006.01) | |
| C12N 9/10 | (2006.01) | |
| C12P 21/00 | (2006.01) | |

(52) U.S. Cl.
CPC ......... C12N 9/1051 (2013.01); *A01K 2217/075* (2013.01); C12P 21/005 (2013.01)
USPC ...... 435/7.31; 435/171; 435/254.1; 435/6.15; 424/1.17; 424/274.1; 424/93.5; 424/93.51; 424/195.15

(58) Field of Classification Search
USPC ............ 435/7.31, 41, 69.9, 254.2; 424/93.51, 424/195.16
See application file for complete search history.

(56) References Cited

U.S. PATENT DOCUMENTS

| | | | |
|---|---|---|---|
| 5,272,070 A * | 12/1993 | Lehrman et al. ............... | 435/440 |
| 5,595,900 A | 1/1997 | Lowe | |
| 6,300,113 B1 | 10/2001 | Landry | |
| 6,803,225 B2 * | 10/2004 | Contreras et al. .......... | 435/254.2 |
| 7,029,872 B2 * | 4/2006 | Gerngross .................... | 435/69.1 |
| 7,064,191 B2 | 6/2006 | Shinkawa et al. | |
| 7,214,775 B2 | 5/2007 | Hanai et al. | |
| 8,445,227 B2 * | 5/2013 | Bobrowicz et al. .......... | 435/69.1 |
| 2004/0018590 A1 | 1/2004 | Gerngross et al. | |
| 2004/0171826 A1 | 9/2004 | Hamilton | |
| 2004/0230042 A1 | 11/2004 | Hamilton | |
| 2005/0170452 A1 | 8/2005 | Wildt et al. | |
| 2005/0208617 A1 | 9/2005 | Bobrowicz et al. | |
| 2005/0260729 A1 | 11/2005 | Hamilton | |
| 2006/0024292 A1 | 2/2006 | Gerngross et al. | |
| 2006/0024304 A1 | 2/2006 | Gerngross et al. | |
| 2006/0029604 A1 | 2/2006 | Gerngross et al. | |
| 2006/0034828 A1 | 2/2006 | Gerngross et al. | |
| 2006/0034829 A1 | 2/2006 | Gerngross et al. | |
| 2006/0034830 A1 | 2/2006 | Gerngross et al. | |
| 2006/0040353 A1 | 2/2006 | Davidson et al. | |
| 2006/0078963 A1 | 4/2006 | Gerngross | |
| 2006/0148035 A1 | 7/2006 | Gerngross | |
| 2006/0160179 A1 | 7/2006 | Bobrowicz et al. | |
| 2006/0177898 A1 | 8/2006 | Gerngross | |

(Continued)

FOREIGN PATENT DOCUMENTS

| | | |
|---|---|---|
| EP | 1211310 | 6/2002 |
| EP | 1211310 A1 | 6/2002 |

(Continued)

OTHER PUBLICATIONS

Nakayama et al. 1992, The EMBO Journal, 11: 2511-2519.*
Cereghino and Cregg, 2000, FEMS Microbiology Reviews, 24: 45-66.*
Wildt and Gerngross, 2005, Nature Review: Microbiology, 3: 119-128.*
Bischoff and Kornfeld, 1983, The Journal of Biological Chemistry, 258: 7907-7910.*
Wagner et al., 1996, Glycobiology, 6: 165-175.*
Velasco et al., 1993, The Journal of Cell Biology, 122: 39-51.*
Goss et al., 1995, Clinical Cancer Research, 1: 935-944.*

(Continued)

*Primary Examiner* — J. Hines
*Assistant Examiner* — Mary Lyons
(74) *Attorney, Agent, or Firm* — Gloria Fuentes; Immac J. Thampoe

(57) ABSTRACT

The present invention relates to host cells having modified lipid-linked oligosaccharides which may be modified further by heterologous expression of a set of glycosyltransferases, sugar transporters and mannosidases to become host-strains for the production of mammalian, e.g., human therapeutic glycoproteins. The process provides an engineered host cell which can be used to express and target any desirable gene(s) involved in glycosylation. Host cells with modified lipid-linked oligosaccharides are created or selected. N-glycans made in the engineered host cells have a $GlcNAcMan_3GlcNAc_2$ core structure which may then be modified further by heterologous expression of one or more enzymes, e.g., glycosyl-transferases, sugar transporters and mannosidases, to yield human-like glycoproteins. For the production of therapeutic proteins, this method may be adapted to engineer cell lines in which any desired glycosylation structure may be obtained.

31 Claims, 56 Drawing Sheets

(56) References Cited

U.S. PATENT DOCUMENTS

| | | |
|---|---|---|
| 2006/0211085 A1 | 9/2006 | Bobrowicz |
| 2006/0286637 A1 | 12/2006 | Hamilton |
| 2007/0105127 A1 | 5/2007 | Gerngross |

FOREIGN PATENT DOCUMENTS

| | | | |
|---|---|---|---|
| EP | 1522590 | | 4/2005 |
| EP | 1297172 | | 11/2005 |
| EP | 1211310 | B1 | 12/2006 |
| JP | 8-336387 | | 12/1996 |
| WO | 9621038 | | 7/1996 |
| WO | WO 9621038 | A1 * | 7/1996 |
| WO | WO 00/34490 | * | 6/2000 |
| WO | WO 00/61739 | | 10/2000 |
| WO | 01/14522 | | 3/2001 |
| WO | 0200856 | | 1/2002 |
| WO | WO 02/00879 | | 1/2002 |
| WO | WO 03/056914 | | 7/2003 |
| WO | WO 2004/074458 | | 9/2004 |
| WO | WO 2004/074461 | | 9/2004 |
| WO | WO 2004/074497 | | 9/2004 |
| WO | WO 2004/074498 | | 9/2004 |
| WO | WO 2004/074499 | | 9/2004 |
| WO | WO 2007/028144 | | 3/2007 |

OTHER PUBLICATIONS

Gemmill et al., 1999, Biochimica et Biophysica Acta, 1426: 227-237.*
Burda et al., 1999a, Biochimica et Biophysica Acta, 1426: 239-257.*
Karaoglu et al., 2001, Biochemistry, 40: 12193-12206.*
Burda et al., 1999b, Glycobiology, 9: 617-625.*
Tremblay et al., 1998, Glycobiology, 8: 585-595.*
Sarkar et al., 1991, PNAS, USA, 88: 234-238.*
Moremen et al., 1991, The Journal of Cell Biology, 115: 1521-1534.*
Roy et al., 2000, Biotechnol. Bioprocess Eng. 5: 219-226.*
Lin et al., 1985, PNAS, USA, 82: 7580-7584.*
Nakanishi-Shindo et al. 1993 (Structure of the N-linked oligosaccharides that show the complete loss of a-1,6-polymannose outer chain from och1, och1, mmn1, and och1 mmnl alg3 mutants of *Saccharomyces cerevisiae*, Journal of Biological Chemistry, 268(1): 26338-26345).*
Wildt et al. 2005 (The humanization of N-glycosylated pathways in yeast; Nature Reviews Microbiology 3:119-128).*
Kainz et al. 2008 (N-Glycan modification in *Aspergillus* species; Applied and Environmental Microbiology, 74(4): 1076-1086.*
Nakayama, "Molecular breeding of a yeast that produces human compatible glycoproteins", Trends in Glycoscience and Glycotech. (2001), vol. 13, pp. 421-431.
Kainuma, "Coexpression of alpha1,2 galactosyltransferase . . . ", Glycobiology (1999), vol. 9, pp. 133-141.
Callewaert et al., "Use of HDEL-tagged *Trichoderma reesei* mannosyl oligosaccharide 1,2-alpha-D-mannosidase for N-glycan engineering in *Pichia pastoris*" FEBS Letter, 503(2-3):173-178 (2001).
Contreras et al. "Modification of the N-glycosylation pathway of lower eukaryotes to a mammalian type" Abstracts of Papers American Chemical Society, 225(1-2):BIOT 30 (2003).
Maras et al., "Filamentous fungi as production organisms for glycoproteins of bio-medical interest" Glycoconjugate Journal, 16(2):99-107 (1999).
Umana et al., "A mathematical model of N-linked glycoform biosynthesis" Biotechnology and Bioengineering, Interscience Publishers, 55(6):890-908 (1997).
Maras, "Structural characterization of N-linked oligosaccharides . . . ", Eur. J. Biochem. (1997), vol. 245, pp. 617-625.
Maras, "In vivo synthesis of complex N-glycans by expression . . . ", FEBS Letters (1999), vol. 452, pp. 365-370.
Salovuori, "Low molecular weight high-mannose type glycans . . . ", Bio/Technology (1987), vol. 5, pp. 152-156.
Aebi et al., "Cloning and charterization of the ALG2 gene of *Saccharomyces cerevisiae*", Glycibiology, 1996, pp. 439-444, vol. 6, No. 4.

Chiba et al., "Production of Human Compatible High Mannose-type (Man5GlcNAc2) Sugar Chains in *Saccharomyces cerevisiae*", The Journal of Biological Chemistry, 1998, pp. 26298-26304, vol. 273, No. 41.
Dean et al., "Asparagine-linked glycosylation in the yeast Golgi", Biochimica et Biophysica Acta, 1999, pp. 309-322, vol. 1426.
Fujiyama et al., "In Vivo Conversion of a Glycan to Human Compatible Type by Transformed Tobacco Cells", Biochemical and Biophysical Research Communication, 2001, pp. 553-557, vol. 289.
Martinet et al., "Modification of the protein glycosylation pathway in the methylotrophic yeast *Pichia pastoris*", Biotechnology Letters, 1998, pp. 1171-1177, vol. 20, No. 12.
Abdel-Salam et al., "Expression of mouse anticreatine kinase (MAK33) monoclonal antibody in the yeast *Hansenula polymorpha*", Appl. Microbiol. Biotechnol., 56:157-164 (2001).
Aebi et al., "Cloning and Characterization of the ALG3 Gene of *Saccharomyces Cerevisiae*" Glycobiology 6(4): 439-444 (1999).
Abeijon et al., "Molecular Cloning of the Golgi apparatus uridine diphosphate-N-acetylglucosamine transporter from *Kluyveromyces lactis*" Proc. Natl. Acad. Sci. USA 93:5963-5968 (1996).
Alverez et al., "Sequences of the mouse N-acetylglucosaminyltransferase V (*Mgat5*) mRNA and an mRNA expressed by an *Mgat*-deficient cell line" Glycobiology 12 (7), 389-394 (2002).
Aoki et al., "Expression and activity of chimeric molecules between human UDP-galactose transporter and CMP-sialic acid transporter", J. Biochem. (Tokyo), 126(5):940-50 (1999).
Beaudet et al., "High-level expression of mouse Mdr3 P-glycoprotein in yeast *Pichia pastoris* and characterization of ATPase activity", Methods Enzymol., 292:397-413 (1998).
Berka et al., "The Filamentous Fungus *Aspergillus niger* var. *Awamori* as Host for the Expression and Secretion of Fungal and Non-Fungal Heterologous Proteins", Abstr. Papers Amer. Chem. Soc. 203:121-BIOT (1992).
Berninsone et al., "The Golgi guanosine diphosphatase is required for transport of GDP-mannose into the lumen of *Saccharomyces cerevisiae* Golgi vesicles", J. Biol. Chem., 269(1):207-211 (1994).
Berninsone et al., "Regulation of Yeast Golgi Glycosylation", J. Biol. Chem., 270 (24): 14564-14567 (1995).
Berninsone et al., "Functional Expression of the Murine Golgi CMP-Sialic Acid Transporter in *Saccharomyces cerevisiae*", J. Biol. Chem. 272(19):12616-9 (1997).
Berninsone, "Nucleotide Sugar Transporters of the Golgi Apparatus." Current opinion in Structural Biology, Biology 10: 542-547 (2000).
Bianchi et al., "Transformation of the yeast *Kluyveromyces lactis* by new vectors derived from the 1.6 μm circular plasmid pKD1", Current Genetics, 12:185-192 (1987).
Boehm et al., "Disruption of the KEX1 Gene in *Pichia pastoris* Allows Expression of Full-Length Murine and Human Endostatin", Yeast, 15:563-572 (1999).
Bretthauer et al., "Glycosylation of *Pichia pastoris*-derived proteins", Biotechnology and Applied Biochemistry 30:193-200 (1999).
Burda et al., "A Novel Carbohydrate-Deficient Glycoprotein Syndrome Characterized by a Deficiency in Glucosylation of the Dolichol-Linked Oligosaccharide", J. Clin. Invest., vol. 102, No. 4, 647-652, Aug. 1998.
Burda et al., "Stepwise Assembly of the Lipid-Linked Oligosaccharide int he Endoplasmic Reticulum of *Saccharomyces cerevisiae:* Idenfication of the ALG9 Gene Encoding a Putative Mannosyl Transferase", Proc. Natl. Acad. Sci, U.S.A., Jul. 1996 (93): 7160-7165.
Cereghino et al., "Heterologous protein expression in the methylotrophic yeast *Pichia pastoris*", FEMS Microbiology Reviews, 24(1):45-66 (2000).
Cereghino et al., "New selectable marker/auxotrophic host strain combinations for molecular genetic manipulation of *Pichia pastoris*", Gene, 263:159-169 (2001).
Chantret et al., "Congenital Disorders of Glycosylation Type Ig is Defined by a Deficiency in Dolichyl-P-mannose: Man7GlcNAc2-PP-dolichyl mannosyltransferase", J. Biol. Chem., Jul. 12, 2002 (277) 28:25815-25822.

(56) References Cited

OTHER PUBLICATIONS

Chiba et al., "Production of Human Compatible High Mannose-type Sugar Chains in *Saccharomyces cerevisiae*", *J. Biol. Chem.*, 273(41):26298-26304 (1998).
Choi et al., "Use of combinatorial genetic libraries to humanize N-linked glycosylation in the yeast *Pichia pastoris*", *Proc. Natl. Acad. Sci.* USA 100:5022-5027 (2003).
Cipollo et al., "The *Saccharomyces cerevisiae alg*12delta Mutant Reveals a Role for the Middle-arm Alpha1,2Man-and Upper-Arm alpha1,2Manalpha1,6Man-Residues of Glc3Man9GlcNAc2-PP-Dol in Regulating Glycoprotein Glycan Processing in the Endloplasmic Reticulum and Golgi Apparatus", *Glycobiology* 2002, (12) 11:749-762.
Cipollo et al., "The Accumulation of Man(6)GlcNAc(2)-PP-dolichol in the *Saccharomyces Cerevisiae* Δ*alg9* Mutant Reveals a Regulatory Role for the Alg3P alpha1,3-Man Middle-Arm Addition in Downstream Oligosaccharide-Lipid and Glycoprotein Glycan Processing", *J. Biol. Chem.*, Feb. 11, 2000 (275) 6:-4267-4277.
Cueva et al., "Preferential Transfer to Truncated Oligosaccharides to the First Sequon of Yeast Exoglucanase in *Saccharomyces cerevisiae* alg3 Cells", *Biochim. Biophys. Acta*, 1289 (3):336-42 (1996).
Davidson et al., "A PCR-based strategy to generate integrative targeting alleles with large regions of homology", *Microbiol.*, 148(Pt8):2607-15 (2002).
Davies et al., "Expression of GnTIII in a Recombinant Anti-CD20 CHO Production Cell Line: Expression of Antibodies with Altered Glycoforms Leads to an Increase in ADCC Through Higher Affinity for FcγRIII", *Biotechnol. Bioeng.*, 74(4):288-294 (2001).
Duman et al., "O-Mannosylation of *Pichia pastoris* Cellular and Recombinant Proteins", *Biotechnology and Applied Biochemistry*, 1998, vol. 28, pp. 39-45.
Eckhardt et al., "Molecular Cloning of the Hamster CMP-Sialic Acid Transporter", *Eur. J. Biochem.*, 248(1):187-192 (1997).
Fukuta et al., "Comparative Study for the N-Glycans of Human Monoclonal Immunogloblulins M Produced by Hybridoma and Parental Cells", *Archives of Biochemistry and Biophysics*, 378(1), 142-150 (2000).
Gibbs et al., "Dolichylpyrophosphate Oligosaccharides: Large-Scale Isolation and Evaluation as Oligosaccharyltransferase Substrates" *Bioorganic & Medical Chemistry* 7 (1999) 441-447.
Gleeson, Paul A. "Targeting of Proteins to the Golgi Apparatus", *Histochem. Cell Biol.*, 109:517-532 (1998).
Graham et al., "Compartmental Organization of Golgi-specific Protein Modification and Vacuolar Protein Sorting Events Defined in Yeast *sec*18 (*NSF*) Mutant", *J. Cell. Biol.*, 114(2):207-218 (1991).
Grimme et al., "The essential Smp3 Protein is Required for Addition of the Side-Branching Fourth Mannose During Assembly of Yeast Glycosylphosphatidylinositols", *J. Biol. Chem.*, Jul. 20, 2001, (276)29:2773-27739.
Guillen et al., "Mammalian Golgi Apparatus UDP-*N*-acetylglucosamine Transporter: Molecular Cloning by Phenotypic Correction of a Yeast Mutant", *Proc. Natl. Acad. Sci. USA*, 95(14):7888-7892 (1998).
Hamilton et al., "Yeast mutants deficient in protein glycosylation", Production of Complex Human Glycoproteins in Yeast, *Science*, 301:1244-46 (2003).
Hernandez et al., "Structure of the Phosphorylated *N*-Linked Oligosaccharides from the *mnn9* and *mnn10* Mutants of *Saccharomyces cerevisiae*", The Journal of Biological Chemistry, 264(23):13648-13659 (1989).
Huffaker et al., "Yeast Mutants Deficient in Protein Glycosylation", Proc. Natl. Acad. Sci. U.S.A., Dec. 1983 (80): 7466-7470.
Imbach, et al. "A Mutation in the Human Ortholog of the *Saccharomyces cerevisiae ALG6* Gene Causes Carbohydrate-Deficient Glycoprotein Syndrome Type-lc.", *Proc, Natl. Acad. Sci.* U.S.A., Jun. 1999 (96), 6981-6987.
Ishida et al., "Molecular Cloning and Characterization of a Novel Isoform of the Human UDP-Galactose Transporter, and of Related Complementary DNAs Belonging to the Nucleotide-Sugar Transporter Gene Family", *J. Biochem.*, (Tokyo) 120(6)1074-1078 (1996).
Ishida et al., "Molecular Cloning and Functional Expression of the Human Golgi UDP-*N*-Acetylglucosamine Transporter", *J. Biochem.*, 126(1):68-77 (1999).
Jarvis et al., "Engineering N-glycosylation pathways in the baculovirus-insect cell system", *Current Opinion in Biotechnology*, 9:528-533 (1998).
Kainuma, "Coexpression of α1,2 galactosyltransferase and UDP-galactose transporter efficiently galatosylates *N*- and *O*-glycan in *Saccharomyces cerevisiae*", *Glycobiology*, 9(2): 133-141 (1999).
Kalsner et al., "Insertion into *Aspergillus nidulans* of functional UDP-GlcNAc: α3-D-mannoside β-1,2-*N*-acetylglucosaminyl-transferase I, the enzyme catalysing the first committed step from oligomannose to hybrid and complex N-glycans", *Glycoconj. J.*, 12(3):360-370 (1995).
Karaoglu et al., "Allosteric Regulation Provides a Molecular Mechanism for Preferential Utilization of the Fully Assembled Dolichol-Linked Oligosaccharide by the Yeast Oligosaccharyltransferase", *Biochemistry*, 2001, 40, 12193-12206.
Kato et al., "Nucleotide Sequence of a Regulatory Region Controlling Alginate Synthesis in *Pseudomonas aeruginosa*: Characterization of the *AlgR2* Gene", *Gene*, 1989, vol. 84, pp. 31-38.
Krezdorn et al., "Human β1,4 galactosyltransferase and α2,6 sialytransferase expressed in *Saccharomyces cerevisiae* are retained as active enzymes in the endoplasmic reticulum", *Eur. J. Biochem.*, 220(3):809-17 (1994).
Malissard et al., "Expression of Functional Soluble Forms of Human β-1,4-Galactosyltransferase I, α-2,6-Sialytransferase, and α-1,3-Fucosyltransferase VI in the Methylotrophic Yeast *Pichia pastoris*", *Biochemical and Biophysical Research Communications*, 267:169-173 (2000).
Maras et al., "In vitro conversion of the carbohydrate moiety of fungal glycoproteins to mammalian-type oligosaccharides", *Eur. J. Biochem.*, 249:701-707 (1997).
Maras et al., "In Vivo Synthesis of Complex *N*-glycans by Expression of Human *N*-acetylglucosaminyltransferase I in the Filamentous Fungus *Trichoderma reesei*", *Febs Letters*, 452(3): 365-370 (1999).
Martinet et al., "Modification of the Protein Glycosylation Pathway in the Methylotrophic Yeast *Pichia pastoris*" *Biotechnology Letters*, 20:1171-1177 (1998).
Miele et al., "Glycosylation properties of the *Pichia pastoris*-expressed recombinant kringle 2 domain of tissue-type plasminogen activator", *Biotechnol. Appl. Biochem.*, 25:151-157 (1997).
Miele et al., "Glycosylation of Asparagine-28 of Recombinant Staphylokinase with High-Mannose-Type Oligosaccharides Results in a Protein with Highly Attenuated Phasminogen Activator Activity", *Journal of Biological Chemistry*, Mar. 19, 1999, vol. 274, No. 12, pp. 7769-7776.
Minowa et al., "cDNA Cloning and Expression of Bovine UDP-N-Acetylglucosamine: α1, 3-D-Mannoside β1,4-N-acetylglucosaminyltransferase IV", *J. Biol. Chem.*, 273 (19), 1998, 11556-11562.
Moller et al., "Control of Glycoprotein Synthesis: Substrate Specificity of Rat Liver UDP-GlcNAc:Man alpha 3R beta 2-N-Acetylglucosaminyltransferase I Using Synthetic Substrate Analogues", *Glycoconj J.*, Aug. 1992; 9(4): 180-90.
Nakanishi-Shindo et al., "Structure of the N-Linked Oligosaccharides That Show the Complete Loss of α-1,6-Polymannose Outer Chain from *och1*, *och1 mnn1*, and *och1 mnn1 alg3* Mutants in *Saccharomyces cerevisiae*" *J. Biol. Chem.*, 268(35):26338-45 (1993).
Omtvedt et al., "Glycosylation of Immunoglobulin Light Chains Associated with Amyloidosis", *Amyloid: International Journal of Experimental and Clinical Investigation*, 2000, vol. 7, pp. 227-244.
Papac et al., "A high-throughput microscale method to release N-linked oligosaccharides from glycoproteins for matrix-assisted laser desorption/ionization time-of-flight mass spectrometric analysis", A.J.S., *Glycobiology*, 8:445-454 (1998).
Perez et al., "Transport of Sugar Nucleotides into the Lumen of Vesicles Derived from Rat Liver Rough Endoplasmic Reticulum and Golgi Apparatus", *Methods in Enzymology*, 138:709-715 (1987).
Puglielli et al., "Reconstitution, Identification, and Purification of the Rat Liver Golgi Membrane GDP-fucose Transporter", *J. Biol. Chem.* 274(50):35596-35600 (1999).
Raju et al., "Species-specific variation in glycosylation of IgG: evidence for the species-specific sialyation and branch-specific galactosylation and importance for engineering recombinant glycoprotein therapeutics", *Glycobiology*, 10(5):477-486 (2000).

(56) References Cited

OTHER PUBLICATIONS

Reiss et al., "Isolation of the ALG6 Locus of Saccharomyces Cerevisiae Required for blycosylation in the N-lined Glycosylation Pathway", *Glycobiology*, Jul. 1996 6(5):493-8.
Runge et al., "A New Yeast Mutant in the Glucosylation Steps for the Asparagine-Linked Glycosylation Pathway", *Journal of Biological Chemistry*, Nov. 25, 1986, vol. 261, No. 33, pp. 15582-15590.
Schachter et al., "The 'Yellow Brick Road' to Branched Complex N-glycans", *Glycobiology* 1(5): 453-461, 1991.
Schwientek et al., "Golgi Localization in Yeast is Mediated by the Membrane Anchor Region in Rat Liver Sialyltransferase", *J. Biol. Chem.*, 270(10):5483-5489 (1995).
Segawa et al., "*Schizosaccharomyces pombe* UDP-galatose transporter: identification of its functional form through cDNA cloning and expression in mammalian cells", *FEBS Letters*, 451(3):295-298 (1999).
Sharma et al., "Biosynthesis of Lipid-Linked Oligosaccharides in Yeast: The ALG3 Gene Encodes the Dol-P-Man: Man(5)GlcNAc(2)-PP-Dol Mannosyltransferase", *Biological Chemistry*, 382(2): 321-328 (2001).
Sommers et al., "Transport of Sugar Nucleotides into Rat Liver Golgi", *J. Cell Biol.*, 91(2):A406 (1981).
Sommers et al., "Transport of Sugar Nucleotides into Rat Liver Golgi. A New Golgi Marker Activity", J. Cell Biol., 257(18):811-817 (1982).
Stagljar et al., "New Phentoype of Mutations Deficient in Glucosylation of the Lipid-Linked Oligosaccharide: Cloning of the *ALG8* Locus", *Proc. Natl. Acad. Sci. USA*, vol. 91, pp. 5977-5981, Jun. 1994.
Suzuki C., "Immunochemical and Mutational Analyses of P-Type ATPase Spflp Involved in the Yeast Secretory Pathway", *Bioscience Biotechnology Biochemistry* 2001, vol. 65, No. 11, 2405-2411.
Takahashi N. et al., "Comparative Structural Study of the N-Linked Oligosaccharides of Human Normal and Pathological Immunoglobulin", *Biochemistry*, 1987, vol. 26, pp. 1137-1144.
Takeuchi, "Trial for Molecular Breeding of Yeast for the Production of Glycoprotein Therapeutics", *Trends in Glycoscience and Glycotechnology*, 9:S29-S35 (1997).
Tremblay et al., "Cloning and Expression of a Specific Human α1,2-Mannosidase that Trims Man9GlcNAc2 to Man8GlcNAc2 Isomer B during N-Glycan Biosynthesis", *Glycobiology*, 1999, vol. 9, No. 10, pp. 1073-1078.
Umana et al., "Tetracycline-Regulated Overexpression of Glycosyltransferase in Chinese Hamster Ovary Cells", *Biotechnol. Bioeng.*, 65(5):542-9 (1999).
Umana et al., "Engineered glycoforms of an antineuroblastoma IgG1 with optimized antibody-dependent cellular cytotoxic activity", Nat. Biotechnol., 17(2):176-80 (1999).
Vasquez-Reyna, et al., "Biosynthesis of Blycoproteins in *Candida albicans*: Biochemical Characterization of a Soluble Alpha-Mannosidase", *FEMS Microbiology Letters*, 1993, vol. 106, pp. 321-326.
Verostek et al., "Glycoprotein Biosynthesis in the alg3 *Saccharomyces cerevisiae* mutant. II. Stucture of Novel Man6-10GlcNAc2 Processing Intermediates on Secreted Invertase", *J. Biol. Chem.*, Jun. 5, 1993 (268) 16:12095-12103.
Weikert, et al., "Engineering Chinese Hamster Ovary Cells to Maximize Sialic Acid Content of Recombinant Glycoproteins", *Nature Biotechnology*, 17(11): 1116-1121 (1999).
Yip et al., "Cloning and analysis of the *Saccharomyces cerevisiae* MNN9 and MNN1 genes required for complex glycosylation of secreted proteins", *Proc. Natl. Acad. Sci. USA*, 91(7):2723-7 (1994).
Yoko-o et al., "*Schizosaccharomyces pombe* Och1(+) Encodes Alpha-1,6-Mannosyltranferase that is involved in Outer Chain Elongation of N-Linked Oligosaccharides", *FEBS Lett.*, 489(1):75-80 (2001).
Yoshida, et al., "1-2-alpha-D-mannosidase from *Penicillium citriunum*: molecular and enzymic properties of two isoenzymes", *Biochem. J.* 290 (Pt2):349-354 (1993).

Yoshida et al. STT3, a Novel Essential Gene Related to the PKC1/STT1 Protein Kinase Pathway, is Involved in Protein Glycosylation in Yeast, *Gene* Oct. 16, 1995;164(1):167-72.
Yoshida, et al., "Expression and characterization of rat EDP-N-acetylgluocosamine: α-3-D-mannoside β-1,2-N-acetylglucosaminyltransferase I in *Saccharomyces cerevisiae*", *Glycobiology*, 9 (1):53-8 (1999).
Segawa, et al., "*Schizosaccharomyces pombe* UDP-galactose transporter: identification of its function form through cDNA cloning and expression in mammalian cells", FEBS Letters 451 (1999) pp. 295-298.
Bobrowicz, "Engineering of an artificial glycosylation pathway . . . ", Glycobiology (2004), vol. 14, pp. 757-766.
Kornfield, "Class E Thy-1 negative mouse lymphoma cells . . . ", J. Biol. Chem. (1979), vol. 254, pp. 11649-11654.
Lehrman, "Pleiotropic resistance to glycoprotein processing . . . ", J. Biol. Chem. (1989), vol. 264, pp. 1584-1593.
Stoll, "Mutant of Chinese hamster ovary cells with altered mannose . . . ", PNAS (1982), vol. 79, pp. 2296-2300.
Vella, "Control of glycoprotein synthesis . . . ", Can. J. Biochem. Cell Biol. (1984), vol. 62, pp. 409-417.
Zhang, "Synthesis of paucimannose N-glycans by Caenorhabditis elegans . . . ", Biochem. J. (2003), vol. 372, pp. 53-64.
Strasser, "Molecular cloning and characterization of cDNA . . . ", Glycobiology (1999), vol. 9, pp. 779-785.
Altmann, "Processing of asparagine-linked oligosaccharides . . . ", Glycobiology (1993), vol. 3, pp. 619-625.
Elbers et al., Plant Plysiol. vol. 126 (2001), pp. 1314-1322.
Li et al., Nature Biotech., vol. 24 (2006), pp. 210-215, "Optimization of humanized IgGs in glycoengineered *Pichia pastoris*".
Lifely et al., Glycobiology, vol. 5 (1995), pp. 813-822, "Glycosylation and biological activity of CAMPATH-1H expressed in different cell lines . . . ".
Yamane-Ohnuki et al., Biotech. Bioengin., vol. 87 (2004), pp. 614-622, "Establishment of FUT8 knockout Chinese hamster ovary cells: An ideal host cell line for producing . . . ".
Weikert et al., Nature Biol., vol. 17 (1999), pp. 1116-1121, "Engineering Chinese hamster ovary cells to maximize sialic acid content of recombinant glycoproteins".
EP 1297172 B1—Glycode Opposition Brief (French), 2007.
EP 1297172 B1—Glycode Opposition Brief (English translation), 2007.
EP 1297172 B1—Novozyme Opposition Brief, 2007.
EP 1297172 B1—Patentee's Reply to the Notice of Opinion, 2007.
EP 1297172 B1—EPO Non-Binding Opinion, 2007.
Maras et al., Glycoconjugate J., vol. 16 (1999), pp. 99-107, "Filamentous fungi as production organisms for glycoproteins of biomedical interest".
Notice of Opposition to EP1467615, filed by Novartis, Oct. 22, 2013.
Schwientek et al., JBC, vol. 271, pp. 3398-3405, 1996.
Tremblay et al., Glycobiology, vol. 8(6), pp. 585-595, 1998.
Chui et al., Cell, vol. 90, pp. 157-167, 1997.
Moreman, et al., Biochimica at Biophysica Acta, vol. 1573, pp. 225-235, 2002.
PNAS, vol. 107(15), p. 7113, 2010.
Kainz et al., Appl. Env. Microbiology, vol. 74(4) pp. 1076-1086, 2008.
Wildt & Gerngross, Nat. Rev. Microbiology, vol. 3(2) pp. 119-128, 2005.
Vervecken et al., Appl. Env. Microbiology, vol. 70%5) pp. 2639-2646, 2004.
Jigami, Protein Nucleic Acid Enzyme, vol. 39(4) pp. 657-666 (Non-English) and English language translation, 1994.
U.S. Appl. No. 10/546,101, filed Aug. 3, 2006.
U.S. Appl. No. 12/313,636, filed Nov. 21, 2008.
U.S. Appl. No. 11/187,113, filed Jul. 21, 2005.
U.S. Appl. No. 11/187,079, filed Jul. 21, 2005.
U.S. Appl. No. 12/287,423, filed Oct. 9, 2008.
U.S. Appl. No. 11/187,065, filed Jul. 21, 2005.
U.S. Appl. No. 12/284,399, filed Sep. 22, 2008.
U.S. Appl. No. 11/187,229, filed Jul. 21, 2005.

* cited by examiner

*ALG3 Blast 05-22-01*

Sequences producing significant alignments:                    (bits)    Value

```
gi|586444|sp|P38179|ALG3_YEAST   DOLICHYL-P-MAN:MAN(5)GLCNAC(...797    0.0
gi|3024226|sp|Q92685|ALG3_HUMAN  DOLICHYL-P-MAN:MAN(5)GLCNAC...173     7e-43
gi|3024221|sp|Q24332|NT56_DROVI  LETHAL(2)NEIGHBOUR OF TID P...145     3e-34
gi|3024222|Sp|Q27333|NT56_DROME  LETHAL(2)NEIGHBOUR OF TID P...121     3e-27
gi|10720153|sp|P82149|NT53_DROME LETHAL(2)NEIGHBOUR OF TID ...121      5e-27
gi|1707982|sp|P40989|GLS2_YEAST  1,3-BETA-GLUCAN SYNTHASE CO... 32
2.8
gi|1346146|sp|P38631|GLS1_YEAST  1,3-BETA-GLUCAN SYNTHASE CO... 31
6.6
```

Alignments

<u>Yeast</u>

```
>gi|586444|sp|P38179|ALG3_YEAST DOLICHYL-P-
MAN:MAN(5)GLCNAC(2)-PP-DOLICHYL MANNOSYLTRANSFERASE
    (DOL-P-MAN DEPENDENT ALPHA(1-3)-MANNOSYLTRANSFERASE)
    (HM-1 KILLER TOXIN RESISTANCE PROTEIN)
    Length = 458

Score = 797 bits (2059), Expect = 0.0
 Identities = 422/458 (92%), Positives = 422/458 (92%)

Query: 1    MEGEQSPQGEKSLQRKQFVRPPLDLWQDLKDGVRYVIFDCRANLIVMPLLILFESMLCKI  60
            MEGEQSPQGEKSLQRKQFVRPPLDLWQDLKDGVRYVIFDCRANLIVMPLLILFESMLCKI
Sbjct: 1    MEGEQSPQGEKSLQRKQFVRPPLDLWQDLKDGVRYVIFDCRANLIVMPLLILFESMLCKI  60

Query: 61   IIKKVAYTEIDYKAYMEQIEMIQLDGMLDYSQVSGGTGPLVYPAGHVLIYKMMYWLTEGM  120
            IIKKVAYTEIDYKAYMEQIEMIQLDGMLDYSQVSGGTGPLVYPAGHVLIYKMMYWLTEGM
Sbjct: 61   IIKKVAYTEIDYKAYMEQIEMIQLDGMLDYSQVSGGTGPLVYPAGHVLIYKMMYWLTEGM  120

Query: 121  DHVERGQVFFRYLYLLTLALQMACYYLLHLPPWCVVLACLSKRLHSIYVLRLFNDCFTTL  180
            DHVERGQVFFRYLYLLTLALQMACYYLLHLPPWCVVLACLSKRLHSIYVLRLFNDCFTTL
Sbjct: 121  DHVERGQVFFRYLYLLTLALQMACYYLLHLPPWCVVLACLSKRLHSIYVLRLFNDCFTTL  180
```

FIG.4A

```
Query: 181  FMVVTVLGAIVASRCHQRPKLKKSLALVISATYSMAVSIKMNALLYFPAMMISLFILNDA  240
            FMVVTVLGAIVASRCHQRPKLKKSLALVISATYSMAVSIKMNALLYFPAMMISLFILNDA
Sbjct: 181  FMVVTVLGAIVASRCHQRPKLKKSLALVISATYSMAVSIKMNALLYFPAMMISLFILNDA  240

Query: 241  NVILTLLDLVAMIAWQVAVAVPFLRSFPQQYLHCAFNFGRKFMYQWSINWQMMDEEAFND  300
            NVILTLLDLVAMIAWQVAVAVPFLRSFPQQYLHCAFNFGRKFMYQWSINWQMMDEEAFND
Sbjct: 241  NVILTLLDLVAMIAWQVAVAVPFLRSFPQQYLHCAFNFGRKFMYQWSINWQMMDEEAFND  300

Query: 301  KRFXXXXXXXXXXXXXXXXXFVTRYPRILPDLWSSLCHPLRKNAVLNANPAKTIPFVLIASN  360
            KRF              FVTRYPRILPDLWSSLCHPLRKNAVLNANPAKTIPFVLIASN
Sbjct: 301  KRFHLALLISHLIALTTLFVTRYPRILPDLWSSLCHPLRKNAVLNANPAKTIPFVLIASN  360

Query: 361  FIGVLFSRSLHYQFLSWYHWTLPILIFWSGMPFFVGPIWYVLHEWCWNSYPPNSQXXXXXX  420
            FIGVLFSRSLHYQFLSWYHWTLPILIFWSGMPFFVGPIWYVLHEWCWNSYPPNSQ
Sbjct: 361  FIGVLFSRSLHYQFLSWYHWTLPILIFWSGMPFFVGPIWYVLHEWCWNSYPPNSQASTLL  420

Query: 421  XXXXXXXXXXXXXXXXXSGSVALAKSHLRTTSSMEKKLN  458
                             SGSVALAKSHLRTTSSMEKKLN
Sbjct: 421  LALNTVLLLLLALTQLSGSVALAKSHLRTTSSMEKKLN  458
```

FIG.4B

Human

>gi|3024226|sp|Q92685|ALG3_HUMAN DOLICHYL-P-MAN:MAN (5) GLCNAC (2)-PP-DOLICHYL MANNOSYLTRANSFERASE
    (DOL-P-MAN DEPENDENT ALPHA(1-3)-MANNOSYLTRANSFERASE)
    (NOT56-LIKE PROTEIN)
  Length = 438

Score = 173 bits (439), Expect = 7e-43
 Identities = 133/396 (33%), Positives = 195/396 (48%), Gaps = 28/396 (7%)

```
Query:  26  WQDLKDGVRYVIFDCRANLIVMPLLILFESMLCKIIIKKVAYTEIDYKAYMEQIEMIQLD   85
            WQ+     R ++ + R L+V   L L E +   +I +VAYTEID+KAYM ++E + ++
Sbjct:  29  WQER----RLLLREPRYTLLVAACLCLAEVGITFWVIHRVAYTEIDWKAYMAEVEGV-IN   83

Query:  86  GMLDYSQVSGGTGPLVYPAGHVLIYKMMYWLTEGMDHVERGQVFFRYLYLLTLALQMACY  145
            G  DY+Q+ G TGPLVYPAG V I+  +Y+ T     +   Q F  LYL TL L    Y
Sbjct:  84  GTYDYTQLQGDTGPLVYPAGFVYIFMGLYYATSRGTDIRMAQNIFAVLYLATLLLVFLIY  143

Query: 146  Y-LLHLPPWC-VVLACLSKRLHSIYVLRLFNDCFTTLFMVVTVLGAIVASRCHQRPKLKK  203
            +    +PP+      + C S R+HSI+VLRLFND      + + +L  +       QR
Sbjct: 144  HQTCKVPPFVFFFMCCASYRVHSIFVLRLFNDP-----VAMVLLFLSINLLLAQRWGWG-  197

Query: 204  SLALVISATYSMAVSIKMNALLYFPAMMISLFILNDANVILTLLDLVAMIAWQVAVAVPF  263
                     +S+AVS+KMN LL+ P ++  L       LL  + A +   QV  +PF
Sbjct: 198  ------CCFFSLAVSVKMNVLLFAPGLLFLLLTQFGFRGALPKLGICAGL--QVVLGLPF  249

Query: 264  LRSFPQQYLHCAFNFGRKFMYQWSINWQMMDEEAFNDKRFXXXXXXXXXXXXXXXXFVTRY  323
            L   P YL +F+ GR+F++ W++NW+ + E F   + F                 + R+
Sbjct: 250  LLENPSGYLSRSFDLGRQFLFHWTVNWRFLPEALFLHRAFHLALLTAHLTLLLLFALCRW  309

Query: 324  PRILPDLWSSLCHPLRKNAVLNANPAKTIPFVLIASNFIGVLFSRSLHYQFLSWYHWTLP  383
             R   + S L P ++          I   L SNFIG+ FSRSLHYQF  WY  TLP
Sbjct: 310  HRTGESILSLLRDPSKRKVPPQPLTPNQIVSTLFTSNFIGICFSRSLHYQFYVWYFHTLP  369

Query: 384  ILIF-----WSGMPFFVGPIWYVLHEWCWNSYPPNS  414
             L++     W    +   +   E WN+YP  S
Sbjct: 370  YLLWAMPARWLTHLLRLLVLGLI--ELSWNTYPSTS  403
```

FIG.4C

Drosophila Vi

>gi|3024221|sp|Q24332|NT56_DROVI LETHAL(2)NEIGHBOUR OF TID PROTEIN (NOT58)
    Length = 526

Score = 145 bits (366), Expect = 3e-34
 Identities = 103/273 (37%), Positives = 157/273 (56%), Gaps = 17/273 (6%)

```
Query:  33  VRYVIFDCRANLIVMPLLILFESMLCKIIIKKVAYTEIDYKAYMEQIEMIQLDGMLDYSQ  92
            ++Y+ F+   A IV  L++L E+++  ++I++V YTEID+KAYM++ E    L+G  +YS
Sbjct:  34  IKYLAFEPAALPIVSVLIVLAEAVINVLVIQRVPYTEIDWKAYMQECEGF-LNGTTNYSL  92

Query:  93  VSGGTGPLVYPAGHVLIYKMMYWLTEGMDHVERGQVFFRYLYLLTLALQMACYYLLH-LP  151
            +  G TGPLVYPA  V IY  +Y+LT    +V   Q  F  +YLL + L +  Y     +P
Sbjct:  93  LRGDTGPLVYPAAFVYIYSGLYYLTGQGTNVRLAQYIFACIYLLQMCLVLRLYTKSRKVP  152

Query: 152  PWCVVLACL-SKRLHSIYVLRLFNDCFTTLFMVVTVLGAIVASRCHQRPKLKKSLALVIS  210
            P+ +VL+   S R+HSIYVLRLFND       L  +L A +       QR  L         S
Sbjct: 153  PYVLVLSAFTSYRIHSIYVLRLFNDPVAIL-----LLYAALNLFLDQRWTLG-------S  200

Query: 211  ATYSMAVSIKMNALLYFPAMMISLFILNDANVILTLLDLVAMIAWQVAVAVPFLRSFPQQ  270
              YS+AV +KMN  +   A + LF L + V+ TL+ L     Q+ +   PFLR+ P +
Sbjct: 201  ICYSLAVGVKMN--ILLFAPALLLFYLANLGVLRTLVQLTICAVLQLFIGAPFLRTHPME  258

Query: 271  YLHCAFNFGRKFMYQWSINWQMMDEEAFNDKRF  303
            YL +F+ GR F ++W++N++  + +E F   + F
Sbjct: 259  YLRGSFDLGRIFEHKWTVNYRFLSKELFEQREF  291
```

Score = 53.3 bits (127), Expect = 1e-06
 Identities = 31/62 (50%), Positives = 41/62 (66%), Gaps = 6/62 (9%)

```
Query: 352  IPFVLIASNFIGVLFSRSLHYQFLSWYHWTLPILIFWSGMPFFVGPIWYVLH--EWCWNS  409
            +PF L   NFIGV  +RSLHYQF  WY +LP L+ WS P+ +G  + +L   E+CWN+
Sbjct: 412  LPFFL--CNFIGVACARSLHYQFYIWYFHSLPYLV-WS-TPYSLGVRYLILGIIEYCWNT  467

Query: 410  YP  411
            YP
Sbjct: 468  YP  469
```

FIG.4D

Drosophila melanogaster

>gi|3024222|sp|Q27333|NT56_DROME LETHAL(2)NEIGHBOUR OF TID PROTEIN (NOT56) (NOT4 5)
          Length = 510

Score = 121 bits (305), Expect = 3e-27
 Identities = 96/272 (35%), Positives = 154/272 (56%), Gaps = 17/272 (6%)

```
Query:  34  RYVIFDCRANLIVMPLLILFESMLCKIIIKKVAYTEIDYKAYMEQIEMIQLDGMLDYSQV  93
            +Y++ + A IV ++L E ++ ++I++V YTEID+ AYM++ E    L+G +YS +
Sbjct:  36  KYLLLEPAALPIVGLFVLLAELVINVVVIQRVPYTEIDWVAYMQECEGF-LNGTTNYSLL  94

Query:  94  SGGTGPLVYPAGHVLIYKMMYWLTEGMDHVERGQVFFRYLYLLTLALQMACYYLLH-LPP  152
            G TGPLVYPA V IY +Y++T  +V  Q F +YLL LAL + Y      +PP
Sbjct:  95  RGDTGPLVYPAAFVYIYSALYYVTSHGTNVRLAQYIFAGIYLLQLALVLRLYSKSRKVPP  154

Query: 153  WCVVLACL-SKRLHSIYVLRLFNDCFTTLFMVVTVLGAIVASRCHQRPKLKKSLALVISA  211
            + +VL+  S R+HSIYVLRLFND    + V +LA +    +R L      S
Sbjct: 155  YVLVLSAFTSYRIHSIYVLRLFNDP.....VAVLLLYAALNLFLDRRWTLG--......ST  202

Query: 212  TYSMAVSIKMNALLYFPAMMISLFILNDANVILTLLDLVAMIAWQVAVAVPFLRSFPQQY  271
            +S+AV +KMN +   A  + LF L + ++ T+L L        Q+ + PFL + P +Y
Sbjct: 203  FFSLAVGVKMN--ILLFAPALLLFYLANLGLLRTILQLAVCGVIQLLLGAPFLLTHPVEY  260

Query: 272  LHCAFNFGRKFMYQWSINWQMMDEEAFNDKRF  303
            L +F+ GR F ++W+++N++ +  + F ++ F
Sbjct: 261  LRGSFDLGRIFEHKWTVNYRFLSRDVFENRTF  292
```

Score = 49.4 bits (117), Expect = 2e-05
 Identities = 27/60 (45%), Positives = 35/60 (58%), Gaps = 2/60 (3%)

```
Query: 352  IPFVLIASNFIGVLFSRSLHYQFLSWYHWTLPILIFWSGMPFFVGPIWYVLHEWCWNSYP  411
            +PF L   N +GV SRSLHYQF WY +LP L + +    V +   L E+CWN+YP
Sbjct: 407  LPFFL--CNLVGVACSRSLHYQFYVWYFHSLPYLAWSTPYSLGVRCLILGLIEYCWNTYP  464
```

FIG.4E

Matrix: BLOSUM62
Gap Penalties: Existence: 11, Extension: 1
Number of Hits to DB: 28883317
Number of Sequences: 96469
Number of extensions: 1107545
Number of successful extensions: 2870
Number of sequences better than 10.0: 16
Number of HSP's better than 10.0 without gapping: 5
Number of HSP's successfully gapped in prelim test: 11
Number of HSP's that attempted gapping in prelim test: 2839
Number of HSP's gapped (non-prelim): 23 length of query: 458
length of database: 35,174,128
effective HSP length: 45
effective length of query: 413
effective length of database: 30,833,023
effective search space: 12734038499
effective search space used: 12734038499
T: 11
A: 40
X1: 15 ( 7.1 bits)
X2: 38 (14.6 bits)
X3: 64 (24.7 bits)
S1: 40 (21.8 bits)
S2: 67 (30.4 bits)

FIG.4F

*S. cerevisiae* ALG3
ATGGAAGGTGAACAGTCTCCGCAAGGTGAAAAGTCTCTGCAAAGGAAGC
AATTTGTCAGACCTCCGCTGGATCTGTGGCAGGATCTCAAGGACGGTGTG
CGCTACGTGATCTTCGATTGTAGGGCCAATCTTATCGTTATGCCCCTTTTG
ATTTTGTTCGAAAGCATGCTGTGCAAGATTATCATTAAGAAGGTAGCTTAC
ACAGAGATCGATTACAAGGCGTACATGGAGCAGATCGAGATGATTCAGCT
CGATGGCATGCTGGACTACTCTCAGGTGAGTGGTGGAACGGGCCCGCTGG
TGTATCCAGCAGGCCACGTCTTGATCTACAAGATGATGTACTGGCTAACA
GAGGGAATGGACCACGTTGAGCGCGGGCAAGTGTTTTTCAGATACTTGTA
TCTCCTTACACTGGCGTTACAAATGGCGTGTTACTACCTTTTACATCTACC
ACCGTGGTGTGTGGTCTTGGCGTGCCTCTCTAAAAGATTGCACTCTATTTA
CGTGCTACGGTTATTCAATGATTGCTTCACTACTTTGTTTATGGTCGTCACG
GTTTTGGGGGCTATCGTGGCCAGCAGGTGCCATCAGCGCCCCAAATTAAA
GAAGTCCCTTGCGCTGGTGATCTCCGCAACATACAGTATGGCTGTGAGCA
TTAAGATGAATGCGCTGTTGTATTTCCCTGCAATGATGATTTCTCTATTCAT
CCTTAATGACGCGAACGTAATCCTTACTTTGTTGGATCTCGTTGCGATGAT
TGCATGGCAAGTCGCAGTTGCAGTGCCCTTCCTGCGCAGCTTTCCGCAACA
GTACCTGCATTGCGCTTTTAATTTCGGCAGGAAGTTTATGTACCAATGGAG
TATCAATTGGCAAATGATGGATGAAGAGGCTTTCAATGATAAGAGGTTCC
ACTTGGCCCTTTTAATCAGCCACCTGATAGCGCTCACCACACTGTTCGTCA
CAAGATACCCTCGCATCCTGCCCGATTTATGGTCTTCCCTGTGCCATCCGC
TGAGGAAAAATGCAGTGCTCAATGCCAATCCCGCCAAGACTATTCCATTC
GTTCTAATCGCATCCAACTTCATCGGCGTCCTATTTTCAAGGTCCCTCCAC
TACCAGTTTCTATCCTGGTATCACTGGACTTTGCCTATACTGATCTTTTGGT
CGGGAATGCCCTTCTTCGTTGGTCCCATTTGGTACGTCTTGCACGAGTGGT
GCTGGAATTCCTATCCACCAAACTCACAAGCAAGCACGCTATTGTTGGCA
TTGAATACTGTTCTGTTGCTTCTATTGGCCTTGACGCAGCTATCTGGTTCGG
TCGCCCTCGCCAAAAGCCATCTTCGTACCACCAGCTCTATGGAAAAAAAG
CTCAACTGA

*S. cerevisiae* Alg3p
MEGEQSPQGEKSLQRKQFVRPPLDLWQDLKDGVRYVIFDCRANLIVMPLLIL
FESMLCKIIIKKVAYTEIDYKAYMEQIEMIQLDGMLDYSQVSGGTGPLVYPAG
HVLIYKMMYWLTEGMDHVERGQVFFRYLYLLTLALQMACYYLLHLPPWCV
VLACLSKRLHSIYVLRLFNDCFTTLFMVVTVLGAIVASRCHQRPKLKKSLALV
ISATYSMAVSIKMNALLYFPAMMISLFILNDANVILTLLDLVAMIAWQVAVA
VPFLRSFPQQYLHCAFNFGRKFMYQWSINWQMMDEEAFNDKRFHLALLISHL
IALTTLFVTRYPRILPDLWSSLCHPLRKNAVLNANPAKTIPFVLIASNFIGVLFS
RSLHYQFLSWYHWTLPILIFWSGMPFFVGPIWYVLHEWCWNSYPPNSQASTL
LLALNTVLLLLLALTQLSGSVALAKSHLRTTSSMEKKLN

FIG.5

*P. pastoris ALG3*
ATGCCTCCGATAGAGCCAGCTGAAAGGCCAAAGCTTACGCTGAAAAATGT
TATCGGTGATCTAGTGGCTCTTATTCAAAACGTTTTATTTAACCCAGATTTT
AGTGTCTTCGTTGCACCTCTTTTATGGTTAGCTGATTCCATTGTTATCAAGG
TGATCATTGGCACTGTTTCCTACACAGATATTGATTTTCTTCATATATGCA
ACAAATCTTTAAAATTCGACAAGGAGAATTAGATTATAGCAACATATTTG
GTGACACCGGTCCATTGGTTTACCCAGCCGGCCATGTTCATGCTTACTCAG
TACTTTCGTGGTACAGTGATGGTGGAGAAGACGTCAGTTTCGTTCAACAA
GCATTTGGTTGGTTATACCTAGGTTGCTTGTTACTATCCATCAGCTCCTACT
TTTTCTCTGGCTTAGGGAAAATACCTCCGGTTTATTTTGTTTTGTTGGTAGC
GTCCAAGAGACTGCATTCAATATTTGTATTGAGACTCTTCAATGACTGTTT
AACAACATTTTTGATGTTGGCAACTATAATCATCCTTCAACAAGCAAGTAG
CTGGAGGAAAGATGGCACAACTATTCCATTATCTGTCCCTGATGCTGCAG
ATACGTACAGTTTAGCCATCTCTGTAAAGATGAATGCGCTGCTATACCTCC
CAGCATTCCTACTACTCATATATCTCATTTGTGACGAAAATTTGATTAAAG
CCTTGGCACCTGTTCTAGTTTTGATATTGGTGCAAGTAGGAGTCGGTTATT
CGTTCATTTTACCGTTGCACTATGATGATCAGGCAAATGAAATTCGTTCTG
CCTACTTTAGACAGGCTTTTGACTTTAGTCGCCAATTTCTTTATAAGTGGA
CGGTTAATTGGCGCTTTTTGAGCCAAGAAACTTTCAACAATGTCCATTTTC
ACCAGCTCCTGTTTGCTCTCCATATTATTACGTTAGTCTTGTTCATCCTCAA
GTTCCTCTCTCCTAAAAACATTGGAAAACCGCTTGGTAGATTTGTGTTGGA
CATTTTCAAATTTTGGAAGCCAACCTTATCTCCAACCAATATTATCAACGA
CCCAGAAAGAAGCCCAGATTTTGTTTACACCGTCATGGCTACTACCAACTT
AATAGGGGTGCTTTTTGCAAGATCTTTACACTACCAGTTCCTAAGCTGGTA
TGCGTTCTCTTTGCCATATCTCCTTTACAAGGCTCGTCTGAACTTTATAGCA
TCTATTATTGTTTATGCCGCTCACGAGTATTGCTGGTTGGTTTTCCCAGCTA
CAGAACAAAGTTCCGCGTTGTTGGTATCTATCTTACTACTTATCCTGATTC
TCATTTTTACCAACGAACAGTTATTTCCTTCTCAATCGGTCCCTGCAGAAA
AAAAGAATACATAA

*P. pastoris* Alg3p
MPPIEPAERPKLTLKNVIGDLVALIQNVLFNPDFSVFVAPLLWLADSIVIKVIIG
TVSYTDIDFSSYMQQIFKIRQGELDYSNIFGDTGPLVYPAGHVHAYSVLSWYS
DGGEDVSFVQQAFGWLYLGCLLLSISSYFFSGLGKIPPVYFVLLVASKRLHSIF
VLRLFNDCLTTFLMLATIIILQQASSWRKDGTTEPLSVPDAADTYSLAISVKMN
ALLYLPAFLLLIYLICDENLIKALAPVLVLILVQVGVGYSFILPLHYDDQANEIR
SAYFRQAFDFSRQFLYKWTVNWRFLSQETFNNVHFHQLLFALHIITLVLFILKF
LSPKMGKPLGRFVLDIFKFWKPTLSPTNIINDPERSPDFVYTVMATTNLIGVLF
ARSLHYQFLSWYAFSLPYLLYKARLNFIASIIVYAAHEYCWLVFPATEQSSAL
LVSILLLILILIFTNEQLFPSQSVPAEKKNT

FIG.6

*P. pastoris* ALG3 BLAST

Sequences producing significant alignments: (bits) Value

```
gi|586444|sp|P38179|ALG3_YEAST    Dolichyl-P-Man:Man(5)GlcNAc(...228    2e-58
gi|12802365|gb|AAK07848.1|AF309689_10    putative NOT-56 manno...212    8e-54
gi|984725|gb|AAA75352.1|    ORF 1                              206    4e-52
gi|7492702|pir||T39084    probable mannosyltransferase - fissi...176    8e-43
gi|16226531|gb|AAL16193.1|AF428424_1    At2g47760/F17A22.15 [A...164    2e-39
gi|25367230|pir||B84919    Not56-like protein [imported] - Ara...164    3e-39
gi|25814791|emb|CAB70171.2|    Hypothetical protein K09E4.2 [C...161    2e-38
gi|17535001|ref|NP_496950.1|    Putative plasma membrane membr...160    3e-38
gi|1654000|emb|CAA70220.1|    Not56-like protein [Homo sapiens...155    2e-36
gi|13279206|gb|AAH04313.1|AAH04313    Unknown (protein for IMA...154    2e-36
gi|22122365|ref|NP_666051.1|    hypothetical protein MGC36684 ...150    3e-35
gi|21292031|gb|EAA04176.1|    agCP3388 [Anopheles gambiae str....120    4e-26
gi|1780792|emb|CAA71167.1|    lethal(2)neighbour of tid [Droso...114    3e-24
```

Alignments

*S. cerevisiae*

```
Score = 228 bits (580), Expect = 2e-58
Identities = 154/429 (35%), Positives = 229/429 (53%), Gaps = 37/429 (8%)

Query:   9  RPKLTLKNVIGDLVALIQNVLFNPDFSVFVAPLLWLADSIVIKVIIGTVSYTDIDFSSYM   68
            RP L L     DL    ++ V+F+    ++ V PLL L +S++ K+II  V+YT+ID+ +YM
Sbjct:  20  RPPLDLWQ---DLKDGVRYVIFDCRANLIVMPLLILFESMLCKIIIKKVAYTEIDYKAYM   76

Query:  69  QQIFKIR-QGELDYSNIFGDTGPLVYPAGHVHAYSVLSWYSDGGEDVSFVQQAFGWLYLG  127
            +QI  I+   G LDYS + G TGPLVYPAGHV  Y ++ W ++G + V   Q F +LYL
Sbjct:  77  EQIEMIQLDGMLDYSQVSGGTGPLVYPAGHVLIYKMMYWLTEGMDHVERGQVFFRYLYLL  136

Query: 128  CLLLSISSYFFSGLGKIPPVYFVLLVASKRLHSIFVLRLFNDCLTTFLMLATI---IILQ  184
              L L ++ Y+   L    +PP   VL    SKRLHSI+VLRLFNDC TT  M+ T   I+
Sbjct: 137  TLALQMACYY---LLHLPPWCVVLACLSKRLHSIYVLRLFNDCFTTLFMVVTVLGAIVAS  193

Query: 185  QASSWRKDGTTIPLSVPDAADTYSLAISVKMNXXXXXXXXXXXXXXXXCDENLIKALAPXX  244
            +           K    ++ L +    + TYS+A+S+KMN                 D N+I  L
Sbjct: 194  RCHQRPKLKKSLALVI---SATYSMAVSIKMNALLYFPAMMISLFILNDANVILTLLDLV  250

Query: 245  XXXXXXXXXXYSFILPLHYDDQANEIRSAYFRQAFDFSRQFLYKWTVNWRFLSQETFNNV  304
                      F+          Y    AF+F R+F+Y+W++NW+ + ++E FN+
Sbjct: 251  AMIAWQVAVAVPFL--------RSFPQQYLHCAFNFGRKFMYQWSINWQMMDEEAFNDK  301
```

FIG.7A

```
Query: 305  HFHQLLFALHIITL-VLFILKFLSPKNIGKPLGRFVLDIFKFWKPTLSPTNIIN-DPERS  362
             FH  L  H+I L  LF+ ++         R + D++      L   ++N +P ++
Sbjct: 302  RFHLALLISHLIALTTLFVTRY..........PRILPDLWSSLCHPLRKNAVLNANPAKT  351

Query: 363  PDFVYTVMATTNLIGVLFARSLHYQFLSWYAFSLPYLLYKARLNFIASIIVYAAHEYCWL  422
             F   V+  +N IGVLF+RSLHYQFLSWY ++LP L++ + + F    I Y  HE+CW
Sbjct: 352  IPF---VLIASNFIGVLFSRSLHYQFLSWYHWTLPILIFWSGMPFFVGPIWYVLHEWCWN  408

Query: 423  VFPATEQSS  431
             +P   Q+S
Sbjct: 409  SYPPNSQAS  417
```

*Neurospora crassa*

Score = 212 bits (540), Expect = 8e-54
Identities = 140/400 (35%), Positives = 212/400 (53%), Gaps = 29/400 (7%)

```
Query: 35   SVFVAPLLWLADSIVIKVIIGTVSYTDIDFSSYMQQIFKIRQGELDYSNIFGDTGPLVYP  94
             S  + P L+L D+++  +II  V YT+ID+++YM+Q+ +I  GE DY+ + G TGPLVYP
Sbjct: 33   SKLIPPALFLVDALLCGLIIWKVPYTEIDWAAYMEQVSQILSGERDYTKVRGGTGPLVYP  92

Query: 95   AGHVHAYSVLSWYSDGGEDVSFVQQAFGWLYLGCLLLSISSYFFSGLGKIPPVYFVLLVA  154
             A HV+ Y+ L  +D G ++   QQ F  LY+ L  + Y+    K PP  F LL
Sbjct: 93   AAHVYIYTGLYHLTDEGRNILLAQQLFAGLYMVTLAVVMGCYW---QAKAPPYLFPLLTL  149

Query: 155  SKRLHSIFVLRLFNDCLTTFLMLATIIILQQASSWRKDGTTIPLSVPDAADTYSLAISVK  214
             SKRLHSIFVLR FNDC     + I  Q+ +W+              A  Y+L + VK
Sbjct: 150  SKRLHSIFVLRCFNDCFAVLFLWLAIFFFQR-RNWQA.........-......GALLYTLGLGVK  197

Query: 215  MNXXXXXXXXXXXXXXCDENLIKALAPXXXXXXXXXXXXXXYSFILPLHYDDQANEIRSAY  274
             M              + + L               F+  HY +         Y
Sbjct: 198  MTLLLSLPAVGIVLFLGSG-SFVTTLQLVATMGLVQILIGVPFL--AHYPTE-------Y  247

Query: 275  FRQAFDFSRQFLYKWTVNWRFLSQETFNNVHFHQLLFALHIITLVLFI-LKFLSPKNIGK  333
             +AF+ SRQF ++KWTVNWRF+ +E F + F   L ALH++ L +FI +++  P  K
Sbjct: 248  LSRAFELSRQFFFKWTVNWRFVGEEIFLSKGFALTLLALHVLVLGIFITTRWIKPAR--K  305

Query: 334  PLGRFVLDIFKFWKPTLS-PTNIINDPERSPDFVYTVMATTNLIGVLFARSLHYQFLSWY  392
              L  + +   KP L+ P +     +P ++ T + + N +G+LFARSLHYQF ++
Sbjct: 306  SLVQLISPVLLAGKPPLTVPEHRAAARDVTPRYIMTTILSANAVGLLFARSLHYQFYAYV  365

Query: 393  AFSLPYLLYKARLNFIASIIVYAAHEYCWLVFPATEQSSA  432
             A+S P+LL++A L+ +    +++A HE+ W VFP+T SSA
Sbjct: 366  AWSTPFLLWRAGLHPVLVYLLWAVHEWAWNVFPSTPASSA  405
```

FIG.7B

*Schizosaccharomyces pombe*

Score = 176 bits (445), Expect = 8e-43
Identities = 132/390 (33%), Positives = 194/390 (49%), Gaps = 35/390 (8%)

```
Query:   42  LWLADSIVIKVIIGTVSYTDIDFSSYMQQIFKIRQGELDYSNIFGDTGPLVYPAGHVHAY  101
             L L +   + II V YT+ID+ +YM+Q+    GE DY ++ G TGPLVYP GHV Y
Sbjct:   30  LLLLEIPFVFAIISKVPYTEIDWIAYMEQVNSFLLGERDYKSLVGCTGPLVYPGGHVFLY  89

Query:  102  SVLSWYSDGGEDVSFVQQAFGWLYLGCLLLSISSYFFSGLGKIPPVYFVLLVASKRLHSI  161
             ++L + +DGG ++    Q  F ++Y  +  +I  Y F  + + P   +VLL+ SKRLHSI
Sbjct:   90  TLLYYLTDGGTNIVRAQYIFAFVYW--ITTAIVGYLFK-IVRAPFYIYVLLILSKRLHSI  146

Query:  162  FVLRLFNDCLTTFLMLATIIILQQASSWRKDGTTIPLSVPDAADTYSLAISVKMNXXXXX  221
             F+LRLFND  +L + I+       W +           A+   S+A SVKM+
Sbjct:  147  FILRLFNDGFNS-LFSSLFILSSCKKKWVR...........ASILLSVACSVKMSSLLYV  194

Query:  222  XXXXXXXXXXCDENLIKALAPXXXXXXXXXXXXXYSFILPLHYDDQANEIRSAYFRQAFDF  281
                       L++ L P             + + +             +Y+ QAFDF
Sbjct:  195  PAYLVL--------LLQILGPKKTWMHIFVIIIVQILFSIPF----LAYFWSYWTQAFDF  242

Query:  282  SRQFLYKWTVNWRFLSQETFNNVHFHQLLFALHIITLVLFILKFLSPKNIGKPLGRFVLD  341
             R F YKWTVNWRF+ + F + F  + LH+ LV F  K  + P
Sbjct:  243  GRAFDYKWTVNWRFIPRSIFESTSFSTSILFLHVALLVAFTCKHWNKLSRATP-------  295

Query:  342  IFKFWKPTLSPTNIINDPERSPDFVYTVMATTNLIGVLFARSLHYQFLSWYAFSLPYLLY  401
                F       L+   +       +P+F++T +AT+NLIG+L ARSLHYQF +W+A+  PYL Y
Sbjct:  296  -FAMVNSMLTLKPLPKLQLATPNFIFTALATSNLIGILCARSLHYQFYAWFAWYSPYLCY  354

Query:  402  KARLNFIASIIVYAAHEYCWLVFPATEQSS  431
             +A      I ++   EY W VFP+T+ SS
Sbjct:  355  QASFPAPIVIGLWMLQEYAWNVFPSTKLSS  384
```

*Arabidopsis thaliana*

Score = 164 bits (415), Expect = 2e-39
Identities = 131/391 (33%), Positives = 194/391 (49%), Gaps = 29/391 (7%)

```
Query:   42  LWLADSIVIKVIIGTVSYTDIDFSSYMQQIFKIRQGELDYSNIFGDTGPLVYPAGHVHAY  101
             L LAD+I++  +II V YT ID+ +YM Q+    GE DY N+ GDTGPLVYPAG ++ Y
Sbjct:   39  LILADAILVAL1IAYVPYTKIDWDAYMSQVSGFLGGERDYGNLKGDTGPLVYPAGFLYVY  98
```

FIG.7C

```
Query: 102  SVLSWYSDGGEDVSFVQQAFGWLYLGCLLLSISSYFFSGLGKIPPVYFVLLVASKRLHSI  161
            S +   + G +V   Q  FG LY+ L + +  Y  + + +P       LL  SKR+HSI
Sbjct:  99  SAVQNLTGG--EVYPAQILFGVLYIVNLGIVLIIYVKTDV--VPWWALSLLCLSKRIHSI  154

Query: 162  FVLRLFNDCLTTFLMLATIIILQQASSWRKDGTTIPLSVPDAADTYSLAISVKMNXXXXX  221
            FVLRLFNDC   L+ A++ +     +RK   + +         +S A+SVKMN
Sbjct: 155  FVLRLFNDCFAMTLLHASMALFL----YRKWHLGMLV--------FSGAVSVKMNVLLYA  202

Query: 222  XXXXXXXXXXCDENLIKALAPXXXXXXXXXXXXXYSFILPLHYDDQANEIRSAYFRQAFDF  281
                      N+I  ++                 F++           +Y   AFD
Sbjct: 203  PTLLLLLLKAM--NIIGVVSALAGAALAQILVGLPFLITYPV.........SYIANAFDL  251

Query: 282  SRQFLYKWTVNWRFLSQETFNNVHFHQLLFALHIITLVLFILKFLSPKNIGKPLGRFVLD  341
            R F++ W+VN++F+ +  F + F L    H+  LV F   +  K+ G +G
Sbjct: 252  GRVFIHFWSVNFKFVPERVFVSKEFAVCLLIAHLFLLVAFA-NYKWCKHEGGIIGFMRSR  310

Query: 342  IFKFWKP-TLSPTNIINDPERSPDFVYTVMATTNLIGVLFARSLHYQFLSWYAFSLPYLL  400
            F     P  +LS +++     + + V T M   N IG++FARSLHYQF SWY +SLPYLL
Sbjct: 311  HFFLTLPSSLSFSDVSASRIITKEHVVTAMFVGNFIGIVFARSLHYQFYSWYFYSLPYLL  370

Query: 401  YKARLNFIASIIVYAAHEYCWLVFPATEQSS  431
            ++         +I++   E CW V+P+T  SS
Sbjct: 371  WRTPFPTWLRLIMFLGIELCWNVYPSTPSSS  401
```

FIG. 7D

*K. lactis* ALG3

TTTGTTTACAAGCTGATACCAACGAACATGAATACACCGGCAGGTTTACT
GAAGATTGGCAAAGCTAACCTTTTACATCCTTTTACCGATGCTGTATTCAG
TGCGATGAGAGTAAACGCAGAACAAATTGCATACATTTTACTTGTTACCA
ATTACATTGGAGTACTATTTGCTCGATCATTACACTACCAATTCCTATCTT
GGTACCATTGGACGTTACCAGTACTATTGAATTGGGCCAATGTTCCGTATC
CGCTATGTGTGCTATGGTACCTAACACATGAGTGGTGCTGGAACAGCTAT
CCGCCAAACGCTACTGCATCCACACTGCTACACGCGTGTAACACATACTG
TTATTGGCTGTATTCTTAAGAGGACCCGCAAACTCGAAAAGTGGTGATAA
CGAAACAACACACGAGAAAGCTGAG

*K. lactis* Alg3p

FVYKLIPTNMNTPAGLLKIGKANLLHPFTDAVFSAMRVNAEQIAYILLVTNYI
GVLFARSLHYQFLSWYHWTLPVLLNWANVPYPLCVLWYLTHEWCWNSYPP
NATASTLLHACNTYCYWLYSZEDPQTRKVVITKQHTRKL

FIG.8

K. lactis ALG3 BLAST

```
                                                             Score    E
Sequences producing significant alignments:                  (bits)   Value gi|586444|sp|P38179|ALG3_YEAST  Dolichyl-P-Man:Man(5)GlcNAc(... 125   1e-28
gi|984725|gb|AAA75352.1|   ORF 1                                94    4e-19
gi|16226531|gb|AAL16193.1|AF428424_1   At2g47760/F17A22.15 [A...72    1e-12
gi|25367230|pir||B84919    Not56-like protein [imported] - Ara...72   1e-12
gi|21292031|gb|EAA04176.1|    agCP3388 [Anopheles gambiae str... 69   2e-11
gi|20892051|ref|XP_148657.1|    similar to Lethal(2)neighbour ...65   2e-10
```

Alignments

*S. cerevisiae*

```
Score = 125 bits (314), Expect = 1e-28
Identities = 60/120 (50%), Positives = 83/120 (69%), Gaps = 1/120 (0%)
Frame = +3

Query: 66   ANLLHPFT-DAVFSAMRVNAEQIAYILLVTNYIGVLFARSLHYQFLSWYHWTLPVLLNWA  242
            ++L HP   +AV +A    A+ I ++L+ +N+1GVLF+RSLHYQFLSWYHWTLP+L+ W+
Sbjct: 332  SSLCHPLRKNAVLNANP--AKTIPFVLIASNFIGVLFSRSLHYQFLSWYHWTLPILIFWS  389

Query: 243  NVPYPLCVLWYLTHEWCWNSYPPNATASTLLHACNTYCYWLYS*EDPQTRKVVITKQHTR  422
              +P+ +  +WY+ HEWCWNSYPPN+ ASTLL A NT    L+      + V +KHR
Sbjct: 390  GMPFFVGPIWYVLHEWCWNSYPPNSQASTLLLALNTVLLLLA-LTQLSGSVALAKSHLR  448
```

*A. thaliana*

```
Score = 72.0 bits (175), Expect = 1e-12
Identities = 42/107 (39%), Positives = 57/107 (53%), Gaps = 3/107 (2%)
Frame = +3

Query: 84   FTDAVFSAMRVNAEQIAYILLVTNYIGVLFARSLHYQFLSWYHWTLPVLLNWANVPYPLC  263
            F+D  S + + E +  + V N+IG++FARSLHYQF SWY ++LP LL     P   L
Sbjct: 322  FSDVSASRI-ITKEHVVTAMFVGNFIGIVFARSLHYQFYSWYFYSLPYLLWRTPFPTWLR  380

Query: 264  VLWYLTHEWCWNSYPPNATASTL---LHACNTYCYWLYS*EDPQTRK  395
            ++ +L  E CWN YP   ++S L   LH        WL   DP  K
Sbjct: 381  LIMFLGIELCWNVYPSTPSSSGLLLCLHLIILVGLWLAPSVDPYQLK  427
```

FIG.9

*S. cerevisiae* ALG9
ATGAATTGCAAGGCGGTAACCATTAGTTTATTACTGTTGTTATTTTTAACAAGAGT
ATATATTCAGCCGACATTCTCGTTAATTTCAGATTGCGATGAAACTTTTAATTATT
GGGAACCATTAAATTTATTGGTACGTGGATTTGGTAAACAAACCTGGGAATATTC
ACCCGAGTATTCTATTAGATCATGGCTTTCTTATTACCTTTTTACTGTATTCTTTA
TCCAGTAAACAAATTTACTGACCTAGAAAGTCATTGGAACTTTTTCATCACAAGA
GCATGCTTAGGCTTTTTTAGTTTTATCATGGAATTTAAACTACATCGTGAAATTGC
AGGCAGCTTGGCATTGCAAATCGCAAATATTTGGATTATTTTCCAATTGTTTAATC
CGGGCTGGTTCCATGCATCTGTGGAATTATTGCCTTCTGCCGTTGCCATGTTGTTG
TATGTAGGTGCCACCAGACACTCTCTACGCTATCTGTCCACTGGGTCTACTTCTAA
CTTTACGAAAAGTTTAGCGTACAATTTCCTGGCTAGTATACTAGGCTGGCCATTTG
TTTTAATTTTAAGCTTGCCATTATGT1TACATTACCTTTTCAACCATAGAATTATTT
CTACCATCAGAACCGCATTCGACTGCTGTTTGATATTTTCATTGACTGCATTTGCT
GTGATTGTCACTGACAGTATATTTTACGGGAAGCTTGCTCCTGTATCATGGAACA
TCTTATTTTACAATGTCAITAATGCAAGTGAGGAATCTGGCCCAAATATTTTCGGG
GTTGAGCCATGGTACTACTATCCACTAAATTTGTTACTGAATTTCCCACTGCCTGT
GCTAGTTTTAGCTATTTTGGGAATTTTCCATTTGAGATTATGGCCATTATGGGCAT
CATTATTCACATGGATTGCCGTTTTCACTCAACAACCTCACAAAGAGGAAAGATT
TCTCTATCCAATTTACGGGTTAATAACTTTGAGTGCAAGTATCGCCTTTTACAAAG
TGTTGAATCTATTCAATAGAAAGCCGATTCTTAAAAAAGGTATAAAGTTGTCAGT
TTTATTAATTGTTGCAGGCCAGGCAATGTCACGGATAGTGGCTTTGGTGAACAAT
TACACAGCTCCTATAGCCGTCTACGAGCAATTTTCTTCACTAAATCAAGGTGGTG
TGAAGGCACCGGTAGTGAATGTATGTACGGGACGTGAATGGTATCACTTCCCAAG
TTCTTTCCTGCTGCCAGATAATCATAGGCTAAAATTTGTTAAATCTGGATTTGATG
GTCTTCTTCCAGGTGATTTTCCAGAGAGTGGTTCTATTTTCAAAAAGATTAGAACT
TTACCTAAGGGAATGAATAACAAGAATATATATGATACCGGTAAAGAGTGGCCG
ATCACTAGATGTGATTATTTTATTGACATCGTCGCCCCAATAAATTTAACAAAAG
ACGTTTTCAACCCTCTACATCTGATGGATAACTGGAATAAGCTGGCATGTGCTGC
ATTCATCGACGGTGAAAATTCTAAGATTTTGGGTAGAGCATTTTACGTACCGGAG
CCAATCAACCGAATCATGCAAATAGTTTTACCAAAACAATGGAATCAAGTGTACG
GTGTTCGTTACATTGATTACTGTTTGTTTGAAAAACCAACTGAGACTACTAATTGA

*S. cerevisiae* Alg9p
MNCKAVTISLLLLLFLTRVYIQPTFSLISDCDETFNYWEPLNLLVRGFGKQTWEYSPE
YSIRSWAFLLPFYCILYPVNKFTDLESHWNFFITRACLGFFSFIMEFKLHREIAGSLALQ
IANIWIIFQLFNPGWFHASVELLPSAVAMLLYVGATRHSLRYLSTGSTSNFTKSLAYN
FLASILGWPFVLILSLPLCLHYLFNHRIISTIRTAFDCCLIFSLTAFAVIVTDSIFYGKLAP
VSWNILFYNVINASEESGPNIFGVEPWYYYPLNLLLNFPLPVLVLAILGIFHLRLWPLW
ASLFTWIAVFTQQPHKEERFLYPIYGLITLSASIAFYKVLNLFNRKPILKKGIKLSVLLI
VAGQAMSRIVALVNNYTAPIAVYEQFSSLNQGGVKAPVVNVCTGREWYHFPSSFLLP
DNHRLKEVKSGFDGLLPGDFPESGSIFKKIRTLPKGMNNKNIYDTGKEWPITRCDYFI
DIVAPINLTKDVFNPLHLMDNWNKLACAAFIDGENSKILGRAFYVPEPINRIMQIVLP
KQWNQVYGVRYIDYCLFEKPTETTN

FIG. 10

*P. pastoris ALG9*
TGGCCTTCCTGTCTGCTCGATACTTCCTTTTACAGTAACCAACATACATGTT
CTCCAACATGCTCTTGTATGTATTGGCCTATTCTATCTTGAGACTTGATATC
AACCTTCTATGGTATTATTTCAGACTGTGATGAAGTGTTCAACTACTGGGA
GCCACTCAACTTCATGCTTAGAGGGTTTGGAAAACAGACTTGGGAGTATT
CTCCAGAGTATGCCATCCGATCTTGGTCCTATCTAGTGCCACTTTGGATAG
CAGGCTATCCACCATTGTTCCTGGATATCCCTTCTTACTACTTTTTCTACTT
TTTCAGACTACTGCTGGTTATTTTTTCATTGGTTGCAGAAGTCAAGTTGTA
CCATAGTTTGAAGAAAAATGTCAGCAGTAAGATCAGTTTCTGGTACCTTCT
ATTTACAACCGTTGCTCCAGGAATGTCTCATAGCACGATAGCCTTATTACC
ATCCTCTTTTGCTATGGTTTGTCACACTTTTGCCATTAGATACGTCATTGAT
TACCTACAATTACCAACATTAATGCGCACAATCAGAGAGACTGCTGCCAT
CTCACCAGCTCACAAACAACAACTAGCCAACTCTCTC

*P. pastoris Alg9p*

WPSCLLDTSFYSNQHTCSPTCSCMYWPILSZDLISTFYGIISDCDEVFNYWEPL
NFMLRGFGKQTWEYSPEYAIRSWSYLVPLWIAGYPPLFLDIPSYYFFYFFRLLL
VIFSLVAEVKLYHSLKKNVSSKISFWYLLFTTVAPGMSHSTIALLPSSFAMVCH
TFAIRYVIDYLQLPTLMRTIRETAAISPAHKQQLANSL

FIG.11

*P. pastoris* ALG9 BLAST

```
                                                              Score    E
Sequences producing significant alignments:                   (bits)   Value gi|6324110|ref|NP_014180.1|    catalyzes the transfer of manno...131    1e-29
gi|21296668|gb|EAA08813.1|     agCP7810 [Anopheles gambiae str....110   2e-23
gi|7019765|emb|CAB75773.1|     putative mannosyltransferase inv...104  1e-21
gi|26341066|dbj|BAC34195.1|    unnamed protein product [Mus mu... 99    4e-20
gi|16551378|gb|AAL25798.1|     DIBD1 [Homo sapiens]               99    4e-20
gi|19527202|ref|NP_598742.1|    RIKEN cDNA 8230402H15 [Mus mus... 99    4e-20
gi|12053349|emb|CAB66861.1|    hypothetical protein [Homo sapi... 99    4e-20
```

Alignments

*S. cerevisiae*

```
 Score = 131 bits (329), Expect = 1e-29
 Identities = 62/141 (43%), Positives = 91/141 (64%), Gaps = 1/141 (0%)
 Frame = +2

Query: 200  ISTFYGIISDCDEVFNYWEPLNFMLRGFGKQTWEYSPEYAIRSWSYLVPLWIAGYP-PLF  376
            I + +ISDCDE FNYWEPLN ++RGFGKQTWEYSPEY+IRSW++L+P +   YP    F
Sbjct: 21   IQPTFSLISDCDETFNYWEPLNLLVRGFGKQTWEYSPEYSIRSWAFLLPFYCILYPVNKF  80

Query: 377  LDIPSXXXXXXXXRLLLVIFSLVAEVKLYHSLKKNVSSKISFWYLLFTTVAPGMSHSTIAL  556
            D+ S     R L FS + E KL+  +  +++ +I+  +++F  PG H+++ L
Sbjct: 81   TDLESHWNFFITRACLGFFSFIMEFKLHREIAGSLALQIANIWIIFQLFNPGWFHASVEL  140

Query: 557  LPSSFAMVCHTFAIRYVIDYL  619
            LPS+ AM+ +  A R+ + YL
Sbjct: 141  LPSAVAMLLYVGATRHSLRYL  161
```

*Anopheles gambiae*

```
 Score = 110 bits (274), Expect = 2e-23
 Identities = 58/130 (44%), Positives = 79/130 (60%), Gaps = 3/130 (2%)
 Frame = +2

Query: 197  LISTFYGIISDCDEVFNYWEPLNFMLRGFGKQTWEYSPEYAIRSWSYLVPLWIAGYPPLF  376
            L S Y IISDCDE +NYWEPL+++L+G G QTWEYSPE+A+RS+SY   LW+ G P
Sbjct: 34   LQSALYSIISDCDETYNYWEPLHYLLKGKGFQTWEYSPEFALRSYSY---LWLHGLPAKV  90
```

FIG.12A

```
Query: 377 LDIPS---XXXXXXXRLLLVIFSLVAEVKLYHSLKKNVSSKISFWYLLFTTVAPGMSHST 547
            L + +        R LL +   + E +LY L +    ++ +LLF    + GM S +
Sbjct: 91  LQLMTDNGVLIFYFVRCLLAVTCALLEYRLYRILGRKCGGGVASLWLLFQLTSAGMFISS 150

Query: 548 IALLPSSFAM 577
            ALLPSSF+M
Sbjct: 151 AALLPSSFSM 160
```

*S. pombe*

```
Score = 104 bits (260), Expect = 1e-21
Identities = 58/157 (36%), Positives = 85/157 (54%)
Frame = +2

Query: 197 LISTFYGIISDCDEVFNYWEPLNFMLRGFGKQTWEYSPEYAIRSWSYLVPLWIAGYPPLF 376
            L S   + +I DCDEV+NYWEPL+++L G+G QTWEYSPEYAIRSW Y+    + G+
Sbjct: 26  LTSASFRVIDDCDEVYNYWEPLHYLLGYGLQTWEYSPEYAIRSWFYIALHAVPGFLARG 85

Query: 377 LDIPSXXXXXXXRLLLVIFSLVAEVKLYHSLKKNVSSKISFWYLLFTTVAPGMSHSTIAL 556
            L +         R +L FS  E L   ++ +N +  ++             V GM ++ +
Sbjct: 86  LGLSRLHVFYFIRGVLACFSAFCETNLILAVARNFNRAVALHLTSVLFVNSGMWSASTSF 145

Query: 557 LPSSFAMVCHTFAIRYVIDYLQLPTLMRTIRETAAIS 667
            LPSSFAM   T A+      L P+  RT++  + I+
Sbjct: 146 LPSSFAMNMVTLALS---AQLSPPSTKRTVKVVSFIT 179
```

*M. musculus*

```
Score = 99.4 bits (246), Expect = 4e-20
Identities = 57/143 (39%), Positives = 76/143 (53%), Gaps = 1/143 (0%)
Frame = +2

Query: 152 SPTCSCMYWPILS*DLISTFYGIISDCDEVFNYWEPLNFMLRGFGKQTWEYSPEYAIRSW 331
            +P  S  + +LS  L +      ISDCDE FNYWEP ++++ G G QTWEYSP YAIRS+
Sbjct: 55  APEGSTAFKCLLSARLCAALLSNISDCDETFNYWEPTHYLIYGKGFQTWEYSPVYAIRSY 114

Query: 332 SY-LVPLWIAGYPPLFLDIPSXXXXXXXRLLLVIFSLVAEVKLYHSLKKNVSSKISFWYL 508
            +Y L+  W A+    L        R LL   S V E+  Y ++ K       +S   L
Sbjct: 115 AYLLLHAWPAAFHARILQTNKILVFYFLRCLLAFVSCVCELYFYKAVCKKFGLHVSRMML 174

Query: 509 LFTTVAPGMSHSTIALLPSSFAM 577
            F ++ GM  S+ A LPSSF M
Sbjct: 175 AFLVLSTGMFCSSSAFLPSSFCM 197
```

FIG. 12B

*H. sapiens*

```
Score = 99.4 bits (246), Expect = 4e-20
Identities = 56/143 (39%), Positives = 76/143 (53%), Gaps = 1/143 (0%)
Frame = +2

Query: 152  SPTCSCMYWPILS*DLISTFYGIISDCDEVFNYWEPLNFMLRGFGKQTWEYSPEYAIRSW  331
            +P S  +  +LS L +      ISDCDE FNYWEP ++++ G G QTWEYSP YAIRS+
Sbjct: 55   APEGSTAFKCLLSARLCAALLSNISDCDETFNYWEPTHYLIYGEGFQTWEYSPAYAIRSY  114

Query: 332  SY-LVPLWIAGYPPLFLDIPSXXXXXXXRLLLVIFSLVAEVKLYHSLKKNVSSKISFWYL  508
            +Y L+  W A +  L             R LL   S + E+ Y ++ K    +S   L
Sbjct: 115  AYLLLHAWPAAFHARILQTNKILVFYFLRCLLAFVSCICELYFYKAVCKKFGLHVSRMML  174

Query: 509  LFTTVAPGMSHSTIALLPSSFAM  577
            F  ++ GM  S+ A LPSSF M
Sbjct: 175  AFLVLSTGMFCSSSAFLPSSFCM  197
```

FIG. 12C

*S. cerevisiae ALG12*
ATGCGTTGGTCTGTCCTTGATACAGTGCTATTGACCGTGATTTCCTTTCATCTAAT
CCAAGCTCCATTCACCAAGGTGGAAGAGAGTTTTAATATTCAAGCCATTCATGAT
ATTTTAACCTACAGCGTATTTGATATCTCCCAATATGACCACTTGAAATTTCCTGG
AGTAGTCCCTAGAACATTCGTTGGTGCTGTGATTATTGCAATGCTTTCGAGACCTT
ATCTTTACTTGAGTTCTTTGATCCAAACTTCCAGGCCTACGTCTATAGATGTTCAA
TTGGTCGTTAGGGGGATTGTTGGCCTCACCAATGGGCTTTCTTTTATCTATTTAAA
GAATTGTTTGCAAGATATGTTTGATGAAATCACTGAAAAGAAAAAGGAAGAAAA
TGAAGACAAGGATATATACATTTACGATAGCGCTGGTACATGGTTTCTTTTATTTT
TAATTGGCAGTTTCCACCTCATGTTCTACAGCACTAGGACTCTGCCTAATTTTGTC
ATGACTCTGCCTCTAACCAACGTCGCATTGGGGTGGGTTTTATTGGGTCGTTATAA
TGCAGCTATATTCCTATCTGCGCTCGTGGCAATTGTATTTAGACTGGAAGTGTCAG
CTCTCAGTGCTGGTATTGCTCTATTTAGCGTCATCTTCAAGAAGATTTCTTTATTC
GATGCTATCAAATTCGGTATCTTTGGCTTGGGACTTGGTTCCGCCATCAGTATCAC
CGTTGATTCATATTTCTGGCAAGAATGGTGTCTACCTGAGGTAGATGGTTTCTTGT
TCAACGTGGTTGCGGGTTACGCTTCCAAGTGGGGTGTGGAGCCAGTTACTGCTTA
TTTCACGCATTACTTGAGAATGATGTTTATGCCACCAACTGTTTTACTATTGAATT
ACTTCGGCTATAAATTAGCACCTGCAAAATTAAAAATTGTCTCACTAGCATCTCTT
TTCCACATTATCGTCTTATCCTTTCAACCTCACAAAGAATGGAGATTCATCATCTA
CGCTGTTCCATCTATCATGTTGCTAGGTGCCACAGGAGCAGCACATCTATGGGAG
AATATGAAAGTAAAAAAGATTACCAATGTTTTATGTTTGGCTATATTGCCCTTATC
TATAATGACCTCCTTTTTCATTTCAATGGCGTTCTTGTATATATCAAGAATGAATT
ATCCAGGCGGCGAGGCTTTAACTTCTTTTAATGACATGATTGTGGAAAAAAATAT
TACAAACGCTACAGTTCATATCAGCATACCTCCTTGCATGACAGGTGTCACTTTAT
TTGGTGAATTGAACTACGGTGTGTACGGCATCAATTACGATAAGACTGAAAATAC
GACTTTACTGCAGGAAATGTGGCCCTCCTTTGATTTCTTGATCACCCACGAGCCA
ACCGCCTCTCAATTGCCATTCGAGAATAAGACTACCAACCATTGGGAGCTAGTTA
ACACAACAAAGATGTTTACTGGATTTGACCCAACCTACATTAAGAACTTTGTTTT
CCAAGAGAGAGTGAATGTTTTGTCTCTACTCAAACAGATCATTTTCGACAAGACC
CCTACCGTTTTTTTGAAAGAATTGACGGCCAATTCGATTGTTAAAAGCGATGTCTT
CTTCACCTATAAGAGAATCAAACAAGATGAAAAAACTGATTGA

*S. cerevisiae* Alg12p

MRWSVLDWLLTVISFHLIQAPFTKVEESFNIQAIHDILTYSVFDISQYDHLKFPGVVP
RTFVGAVIIAMLSRPYLYLSSLIQTSRPTSIDVQLWRGIVGLTNGLSFIYLKNCLQDM
FDEITEKKKEENEDKDIYIYDSAGTWFLLFLIGSFHLMFYSTRTLPNFVMTLPLTNVAL
GWVLLGRYNAAIFLSALVAIVFRLEVSALSAGIALFSVIFKKISLFDAIKFGIFGLGLGS
AISITVDSYFWQEWCLPEVDGFLFNWAGYASKWGVEPVTAYFTHYLRMMFMPPTV
LLLNYFGYKLAPAKLKIVSLASLFHUVLSFQPHKEWRFIIYAVPSIMLLGATGAAHLW
ENMKVKKITNVLCLAILPLSIMTSFFISMAFLYISRMNYPGGEALTSFNDMIVEKNITN
ATVHISIPPCMTGVTLFGELNYGVYGINYDKTENTTLLQEMWPSFDFLITHEPTASQLP
FENKTTNHWELVNTTKMFTGFDPTYIKNFVFQERVNVLSLLKQIIFDKTPTVFLKELT
ANSIVKSDVFFTYKRIKQDEKTD

FIG.13

*P. pastoris ALG12*
TCGGTCGAGAATGATAACTGAAGAACTCAAAATCTCTCACACTTTCATCGT
TACTGTACTGGCAATCATTGCATTTCAGCCTCATAAAGAATGGAGATTTAT
AGTTTACATTGTTCCACCACTTGTCATCACCATATCTACAGTACTTGCACA
ACTACCCAGGAGATTCACAATCGTCAAAGTTGCTGTTTTTCTCCTAAGTTT
CGGCTCTTTGCTCATATCCCTGTCGTTTCTTTTCATCTCATCGTATAACTAC
CCTGGGGGTGAAGCTTTACAGCATTTGAACGAGAAACTCCTTCTACTGGA
CCAAAGTTCCCTACCTGTTGATATTAAGGTTCATATGGATGTCCCTGCATG
CATGACTGGGGTGACTTTATTTGGTTACTTGGATAACTCAAAATTGAACAA
TTTAAGAATTGTCTATGATAAAACAGAAGACGAGTCGCTGGACACAATCT
GGGATTCTTTCAATTATGTCATCTCCGAAATTGACTTGGATTCTTCGACTG
CTCCCAAATGGGAGGGGGATTGGCTGAAGATTGATGTTGTCCAAGGCTAC
AACGGCATCAATAAACAATCTATCAAAAATACAATTTTCAATTATGGAAT
ACTTAAACGGATGATAAGAGACGCAACCAAACTTGATGTTGGATTTATTC
GTACGGTCTTTCGATCCTTCATAAAATTTGATGATAAATTATTCATTTATG
AGAGGAGCAGTCAAACCTGAAAATATATACCTCATTTGTTCAATTTGGTGT
AAAGAGTGTGGCGGATAGACTTCTTGTAAATCAGGAAAGCTACAATTCCA
ATTGCTGCAAAAAATACCAATGCCCATAA

*P. pastoris Alg12p*
RMITEELKISHTFIVTVLAIIAFQPHKEWRFIVYIVPPLVITISTVLAQLPRRFTIV
KVAVFLLSFGSLLISLSFLFISSYNYPGGEALQHLNEKLLLLDQSSLPVDIKVH
MDVPACMTGVTLFGYLDNSKLNNLRIVYDKTEDESLDTIWDSFNYVISEIDLD
SSTAPKWEGDWLKIDVVQGYNGINKQSIKNTIFNYGILKRMIRDATKLDVGFI
RTVFRSFIKFDDKLFIYERSSQ

FIG.14

*P. pastoris* ALG12 BLAST

```
                                                           Score      E
Sequences producing significant alignments:                (bits)    Value gi|1302525|emb|CAA96310.1|   ORF YNR030w [Saccharomyces cerev... 102   5e-21
gi|19112221|ref|NP_595429.1| putative involvement in cell w...   56   5e-07
gi|15864569|emb|CAC83681.1|  putative dolichyl-p-man: Man7Gl...  53   4e-06
gi|13129114|ref|NP_077010.1| dolichyl-p-mannose:Man7GlcNAc2...   53   4e-06
gi|22266724|gb|AAM94_900.1|AF311904_1 membrane protein SB87 ...  53   4e-06
gi|118478284|emb|CAD22101.1| putative mannosyltransferase [M... 52    8e-06
```

Alignments

*S. cerevisiae*

```
 Score =  102 bits (255), Expect = 5e-21
 Identities = 74/258 (28%), Positives = 121/258 (46%), Gaps = 19/258 (7%)

Query: 8    RMITEELKISHTFIVTVLAIIAFQPHKEWRFIVYIVPPLVITISTVLAQLPRRFTIVKVA  187
            ++  +LKI    +  + +++FQPHKEWRFI+Y VP +++  +T  A L    +  K+
Sbjct: 302  KLAPAKLKIVSLASLFHIIVLSFQPHKEWRFIIYAVPSIMLLGATGAAHLWENMKVKKIT 361

Query: 188  -------VXXXXXXXXXXXXXXXXXXXXXYNYPGGEALQHLNEKLLLLDQSSLPVDIKVHMD 346
                   +                     NYPGGEAL   N+ ++       +  VH+
Sbjct: 362  NVLCLAILPLSIMTSFFISMAFLYISRMNYPGGEALTSFNDMIV----EKNITNATVHIS 417

Query: 347  VPACMTGVTLFGYLDNSKLNNLRIVYDKTEDES-LDTIWDSFNYVI------SEIDLDSS 505
            +P CMTGVTLFG L+         I YDKTE+ + L +W SF+++I      S++  ++
Sbjct: 418  IPPCMTGVTLFGELNYGVYG---INYDKTENTTLLQEMWPSFDFLITHEPTASQLPFENK 474

Query: 506  TAPKWEGDWLKIDVVQGYNGINKQSIKNTIFN-----YGILKRMIRDATKLDVGFIRTVF 670
            T  WE    ++  + + G +  IKN +F        +LK++I D K    F++ +
Sbjct: 475  TTNHWE----LVNTTKMFTGFDPTYIKNFVFQERVNVLSLLKQIIFD--KTPTVFLKELT 528

Query: 671  RSFIKFDDKLFIYERSSQ 724
             + I    D  F Y+R Q
Sbjct: 529  ANSIVKSDVFFTYKRIKQ 546
```

FIG.15A

*S. pombe*

```
 Score = 56.2 bits (134), Expect = 5e-07
 Identities = 46/152 (30%), Positives = 62/152 (40%), Gaps = 11/152 (7%)

Query:  65  IIAFQPHKEWRFIVYIVPPLVITISTVLAQL--------PRRFTIVKVAVXXXXXXXXXX  220
            + +F HKEWRFI+Y + P    S + A L         + F I+++
Sbjct: 295  VYSFLGHKEWRFIIYSI-PWFNAASAIGASLCFNASKFGKKIFEILRLMFFSGIIFGFIG  353

Query: 221  XXXXXXXXXXYNYPGGEALQHLNEKLLLLDQSSLPVDIKVHMDVPACMTGVTLFGYLDNSK  400
                      Y YPGG AL   L E           + VHMDV  CMTG+T F  L +
Sbjct: 354  SSFLLYVFQYAYPGGLALTRLYE-------IENHPQVSVHMDVYPCMTGITRFSQLPS--  404

Query: 401  LNNLRIVYDKTEDESL---DTIWDSFNYVISE  487
                     YDKTED +        F+Y+I+E
Sbjct: 405  .....WYYDKTEDPKMLSNSLFISQFDYLITE  431
```

*Homo sapiens*

```
 Score = 53.1 bits (126), Expect = 4e-06
 Identities = 41/149 (27%), Positives = 68/149 (45%), Gaps = 6/149 (4%)

Query:  59  LAIIAFQPHKEWRFIVYIVPPLVITISTVLAQLPRR......FTIVKVAVXXXXXXXXXX  220
            +A+ + PHKE RFI+Y  P L IT +   + L          +   + V
Sbjct: 299  MALYSLLPHKELRFIIYAFPMLNITAARGCSYLLNNYKKSWLYKAGSLLVIGHLVVNAAY  358

Query: 221  XXXXXXXXXXYNYPGGEALQHLNEKLLLLDQSSLPVDIKVHMDVPACMTGVTLFGYLDNSK  400
                      +NYPGG A+Q L++  L+ Q+     D+ +H+DV A  TGV+ F  ++++
Sbjct: 359  SATALYVSHFNYPGGVAMQRLHQ--LVPPQT----DVLLHIDVAAAQTGVSRFLQVNSAW  412

Query: 401  LNNLRIVYDKTEDESLDTIWDSFNYVISE  487
                  YDK ED   T  ++ +++ E
Sbjct: 413  R------YDKREDVQPGTGMLAYTHILME  435
```

FIG. 15B

*S. cerevisiae ALG6*
ATGGCCATTGGCAAAAGGTTACTGGTGAACAAACCAGCAGAAGAATCATT
TTATGCTTCTCCAATGTATGATTTTTTGTATCCGTTTAGGCCAGTGGGGAA
CCAATGGCTGCCAGAATATATTATCTTTGTATGTGCTGTAATACTGAGGTG
CACAATTGGACTTGGTCCATATTCTGGGAAAGGCAGTCCACCGCTGTACG
GCGATTTTGAGGCTCAGAGACATTGGATGGAAATTACGCAACATTTACCG
CTTTCTAAGTGGTACTGGTATGATTTGCAATACTGGGGATTGGACTATCCA
CCATTAACAGCATTTCATTCGTACCTTCTGGGCCTAATTGGATCTTTTTTCA
ATCCATCTTGGTTTGCACTAGAAAAGTCACGTGGCTTTGAATCCCCCGATA
ATGGCCTGAAAACATATATGCGTTCTACTGTCATCATTAGCGACATATTGT
TTTACTTTCCTGCAGTAATATACTTTACTAAGTGGCTTGGTAGATATCGAA
ACCAGTCGCCCATAGGACAATCTATTGCGGCATCAGCGATTTTGTTCCAAC
CTTCATTAATGCTCATTGACCATGGGCACTTTCAATATAATTCAGTCATGC
TTGGCCTTACTGCTTATGCCATAAATAACTTATTAGATGAGTATTATGCTA
TGGCGGCCGTTTGTTTTGTCCTATCCATTTGTTTTAAACAAATGGCATTGTA
TTATGCACCGATTTTTTTTGCTTATCTATTAAGTCGATCATTGCTGTTCCCC
AAATTTAACATAGCTAGATTGACGGTTATTGCGTTTGCAACACTCGCAACT
TTTGCTATAATATTTGCGCCATTATATTTCTTGGGAGGAGGATTAAAGAAT
ATTCACCAATGTATTCACAGGATATTCCCTTTTGCCAGGGGCATCTTCGAA
GACAAGGTTGCTAACTTCTGGTGCGTTACGAACGTGTTTGTAAAATACAA
GGAAAGATTCACTATACAACAACTCCAGCTATATTCATTGATTGCCACCGT
GATTGGTTTCTTACCAGCCATGATAATGACATTACTTCATCCCAAAAAGCA
TCTTCTCCCATACGTGTTAATCGCATGTTCGATGTCCTTTTTTCTTTTTAGC
TTTCAAGTACATGAGAAAACTATCCTCATCCCACTTTTGCCTATTACACTA
CTCTACTCCTCTACTGATTGGAATGTTCTATCTCTTGTAAGTTGGATAAAC
AATGTGGCTTTGTTTACGCTATGGCCTTTGTTGAAAAAGGACGGTCTTCAT
TTACAGTATGCCGTATCTTTCTTACTAAGCAATTGGCTGATTGGAAATTTC
AGTTTTATTACACCAAGGTTCTTGCCAAAATCTTTAACTCCTGGCCCTTCT
ATCAGCAGCATCAATAGCGACTATAGAAGAAGAAGCTTACTGCCATATAA
TGTGGTTTGGAAAAGTTTTATCATAGGAACGTATATTGCTATGGGCTTTTA
TCATTTCTTAGATCAATTTGTAGCACCTCCATCGAAATATCCAGACTTGTG
GGTGTTGTTGAACTGTGCTGTTGGGTTCATTTGCTTTAGCATATTTTGGCTA
TGGTCTTATTACAAGATATTCACTTCCGGTAGCAAATCCATGAAGGACTTG
TAG

FIG.25A

*S. cerevisiae* ALG6p
MAIGKRLLVNKPAEESFYASPMYDFLYPFRPVGNQWLPEYIIFVCAVILRCTIG
LGPYSGKGSPPLYGDFEAQRHWMEITQHLPLSKWYWYDLQYWGLDYPPLTA
FHSYLLGLIGSFFNPSWFALEKSRGFESPDNGLKTYMRSTVIISDILFYFPAVIY
FTKWLGRYRNQSPIGQSIAASAILFQPSLMLIDHGHFQYNSVMLGLTAYAINN
LLDEYYAMAAVCFVLSICFKQMALYYAPIFFAYLLSRSLLFPKFNIARLTVIAF
ATLATFAIIFAPLYFLGGGLKNIHQCIHRIFPFARGIFEDKVANFWCVTNVFVK
YKERFTIQQLQLYSLIATVIGFLPAMIMTLLHPKKHLLPYVLIACSMSFFLFSFQ
VHEKTILIPLLPITLLYSSTDWNVLSLVSWINNVALFTLWPLLKKDGLHLQYA
VSFLLSNWLIGNFSFITPRFLPKSLTPGPSISSINSDYRRRSLLPYNVVWKSFIIGT
YIAMGFYHFLDQFVAPPSKYPDLWVLLNCAVGFICFSIFWLWSYYKIFTSGSK
SMKDL

FIG. 25B

*P. pastoris ALG6*
ATGCCACATAAAAGAACGCCCTCTAGCAGTCTGCTGTATGCAAGAATTCC
AGGGATCTCTTTTGAAAACTCTCCGGTGTTTGATTTTTTGTCTCCTTTTGGA
CCCGCTCCTAATCAATGGGTAGCACGATACATCATCATCTTTGCAATT
CTCATCAGATTGGCAGTTGGGCTGGGCTCCTATTCCGGCTTCAACACCCCT
CCAATGTATGGGGATTTTGAAGCTCAGAGGCATTGGATGGAAATTACTCA
GCATTTATCCATAGAAAATGGTACTTCTACGACTTGCAATATTGGGGGCT
TGACTATCCTCCCTTGACAGCCTTTCATTCATACTTCTTTGGCAAATTAGGC
AGCTTCATCAATCCAGCATGGTTTGCTTTAGACGTCTCCAGAGGGTTTGAA
TCAGTGGATCTAAAATCGTACATGAGGGCGACCGCAATTCTCAGTGAGCT
GTTATGTTTTATTCCAGCTGTCATTTGGTATTGTCGTTGGATGGGACTTAAC
TACTTCAATCAAAACGCCATTGAGCAAACTATAATAGCGTCTGCTATTCTT
TTCAATCCATCTTTAATTATCATAGATCATGGCCACTTCCAGTACAACTCA
GTTATGCTAGGTTTTGCTTTATTATCCATATTAAATCTGTTGTACGATAATT
TTGCATTAGCGGCTATTTTTTCGTTCTTTCAATAAGCTTTAAGCAAATGGC
TCTCTATTATAGCCCCATCATGTTTTTTTACATGCTGAGTGTGAGTTGTTGG
CCTTTGAAAAACTTCAACTTGTTGAGATTGGCTACTATCAGTATTGCAGTA
CTCTTGACTTTTGCAACTCTATTACTGCCTTTTGTATTAGTAGATGGGATGT
CACAAATTGGCCAAATATTATTCAGAGTTTTCCCGTTTTCAAGAGGCTTGT
TTGAGGATAAGGTGGCCAACTTTTGGTGTACAACGAATATACTGGTAAAG
TACAAACAGTTATTCACTGACAAAACCCTTACTAGGATATCGCTAGTAGC
AACTTTGATTGCAATTAGTCCGTCTTGCTTCATCATTTTTACTCACCCAAAG
AAGGTTTTACTACCGTGGGCTTTTGCTGCTTGCTCTTGGGCGTTCTATCTTT
TCTCTTTCCAAGTCCACGAGAAATCAGTTTTAGTTCCATTGATGCCTACCA
CTCTATTACTGGTAGAAAAAGACTTGGACATCATCTCAATGGTCTGCTGGA
TTTCTAATATTGCCTTCTTCAGCATGTGGCCTCTATTAAAAAGAGACGGGC
TGGCTTTGGAATATTTTGTCTTGGGAATATTGAGTAATTGGCTGATTGGAA
ACCTCAATTGGATTAGTAAATGGCTTGTCCCAGTTTCCTGATTCCAGGGC
CTACTCTCTCCAAAAAAGTTCCTAAAAGAGATACTAAAACAGTTGTTCAT
ACTCACTGGTTTTGGGGGTCAGTAACATTCGTTTCATACCTCGGAGCTACA
GTTATCCAGTTCGTAGATTGGCTGTACCTTCCACCTGCCAAGTATCCAGAT
TTGTGGGTTATTTTGAACACTACATTGTCGTTTGCTTGTTTCGGGTTGTTTT
GGCTATGGATTAACTACAATCTGTACATTTTGCGTGATTTTAAGCTTAAAG
ATGCTTAG

FIG.26A

*P. pastoris* Alg6
MPHKRTPSSSLLYARIPGISFENSPVFDFLSPFGPAPNQWVARYIIIIFAILIRLAV
GLGSYSGFNTPPMYGDFEAQRHWMEITQHLSIEKWYFYDLQYWGLDYPPLT
AFHSYFFGKLGSFINPAWFALDVSRGFESVDLKSYMRATAILSELLCFIPAVIW
YCRWMGLNYFNQNAIEQTIIASAILFNPSLIIIDHGHFQYNSVMLGFALLSILNL
LYDNFALAAIFFVLSISFKQMALYYSPIMFFYMLSVSCWPLKNFNLLRLATISI
AVLLTFATLLLPFVLVDGMSQIGQILFRVFPFSRGLFEDKVANFWCTTNILVK
YKQLFTDKTLTRISLVATLIAISPSCFIIFTHPKKVLLPWAFAACSWAFYLFSFQ
VHEKSVLVPLMPTTLLLVEKDLDIISMVCWISNIAFFSMWPLLKRDGLALEYF
VLGILSNWLIGNLNWISKWLVPSFLIPGPTLSKKVPKRDTKTVVHTHWFWGS
VTFVSYLGATVIQFVDWLYLPPAKYPDLWVILNTTLSFACFGLFWLWINYNL
YILRDFKLKDA

FIG.26B

*P. pastoris* ALG6 BLAST

```
                                                                Score    E
Sequences producing significant alignments:             (bits)   Value gi|1420090|emb|CAA99190.1|   ORF YOR002w [Saccharomyces cerev...489    e-137
gi|7490584|pir|T40396        glucosyltransferase - fission yeast ...369    e-101
gi|19921070|ref|NP_609393.1|  CG5091-PA [Drosophila melanoga...47     4e-64
gi|15240920|ref|NP_198662.1|  glucosyltransferase-like prote...244    3e-63
gi|7019325|ref|NP_037471.1|   dolichyl-P-Glc:Man9GlcNAc2-PP-d...238    2e-61
gi|12002040|gb|AAG43163.1|AF063604_1  brain my046 protein [H...236    7e-61
gi|1176671|sp|Q09226|ALG6_CAEEL  Probable dolichyl pyrophosp...222    9e-57
gi|21302638|gb|EAA14783.1|    agCP4617 [Anopheles gambiae str....219    8e-56
gi|5441788|emb|CAB4_6771.1|   probable glucosyltransferase [Sc...192    1e-47
gi|13129070|ref|NP_076984.1|  hypothetical protein MGC2840 s...112    1e-23
gi|2996578|emb|CAA12176.1|    glucosyltransferase [Homo sapiens] 112   1e-23
gi|20835439|ref|XP_131506.1|  similar to Dolichyl pyrophosph...104    3e-21
```

Alignments

*S. cerevisiae*

```
Score = 489 bits (1259), Expect = e-137
Identities = 274/530 (51%), Positives = 358/530 (67%), Gaps = 5/530 (0%)

Query:  20  SFENSPVFDFLSPFGPAPNQWVXXXXXXXXXXXXXXXXXXVGLGSYSGFNTPPMYGDFEAQRH  79
            SF  SP++DFL PF P  NQW+                  +GLG YSG  +PP+YGDFEAQRH
Sbjct:  16  SFYASPMYDFLYPFRPVGNQWLPEYIIFVCAVILRCTIGLGPYSGKGSPPLYGDFEAQRH  75

Query:  80  WMEITQHLSIEKWYFYDLQYWGLDYPPLTAFHSYFFGKLGSFINPAWFALDVSRGFESVD  139
            WMEITQHL + KWY+YDLQYWGLDYPPLTAFHSY  G +GSF NP+WFAL+ SRGFES D
Sbjct:  76  WMEITQHLPLSKWYWYDLQYWGLDYPPLTAFHSYLLGLIGSFFNPSWFALEKSRGFESPD  135

Query: 140  --LKSYMRATAILSELLCFIPAVIWYCRWMGLNYFNQNAIEQTIIASAILFNPSLIIIDH  197
              LK+YMR+T I+S++L + PAVI++ +W+G  Y NQ+ I Q+I ASAILF PSL++IDH
Sbjct: 136  NGLKTYMRSTVIISDILFYFPAVIYFTKWLG-RYRNQSPIGQSIAASAILFQPSLMLIDH  194

Query: 198  GHFQYNSVMLGFALLSILNLLYDNFALAAIFFVLSISFKQMALYYSPIMFFYMLSVSCWP  257
            GHFQYNSVMLG     +I NLL + +A+AA+ FVLSI FKQMALYY+PI F Y+LS S
Sbjct: 195  GHFQYNSVMLGLTAYAINNLLDEYYAMAAVCFVLSICFKQMALYYAPIFFAYLLSRSLL-  253
```

FIG.27A

```
Query:  258 LKNFNLLRLATISIAVLLTFATLLLP-FVLVDGMSQIGQILFRVFPFSRGLFEDKVANFW  316
             FN+ RL  I+ A L TFA +  P + L  G+  I Q + R+FPF+RG+FEDKVANFW
Sbjct:  254 FPKFNIARLTVIAFATLATFAIIFAPLYFLGGGLKNIHQCIHRIFPFARGIFEDKVANFW  313

Query:  317 CTTNILVKYKQLFTDKTLTRISLVATLIAISPSCFIIFTHPKKVLLPWAFAACSWAFYLF  376
             C TN+ VKYK+ FT + L    SL+AT+I P+   +   HPKK LLP+   ACS +F+LF
Sbjct:  314 CVTNVFVKYKERFTIQQLQLYSLIATVIGFLPAMIMTLLHPKKHLLPYVLIACSMSFFLF  373

Query:  377 SFQVHEKSXXXXXXXXXXXXXXXEKDLDIISMVCWISNIAFFSMWPLLKRDGLALEYFVLGI  436
             SFQVHEK+             D  +++S+V WI+N+A F++WPLLK+DGL L+Y V  +
Sbjct:  374 SFQVHEKTILIPLLPITLLYSSTDWNVLSLVSWINNVALFTLWPLLKKDGLHLQYAVSFL  433

Query:  437 LSNWLIGNLNWISKWLVPSFLIPGPTLSKKVPKRDTKTVVHTHWFWGSVTFVSYLGATVI  496
             LSNWLIGN ++I+  +P L PGP++S       ++++  +   W S    +Y+
Sbjct:  434 LSNWLIGNFSFITPRFLPKSLTPGPSISSINSDYRRRSLLPYNWWKSFIIGTYIAMGFY  493

Query:  497 QFVDWLYLPPAKYPDLWVILNTTLSFACFGLFWLWINYNLYILRDFKLKD  546
             F+D     PP+KYPDLWV+LN + F CF+ FWLW Y ++    +KD
Sbjct:  494 HFLDQFVAPPSKYPDLWVLLNCAVGFICFSIFWLWSYYKIFTSGSKSMKD  543

S. pombe

Score =  369 bits (946), Expect = e-101
Identities = 228/513 (44%), Positives = 315/513 (61%), Gaps = 35/513 (6%)

Query:   21 FEN-SPVFDFLSPFGPAPNQWVXXXXXXXXXXXXXXXXXVGLGSYSGFNTPPMYGDFEAQRH   79
             FEN +PV  F+S F    ++++                + +G  YSG+NTPPMYGDFEAQRH
Sbjct:    5 FENGAPVQQFVSRFRSYSSKFLFFPCLIMSLVFMQWLISIGPYSGYNTPPMYGDFEAQRH   64

Query:   80 WMEITQHLSIEKWYFYDLQYWGLDYPPLTAFHSYFFGKLGS-FINPAWFALDVSRGFESV  138
             WME+T H + +WYF DLQ+WGLDYPPLTA+ S+FFG +G  F NP WFA   SRGFES+
Sbjct:   65 WMELTLHTPVSQWYFRDLQWWGLDYPPLTAYVSWFFGIIGHYFFNPEWFADVTSRGFESL  124

Query:  139 DLKSYMRATAILSELLCFIPAVIWYCRWMGLNYFNQNAIEQTIIASAILFNPSLIIIDHG  198
             +LK +MR+T I S LL  +P +++Y +W     N +++        +LF P+L++++IDHG
Sbjct:  125 ELKLFMRSTVIASHLLILVPPLMFYSKWWSRRI--PNFVDRNASLIMVLFQPALLLIDHG  182

Query:  199 HFQYNSVMLGFALLSILNLLYDNFALAAIFFVLSISFKQMALYYSPIMFFYMLSVSCWPL  258
             HFQYN VMLG  + I NLL + + A  FF L+++FKQMALY++P +FFY+L     P
Sbjct:  183 HFQYNCVMLGLVMYAIANLLKNQYVAATFFFCLALTFKQMALYFAPPIFFYLLGTCVKPK  242
```

FIG.27B

```
Query: 259 KNFNLLRLATISIAVLLTFATLLLPFVLVDGMSQIGQILFRVFPFSRGLFEDKVANFWCT 318
            F+  R  +S+ V+ TF+ +L P++ +D  + + QIL RVFPF+RGL+EDKVANFWCT
Sbjct: 243 IRFS--RFILLSVTVVFTFSLILFPWIYMDYKTLLPQILHRVFPFARGLWEDKVANFWCT 300

Query: 319 TNILVKYKQLFTDKTLTRISLVATLIAISPSCFIIFTHPKKVLLPWAFAACSWAFYLFSF 378
            N + K +++FT   L  ISL+ TLI+I PSC I+F +P+K LL   FA+ SW F+LFSF
Sbjct: 301 LNTVFKIREVFTLHQLQVISLIFTLISILPSCVILFLYPRKRLLALGFASASWGFFLFSF 360

Query: 379 QVHEKSXXXXXXXXXXXXXXXEKDLDIISMVCWISNIAFFSMWPLLKRDGLALEYFVLGILS 438
            QVHEKS               ++          N+A FS+WPLLK+DGL L+YF L ++
Sbjct: 361 QVHEKSVLLPLLPTSILLCHGNITTKPWIALANNLAVFSLWPLLKKDGLGLQYFTLVLMW 420

Query: 439 NWLIGNLNWISKWLVPSFLIPGPTLSKKVPKRDTKTVVHTHWFWGSVTFVSYLGATVIQF 498
            NW IG++   SK ++  F                      +    Y+G VI
Sbjct: 421 NW -1GDMWFSKNVLFRF.......-..................IQLSFYVGMIVILG 451

Query: 499 VDWLYLPPAKYPDLWVILNTTLSFACFGLFWLW   531
            +D   PP++YPDLWVILN TLSFA F   +LW
Sbjct: 452 IDLFIPPPSRYPDLWVILNVTLSFAGFFTIYLW   484

D. melanogaster

Score = 247 bits (630), Expect = 4e-64
 Identities = 175/490 (35%), Positives = 267/490 (54%), Gaps = 55/490 (11%)

Query:  57 VGLGSYSGFNTPPMYGDFEAQRHWMEITQHLSIEKWYF----YDLQYWGLDYPPLTAFHS 112
            + L SYSGF++PPM+GD+EAQRHW EIT +L++  +WY    DLQYWGLDYPPLTA+HS
Sbjct:  19 ISLYSYSGFDSPPMHGDYEAQRHWQEITVNLAVGEWYTNSSNNDLQYWGLDYPPLTAYHS  78

Query: 113 YFFGKLGSFINPAWFALDVSRGFESVDLKSYMRATAILSELLCFIPAVIWYCRWMGLNYF 172
            Y G++G I+P + L    SRGFES + K +MRAT +++L ++PA++     +    +
Sbjct:  79 YLVGRIGASIDPRFVELHKSRGFESKEHKRFMRATVVSADVLIYLPAMLLLAYSLDKAFR 138

Query: 173 NQNAIEQTIIASAILFNPSLIIIDHGHFQYNSVMLGFALLSILNLLYDNFALAAIFFVLS 232
            + + +   + +A   P  +ID+GHFQYN++  LGFA ++I  +L   F  AA FF L+
Sbjct: 139 SDDKLFLFTLVAAY---PGQTLIDNGHFQYNNISLGFAAVAIAAILRRRFYAAAFFFTLA 195

Query: 233 ISFKQMALYYSPIMFFYMLSVSCWPLKNFN--LLRLATISIAVLLTFATLLLPFVLVDGM 290
             +++KQM LY+S + FF  L  C   K+F  + ++ I+ VL TFA L+P+  +
Sbjct: 196 LNYKQMELYHS-LPFFAFLLGECVSQKSFASFIAEISRIAAVVLGTFAILWVPW--LGSL 252
```

FIG.27C

```
Query:  291  SQIGQILFRVFPFSRGLFEDKVANFWCTTNILVKYKQLFTDKTLTRISLVATLIAISPSC  350
              + Q+L R+FP +RG+FEDKVAN WC N++ K K+  ++  + + + TLIA  P+
Sbjct:  253  QAVLQVLHRLFPVARGVFEDKVANVWCAVNVVWKLKKHISNDQMALVCIACTLIASLPTN  312

Query:  351  FIIFTHPKKVLLPWAFAACSWAFYLFSFQVHEKSXXXXXXXXXXXXXXEKDLDIISMVCW-  409
              ++F     V   A   S AF+LFSFQVHEK+                  + + CW
Sbjct:  313  VLLFRRRTNVGFLLALFNTSLAFFLFSFQVHEKTILLTALPA----------LFLLKCWP  362

Query:  410  -----ISNIAFFSMWPLLKRDGLALEYFVLGILSNWLIGNLNWISKWLVPSFLIPGPTLS  464
                   + FSM PLL RD L  +  V  + ++    + SK              LS
Sbjct:  363  DEMILFLEVTVFSMLPLLARDELLVPAVVATVAFHLIFKCFDSKSK------------LS  410

Query:  465  KKVPKRDTKTVVHTHWFWGSVTFVSYLGATVIQFVDWLYLP-PAKYPDLWVILNTTLSFA  523
              + P +    +          + +S + A+       L +P P KYPDLW ++ + S
Sbjct:  411  NEYPLKYIANI--------SQILMISVVVAS------LTVPAPTKYPDLWPLIISVTSCG  456

Query:  524  CFGLFWLWIN  533
              F LF+LW N
Sbjct:  457  HFFLFFLWGN  466

A. thaliana

Score = 244 bits (622), Expect = 3e-63
Identities = 187/488 (38%), Positives = 248/488 (50%), Gaps = 39/488 (7%)

Query:   62  YSGFNTPPMYGDFEAQRHWMEITQHLSIEKWY----FYDLQYWGLDYPPLTAFHSYFFGK  117
             YSG   PP +GDFEAQRHWMEIT +L +  WY     + DL YWGLDYPPLTA+ SY  G
Sbjct:   61  YSGAGIPPKFGDFEAQRHWMEITTNLPVIDWYRNGTYNDLTYWGLDYPPLTAYQSYIHGI  120

Query:  118  LGSFINPAWFALDVSRGFESVDLKSYMRATAILSELLCFIPAVIWYCRWMGLNYFNQNAI  177
                F NP    AL  SRG ES   K MR T + S+    F PA +++        N
Sbjct:  121  FLRFFNPESVALLSSRGHESYLGKLLMRWTVLSSDAFIFFPAALFFVLVYHRNRTRGGKS  180

Query:  178  EQTIIASAILFNPSLIIIDHGHFQYNSVMLGFALLSILNLLYDNFALAAIFFVLSISFKQ  237
             E     + IL NP LI+IDHGHFQYN + LG  + +I +L ++ L  + F L++S KQ
Sbjct:  181  EVAWHIAMILLNPCLILIDHGHFQYNCISLGLTVGAIAAVLCESEVLTCVLFSLALSHKQ  240

Query:  238  MALYYSPIMFFYMLSVSCWPLKNFNLLRLATISIAVLLTFATLLLPFVLVDGMSQIGQIL  297
             M+ Y++P F ++L  C  K+ +L + + IAV++TF     P+ V +      +L
Sbjct:  241  MSAYFAPAFFSHLLG-KCLRRKS-PILSVIKLGIAVIVTFVIFWWPY--VHSLDDFLMVL  296
```

FIG.27D

```
Query: 298  FRVFPFSRGLFEDKVANFWCTTNILVKYKQLFTDKTLTRISLVATLIAISPSCFIIFTHP  357
            R+ PF RG++ED VANFWCTT+IL+K+K LFT ++L  ISL AT++A PS       P
Sbjct: 297  SRLAPFERGIYEDVANFWCTTSILIKWKNLFTTQSLKSISLAATILASLPSMVQQILSP  356

Query: 358  KKVLLPWAFAACSWAFYLFSFQVHEKSXXXXXXXXXXXXXXXEKDLDIISMVCWISNIAFFS  417
                     S AFYLFSFQVHEKS               L +      ++ A FS
Sbjct: 357  SNEGFLYGLLNSSMAFYLFSFQVHEKSILMPFLSATLLA----LKLPDHFSHLTYYALFS  412

Query: 418  MWPLLKRDGLALEYFVLGILSNWLI---GNLNWISKWLVPSFL---IPGPTLSKKVPKRD  471
            M+PLL RD L + Y L  L   +     GN + IKV     F      PG
Sbjct: 413  MFPLLCRDKLLIPYLTLSFLFTVIYHSPGNHHAIQKTDVSFFSFKNFPGYVF--------  464

Query: 472  TKTVVHTHWFWGSVTFVSYLGATVIQFVDWLYLPPAKYPDLWVILNTTLSFACFGLFWLW  531
            ++ TH+F   V V YL           PP KYP L+   L F+ F +F +
Sbjct: 465  ---LLRTHFFISVVLHVLYLTILK--------PPQKYPFLFEALIMILCFSYFIMFAFY  511

Query: 532  INYNLYIL  539
            NY + L
Sbjct: 512  TNYTQWTL  519
```

FIG.27E

*K. lactis ALG6*
ATCTCTGTTTCAACAGCTCTTGCATTCATTGGTTCTTTCGGTCCAATCTATA
TCTTTGGAGGATACAAGAACTTAGTGCAATCAATGCACAGGATTTTTCCAT
TTGCCAGGGGTATCTTTGAAGATAAAGTTGCGAATTTTTGGTGCGTTTCTA
ATATTTTCATCAAATATAGAAATCTATTCACTCAGAAGGATCTTCAATTAT
ACTCATTACTCGCAACAGTTATTGGGCTTTTACCATCATTCATTATAACAT
TTTTATACCCGAAGAGACATTTACTACCATATGCTTTGGCCGCATGTTCGA
TGTCATTCTTCTTATTCAGCTTCCAGGTTCATGAAAAGACAATCTTATTAC
CTTTACTTCCTATTACACTCTTGTACACGTCAAGAGATTGGAATGTTCTAT
CATTGGTTTGTTGGATTAACAACGTGGCATTGTTTACACTCTGGCCATTAC
TGAAAAAGGACAATCTAGTATTGCAATATGGAGTCATGTTCATGTTTAGC
AATTGGTTGATCGGTAACTTCAGTTTCGTCACACCACGCTTCCTCCCAAAA
TTTTTGACACCAGGGCCATCCATCAGTGATATAGATGTTGATTATAGACGG
GCAAGTTTACTACCCAAGAGCCTAATATGGAGATTAATCATTGTTGGCTCA
TATATTGCAATGGGGATTATTCATTTTCTAGACTATTACGTCTCCCCGCCA
TCAAAATACCCTGATTTATGGGTGCTTGCCAATTGTTCCTTGGGCTTCTCA
TGTTTTGTGACATTTTGGATATGGAACAATTATAATTATTCGAAATGAGAA
ACAGCACTTTGCAAGATTTA

*K. lactis Alg6p*
ISVSTALAFIGSFGPIYIFGGYKNLVQSMHRIFPFARGIFEDKVANFWCVSNIFIK
YRNLFTQKDLQLYSLLATVIGLLPSFIITFLYPKRHLLPYALAACSMSFFLFSFQ
VHEKTILLPLLPITLLYTSRDWNVLSLVCWINNVALFTLWPLLKKDNLVLQYG
VMFMFSNWLIGNFSFVTPRFLPKFLTPGPSISDIDVDYRRASLLPKSLIWRLIIV
GSYIAMGIIHFLDYYVSPPSKYPDLWVLANCSLGFSCFVTFWIWNNYNYSKZE
TALCKI

FIG.28

*K. lactis* ALG6 BLAST

```
                                                              Score      E
Sequences producing significant alignments:                   (bits)   Value gi|1420090|emb|CAA99190.1|   ORF YC)R002w [Saccharomyces cerev... 392   e-108
gi|7490584|pir|T40396        glucosyltransferase - fission yeast ...187  2e-46
gi|15240920|ref|NP_198662.1| glucosyltransferase-like prote...117       2e-25
gi|7019325|ref|NP_037471.1|  dolichyl-P-Glc:Man9GlcNAc2-PP-d...102      2e-21
gi|12_002040|gb|AAG4_3163.1|AF063604_1  brain my046 protein [H...102    8e-21
gi|19921070|ref|NP_609393.1| CG5091-PA [Drosophila melanoga...101       1e-20
```

Alignments

*S. cerevisiae*

```
 Score = 392 bits (1006), Expect = e-108
 Identities = 182/280 (65%), Positives = 218/280 (77%), Gaps = 1/280 (0%)
 Frame = +1

Query: 1    ISVSTALAFIGSFGPIYIFGG-YKNLVQSMHRIFPFARGIFEDKVANFWCVSNIFIKYRN   177
            I+ +T  F   F P+Y  GG  KN+ Q +HRIFPFARGIFEDKVANFWCV+N+F+KY+
Sbjct: 265  IAFATLATFAIIFAPLYFLGGGLKNIHQCIHRIFPFARGIFEDKVANFWCVTNVFVKYKE  324

Query: 178  LFTQKDLQLYSLLATVIGLLPSFIITFLYPKRHLLPYALAACSMSFFLFSFQVHEKXXXX  357
            FT + LQLYSL+ATVIG LP+ I+T L+PK+HLLPY L ACSMSFFLFSFQVHEK
Sbjct: 325  RFTIQQLQLYSLIATVIGFLPAMIMTLLHPKKHLLPYVLIACSMSFFLFSFQVHEKTILI  384

Query: 358  XXXXXXXXYTSRDWNVLSLVCWINNVALFTLWPLLKKDNLVLQYGVMFMFSNWLIGNFSF  537
                    Y+S DWNVLSLV WINNVALFTLWPLLKKD L LQY V F+ SNWLIGNFSF
Sbjct: 385  PLLPITLLYSSTDWNVLSLVSWINNVALFTLWPLLKKDGLHLQYAVSFLLSNWLIGNFSF  444

Query: 538  VTPRFLPKFLTPGPSISDIDVDYRRASLLPKSLIWRLIIVGSYIAMGIIHFLDYYVSPPS  717
            +TPRFLPK LTPGPSIS 1+ DYRR SLLP +++W+  I+G+YIAMG  HFLD +V PPS
Sbjct: 445  ITPRFLPKSLTPGPSISSINSDYRRRSLLPYNVvWKSFIIGTYIAMGFYHFLDQFVAPPS  504

Query: 718  KYPDLWvLANCSLGFSCFVTFWIWNNYXLFEMRNSTLQDL  837
            KYPDLWVL NC++GF CF FW+W+  Y +F +  +++DL
Sbjct: 505  KYPDLWVLLNCAVGFICFSIFWLWSYYKIFTSGSKSMKDL  544
```

FIG.29A

*S. pombe*

```
Score = 187 bits (475), Expect = 2e-46
Identities = 106/280 (37%), Positives = 150/280 (53%), Gaps = 1/280 (0%)
Frame = +1

Query: 1    ISVSTALAFIGSFGPIYIFGGYKNLV-QSMHRIFPFARGIFEDKVANFWCVSNIFIKYRN  177
            +SV+     F    P +I+   YK L+ Q +HR+FPFARG++EDKVANFWC  N   K R
Sbjct: 251  LSVTVVFTFSLILFP-WIYMDYKTLLPQILHRVFPFARGLWEDKVANFWCTLNTVFKIRE  309

Query: 178  LFTQKDLQLYSLLATVIGLLPSFIITFLYPKRHLLPYALAACSMSFFLFSFQVHEKXXXX  357
            +FT  LQ+ SL+ T+I +LPS +I FLYP++ LL A+   S FFLFSFQVHEK
Sbjct: 310  VFTLHQLQVISLIFTLISILPSCVILFLYPRKRLLALGFASASWGFFLFSFQVHEKSVLL  369

Query: 358  XXXXXXXXXYTSRDWNVLSLVCWINNVALFTLWPLLKKDNLVLQYGVMFMFSNWLIGNFSF  537
                     +    +   NN+A+F+LWPLLKKD L LQY  + +  NW
Sbjct: 370  PLLPTSILLCHGNITTKPWIALANNLAVFSLWPLLKKDGLGLQYFTLVLMWNW-------  422

Query: 538  VTPRFLPKFLTPGPSISDIDVDYRRASLLPKSLIWRLIIVGSYIAMGIIHFLDYYVSPPS  717
                            I D+ V         K++++R I +  Y+ M +I + D ++ PPS
Sbjct: 423  ---------------IGDMVV-------FSKNVLFRFIQLSFYVGMIVILGIDLFIPPPS  460

Query: 718  KYPDLWVLANCSLGFSCFVTFWIWNNYXLFEMRNSTLQDL  837
            +YPDLWV+ N +L F+ F T ++W   L  + +    DL
Sbjct: 461  RYPDLWVILNVTLSFAGFFTIYLWTLGRLLHISSKLSTDL  500
```

*A. thaliana*

```
Score = 117 bits (292), Expect = 2e-25
Identities = 81/240 (33%), Positives = 120/240 (50%), Gaps = 2/240 (0%)
Frame = +1

Query: 85   MHRIFPFARGIFEDKVANFWCVSNIFIKYRNLFTQKDLQLYSLLATVIGLLPSFIITFLY  264
            + R+ PF RGI+ED VANFWC ++I IK++NLFT + L+  SL AT++  LPS +    L
Sbjct: 296  LSRIAPFERGIYEDYVANFWCTTSILIKWKNLFTTQSLKSISLAATILASLPSMVQQILS  355

Query: 265  PKRHLLPYALAACSMSFFLFSFQVHEKXXXXXXXXXXXXXXXYTSRDWNVLSLVCWINNVALF  444
             P    Y L  SM+F+LFSFQVHEK                     + L  +   ALF
Sbjct: 356  PSNEGFLYGLLNSSMAFYLFSFQVHEKSILMPFLSATLLALKLPDHFSHLTYY----ALF  411

Query: 445  TLWPLLKKDNLVLQYGVMFMFSNWLIGNFSFVTPRFLPKFLTPG--PSISDIDVDYRRAS  618
            +++PLL +D L++  Y +       SF+  F   ++PG  +I   DV  +
Sbjct: 412  SMFPLLCRDKLLIPYLTL...........SFL---FTVIYHSPGNHHAIQKTDVSFFSFK  457
```

FIG.29B

```
Query: 619 LLPKSLIWRLIIVGSYIAMGIIHFLDYYVSPPSKYPDLWVLANCSLGFSCFVTFWIWNNY 798
            P  +  L+    +I++ ++H L  + PP KYP L+    L FS F+ F + NY
Sbjct: 458 NFPGYVF--LLRTHFFISV-VLHVLYLTIKPPQKYPFLFEALIMILCFSYFIMFAFYTNY 514
```

*H. sapiens*

```
  Score = 103 bits (258), Expect = 2e-21
  Identities = 78/266 (29%), Positives = 123/266 (46%), Gaps = 3/266 (1%)
  Frame = +1

Query: 7   VSTALAFIGSFGPIYI--FGGYKNLVQSMHRIFPFARGIFEDKVANFWCVSNIFIKYRNL 180
           V  A   + SF    ++  F   +  +Q +  R+FP   RG+FEDKVAN WC  N+F+K +++
Sbjct: 232 VKLACIVVASFVLCWLPFFTEREQTLQVLRRLFPVDRGLFEDKVANIWCSFNVFLKIKDI 291

Query: 181 FTQKDLQLYSLLATVIGLLPSFIITFLYPKRHLLPYALAACSMSFFLFSFQVHEKXXXXX 360
           +   + S   T + LLP+ I   L P      + L +C++SFFLFSFQVHEK
Sbjct: 292 LPRHIQLIMSFCFTFLSLLPACIKLILQPSSKGFKFTLVSCALSFFLFSFQVHEKSILLV 351

Query: 361 XXXXXXXYTSRDWNVLSLVCWINNVALFTLWPLLKKDNLVLQYGVMFM-FSNWLIGNFSF 537
                     +  +  W  V+ F++ PLL KD L++    V  M F  + +FS
Sbjct: 352 SLPVCLVLS----EIPFMSTWFLLVSTFSMLPLLLKDELLMPSVVTTMAFFIACVTSFSI 407

Query: 538 VTPRFLPKFLTPGPSISDIDVDYRRASLLPKSLIWRLIIVGSYIAMGIIHFLDYYVSPPS 717
           +           SIS    V                 S I+ + + S I M ++ +  + PP
Sbjct: 408 FEKTSEEELQLKSFSIS---VRKYLPCFTFLSRIIQYLFLISVITMVLLTLMTVTLDPPQ 464

Query: 718 KYPDLWVLANCSLGFSCFVTFWIWNN 795
           K PDL+ +  C +     F+ F ++ N
Sbjct: 465 KLPDLFSVLVCFVSCLNFLFFLVYFN 490
```

FIG.29C

>gi|6754685|ref|NM_010795.1| Mus musculus mannoside acetyl
glucosaminyltransferase 3 (Mgat3), mRNA

```
ATGAAGATGAGACGCTACAAGCTCTTTCTCATGTTCTGTATGGCTGGCCTGTGCCTCATATCCTTCCTGC
ACTTCTTTAAGACCTTATCCTATGTCACCTTCCCGAGAGAACTGGCCTCCCTCAGCCCTAACCTCGTATC
CAGCTTCTTCTGGAACAATGCCCCTGTCACTCCCCAGGCCAGTCCGGAGCCGGGTGGCCCCGACCTATTG
CGGACACCCCTCTACTCCCACTCTCCCCTGCTCCAGCCACTGTCCCCGAGCAAGGCCACAGAGGAACTGC
ACCGGGTGGACTTCGTGTTGCCGGAGGACACCACGGAGTATTTTGTGCGCACCAAAGCTGGTGGTGTGTG
CTTCAAACCAGGTACCAGGATGCTGGAGAAACCTTCGCCAGGGCGGACAGAGGAGAAGCCCGAAGTGTCT
GAGGGCTCCTCAGCCCGGGGACCTGCTCGGAGGCCCATGAGGCACGTGTTGAGTACGCGGGAGCGCCTGG
GCAGCCGGGGCACTAGGCGCAAGTGGGTTGAGTGTGTGTGCCTGCCAGGCTGGCACGGGCCCAGTTGCGG
GGTGCCCACGGTGGTGCAGTATTCCAACCTGCCCACCAAGGAACGCCTGGTACCCAGGGAGGTACCGAGG
CGGGTTATCAACGCCATCAACATCAACCACGAGTTCGACCTGCTGGATGTGCGCTTCCATGAGCTGGGAG
ATGTTGTGGACGCCTTCGTGGTCTGTGAATCTAATTTCACCGCCTACGGGGAGCCTCGGCCGCTCAAGTT
CCGAGAGATGCTGACCAATGGCACCTTCGAGTACATCCGCCACAAGGTGCTCTATGTCTTCCTGGACCAT
TTCCCACCTGGTGGCCGTCAGGACGGCTGGATTGCGGATGACTACCTGCGCACCTTCCTCACCCAGGATG
GCGTCTCCCGCCTGCGCAACCTGCGGCCCGATGACGTCTTTATCATCGACGATGCGGACGAGATCCCTGC
GCGTGATGGTGTGCTGTTCCTCAAACTCTACGATGGCTGGACAGAGCCCTTCGCCTTCCACATGCGGAAG
TCCCTGTATGGTTTCTTCTGGAAGCAGCCGGGCACACTGGAGGTGGTGTCAGGCTGCACCATGGACATGC
TGCAGGCCGTGTATGGGCTGGATGGCATCCGCCTGCGCCGCCGCCAGTACTACACCATGCCCAACTTCCG
GCAGTATGAGAACCGCACCGGCCACATCCTAGTGCAGTGGTCTCTCGGCAGCCCCCTGCACTTCGCGGGC
TGGCATTGCTCCTGGTGCTTCACACCCGAGGGCATCTACTTTAAACTCGTGTCAGCCCAGAATGGCGACT
TCCCCCGCTGGGGTGACTATGAGGACAAGAGGGACCTCAATTACATCCGCAGCTTGATCCGCACTGGGGG
ATGGTTCGACGGAACGCAGCAGGAGTACCCTCCTGCGGACCCCAGTGAGCACATGTATGCTCCTAAATAC
CTGCTCAAGAACTATGACCAGTTCCGCTACTTGCTGGAAAATCCCTACCGGGAGCCCAAGAGCACTGTAG
AGGGTGGGCGCCAGAACCAGGGCTCAGATGGAAGGCCATCTGCTGTCAGGGGCAAGTTGGATACAGTGGA
GGGCTAG
```

>gi|2117717|pir||JC4362 beta-1,4-mannosyl-glycoprotein 4-beta-N-
acetylglucosaminyltransferase (EC 2.4.1.144) III - mouse
MRRYKLFLMFCMAGLCLISFLHFFKTLSYVTFPRELASLSPNLISSFFWNNAPVTPQASPEPGDPDLLRT
PLYSHSPLLQPLSPSKATEELHRVDFVLPEDTTEYFVRTKAGGVCFKPGTRMLEKPSPGRTEEKTEVSEG
SSARGPARRPMRHVLSSRERLGSRGTRRKWVECVCLPGWHGPSCGVPTVVQYSNLPTKERLVPREVPRRV
INAININHEFDLLDVRFHELGDVVDAFVVCDSNFTAYGEPRPLKFREMLTNGTFEYIRHKVLYVFLDHFP
PGGRQDGWIADDYLRTFLTQDGVSRLRNLRPDDVFIIDDADEIPARDGVLFLKLYDGWTEPFAFHMRKSL
YGFFWKQPGTLEVVSGCTMDMLQAVYGLDGIRLRRRQYYTMPNFRQYENRTGHILVQWSLGSPLHFAGWH
CSWCFTPEGIYFKLVSAQNGDFPRWGDYEDKRDLNYIRSLIRTGGWFDGTQQEYPPADPSEHMYAPKYLL
KNYDQFRYLLENPYREPKSTVEGGRQNQGSDGRSSAVRGKLDTAEG

FIG.32

>gi|6912501|ref|NM_012214.1| Homo sapiens mannosyl
(alpha-1,3-)-glycoprotein beta-1,4-N-
acetylglucosaminyltransferase, isoenzyme A (MGAT4A), mRNA

```
GAAATGAACCTCTCTTATTGATTTTTATTGGCCTAGAGCCAGGAGTACTGCATTCAGTTGACTTTCAGG
GTAAAAAGAAAACAGTCCTGGTTGTTGTCATCATAAACATATGGACCAGTGTGATGGTGAAATGAGATG
AGGCTCCGCAATGGAACTGTAGCCACTGCTTTAGCATTTATCACTTCCTTCCTTACTTTGTCTTGGTAT
ACTACATGGCAAAATGGGAAAGAAAAACTGATTGCTTATCAACGAGAATTCCTTGCTTTGAAAGAACGT
CTTCGAATAGCTGAACACAGAATCTCACAGCGCTCTTCTGAATTAAATACGATTGTGCAACAGTTCAAG
CGTGTAGGAGCAGAAACAAATGGAAGTAAGGATGCGTTGAATAAGTTTTCAGATAATACCCTAAAGCTG
TTAAAGGAGTTAACAAGCAAAAAATCTCTTCAAGTGCCAAGTATTTATTATCATTTGCCTCATTTATTG
AAAAATGAAGGAAGTCTTCAACCTGCTGTACAGATTGGCAACGGAAGAACAGGAGTTTCAATAGTCATG
GGCATTCCCACAGTGAAGAGAGAAGTTAAATCTTACCTCATAGAAACTCTTCATTCCCTTATTGATAAC
CTGTATCCTGAAGAGAAGTTGGACTGTGTTATAGTAGTCTTCATAGGAGAGACAGATATTGATTATGTA
CATGGTGTTGTAGCCAACCTGGAGAAAGAATTTTCTAAAGAAATCAGTTCTGGCTTGGTGGAAGTCATA
TCACCCCCTGAAAGCTATTATCCTGACTTGACAAACCTAAAGGAGACATTTGGAGACTCCAAAGAAAGA
GTAAGATGGAGAACAAAGCAAAACCTAGATTACTGTTTTCTAATGATGTATGCTCAAGAAAAGGGCATA
TATTACATTCAGCTTGAAGATGATATTATTGTCAAACAAAATTATTTTAATACCATAAAAAATTTTGCA
CTTCAACTTTCTTCTGAGGAATGGATGATTCTAGAGTTTTCCCAGCTGGGCTTCATTGGTAAAATGTTT
CAAGCGCCGGATCTTACTCTGATTGTAGAATTCATATTCATGTTTTACAAGGAGAAACCCATTGATTGG
CTCCTGGACCATATTCTCTGGGTGAAAGTCTGCAACCCTGAAAAAGATGCAAAACATTGTGATAGACAG
AAAGCAAATCTGCGAATTCGCTTCAGACCTTCCCTTTTCCAACATGTTGGTCTGCACTCATCACTATCA
GGAALAATCCAAAAACTCACGGATAAAGATTATATGAAACCATTACTTCTTAAAATCCATGTAAACCCA
CCTGCGGAGGTATCTACTTCCTTGAAGGTCTACCAAGGGCATACGCTGGAGAAAACTTACATGGGAGAG
GATTTCTTCTGGGCTATCACACCGATAGCTGGAGACTACATCTTGTTTAAATTTGATAAACCAGTCAAT
GTAGAAAGTTATTTGTTCCATAGCGGCAACCAAGAACATCCTGGAGATATTCTGCTAAACACAACTGTG
GAAGTTTTGCCTTTTAAGAGTGAAGGTTTGGAAATAAGCAAAGAAACCAAAGACAAACGATTAGAAGAT
GGCTATTTCAGAATAGGAAAATTTGAGAATGGTGTTGCAGAAGGAATGGTGGATCCAAGTCTCAATCCC
ATTTCAGCCTTTCGACTTTCAGTTATTCAGAATTCTGCTGTTTGGGCCATTCTTAATGAGATTCATATT
AAAAAAGCCACCAACTGATCATCTGAGAAACCAACACATTTTTTCCTGTGAATTTGTTAATTAAAGATA
GTTAAGCATGTATCTTTTTTTATTTCTACTTGAACACTACCTCTTGTGAAGTCTACTGTAGATAAGAC
GATTGTCATTTCCACTTGGAAAGTGAATCTCCCATAATAATTGTATTTGTTTGAAACTAAGCTGTCCTC
AGATTTTAACTTGACTCAAACATTTTTCAATTATGACAGCCTGTTAATATGACTTGTACTATTTTGGTA
TTATACTAATACATAAGAGTTGTACATATTGTTACATTCTTTAAATTTGAGAAAAACTAATGTTACATA
CATTTTATGAAGGGGGTACTTTTGAGGTTCACTTATTTTACTATT
```

FIG.33A

>gi|6912502|ref|NP_036346.1| mannosyl (alpha-1,3-)-
glycoprotein beta-1,4-N-acetylglucosaminyltransferase,
isoenzyme A; UDP-N-acetylglucosamine:alpha1,3-d-mannoside
beta1,4-N-acetylglucosaminyltransferase; alpha-1,3-
mannosyl-glycoprotein beta-1,4-N-
acetylglucosaminyltransferase [Homo sapiens]

MRLRNGTVATALAFITSFLTLSWYTTWQNGKEKLIAYQREFLALKERLRIAEHRISQ
RSSELNTIVQQFKRVGAETNGSKDALNKFSDNTLKLLKELTSKKSLQVPSIYYHLPH
LLKNEGSLQPAVQIGNGRTGVSIVMGIPTVKREVKSYLIETLHSLIDNLYPEEKLDC
VIVVFIGETDIDYVHGVVANLEKEFSKEISSGLVEVISPPESYYPDLTNLKETFGDS
KERVRWRTKQNLDYCFLMMYAQEKGIYYIQLEDDIIVKQNYFNTIKNFALQLSSEEW
MILEFSQLGFIGKMFQAPDLTLIVEFIFMFYKEKPIDWLLDHILWVKVCNPEKDAKH
CDRQKANLRIRFRPSLFQHVGLHSSLSGKIQKLTDKDYMKPLLLKIHVNPPAEVSTS
LKVYQGHTLEKTYMGEDFFWAITPIAGDYILFKFDKPVNVESYLFHSGNQEHPGDIL
LNTTVEVLPFKSEGLEISKETKDKRLEDGYFRIGKFENGVAEGMVDPSLNPISAFRL
SVIQNSAVWAILNEIHIKKATN

FIG.33B

>gi|18997006|gb|AF474154.1| Mus musculus N-acetylglucosaminyltransferase V (Mgat5) mRNA, complete cds

```
ATTGCTAGAGAGAGATGGCTTTCTTTTCTCCCTGGAAGTTGTCCTCTCAGAAGCTGG
GCTTTTTCCTGGTGACTTTCGGCTTCATCTGGGGCATGATGCTTCTGCACTTCACCA
TCCAGCAGCGGACTCAGCCCGAGAGCAGCTCCATGTTACGGGAGCAGATCCTTGACC
TCAGCAAGAGGTACATTAAGGCACTGGCAGAGGAGAACAGGGACGTGGTGGATGGCC
CCTACGCTGGTGTCATGACAGCCTATGATCTGAAGAAAACGCTCGCCGTCTTGCTGG
ATAACATCCTGCAGCGCATTGGCAAGCTCGAGTCAAAGGTGGACAATCTGGTCAACG
GCACAGGAGCGAACTCCACCAACTCCACCACGGCTGTCCCCAGCTTGGTGTCGCTTG
AGAAAATTAATGTGGCAGATATCATTAATGGAGTTCAGGAAAAATGTGTATTGCCTC
CTATGGATGGCTACCCCACTGCGAGGGGAAAATCAAGTGGATGAAGGACATGTGGC
GCTCGGACCCCTGCTACGCAGACTATGGAGTGGACGGGACCTCCTGCTCCTTTTTTA
TTTACCTCAGTGAGGTTGAAAATTGGTGTCCTCGTTTACCTTGGAGAGCAAAAAATC
CCTATGAAGAAGCTGATCATAACTCATTGGCGGAAATCCGTACGGATTTTAACATTC
TCTACGGCATGATGAAGAAGCACGAGGAGTTCCGTTGGATGAGGCTTCGGATCCGGC
GAATGGCTGACGCGTGGATCCAAGCTATCAAGTCTCTGGCGGAGAAACAAAACCTTG
AGAAGAGGAAACGGAAGAAAATCCTTGTTCACCTGGGGCTCCTGACCAAGGAATCGG
GCTTCAAGATTGCGGAGACAGCATTCAGCGGTGGCCCTCTGGGTGAACTCGTTCAGT
GGAGTGACTTAATCACATCTCTGTACCTGCTGGGCCATGACATCCGGATCTCGGCCT
CACTGGCTGAGCTCAAGGAGATAATGAAGAAGGTTGTTGGAAACCGGTCTGGCTGTC
CAACTGTAGGAGACAGAATCGTTGAGCTGATTTATATCGATATTGTGGGACTTGCTC
AATTTAAGAAAACACTAGGGCCATCCTGGGTTCATTACCAGTGCATGCTCCGGGTGC
TAGACTCCTTTGGAACAGAACCTGAGTTCAATCATGCGAGCTATGCCCAGTCAAAAG
GCCACAAGACCCCCTGGGGAAAGTGGAATCTGAACCCGCAGCAGTTTTACACCATGT
TCCCTCATACCCCAGACAACAGCTTTCTGGGCTTCGTGGTGGAGCAGCACCTGAACT
CCAGCGACATTCACCACATCAACGAGATCAAAAGGCAGAACCAGTCCCTTGTGTATG
GCAAAGTGGATAGTTTCTGGAAGAATAAGAAAATCTACCTGGATATCATTCACACGT
ACATGGAAGTGCACGCCACTGTTTATGGCTCCAGTACCAAGAACATTCCCAGTTACG
TGAAAAACCATGGCATTCTCAGTGGACGTGACCTGCAGTTTCTTCTCCGGGAAACCA
AGCTGTTCGTTGGGCTCGGATTCCCTTATGAAGGCCCAGCTCCCCTGGAGGCCATCG
CGAATGGATGTGCTTTCCTGAACCCCAAGTTCAACCCTCCCAAAAGCAGCAAAAACA
CAGACTTCTTCATTGGCAAGCCAACACTGAGAGAGCTGACATCCCAGCATCCTTACG
CAGAAGTCTTCATCGGCCGGCCACACGTCTGGACTGTGGATCTCAATAACCGAGAGG
AAGTAGAAGATGCAGTAAAAGCCATCTTAAACCAGAAGATTGAGCCGTATATGCCAT
ATGAGTTCACATGTGAAGGCATGCTGCAGAGAATCAACGCTTTCATTGAAAAACAGG
ACTTCTGCCATGGCCAAGTGATGTGGCCGCCCCTCAGCGCCCTGCAGGTTAAGCTGG
CTGAGCCAGGGCAGTCCTGCAAACAGGTGTGCCAGGAGAGCCAGCTCATCTGCGAGC
CATCCTTCTTTCAACACCTCAACAAGGAAAAGGACCTGCTGAAGTATAAGGTGACCT
GCCAAAGCTCAGAACTGTACAAGGACATCCTGGTGCCCTCCTTCTACCCCAAGAGCA
AGCACTGTGTGTTCCAAGGGGACCTCCTGCTCTTCAGTTGTGCCGGAGCCCATCCCA
CACACCAGCGGATCTGCCCCTGCCGGGACTTCATCAAGGGCCAAGTGGCCCTCTGCA
```

FIG.34A

AAGACTGCCTATAGCATCGCTGCCCTGAATTAACTCAGACGGGAAAGACGTGGCTCC
ACTGGGCAGGGCCAAGGGGCACAAAGACATTCAGGGACTCTGACCAGAGCCTGAGAT
CTTTGGTCCAGGGCTTGAGTTTAGTACCGCTCCAGCCACAGCCAGTGCATCCCAGTT
TACACCAAAACCACAAGGGAACAGGTTAGAACAGGAACCTGGGTTCTCCTCAGTGTA
AGGAATGTCCTCTCTGTCTGGGAGATCGAGCGACTGTAGGGAAAGGATCCAGGCAGT
TGCTCCCGGGAATTTTTTTTTTTTTTTTTAAAGAAGGGATAAAAGTCCGGAGAC
TCATTCAAACTGAAAACAAAACAGGAAGAGGGAATTGAGCCAATTGGGAAGGACTTT
GGGGCCGATCCTAAACCAATTAATTTATTTATTTGGGAGGATGGGGGCGGGCTCGGG
AGGGAGGAGAGGGGTTGAACAGTTTCCTTTTGTTCCTCACTGTTAATTCGCCCACCT
TCGGGCCCTTCTTGTTCTGCAGCGCCAAGCAGGGTGCAGAGGGGCTGTGGCTTGCTT
GAGGGGCCACTGTGGGGCTTCACTCCTGGTCACAGGTGGCAGCAGAGAAAAGAGATG
TCTATAAGCAGGGGATGTAGCTCAGTTTGTAGAATGCTTGCATAGCATAAATGAAG
TCCTGGGTTCCATCCCCAGCACCACATAAATGCAGGTAAGAAACAGAGTCAGGAGGA
CCAAGCATTCTCCTTGGCTACATAACAAAAGCAAGGCCTTTGTCCCCATGTCTTGGC
TACAAGAGACCCTATCTCAGAAAATTGTGGGGGGGAGGGGGGGGAAATGGCCTTGA
AAACACAGCCAGTCACTGTCACTGCATTGCCAGAACTGGTGGATCCCAGGTGTGCTT
GGCAGATAACAGCTAAAAGGCACATAACCTTGGTGGGGAAATAAATGCCTGTGGTGT
CCTGAGGGCCCCACCAAGTTCCAAAAAAAAAAAA

>gi|18997007|gb|AAL8324 9.1|AF474154_1 N-
acetylglucosaminyltransferase V [Mus musculus]

MAFFSPWKLSSQKLGFFLVTFGFIWGMMLLHFTIQQRTQPESSSMLREQILDLSKRY
IKALAEENRDWDGPYAGVMTAYDLKKTLAVLLDNILQRIGKLES KVDNLVNGTGAN
STNSTTAVPSLVSLEKINVADIINGVQEKCVLPPMDGYPHCEGKIKWMKDMWRSDPC
YADYGVDGTSCSFFIYLSEVENWCPRLPWRAKNPYEEADHNSLAEIRTDFNILYGMM
KKHEEFRWMRLRIRRMADAWIQAIKSLAEKQNLEKRKRKKILVHLGLLTKESGFKIA
ETAFSGGPLGELVQWSDLITSLYLLGHDIRISASLAELKEIMKKVVGNRSGCPTVGD
RIVELIYIDIVGLAQFKKTLGPSWVHYQCMLRVLDSFGTEPEFNHASYAQSKGHKTP
WGKWNLNPQQFYTMFPHTPDNSFLGFVVEQHLNSSDIHHINEIKRQNQSLVYGKVDS
FWKNKKIYLDIIHTYMEVHATVYGSSTKNIPSYVKNHGILSGRDLQFLLRETKLFVG
LGFPYEGPAPLEAIANGCAFLNPKFNPPKSSKNTDFFIGKPTLRELTSQHPYAEVFI
GRPHVWTVDLNNREEVEDAVKAILNQKIEPYMPYEFTCEGMLQRINAFIEKQDFCHG
QVMWPPLSALQVKLAEPGQSCKQVCQESQLICEPSFFQHLNKEKDLLKYKVTCQSSE
LYKDILVPSFYPKSKHCVFQGDLLLFSCAGAHPTHQRICPCRDFIKGQVALCKDCL

FIG.34B

SEQUENCE LISTING

```
<160> NUMBER OF SEQ ID NOS: 106

<210> SEQ ID NO 1
<211> LENGTH: 35
<212> TYPE: DNA
<213> ORGANISM: Artificial Sequence
<220> FEATURE:
<223> OTHER INFORMATION: Primer

<400> SEQUENCE: 1
ggtgttttgt tttctagatc tttgcaytay cartt                                35
```

<210> SEQ ID NO 2
<211> LENGTH: 36
<212> TYPE: DNA
<213> ORGANISM: Artificial Sequence
<220> FEATURE:
<223> OTHER INFORMATION: Primer

<400> SEQUENCE: 2
agaatttggt gggtaagaat tccarcacca ytcrtg    36

<210> SEQ ID NO 3
<211> LENGTH: 32
<212> TYPE: DNA
<213> ORGANISM: Artificial Sequence
<220> FEATURE:
<223> OTHER INFORMATION: Primer

<400> SEQUENCE: 3
cctaagctgg tatgcgttct ctttgccata tc    32

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
gcggcataaa caataataga tgctataaag    30

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
aattaaccct cactaaaggg    20

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
gtaatacgac tcactatagg gc    22

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
ccacatcatc cgtgctacat atag    24

<210> SEQ ID NO 8
<211> LENGTH: 44
<212> TYPE: DNA
<213> ORGANISM: Artificial Sequence
<220> FEATURE:

<223> OTHER INFORMATION: Primer

<400> SEQUENCE: 8
acgaggcaag ctaaacagat ctcgaagtat cgagggttat ccag        44

<210> SEQ ID NO 9
<211> LENGTH: 44
<212> TYPE: DNA
<213> ORGANISM: Artificial Sequence
<220> FEATURE:
<223> OTHER INFORMATION: Primer

<400> SEQUENCE: 9
ccatccagtg tcgaaaacga gccaatggtt catgtctata aatc        44

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
agcctcagcg ccaacaagcg atgg        24

<210> SEQ ID NO 11
<211> LENGTH: 44
<212> TYPE: DNA
<213> ORGANISM: Artificial Sequence
<220> FEATURE:
<223> OTHER INFORMATION: Primer

<400> SEQUENCE: 11
ctggataacc ctcgatactt cgagatctgt ttagcttgcc tcgt        44

<210> SEQ ID NO 12
<211> LENGTH: 44
<212> TYPE: DNA
<213> ORGANISM: Artificial Sequence
<220> FEATURE:
<223> OTHER INFORMATION: Primer

<400> SEQUENCE: 12
gatttataga catgaaccat tggctcgttt tcgacactgg atgg        44

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
atcctttacc gatgctgtat        20

<210> SEQ ID NO 14
<211> LENGTH: 27
<212> TYPE: DNA
<213> ORGANISM: Artificial Sequence
<220> FEATURE:
<223> OTHER INFORMATION: Primer

<400> SEQUENCE: 14
ataacagtat gtgttacacg cgtgtag        27

```
<210> SEQ ID NO 15
<211> LENGTH: 36
<212> TYPE: DNA
<213> ORGANISM: Artificial Sequence
<220> FEATURE:
<223> OTHER INFORMATION: Primer

<400> SEQUENCE: 15
tcctggcgcg ccttcccgag agaactggcc tccctc                              36

<210> SEQ ID NO 16
<211> LENGTH: 37
<212> TYPE: DNA
<213> ORGANISM: Artificial Sequence
<220> FEATURE:
<223> OTHER INFORMATION: Primer

<400> SEQUENCE: 16
aattaattaa ccctagccct ccgctgtatc caacttg                             37

<210> SEQ ID NO 17
<211> LENGTH: 28
<212> TYPE: DNA
<213> ORGANISM: Artificial Sequence
<220> FEATURE:
<223> OTHER INFORMATION: Primer

<400> SEQUENCE: 17
aatgagatga ggctccgcaa tggaactg                                       28

<210> SEQ ID NO 18
<211> LENGTH: 28
<212> TYPE: DNA
<213> ORGANISM: Artificial Sequence
<220> FEATURE:
<223> OTHER INFORMATION: Primer

<400> SEQUENCE: 18
ctgattgctt atcaacgaga attccttg                                       28

<210> SEQ ID NO 19
<211> LENGTH: 28
<212> TYPE: DNA
<213> ORGANISM: Artificial Sequence
<220> FEATURE:
<223> OTHER INFORMATION: Primer

<400> SEQUENCE: 19
tgttggtttc tcagatgatc agttggtg                                       28

<210> SEQ ID NO 20
<211> LENGTH: 29
<212> TYPE: DNA
<213> ORGANISM: Artificial Sequence
<220> FEATURE:
<223> OTHER INFORMATION: Primer

<400> SEQUENCE: 20
agagagagat ggctttcttt tctccctgg                                      29

<210> SEQ ID NO 21
<211> LENGTH: 27
<212> TYPE: DNA
<213> ORGANISM: Artificial Sequence
<220> FEATURE:
<223> OTHER INFORMATION: Primer
```

```
<400> SEQUENCE: 21
aaatcaagtg gatgaaggac atgtggc                                              27

<210> SEQ ID NO 22
<211> LENGTH: 28
<212> TYPE: DNA
<213> ORGANISM: Artificial Sequence
<220> FEATURE:
<223> OTHER INFORMATION: Primer

<400> SEQUENCE: 22
agcgatgcta taggcagtct ttgcagag                                             28

<210> SEQ ID NO 23
<211> LENGTH: 4
<212> TYPE: PRT
<213> ORGANISM: Saccharomyces cerevisiae

<400> SEQUENCE: 23

His Asp Glu Leu
 1

<210> SEQ ID NO 24
<211> LENGTH: 458
<212> TYPE: PRT
<213> ORGANISM: Saccharomyces cerevisiae
<220> FEATURE:
<221> NAME/KEY: MOD_RES
<222> LOCATION: (304)...(318)
<223> OTHER INFORMATION: Xaa is a variable amino acid
<220> FEATURE:
<221> NAME/KEY: MOD_RES
<222> LOCATION: (416)...(436)
<223> OTHER INFORMATION: Xaa is a variable amino acid

<400> SEQUENCE: 24

Met Glu Gly Glu Gln Ser Pro Gln Gly Glu Lys Ser Leu Gln Arg Lys
 1               5                  10                  15

Gln Phe Val Arg Pro Pro Leu Asp Leu Trp Gln Asp Leu Lys Asp Gly
                20                  25                  30

Val Arg Tyr Val Ile Phe Asp Cys Arg Ala Asn Leu Ile Val Met Pro
            35                  40                  45

Leu Leu Ile Leu Phe Glu Ser Met Leu Cys Lys Ile Ile Ile Lys Lys
        50                  55                  60

Val Ala Tyr Thr Glu Ile Asp Tyr Lys Ala Tyr Met Glu Gln Ile Glu
 65                 70                  75                  80

Met Ile Gln Leu Asp Gly Met Leu Asp Tyr Ser Gln Val Ser Gly Gly
                85                  90                  95

Thr Gly Pro Leu Val Tyr Pro Ala Gly His Val Leu Ile Tyr Lys Met
               100                 105                 110

Met Tyr Trp Leu Thr Glu Gly Met Asp His Val Glu Arg Gly Gln Val
            115                 120                 125

Phe Phe Arg Tyr Leu Tyr Leu Leu Thr Leu Ala Leu Gln Met Ala Cys
        130                 135                 140

Tyr Tyr Leu Leu His Leu Pro Pro Trp Cys Val Val Leu Ala Cys Leu
145                 150                 155                 160

Ser Lys Arg Leu His Ser Ile Tyr Val Leu Arg Leu Phe Asn Asp Cys
                165                 170                 175

Phe Thr Thr Leu Phe Met Val Val Thr Val Leu Gly Ala Ile Val Ala
            180                 185                 190
```

```
Ser Arg Cys His Gln Arg Pro Lys Leu Lys Ser Leu Ala Leu Val
        195                 200                 205
Ile Ser Ala Thr Tyr Ser Met Ala Val Ser Ile Lys Met Asn Ala Leu
210                 215                 220
Leu Tyr Phe Pro Ala Met Met Ile Ser Leu Phe Ile Leu Asn Asp Ala
225                 230                 235                 240
Asn Val Ile Leu Thr Leu Leu Asp Leu Val Ala Met Ile Ala Trp Gln
                245                 250                 255
Val Ala Val Ala Val Pro Phe Leu Arg Ser Phe Pro Gln Gln Tyr Leu
                260                 265                 270
His Cys Ala Phe Asn Phe Gly Arg Lys Phe Met Tyr Gln Trp Ser Ile
            275                 280                 285
Asn Trp Gln Met Met Asp Glu Glu Ala Phe Asn Asp Lys Arg Phe Xaa
        290                 295                 300
Xaa Xaa Xaa Xaa Xaa Xaa Xaa Xaa Xaa Xaa Xaa Xaa Xaa Phe Val
305                 310                 315                 320
Thr Arg Tyr Pro Arg Ile Leu Pro Asp Leu Trp Ser Ser Leu Cys His
                325                 330                 335
Pro Leu Arg Lys Asn Ala Val Leu Asn Ala Asn Pro Ala Lys Thr Ile
            340                 345                 350
Pro Phe Val Leu Ile Ala Ser Asn Phe Ile Gly Val Leu Phe Ser Arg
        355                 360                 365
Ser Leu His Tyr Gln Phe Leu Ser Trp Tyr His Trp Thr Leu Pro Ile
    370                 375                 380
Leu Ile Phe Trp Ser Gly Met Pro Phe Phe Val Gly Pro Ile Trp Tyr
385                 390                 395                 400
Val Leu His Glu Trp Cys Trp Asn Ser Tyr Pro Pro Asn Ser Gln Xaa
                405                 410                 415
Xaa Xaa Xaa Xaa Xaa Xaa Xaa Xaa Xaa Xaa Xaa Xaa Xaa Xaa Xaa
            420                 425                 430
Xaa Xaa Xaa Xaa Ser Gly Ser Val Ala Leu Ala Lys Ser His Leu Arg
        435                 440                 445
Thr Thr Ser Ser Met Glu Lys Lys Leu Asn
    450                 455

<210> SEQ ID NO 25
<211> LENGTH: 458
<212> TYPE: PRT
<213> ORGANISM: Saccharomyces cerevisiae

<400> SEQUENCE: 25

Met Glu Gly Glu Gln Ser Pro Gln Gly Glu Lys Ser Leu Gln Arg Lys
1               5                   10                  15
Gln Phe Val Arg Pro Pro Leu Asp Leu Trp Gln Asp Leu Lys Asp Gly
                20                  25                  30
Val Arg Tyr Val Ile Phe Asp Cys Arg Ala Asn Leu Ile Val Met Pro
            35                  40                  45
Leu Leu Ile Leu Phe Glu Ser Met Leu Cys Lys Ile Ile Lys Lys
50                  55                  60
Val Ala Tyr Thr Glu Ile Asp Tyr Lys Ala Tyr Met Glu Gln Ile Glu
65                  70                  75                  80
Met Ile Gln Leu Asp Gly Met Leu Asp Tyr Ser Gln Val Ser Gly Gly
                85                  90                  95
Thr Gly Pro Leu Val Tyr Pro Ala Gly His Val Leu Ile Tyr Lys Met
            100                 105                 110
```

Met Tyr Trp Leu Thr Glu Gly Met Asp His Val Glu Arg Gly Gln Val
            115                 120                 125

Phe Phe Arg Tyr Leu Tyr Leu Leu Thr Leu Ala Leu Gln Met Ala Cys
130                 135                 140

Tyr Tyr Leu Leu His Leu Pro Pro Trp Cys Val Val Leu Ala Cys Leu
145                 150                 155                 160

Ser Lys Arg Leu His Ser Ile Tyr Val Leu Arg Leu Phe Asn Asp Cys
            165                 170                 175

Phe Thr Thr Leu Phe Met Val Val Thr Val Leu Gly Ala Ile Val Ala
            180                 185                 190

Ser Arg Cys His Gln Arg Pro Lys Leu Lys Ser Leu Ala Leu Val
            195                 200                 205

Ile Ser Ala Thr Tyr Ser Met Ala Val Ser Ile Lys Met Asn Ala Leu
            210                 215                 220

Leu Tyr Phe Pro Ala Met Met Ile Ser Leu Phe Ile Leu Asn Asp Ala
225                 230                 235                 240

Asn Val Ile Leu Thr Leu Leu Asp Leu Val Ala Met Ile Ala Trp Gln
            245                 250                 255

Val Ala Val Ala Val Pro Phe Leu Arg Ser Phe Pro Gln Gln Tyr Leu
            260                 265                 270

His Cys Ala Phe Asn Phe Gly Arg Lys Phe Met Tyr Gln Trp Ser Ile
            275                 280                 285

Asn Trp Gln Met Met Asp Glu Glu Ala Phe Asn Asp Lys Arg Phe His
            290                 295                 300

Leu Ala Leu Leu Ile Ser His Leu Ile Ala Leu Thr Thr Leu Phe Val
305                 310                 315                 320

Thr Arg Tyr Pro Arg Ile Leu Pro Asp Leu Trp Ser Ser Leu Cys His
            325                 330                 335

Pro Leu Arg Lys Asn Ala Val Leu Asn Ala Asn Pro Ala Lys Thr Ile
            340                 345                 350

Pro Phe Val Leu Ile Ala Ser Asn Phe Ile Gly Val Leu Phe Ser Arg
            355                 360                 365

Ser Leu His Tyr Gln Phe Leu Ser Trp Tyr His Trp Thr Leu Pro Ile
            370                 375                 380

Leu Ile Phe Trp Ser Gly Met Pro Phe Phe Val Gly Pro Ile Trp Tyr
385                 390                 395                 400

Val Leu His Glu Trp Cys Trp Asn Ser Tyr Pro Pro Asn Ser Gln Ala
            405                 410                 415

Ser Thr Leu Leu Leu Ala Leu Asn Thr Val Leu Leu Leu Leu Ala
            420                 425                 430

Leu Thr Gln Leu Ser Gly Ser Val Ala Leu Ala Lys Ser His Leu Arg
            435                 440                 445

Thr Thr Ser Ser Met Glu Lys Lys Leu Asn
450                 455

<210> SEQ ID NO 26
<211> LENGTH: 443
<212> TYPE: PRT
<213> ORGANISM: Saccharomyces cerevisiae
<220> FEATURE:
<221> NAME/KEY: MOD_RES
<222> LOCATION: (333)...(347)
<223> OTHER INFORMATION: Xaa is a variable amino acid

<400> SEQUENCE: 26

```
Trp Gln Asp Leu Lys Asp Gly Val Arg Tyr Val Ile Phe Asp Cys Arg
 1               5                  10                  15

Ala Asn Leu Ile Val Met Pro Leu Leu Ile Leu Phe Glu Ser Met Leu
             20                  25                  30

Cys Lys Ile Ile Ile Lys Lys Val Ala Tyr Thr Glu Ile Asp Tyr Lys
             35                  40                  45

Ala Tyr Met Glu Gln Ile Glu Met Ile Gln Leu Asp Gly Met Leu Asp
         50                  55                  60

Tyr Ser Gln Val Ser Gly Gly Thr Gly Pro Leu Val Tyr Pro Ala Gly
 65                  70                  75                  80

His Val Leu Ile Tyr Lys Met Met Tyr Trp Leu Thr Glu Gly Met Asp
                 85                  90                  95

His Val Glu Arg Gly Gln Val Phe Phe Arg Tyr Leu Tyr Leu Leu Thr
            100                 105                 110

Leu Ala Leu Gln Met Ala Cys Tyr Tyr Leu Leu His Leu Pro Pro Trp
        115                 120                 125

Cys Val Val Leu Ala Cys Leu Ser Lys Arg Leu His Ser Ile Tyr Val
    130                 135                 140

Leu Arg Leu Phe Asn Asp Cys Phe Thr Thr Leu Phe Met Val Val Thr
145                 150                 155                 160

Val Leu Gly Ala Ile Val Ala Ser Arg Cys His Gln Arg Pro Lys Leu
                165                 170                 175

Lys Lys His Gln Thr Cys Lys Val Pro Pro Phe Val Phe Phe Phe Met
            180                 185                 190

Cys Cys Ala Ser Tyr Arg Val His Ser Ile Phe Val Leu Arg Leu Phe
        195                 200                 205

Asn Asp Pro Val Ala Met Val Leu Leu Phe Leu Ser Ile Asn Leu Leu
    210                 215                 220

Leu Ala Gln Arg Trp Gly Trp Gly Ser Leu Ala Leu Val Ile Ser Ala
225                 230                 235                 240

Thr Tyr Ser Met Ala Val Ser Ile Lys Met Asn Ala Leu Leu Tyr Phe
                245                 250                 255

Pro Ala Met Met Ile Ser Leu Phe Ile Leu Asn Asp Ala Asn Val Ile
            260                 265                 270

Leu Thr Leu Leu Asp Leu Val Ala Met Ile Ala Trp Gln Val Ala Val
        275                 280                 285

Ala Val Pro Phe Leu Arg Ser Phe Pro Gln Gln Tyr Leu His Cys Ala
    290                 295                 300

Phe Asn Phe Gly Arg Lys Phe Met Tyr Gln Trp Ser Ile Asn Trp Gln
305                 310                 315                 320

Met Met Asp Glu Glu Ala Phe Asn Asp Lys Arg Phe Xaa Xaa Xaa Xaa
                325                 330                 335

Xaa Xaa Xaa Xaa Xaa Xaa Xaa Xaa Xaa Xaa Phe Val Thr Arg Tyr
            340                 345                 350

Pro Arg Ile Leu Pro Asp Leu Trp Ser Leu Cys His Pro Leu Arg
    355                 360                 365

Lys Asn Ala Val Leu Asn Ala Asn Pro Ala Lys Thr Ile Pro Phe Val
    370                 375                 380

Leu Ile Ala Ser Asn Phe Ile Gly Val Leu Phe Ser Arg Ser Leu His
385                 390                 395                 400

Tyr Gln Phe Leu Ser Trp Tyr His Trp Thr Leu Pro Ile Leu Ile Phe
                405                 410                 415

Trp Ser Gly Met Pro Phe Phe Val Gly Pro Ile Trp Tyr Val Leu His
```

```
                    420                 425                 430
Glu Trp Cys Trp Asn Ser Tyr Pro Pro Asn Ser
            435                 440

<210> SEQ ID NO 27
<211> LENGTH: 373
<212> TYPE: PRT
<213> ORGANISM: Homo sapiens

<400> SEQUENCE: 27

Trp Gln Glu Arg Arg Leu Leu Arg Glu Pro Arg Tyr Thr Leu Leu
 1               5                  10                  15

Val Ala Ala Cys Leu Cys Leu Ala Glu Val Gly Ile Thr Phe Trp Val
                20                  25                  30

Ile His Arg Val Ala Tyr Thr Glu Ile Asp Trp Lys Ala Tyr Met Ala
                35                  40                  45

Glu Val Glu Gly Val Gly Thr Tyr Asp Tyr Thr Gln Leu Gln Gly Asp
 50                  55                  60

Thr Gly Pro Leu Val Tyr Pro Ala Gly Phe Val Tyr Ile Phe Met Gly
 65                  70                  75                  80

Leu Tyr Tyr Ala Thr Ser Arg Gly Thr Asp Ile Arg Met Ala Gln Asn
                85                  90                  95

Ile Phe Ala Val Leu Tyr Leu Ala Thr Leu Leu Val Phe Leu Ile
                100                 105                 110

Tyr His Gln Thr Cys Lys Val Pro Pro Phe Val Phe Phe Met Cys
                115                 120                 125

Cys Ala Ser Tyr Arg Val His Ser Ile Phe Val Leu Arg Leu Phe Asn
 130                 135                 140

Asp Pro Val Ala Met Val Leu Leu Phe Leu Ser Ile Asn Leu Leu
 145                 150                 155                 160

Ala Gln Arg Trp Gly Trp Gly Cys Cys Phe Phe Ser Leu Ala Val Ser
                165                 170                 175

Val Lys Met Asn Val Leu Leu Phe Ala Pro Gly Leu Leu Phe Leu Leu
                180                 185                 190

Leu Thr Gln Phe Gly Phe Arg Gly Ala Leu Pro Lys Leu Gly Ile Cys
                195                 200                 205

Ala Gly Leu Gln Val Val Leu Gly Leu Pro Phe Leu Leu Glu Asn Pro
 210                 215                 220

Ser Gly Tyr Leu Ser Arg Ser Phe Asp Leu Gly Arg Gln Phe Leu Phe
 225                 230                 235                 240

His Trp Thr Val Asn Trp Arg Phe Leu Pro Glu Ala Leu Phe Leu His
                245                 250                 255

Arg Ala Phe His Leu Ala Leu Leu Thr Ala His Leu Thr Leu Leu Leu
 260                 265                 270

Leu Phe Ala Leu Cys Arg Trp His Arg Thr Gly Glu Ser Ile Leu Ser
                275                 280                 285

Leu Leu Arg Asp Pro Ser Lys Arg Lys Val Pro Pro Gln Pro Leu Thr
                290                 295                 300

Pro Asn Gln Ile Val Ser Thr Leu Phe Thr Ser Asn Phe Ile Gly Ile
 305                 310                 315                 320

Cys Phe Ser Arg Ser Leu His Tyr Gln Phe Tyr Val Trp Tyr Phe His
                325                 330                 335

Thr Leu Pro Tyr Leu Leu Trp Ala Met Pro Ala Arg Thr Leu Thr His
                340                 345                 350
```

```
Leu Leu Arg Leu Leu Val Leu Gly Leu Ile Glu Leu Ser Trp Asn Thr
            355                 360                 365

Tyr Pro Ser Thr Ser
    370

<210> SEQ ID NO 28
<211> LENGTH: 269
<212> TYPE: PRT
<213> ORGANISM: Saccharomyces cerevisiae

<400> SEQUENCE: 28

Val Arg Tyr Val Ile Phe Asp Cys Arg Ala Asn Leu Ile Val Met Pro
  1               5                  10                  15

Leu Leu Ile Leu Phe Glu Ser Met Leu Cys Lys Ile Ile Lys Lys
                20                  25                  30

Val Ala Tyr Thr Glu Ile Asp Tyr Lys Ala Tyr Met Glu Gln Ile Glu
             35                  40                  45

Met Ile Gln Leu Asp Gly Met Leu Asp Tyr Ser Gln Val Ser Gly Gly
         50                  55                  60

Thr Gly Pro Leu Val Tyr Pro Ala Gly His Val Leu Ile Tyr Lys Met
 65                  70                  75                  80

Met Tyr Trp Leu Thr Glu Gly Met Asp His Val Glu Arg Gly Gln Val
                 85                  90                  95

Phe Phe Arg Tyr Leu Tyr Leu Leu Thr Leu Ala Leu Gln Met Ala Cys
                100                 105                 110

Tyr Tyr Leu Leu His Pro Trp Cys Val Val Leu Ala Cys Leu Ser Lys
            115                 120                 125

Arg Leu His Ser Ile Tyr Val Leu Arg Leu Phe Asn Asp Cys Phe Thr
        130                 135                 140

Thr Leu Phe Met Val Val Thr Val Leu Gly Ala Ile Val Ala Ser Arg
145                 150                 155                 160

Cys His Gln Arg Pro Lys Leu Lys Lys Ser Leu Ala Leu Val Ile Ser
                165                 170                 175

Ala Thr Tyr Ser Met Ala Val Ser Ile Lys Met Asn Ala Leu Leu Tyr
            180                 185                 190

Phe Pro Ala Met Met Ile Ser Leu Phe Ile Leu Asn Asp Ala Asn Val
        195                 200                 205

Ile Leu Thr Leu Leu Asp Leu Val Ala Met Ile Ala Trp Gln Val Ala
    210                 215                 220

Val Ala Val Pro Phe Leu Arg Ser Phe Pro Gln Gln Tyr Leu His Cys
225                 230                 235                 240

Ala Phe Asn Phe Gly Arg Lys Phe Met Tyr Gln Trp Ser Ile Asn Trp
                245                 250                 255

Gln Met Met Asp Glu Glu Ala Phe Asn Asp Lys Arg Phe
                260                 265

<210> SEQ ID NO 29
<211> LENGTH: 258
<212> TYPE: PRT
<213> ORGANISM: Drosophila virilis

<400> SEQUENCE: 29

Ile Lys Tyr Leu Ala Phe Glu Pro Ala Ala Leu Pro Ile Val Ser Val
  1               5                  10                  15

Leu Ile Val Leu Ala Glu Ala Val Ile Asn Val Leu Val Ile Gln Arg
                20                  25                  30
```

Val Pro Tyr Thr Glu Ile Asp Trp Lys Ala Tyr Met Gln Glu Cys Glu
         35                  40                  45

Gly Phe Leu Asn Gly Thr Thr Asn Tyr Ser Leu Leu Arg Gly Asp Thr
 50                      55                  60

Gly Pro Leu Val Tyr Pro Ala Ala Phe Val Tyr Ile Tyr Ser Gly Leu
 65                  70                  75                  80

Tyr Tyr Leu Thr Gly Gln Gly Thr Asn Val Arg Leu Ala Gln Tyr Ile
                 85                  90                  95

Phe Ala Cys Ile Tyr Leu Leu Gln Met Cys Leu Val Leu Arg Leu Tyr
             100                 105                 110

Thr Lys Ser Arg Lys Val Pro Pro Tyr Val Leu Val Leu Ser Ala Phe
         115                 120                 125

Thr Ser Tyr Arg Ile His Ser Ile Tyr Val Leu Arg Leu Phe Asn Asp
 130                     135                 140

Pro Val Ala Ile Leu Leu Leu Tyr Ala Ala Leu Asn Leu Phe Leu Asp
145                 150                 155                 160

Gln Arg Trp Thr Leu Gly Ser Ile Cys Tyr Ser Leu Ala Val Gly Val
                 165                 170                 175

Lys Met Asn Ile Leu Leu Phe Ala Pro Ala Leu Leu Leu Phe Tyr Leu
             180                 185                 190

Ala Asn Leu Gly Val Leu Arg Thr Leu Val Gln Leu Thr Ile Cys Ala
         195                 200                 205

Val Leu Gln Leu Phe Ile Gly Ala Pro Phe Leu Arg Thr His Pro Met
210                 215                 220

Glu Tyr Leu Arg Gly Ser Phe Asp Leu Gly Arg Ile Phe Glu His Lys
225                 230                 235                 240

Trp Thr Val Asn Tyr Arg Phe Leu Ser Lys Glu Leu Phe Glu Gln Arg
                 245                 250                 255

Glu Phe

<210> SEQ ID NO 30
<211> LENGTH: 267
<212> TYPE: PRT
<213> ORGANISM: Saccharomyces cerevisiae

<400> SEQUENCE: 30

Arg Tyr Val Ile Phe Asp Cys Arg Ala Asn Leu Ile Val Met Pro Leu
 1               5                  10                  15

Leu Ile Leu Phe Glu Ser Met Leu Cys Lys Ile Ile Lys Lys Val
             20                  25                  30

Ala Tyr Thr Glu Ile Asp Tyr Lys Ala Tyr Met Gln Ile Glu Met
         35                  40                  45

Ile Gln Leu Asp Gly Met Leu Asp Tyr Ser Gln Val Ser Gly Gly Thr
 50                      55                  60

Gly Pro Leu Val Tyr Pro Ala Gly His Val Leu Ile Tyr Lys Met Met
 65                  70                  75                  80

Tyr Trp Leu Thr Glu Gly Met Asp His Val Glu Arg Gly Gln Val Phe
                 85                  90                  95

Phe Arg Tyr Leu Tyr Leu Leu Thr Leu Ala Leu Gln Met Ala Cys Tyr
             100                 105                 110

Tyr Leu Leu His Trp Cys Val Val Leu Ala Cys Leu Ser Lys Arg Leu
         115                 120                 125

His Ser Ile Tyr Val Leu Arg Leu Phe Asn Asp Cys Phe Thr Thr Leu
 130                     135                 140

```
Phe Met Val Val Thr Val Leu Gly Ala Ile Val Ala Ser Arg Cys His
145                 150                 155                 160

Gln Arg Pro Lys Leu Lys Lys Ser Leu Ala Leu Val Ile Ser Ala Thr
            165                 170                 175

Tyr Ser Met Ala Val Ser Ile Lys Met Asn Ala Leu Leu Tyr Phe Pro
            180                 185                 190

Ala Met Met Ile Ser Leu Phe Ile Leu Asn Asp Ala Asn Val Ile Leu
            195                 200                 205

Thr Leu Leu Asp Leu Val Ala Met Ile Ala Trp Gln Val Ala Val Ala
            210                 215                 220

Val Pro Phe Leu Arg Ser Phe Pro Gln Gln Tyr Leu His Cys Ala Phe
225                 230                 235                 240

Asn Phe Gly Arg Lys Phe Met Tyr Gln Trp Ser Ile Asn Trp Gln Met
                245                 250                 255

Met Asp Glu Glu Ala Phe Asn Asp Lys Arg Phe
            260                 265

<210> SEQ ID NO 31
<211> LENGTH: 257
<212> TYPE: PRT
<213> ORGANISM: Drosophila melanogaster

<400> SEQUENCE: 31

Lys Tyr Leu Leu Leu Glu Pro Ala Ala Leu Pro Ile Val Gly Leu Phe
1               5                   10                  15

Val Leu Leu Ala Glu Leu Val Ile Asn Val Val Ile Gln Arg Val
            20                  25                  30

Pro Tyr Thr Glu Ile Asp Trp Val Ala Tyr Met Gln Glu Cys Glu Gly
            35                  40                  45

Phe Leu Asn Gly Thr Thr Asn Tyr Ser Leu Leu Arg Gly Asp Thr Gly
50                  55                  60

Pro Leu Val Tyr Pro Ala Ala Phe Val Tyr Ile Tyr Ser Ala Leu Tyr
65                  70                  75                  80

Tyr Val Thr Ser His Gly Thr Asn Val Arg Leu Ala Gln Tyr Ile Phe
                85                  90                  95

Ala Gly Ile Tyr Leu Leu Gln Leu Ala Leu Val Leu Arg Leu Tyr Ser
            100                 105                 110

Lys Ser Arg Lys Val Pro Pro Tyr Val Leu Val Leu Ser Ala Phe Thr
            115                 120                 125

Ser Tyr Arg Ile His Ser Ile Tyr Val Leu Arg Leu Phe Asn Asp Pro
130                 135                 140

Val Ala Val Leu Leu Leu Tyr Ala Ala Leu Asn Leu Phe Leu Asp Arg
145                 150                 155                 160

Arg Trp Thr Leu Gly Ser Thr Phe Phe Ser Leu Ala Val Gly Val Lys
                165                 170                 175

Met Asn Ile Leu Leu Phe Ala Pro Ala Leu Leu Phe Tyr Leu Ala
            180                 185                 190

Asn Leu Gly Leu Leu Arg Thr Ile Leu Gln Leu Ala Val Cys Gly Val
            195                 200                 205

Ile Gln Leu Leu Leu Gly Ala Pro Phe Leu Leu Thr His Pro Val Glu
            210                 215                 220

Tyr Leu Arg Gly Ser Phe Asp Leu Gly Arg Ile Phe Glu His Lys Trp
225                 230                 235                 240

Thr Val Asn Tyr Arg Phe Leu Ser Arg Asp Val Phe Glu Asn Arg Thr
                245                 250                 255
```

Phe

```
<210> SEQ ID NO 32
<211> LENGTH: 1377
<212> TYPE: DNA
<213> ORGANISM: Saccharomyces cerevisiae

<400> SEQUENCE: 32
```

| | | | | | |
|---|---|---|---|---|---|
| atggaaggtg | aacagtctcc | gcaaggtgaa | aagtctctgc | aaaggaagca | atttgtcaga | 60 |
| cctccgctgg | atctgtggca | ggatctcaag | gacggtgtgc | gctacgtgat | cttcgattgt | 120 |
| agggccaatc | ttatcgttat | gcccctttg | attttgttcg | aaagcatgct | gtgcaagatt | 180 |
| atcattaaga | aggtagctta | cacagagatc | gattacaagg | cgtacatgga | gcagatcgag | 240 |
| atgattcagc | tcgatggcat | gctggactac | tctcaggtga | gtggtggaac | gggcccgctg | 300 |
| gtgtatccag | caggccacgt | cttgatctac | aagatgatgt | actggctaac | agagggaatg | 360 |
| gaccacgttg | agcgcgggca | gtgttttc | agatacttgt | atctccttac | actggcgtta | 420 |
| caaatggcgt | gttactacct | tttacatcta | ccaccgtggt | gtgtggtctt | ggcgtgcctc | 480 |
| tctaaaagat | tgcactctat | ttacgtgcta | cggttattca | atgattgctt | cactactttg | 540 |
| tttatggtcg | tcacggtttt | ggggctatc | gtggccagca | ggtgccatca | gcgccccaaa | 600 |
| ttaaagaagt | cccttgcgct | ggtgatctcc | gcaacataca | gtatggctgt | gagcattaag | 660 |
| atgaatgcgc | tgttgtattt | ccctgcaatg | atgatttctc | tattcatcct | taatgacgcg | 720 |
| aacgtaatcc | ttactttgtt | ggatctcgtt | gcgatgattg | catggcaagt | cgcagttgca | 780 |
| gtgcccttcc | tgcgcagctt | tccgcaacag | tacctgcatt | gcgcttttaa | tttcggcagg | 840 |
| aagtttatgt | accaatggag | tatcaattgg | caaatgatgg | atgaagaggc | tttcaatgat | 900 |
| aagaggttcc | acttggccct | tttaatcagc | cacctgatag | cgctcaccac | actgttcgtc | 960 |
| acaagatacc | ctcgcatcct | gcccgattta | tggtcttccc | tgtgccatcc | gctgaggaaa | 1020 |
| aatgcagtgc | tcaatgccaa | tcccgccaag | actattccat | tcgttctaat | cgcatccaac | 1080 |
| ttcatcggcg | tcctatttc | aaggtccctc | cactaccagt | ttctatcctg | gtatcactgg | 1140 |
| actttgccta | tactgatctt | ttggtcggga | atgcccttct | tcgttggtcc | catttggtac | 1200 |
| gtcttgcacg | agtggtgctg | gaattcctat | ccaccaaact | cacaagcaag | cacgctattg | 1260 |
| ttggcattga | atactgttct | gttgcttcta | ttggccttga | cgcagctatc | tggttcggtc | 1320 |
| gccctcgcca | aaagccatct | tcgtaccacc | agctctatgg | aaaaaaagct | caactga | 1377 |

```
<210> SEQ ID NO 33
<211> LENGTH: 458
<212> TYPE: PRT
<213> ORGANISM: Saccharomyces cerevisiae

<400> SEQUENCE: 33
```

Met Glu Gly Glu Gln Ser Pro Gln Gly Glu Lys Ser Leu Gln Arg Lys
 1               5                  10                  15

Gln Phe Val Arg Pro Pro Leu Asp Leu Trp Gln Asp Leu Lys Asp Gly
            20                  25                  30

Val Arg Tyr Val Ile Phe Asp Cys Arg Ala Asn Leu Ile Val Met Pro
        35                  40                  45

Leu Leu Ile Leu Phe Glu Ser Met Leu Cys Lys Ile Ile Lys Lys
    50                  55                  60

Val Ala Tyr Thr Glu Ile Asp Tyr Lys Ala Tyr Met Glu Gln Ile Glu
65                  70                  75                  80

Met Ile Gln Leu Asp Gly Met Leu Asp Tyr Ser Gln Val Ser Gly
                 85                  90                  95

Thr Gly Pro Leu Val Tyr Pro Ala Gly His Val Leu Ile Tyr Lys Met
            100                 105                 110

Met Tyr Trp Leu Thr Glu Gly Met Asp His Val Glu Arg Gly Gln Val
        115                 120                 125

Phe Phe Arg Tyr Leu Tyr Leu Leu Thr Leu Ala Leu Gln Met Ala Cys
    130                 135                 140

Tyr Tyr Leu Leu His Leu Pro Pro Trp Cys Val Val Leu Ala Cys Leu
145                 150                 155                 160

Ser Lys Arg Leu His Ser Ile Tyr Val Leu Arg Leu Phe Asn Asp Cys
                165                 170                 175

Phe Thr Thr Leu Phe Met Val Val Thr Val Leu Gly Ala Ile Val Ala
            180                 185                 190

Ser Arg Cys His Gln Arg Pro Lys Leu Lys Lys Ser Leu Ala Leu Val
        195                 200                 205

Ile Ser Ala Thr Tyr Ser Met Ala Val Ser Ile Lys Met Asn Ala Leu
    210                 215                 220

Leu Tyr Phe Pro Ala Met Met Ile Ser Leu Phe Ile Leu Asn Asp Ala
225                 230                 235                 240

Asn Val Ile Leu Thr Leu Leu Asp Leu Val Ala Met Ile Ala Trp Gln
                245                 250                 255

Val Ala Val Ala Val Pro Phe Leu Arg Ser Phe Pro Gln Gln Tyr Leu
            260                 265                 270

His Cys Ala Phe Asn Phe Gly Arg Lys Phe Met Tyr Gln Trp Ser Ile
        275                 280                 285

Asn Trp Gln Met Met Asp Glu Glu Ala Phe Asn Asp Lys Arg Phe His
    290                 295                 300

Leu Ala Leu Leu Ile Ser His Leu Ile Ala Leu Thr Thr Leu Phe Val
305                 310                 315                 320

Thr Arg Tyr Pro Arg Ile Leu Pro Asp Leu Trp Ser Ser Leu Cys His
                325                 330                 335

Pro Leu Arg Lys Asn Ala Val Leu Asn Ala Asn Pro Ala Lys Thr Ile
            340                 345                 350

Pro Phe Val Leu Ile Ala Ser Asn Phe Ile Gly Val Leu Phe Ser Arg
        355                 360                 365

Ser Leu His Tyr Gln Phe Leu Ser Trp Tyr His Trp Thr Leu Pro Ile
    370                 375                 380

Leu Ile Phe Trp Ser Gly Met Pro Phe Phe Val Gly Pro Ile Trp Tyr
385                 390                 395                 400

Val Leu His Glu Trp Cys Trp Asn Ser Tyr Pro Pro Asn Ser Gln Ala
                405                 410                 415

Ser Thr Leu Leu Leu Ala Leu Asn Thr Val Leu Leu Leu Leu Ala
            420                 425                 430

Leu Thr Gln Leu Ser Gly Ser Val Ala Leu Ala Lys Ser His Leu Arg
        435                 440                 445

Thr Thr Ser Ser Met Glu Lys Lys Leu Asn
    450                 455

<210> SEQ ID NO 34
<211> LENGTH: 1395
<212> TYPE: DNA
<213> ORGANISM: Pichia pastoris

<400> SEQUENCE: 34

```
atgcctccga tagagccagc tgaaaggcca aagcttacgc tgaaaaatgt tatcggtgat      60
ctagtggctc ttattcaaaa cgttttattt aacccagatt ttagtgtctt cgttgcacct     120
cttttatggt tagctgattc cattgttatc aaggtgatca ttggcactgt ttcctacaca     180
gatattgatt tttcttcata tatgcaacaa atctttaaaa ttcgacaagg agaattagat     240
tatagcaaca tatttggtga caccggtcca ttggtttacc cagccggcca tgttcatgct     300
tactcagtac tttcgtggta cagtgatggt ggagaagacg tcagtttcgt tcaacaagca     360
tttggttggt tataccctagg ttgcttgtta ctatccatca gctcctactt tttctctggc     420
ttagggaaaa tacctccggt ttatttttgtt ttgttggtag cgtccaagag actgcattca     480
atatttgtat tgagactctt caatgactgt taacaacat tttgatgtt ggcaactata     540
atcatcctta acaagcaag tagctggagg aaagatggca caactattcc attatctgtc     600
cctgatgctg cagatacgta cagtttagcc atctctgtaa agatgaatgc gctgctatac     660
ctcccagcat tcctactact catatatctc atttgtgacg aaaatttgat taaagccttg     720
gcacctgttc tagttttgat attggtgcaa gtaggagtcg ttattcgtt catttttaccg     780
ttgcactatg atgatcaggc aaatgaaatt cgttctgcct actttagaca ggcttttgac     840
tttagtcgcc aatttcttta taagtggacg gttaattggc gctttttgag ccaagaaact     900
ttcaacaatg tccattttca ccagctcctg tttgctctcc atattattac gttagtcttg     960
ttcatcctca agttcctctc tcctaaaaac attggaaaac cgcttggtag atttgtgttg    1020
gacattttca aattttggaa gccaaccctta tctccaacca atattatcaa cgacccagaa    1080
agaagcccag attttgttta caccgtcatg gctactacca acttaatagg ggtgcttttt    1140
gcaagatctt tacactacca gttcctaagc tggtatgcgt tctctttgcc atatctcctt    1200
tacaaggctc gtctgaactt tatagcatct attattgttt atgccgctca cgagtattgc    1260
tggttggttt tcccagctac agaacaaagt tccgcgttgt tggtatctat cttactactt    1320
atcctgattc tcatttttac caacgaacag ttatttcctt ctcaatcggt ccctgcagaa    1380
aaaaagaata cataa                                                      1395
```

<210> SEQ ID NO 35
<211> LENGTH: 464
<212> TYPE: PRT
<213> ORGANISM: Pichia pastoris

<400> SEQUENCE: 35

```
Met Pro Pro Ile Glu Pro Ala Glu Arg Pro Lys Leu Thr Leu Lys Asn
  1               5                  10                  15

Val Ile Gly Asp Leu Val Ala Leu Ile Gln Asn Val Leu Phe Asn Pro
             20                  25                  30

Asp Phe Ser Val Phe Val Ala Pro Leu Leu Trp Leu Ala Asp Ser Ile
         35                  40                  45

Val Ile Lys Val Ile Ile Gly Thr Val Ser Tyr Thr Asp Ile Asp Phe
     50                  55                  60

Ser Ser Tyr Met Gln Gln Ile Phe Lys Ile Arg Gln Gly Glu Leu Asp
 65                  70                  75                  80

Tyr Ser Asn Ile Phe Gly Asp Thr Gly Pro Leu Val Tyr Pro Ala Gly
                 85                  90                  95

His Val His Ala Tyr Ser Val Leu Ser Trp Tyr Ser Asp Gly Gly Glu
            100                 105                 110
```

Asp Val Ser Phe Val Gln Gln Ala Phe Gly Trp Leu Tyr Leu Gly Cys
            115                 120                 125

Leu Leu Leu Ser Ile Ser Ser Tyr Phe Ser Gly Leu Gly Lys Ile
130                 135                 140

Pro Pro Val Tyr Phe Val Leu Val Ala Ser Lys Arg Leu His Ser
145                 150                 155                 160

Ile Phe Val Leu Arg Leu Phe Asn Asp Cys Leu Thr Thr Phe Leu Met
                165                 170                 175

Leu Ala Thr Ile Ile Leu Gln Gln Ala Ser Ser Trp Arg Lys Asp
            180                 185                 190

Gly Thr Thr Ile Pro Leu Ser Val Pro Asp Ala Ala Asp Thr Tyr Ser
            195                 200                 205

Leu Ala Ile Ser Val Lys Met Asn Ala Leu Leu Tyr Leu Pro Ala Phe
210                 215                 220

Leu Leu Leu Ile Tyr Leu Ile Cys Asp Glu Asn Leu Ile Lys Ala Leu
225                 230                 235                 240

Ala Pro Val Leu Val Leu Ile Leu Val Gln Val Gly Val Gly Tyr Ser
                245                 250                 255

Phe Ile Leu Pro Leu His Tyr Asp Asp Gln Ala Asn Glu Ile Arg Ser
            260                 265                 270

Ala Tyr Phe Arg Gln Ala Phe Asp Phe Ser Arg Gln Phe Leu Tyr Lys
            275                 280                 285

Trp Thr Val Asn Trp Arg Phe Leu Ser Gln Glu Thr Phe Asn Asn Val
            290                 295                 300

His Phe His Gln Leu Leu Phe Ala Leu His Ile Ile Thr Leu Val Leu
305                 310                 315                 320

Phe Ile Leu Lys Phe Leu Ser Pro Lys Asn Ile Gly Lys Pro Leu Gly
                325                 330                 335

Arg Phe Val Leu Asp Ile Phe Lys Phe Trp Lys Pro Thr Leu Ser Pro
            340                 345                 350

Thr Asn Ile Ile Asn Asp Pro Glu Arg Ser Pro Asp Phe Val Tyr Thr
            355                 360                 365

Val Met Ala Thr Thr Asn Leu Ile Gly Val Leu Phe Ala Arg Ser Leu
370                 375                 380

His Tyr Gln Phe Leu Ser Trp Tyr Ala Phe Ser Leu Pro Tyr Leu Leu
385                 390                 395                 400

Tyr Lys Ala Arg Leu Asn Phe Ile Ala Ser Ile Val Tyr Ala Ala
                405                 410                 415

His Glu Tyr Cys Trp Leu Val Phe Pro Ala Thr Glu Gln Ser Ser Ala
            420                 425                 430

Leu Leu Val Ser Ile Leu Leu Ile Leu Ile Leu Ile Phe Thr Asn
            435                 440                 445

Glu Gln Leu Phe Pro Ser Gln Ser Val Pro Ala Glu Lys Lys Asn Thr
450                 455                 460

<210> SEQ ID NO 36
<211> LENGTH: 418
<212> TYPE: PRT
<213> ORGANISM: Pichia pastoris
<220> FEATURE:
<221> NAME/KEY: MUTAGEN
<222> LOCATION: (209)...(223)
<223> OTHER INFORMATION: Xaa is a variable amino acid
<220> FEATURE:
<221> NAME/KEY: MOD_RES
<222> LOCATION: (235)...(246)
<223> OTHER INFORMATION: Xaa is a variable amino acid

<400> SEQUENCE: 36

```
Arg Pro Lys Leu Thr Leu Lys Asn Val Ile Gly Asp Leu Val Ala Leu
 1               5                   10                  15

Ile Gln Asn Val Leu Phe Asn Pro Asp Phe Ser Val Phe Val Ala Pro
             20                  25                  30

Leu Leu Trp Leu Ala Asp Ser Ile Val Ile Lys Val Ile Ile Gly Thr
         35                  40                  45

Val Ser Tyr Thr Asp Ile Asp Phe Ser Ser Tyr Met Gln Gln Ile Phe
     50                  55                  60

Lys Ile Arg Gln Gly Glu Leu Asp Tyr Ser Asn Ile Phe Gly Asp Thr
 65                  70                  75                  80

Gly Pro Leu Val Tyr Pro Ala Gly His Val His Ala Tyr Ser Val Leu
                 85                  90                  95

Ser Trp Tyr Ser Asp Gly Gly Glu Asp Val Ser Phe Val Gln Gln Ala
            100                 105                 110

Phe Gly Trp Leu Tyr Leu Gly Cys Leu Leu Ser Ile Ser Ser Tyr
        115                 120                 125

Phe Phe Ser Gly Leu Gly Lys Ile Pro Pro Val Tyr Phe Val Leu Leu
130                 135                 140

Val Ala Ser Lys Arg Leu His Ser Ile Phe Val Leu Arg Leu Phe Asn
145                 150                 155                 160

Asp Cys Leu Thr Thr Phe Leu Met Leu Ala Thr Ile Ile Leu Gln
                165                 170                 175

Gln Ala Ser Ser Trp Arg Lys Asp Gly Thr Thr Ile Pro Leu Ser Val
            180                 185                 190

Pro Asp Ala Ala Asp Thr Tyr Ser Leu Ala Ile Ser Val Lys Met Asn
        195                 200                 205

Xaa Xaa Xaa Xaa Xaa Xaa Xaa Xaa Xaa Xaa Xaa Xaa Xaa Cys
        210                 215                 220

Asp Glu Asn Leu Ile Lys Ala Leu Ala Pro Xaa Xaa Xaa Xaa Xaa
225                 230                 235                 240

Xaa Xaa Xaa Xaa Xaa Xaa Tyr Ser Phe Ile Leu Pro Leu His Tyr Asp
                245                 250                 255

Asp Gln Ala Asn Glu Ile Arg Ser Ala Tyr Phe Arg Gln Ala Phe Asp
            260                 265                 270

Phe Ser Arg Gln Phe Leu Tyr Lys Trp Thr Val Asn Arg Phe Leu
        275                 280                 285

Ser Gln Glu Thr Phe Asn Asn Val His Phe His Gln Leu Leu Phe Ala
290                 295                 300

Leu His Ile Ile Thr Leu Val Leu Phe Ile Leu Lys Phe Leu Ser Pro
305                 310                 315                 320

Lys Asn Ile Gly Lys Pro Leu Gly Arg Phe Val Leu Asp Ile Phe Lys
                325                 330                 335

Phe Trp Lys Pro Thr Leu Ser Pro Thr Asn Ile Ile Asn Pro Asp Phe
            340                 345                 350

Val Tyr Thr Val Met Ala Thr Thr Asn Leu Ile Gly Val Leu Phe Ala
        355                 360                 365

Arg Ser Leu His Tyr Gln Phe Leu Ser Trp Tyr Ala Phe Ser Leu Pro
    370                 375                 380

Tyr Leu Leu Tyr Lys Ala Arg Leu Asn Phe Ile Ala Ser Ile Ile Val
385                 390                 395                 400

Tyr Ala Ala His Glu Tyr Cys Trp Leu Val Phe Pro Ala Thr Glu Gln
```

405                 410                 415

Ser Ser

<210> SEQ ID NO 37
<211> LENGTH: 398
<212> TYPE: PRT
<213> ORGANISM: Saccharomyces cerevisiae

<400> SEQUENCE: 37

Arg Pro Pro Leu Asp Leu Trp Gln Asp Leu Lys Asp Gly Val Arg Tyr
 1               5                  10                  15

Val Ile Phe Asp Cys Arg Ala Asn Leu Ile Val Met Pro Leu Leu Ile
             20                  25                  30

Leu Phe Glu Ser Met Leu Cys Lys Ile Ile Lys Lys Val Ala Tyr
         35                  40                  45

Thr Glu Ile Asp Tyr Lys Ala Tyr Met Glu Gln Ile Glu Met Ile Gln
     50                  55                  60

Leu Asp Gly Met Leu Asp Tyr Ser Gln Val Ser Gly Thr Gly Pro
 65                  70                  75                  80

Leu Val Tyr Pro Ala Gly His Val Leu Ile Tyr Lys Met Met Tyr Trp
                 85                  90                  95

Leu Thr Glu Gly Met Asp His Val Glu Arg Gly Gln Val Phe Phe Arg
            100                 105                 110

Tyr Leu Tyr Leu Leu Thr Leu Ala Leu Gln Met Ala Cys Tyr Tyr Leu
        115                 120                 125

Leu His Leu Pro Pro Trp Cys Val Val Leu Ala Cys Leu Ser Lys Arg
130                 135                 140

Leu His Ser Ile Tyr Val Leu Arg Leu Phe Asn Asp Cys Phe Thr Thr
145                 150                 155                 160

Leu Phe Met Val Val Thr Val Leu Gly Ala Ile Val Ala Ser Arg Cys
                165                 170                 175

His Gln Arg Pro Lys Leu Lys Lys Ser Leu Ala Leu Val Ile Ser Ala
            180                 185                 190

Thr Tyr Ser Met Ala Val Ser Ile Lys Met Asn Ala Leu Leu Tyr Phe
        195                 200                 205

Pro Ala Met Met Ile Ser Leu Phe Ile Leu Asn Asp Ala Asn Val Ile
    210                 215                 220

Leu Thr Leu Leu Asp Leu Val Ala Met Ile Ala Trp Gln Val Ala Val
225                 230                 235                 240

Ala Val Pro Phe Leu Arg Ser Phe Pro Gln Gln Tyr Leu His Cys Ala
                245                 250                 255

Phe Asn Phe Gly Arg Lys Phe Met Tyr Gln Trp Ser Ile Asn Trp Gln
            260                 265                 270

Met Met Asp Glu Glu Ala Phe Asn Asp Lys Arg Phe His Leu Ala Leu
        275                 280                 285

Leu Ile Ser His Leu Ile Ala Leu Thr Thr Leu Phe Val Thr Arg Tyr
    290                 295                 300

Pro Arg Ile Leu Pro Asp Leu Trp Ser Ser Leu Cys His Pro Leu Arg
305                 310                 315                 320

Lys Asn Ala Val Leu Asn Ala Asn Pro Ala Lys Thr Ile Pro Phe Val
                325                 330                 335

Leu Ile Ala Ser Asn Phe Ile Gly Val Leu Phe Ser Arg Ser Leu His
            340                 345                 350

Tyr Gln Phe Leu Ser Trp Tyr His Trp Thr Leu Pro Ile Leu Ile Phe

-continued

```
            355                 360                 365
Trp Ser Gly Met Pro Phe Phe Val Gly Pro Ile Trp Tyr Val Leu His
    370                 375                 380
Glu Trp Cys Trp Asn Ser Tyr Pro Pro Asn Ser Gln Ala Ser
385                 390                 395

<210> SEQ ID NO 38
<211> LENGTH: 387
<212> TYPE: PRT
<213> ORGANISM: Pichia pastoris
<220> FEATURE:
<221> NAME/KEY: MOD_RES
<222> LOCATION: (183)...(197)
<223> OTHER INFORMATION: Xaa is a variable amino acid
<220> FEATURE:
<221> NAME/KEY: MOD_RES
<222> LOCATION: (209)...(220)
<223> OTHER INFORMATION: Xaa is a variable amino acid

<400> SEQUENCE: 38

Ser Val Phe Val Ala Pro Leu Leu Trp Leu Ala Asp Ser Ile Val Ile
  1               5                  10                  15
Lys Val Ile Ile Gly Thr Val Ser Tyr Thr Asp Ile Asp Phe Ser Ser
                 20                  25                  30
Tyr Met Gln Gln Ile Phe Lys Ile Arg Gln Gly Glu Leu Asp Tyr Ser
             35                  40                  45
Asn Ile Phe Gly Asp Thr Gly Pro Leu Val Tyr Pro Ala Gly His Val
 50                  55                  60
His Ala Tyr Ser Val Leu Ser Trp Tyr Ser Asp Gly Gly Glu Asp Val
 65                  70                  75                  80
Ser Phe Val Gln Gln Ala Phe Gly Trp Leu Tyr Leu Gly Cys Leu Leu
                 85                  90                  95
Leu Ser Ile Ser Ser Tyr Phe Phe Ser Gly Leu Gly Lys Ile Pro Pro
            100                 105                 110
Val Tyr Phe Val Leu Leu Val Ala Ser Lys Arg Leu His Ser Ile Phe
        115                 120                 125
Val Leu Arg Leu Phe Asn Asp Cys Leu Thr Thr Phe Leu Met Leu Ala
130                 135                 140
Thr Ile Ile Ile Leu Gln Gln Ala Ser Ser Trp Arg Lys Asp Gly Thr
145                 150                 155                 160
Thr Ile Pro Leu Ser Val Pro Asp Ala Ala Asp Thr Tyr Ser Leu Ala
                165                 170                 175
Ile Ser Val Lys Met Asn Xaa Xaa Xaa Xaa Xaa Xaa Xaa Xaa Xaa Xaa
            180                 185                 190
Xaa Xaa Xaa Xaa Xaa Cys Asp Glu Asn Leu Ile Lys Ala Leu Ala Pro
        195                 200                 205
Xaa Xaa Xaa Xaa Xaa Xaa Xaa Xaa Xaa Xaa Xaa Tyr Ser Phe Ile
210                 215                 220
Leu Pro Leu His Tyr Asp Asp Gln Ala Asn Glu Ile Arg Ser Ala Tyr
225                 230                 235                 240
Phe Arg Gln Ala Phe Asp Phe Ser Arg Gln Phe Leu Tyr Lys Trp Thr
                245                 250                 255
Val Asn Trp Arg Phe Leu Ser Gln Glu Thr Phe Asn Asn Val His Phe
            260                 265                 270
His Gln Leu Leu Phe Ala Leu His Ile Ile Thr Leu Val Leu Phe Ile
        275                 280                 285
Pro Leu Gly Arg Phe Val Leu Asp Ile Phe Lys Phe Trp Lys Pro Thr
```

```
            290                 295                 300
Leu Ser Pro Thr Asn Ile Ile Asn Asp Pro Glu Arg Ser Pro Asp Phe
305                 310                 315                 320

Val Tyr Thr Val Met Ala Thr Thr Asn Leu Ile Gly Val Leu Phe Ala
                325                 330                 335

Arg Ser Leu His Tyr Gln Phe Leu Ser Trp Tyr Ala Phe Ser Leu Pro
                340                 345                 350

Tyr Leu Leu Tyr Lys Ala Arg Leu Asn Phe Ile Ala Ser Ile Ile Val
            355                 360                 365

Tyr Ala Ala His Glu Tyr Cys Trp Leu Val Phe Pro Ala Thr Glu Gln
        370                 375                 380

Ser Ser Ala
385

<210> SEQ ID NO 39
<211> LENGTH: 373
<212> TYPE: PRT
<213> ORGANISM: Neurospora crassa

<400> SEQUENCE: 39

Ser Lys Leu Ile Pro Pro Ala Leu Phe Leu Val Asp Ala Leu Leu Cys
1               5                   10                  15

Gly Leu Ile Ile Trp Lys Val Pro Tyr Thr Glu Ile Asp Trp Ala Ala
            20                  25                  30

Tyr Met Glu Gln Val Ser Gln Ile Leu Ser Gly Glu Arg Asp Tyr Thr
        35                  40                  45

Lys Val Arg Gly Gly Thr Gly Pro Leu Val Tyr Pro Ala Ala His Val
    50                  55                  60

Tyr Ile Tyr Thr Gly Leu Tyr His Leu Thr Asp Glu Gly Arg Asn Ile
65                  70                  75                  80

Leu Leu Ala Gln Gln Leu Phe Ala Gly Leu Tyr Met Val Thr Leu Ala
                85                  90                  95

Val Val Met Gly Cys Tyr Trp Gln Ala Lys Ala Pro Pro Tyr Leu Phe
            100                 105                 110

Pro Leu Leu Thr Leu Ser Lys Arg Leu His Ser Ile Phe Val Leu Arg
        115                 120                 125

Cys Phe Asn Asp Cys Phe Ala Val Leu Phe Leu Trp Leu Ala Ile Phe
    130                 135                 140

Phe Phe Gln Arg Arg Asn Trp Gln Ala Gly Ala Leu Leu Tyr Thr Leu
145                 150                 155                 160

Gly Leu Gly Val Lys Met Thr Leu Leu Leu Ser Leu Pro Ala Val Gly
                165                 170                 175

Ile Val Leu Phe Leu Gly Ser Gly Ser Phe Val Thr Thr Leu Gln Leu
            180                 185                 190

Val Ala Thr Met Gly Leu Val Gln Ile Leu Ile Gly Val Pro Phe Leu
        195                 200                 205

Ala His Tyr Pro Thr Glu Tyr Leu Ser Arg Ala Phe Glu Leu Ser Arg
    210                 215                 220

Gln Phe Phe Phe Lys Trp Thr Val Asn Trp Arg Phe Val Gly Glu Glu
225                 230                 235                 240

Ile Phe Leu Ser Lys Gly Phe Ala Leu Thr Leu Leu Ala Leu His Val
                245                 250                 255

Leu Val Leu Gly Ile Phe Ile Thr Thr Arg Trp Ile Lys Pro Ala Arg
            260                 265                 270
```

```
Lys Ser Leu Val Gln Leu Ile Ser Pro Val Leu Leu Ala Gly Lys Pro
            275                 280                 285

Pro Leu Thr Val Pro Glu His Arg Ala Ala Arg Asp Val Thr Pro
        290                 295                 300

Arg Tyr Ile Met Thr Thr Ile Leu Ser Ala Asn Ala Val Gly Leu Leu
305                 310                 315                 320

Phe Ala Arg Ser Leu His Tyr Gln Phe Tyr Ala Tyr Val Ala Trp Ser
                325                 330                 335

Thr Pro Phe Leu Leu Trp Arg Ala Gly Leu His Pro Val Leu Val Tyr
                340                 345                 350

Leu Leu Trp Ala Val His Glu Trp Ala Trp Asn Val Phe Pro Ser Thr
                355                 360                 365

Pro Ala Ser Ser Ala
            370

<210> SEQ ID NO 40
<211> LENGTH: 374
<212> TYPE: PRT
<213> ORGANISM: Pichia pastoris
<220> FEATURE:
<221> NAME/KEY: MOD_RES
<222> LOCATION: (160)...(174)
<223> OTHER INFORMATION: Xaa is a variable amino acid
<220> FEATURE:
<221> NAME/KEY: MOD_RES
<222> LOCATION: (186)...(197)
<223> OTHER INFORMATION: Xaa is a variable amino acid

<400> SEQUENCE: 40

Ser Tyr Thr Asp Ile Asp Phe Ser Ser Tyr Met Gln Gln Ile Phe Lys
1               5                   10                  15

Ile Arg Gln Gly Glu Leu Asp Tyr Ser Asn Ile Phe Gly Asp Thr Gly
            20                  25                  30

Pro Leu Val Tyr Pro Ala Gly His Val His Ala Tyr Ser Val Leu Ser
            35                  40                  45

Trp Tyr Ser Asp Gly Gly Glu Asp Val Ser Phe Val Gln Gln Ala Phe
    50                  55                  60

Gly Trp Leu Tyr Leu Gly Cys Leu Leu Leu Ser Ile Ser Ser Tyr Phe
65                  70                  75                  80

Phe Ser Gly Leu Gly Lys Ile Pro Pro Val Tyr Phe Val Leu Leu Val
                85                  90                  95

Ala Ser Lys Arg Leu His Ser Ile Phe Val Leu Arg Leu Phe Asn Asp
            100                 105                 110

Cys Leu Thr Thr Phe Leu Met Leu Ala Thr Ile Ile Leu Gln Gln
            115                 120                 125

Ala Ser Ser Trp Arg Lys Asp Gly Thr Thr Ile Pro Leu Ser Val Pro
    130                 135                 140

Asp Ala Ala Asp Thr Tyr Ser Leu Ala Ile Ser Val Lys Met Asn Xaa
145                 150                 155                 160

Xaa Xaa Xaa Xaa Xaa Xaa Xaa Xaa Xaa Xaa Xaa Xaa Xaa Cys Asp
            165                 170                 175

Glu Asn Leu Ile Lys Ala Leu Ala Pro Xaa Xaa Xaa Xaa Xaa Xaa
            180                 185                 190

Xaa Xaa Xaa Xaa Xaa Tyr Ser Phe Ile Leu Pro Leu His Tyr Asp Asp
            195                 200                 205

Gln Ala Asn Glu Ile Arg Ser Ala Tyr Phe Arg Gln Ala Phe Asp Phe
    210                 215                 220
```

```
Ser Arg Gln Phe Leu Tyr Lys Trp Thr Val Asn Trp Arg Phe Leu Ser
225                 230                 235                 240

Gln Glu Thr Phe Asn Asn Val His Phe Gln Leu Leu Phe Ala Leu
            245                 250                 255

His Ile Ile Thr Leu Val Leu Phe Ile Leu Lys Phe Leu Ser Pro Lys
            260                 265                 270

Asn Ile Gly Lys Pro Leu Gly Arg Phe Val Leu Asp Ile Phe Lys Phe
            275                 280                 285

Trp Lys Pro Thr Leu Ser Pro Thr Asn Ile Ile Asn Asp Pro Glu Arg
            290                 295                 300

Ser Pro Asp Phe Val Tyr Thr Val Met Ala Thr Thr Asn Leu Ile Gly
305                 310                 315                 320

Val Leu Phe Ala Arg Ser Leu His Tyr Gln Phe Leu Ser Trp Tyr Ala
                325                 330                 335

Phe Ser Leu Pro Tyr Leu Leu Tyr Lys Ala Arg Leu Asn Phe Ile Ala
                340                 345                 350

Ser Ile Ile Val Tyr Ala Ala His Glu Tyr Cys Trp Leu Val Phe Pro
                355                 360                 365

Ala Thr Glu Gln Ser Ser
    370

<210> SEQ ID NO 41
<211> LENGTH: 355
<212> TYPE: PRT
<213> ORGANISM: Schizosaccharomyces pombe

<400> SEQUENCE: 41

Leu Leu Leu Leu Glu Ile Pro Phe Val Phe Ala Ile Ile Ser Lys Val
1               5                   10                  15

Pro Tyr Thr Glu Ile Asp Trp Ile Ala Tyr Met Glu Gln Val Asn Ser
            20                  25                  30

Phe Leu Leu Gly Glu Arg Asp Tyr Lys Ser Leu Val Gly Cys Thr Gly
        35                  40                  45

Pro Leu Val Tyr Pro Gly Gly His Val Phe Leu Tyr Thr Leu Leu Tyr
    50                  55                  60

Tyr Leu Thr Asp Gly Gly Thr Asn Ile Val Arg Ala Gln Tyr Ile Phe
65                  70                  75                  80

Ala Phe Val Tyr Trp Ile Thr Thr Ala Ile Val Gly Tyr Leu Phe Lys
                85                  90                  95

Ile Val Arg Ala Pro Phe Tyr Ile Tyr Val Leu Leu Ile Leu Ser Lys
            100                 105                 110

Arg Leu His Ser Ile Phe Ile Leu Arg Leu Phe Asn Asp Gly Phe Asn
        115                 120                 125

Ser Leu Phe Ser Ser Leu Phe Ile Leu Ser Ser Cys Lys Lys Lys Trp
    130                 135                 140

Val Arg Ala Ser Ile Leu Leu Ser Val Ala Cys Ser Val Lys Met Ser
145                 150                 155                 160

Ser Leu Leu Tyr Val Pro Ala Tyr Leu Val Leu Leu Gln Ile Leu
                165                 170                 175

Gly Pro Lys Lys Thr Trp Met His Ile Phe Val Ile Ile Ile Val Gln
            180                 185                 190

Ile Leu Phe Ser Ile Pro Phe Leu Ala Tyr Phe Ser Tyr Trp Thr
        195                 200                 205

Gln Ala Phe Asp Phe Gly Arg Ala Phe Asp Tyr Lys Trp Thr Val Asn
    210                 215                 220
```

```
Trp Arg Phe Ile Pro Arg Ser Ile Phe Glu Ser Thr Ser Phe Ser Thr
225                 230                 235                 240

Ser Ile Leu Phe Leu His Val Ala Leu Leu Val Ala Phe Thr Cys Lys
            245                 250                 255

His Trp Asn Lys Leu Ser Arg Ala Thr Pro Phe Ala Met Val Asn Ser
        260                 265                 270

Met Leu Thr Leu Lys Pro Leu Pro Lys Leu Gln Leu Ala Thr Pro Asn
    275                 280                 285

Phe Ile Phe Thr Ala Leu Ala Thr Ser Asn Leu Ile Gly Ile Leu Cys
290                 295                 300

Ala Arg Ser Leu His Tyr Gln Phe Tyr Ala Trp Phe Ala Trp Tyr Ser
305                 310                 315                 320

Pro Tyr Leu Cys Tyr Gln Ala Ser Phe Pro Ala Pro Ile Val Ile Gly
                325                 330                 335

Leu Trp Met Leu Gln Glu Tyr Ala Trp Asn Val Phe Pro Ser Thr Lys
                340                 345                 350

Leu Ser Ser
        355

<210> SEQ ID NO 42
<211> LENGTH: 390
<212> TYPE: PRT
<213> ORGANISM: Pichia pastoris
<220> FEATURE:
<221> NAME/KEY: MOD_RES
<222> LOCATION: (176)...(190)
<223> OTHER INFORMATION: Xaa is a variable amino acid
<220> FEATURE:
<221> NAME/KEY: MOD_RES
<222> LOCATION: (202)...(213)
<223> OTHER INFORMATION: Xaa is a variable amino acid

<400> SEQUENCE: 42

Leu Trp Leu Ala Asp Ser Ile Val Ile Lys Val Ile Ile Gly Thr Val
1               5                   10                  15

Ser Tyr Thr Asp Ile Asp Phe Ser Ser Tyr Met Gln Gln Ile Phe Lys
            20                  25                  30

Ile Arg Gln Gly Glu Leu Asp Tyr Ser Asn Ile Phe Gly Asp Thr Gly
        35                  40                  45

Pro Leu Val Tyr Pro Ala Gly His Val His Ala Tyr Ser Val Leu Ser
    50                  55                  60

Trp Tyr Ser Asp Gly Gly Glu Asp Val Ser Phe Val Gln Gln Ala Phe
65                  70                  75                  80

Gly Trp Leu Tyr Leu Gly Cys Leu Leu Ser Ile Ser Ser Tyr Phe
                85                  90                  95

Phe Ser Gly Leu Gly Lys Ile Pro Pro Val Tyr Phe Val Leu Leu Val
                100                 105                 110

Ala Ser Lys Arg Leu His Ser Ile Phe Val Leu Arg Leu Phe Asn Asp
            115                 120                 125

Cys Leu Thr Thr Phe Leu Met Leu Ala Thr Ile Ile Ile Leu Gln Gln
130                 135                 140

Ala Ser Ser Trp Arg Lys Asp Gly Thr Thr Ile Pro Leu Ser Val Pro
145                 150                 155                 160

Asp Ala Ala Asp Thr Tyr Ser Leu Ala Ile Ser Val Lys Met Asn Xaa
                165                 170                 175

Xaa Xaa Xaa Xaa Xaa Xaa Xaa Xaa Xaa Xaa Xaa Xaa Xaa Xaa Cys Asp
                180                 185                 190
```

```
Glu Asn Leu Ile Lys Ala Leu Ala Pro Xaa Xaa Xaa Xaa Xaa Xaa
            195                 200                 205

Xaa Xaa Xaa Xaa Xaa Tyr Ser Phe Ile Leu Pro Leu His Tyr Asp Asp
210                     215                 220

Gln Ala Asn Glu Ile Arg Ser Ala Tyr Phe Arg Gln Ala Phe Asp Phe
225                 230                 235                 240

Ser Arg Gln Phe Leu Tyr Lys Trp Thr Val Asn Trp Arg Phe Leu Ser
            245                 250                 255

Gln Glu Thr Phe Asn Asn Val His Phe His Gln Leu Leu Phe Ala Leu
            260                 265                 270

His Ile Ile Thr Leu Val Leu Phe Ile Leu Lys Phe Leu Ser Pro Lys
            275                 280                 285

Asn Ile Gly Lys Pro Leu Gly Arg Phe Val Leu Asp Ile Phe Lys Phe
290                 295                 300

Trp Lys Pro Thr Leu Ser Pro Thr Asn Ile Ile Asn Asp Pro Glu Arg
305                 310                 315                 320

Ser Pro Asp Phe Val Tyr Thr Val Met Ala Thr Thr Asn Leu Ile Gly
            325                 330                 335

Val Leu Phe Ala Arg Ser Leu His Tyr Gln Phe Leu Ser Trp Tyr Ala
            340                 345                 350

Phe Ser Leu Pro Tyr Leu Leu Tyr Lys Ala Arg Leu Asn Phe Ile Ala
            355                 360                 365

Ser Ile Ile Val Tyr Ala Ala His Glu Tyr Cys Trp Leu Val Phe Pro
370                 375                 380

Ala Thr Glu Gln Ser Ser
385                 390

<210> SEQ ID NO 43
<211> LENGTH: 363
<212> TYPE: PRT
<213> ORGANISM: Arabidopsis thaliana

<400> SEQUENCE: 43

Leu Ile Leu Ala Asp Ala Ile Leu Val Ala Leu Ile Ile Ala Tyr Val
 1               5                  10                  15

Pro Tyr Thr Lys Ile Asp Trp Asp Ala Tyr Met Ser Gln Val Ser Gly
            20                  25                  30

Phe Leu Gly Gly Glu Arg Asp Tyr Gly Asn Leu Lys Gly Asp Thr Gly
            35                  40                  45

Pro Leu Val Tyr Pro Ala Gly Phe Leu Tyr Val Tyr Ser Ala Val Gln
 50                  55                  60

Asn Leu Thr Gly Gly Glu Val Tyr Pro Ala Gln Ile Leu Phe Gly Val
 65                  70                  75                  80

Leu Tyr Ile Val Asn Leu Gly Ile Val Leu Ile Ile Tyr Val Lys Thr
                85                  90                  95

Asp Val Val Pro Trp Trp Ala Leu Ser Leu Leu Cys Leu Ser Lys Arg
            100                 105                 110

Ile His Ser Ile Phe Val Leu Arg Leu Phe Asn Asp Cys Phe Ala Met
        115                 120                 125

Thr Leu Leu His Ala Ser Met Ala Leu Phe Leu Tyr Arg Lys Trp His
        130                 135                 140

Leu Gly Met Leu Val Phe Ser Gly Ala Val Ser Val Lys Met Asn Val
145                 150                 155                 160

Leu Leu Tyr Ala Pro Thr Leu Leu Leu Leu Leu Leu Lys Ala Met Asn
```

```
            165                 170                 175
Ile Ile Gly Val Val Ser Ala Leu Ala Gly Ala Leu Ala Gln Ile
            180                 185                 190

Leu Val Gly Leu Pro Phe Leu Ile Thr Tyr Pro Val Ser Tyr Ile Ala
            195                 200                 205

Asn Ala Phe Asp Leu Gly Arg Val Phe Ile His Phe Trp Ser Val Asn
            210                 215                 220

Phe Lys Phe Val Pro Glu Arg Val Phe Ser Lys Glu Phe Ala Val
225                 230                 235                 240

Cys Leu Leu Ile Ala His Leu Phe Leu Leu Val Ala Phe Ala Asn Tyr
                    245                 250                 255

Lys Trp Cys Lys His Glu Gly Gly Ile Ile Gly Phe Met Arg Ser Arg
                    260                 265                 270

His Phe Phe Leu Thr Leu Pro Ser Ser Leu Ser Phe Ser Asp Val Ser
                    275                 280                 285

Ala Ser Arg Ile Ile Thr Lys Glu His Val Val Thr Ala Met Phe Val
            290                 295                 300

Gly Asn Phe Ile Gly Ile Val Phe Ala Arg Ser Leu His Tyr Gln Phe
305                 310                 315                 320

Tyr Ser Trp Tyr Phe Tyr Ser Leu Pro Tyr Leu Leu Trp Arg Thr Pro
                    325                 330                 335

Phe Pro Thr Trp Leu Arg Leu Ile Met Phe Leu Gly Ile Glu Leu Cys
                    340                 345                 350

Trp Asn Val Tyr Pro Ser Thr Pro Ser Ser Ser
                    355                 360

<210> SEQ ID NO 44
<211> LENGTH: 428
<212> TYPE: DNA
<213> ORGANISM: Kluyveromyces lactis

<400> SEQUENCE: 44
tttgtttaca agctgatacc aacgaacatg aatacaccgg caggtttact gaagattggc    60
aaagctaacc ttttacatcc ttttaccgat gctgtattca gtgcgatgag agtaaacgca   120
gaacaaattg catacatttt acttgttacc aattacattg gagtactatt tgctcgatca   180
ttacactacc aattcctatc ttggtaccat tggacgttac cagtactatt gaattgggcc   240
aatgttccgt atccgctatg tgtgctatgg tacctaacac atgagtggtg ctggaacagc   300
tatccgccaa acgctactgc atccacactg ctacacgcgt gtaacacata ctgttattgg   360
ctgtattctt aagaggaccc gcaaactcga aaagtggtga taacgaaaca acacacgaga   420
aagctgag                                                           428

<210> SEQ ID NO 45
<211> LENGTH: 141
<212> TYPE: PRT
<213> ORGANISM: Kluyveromyces lactis

<400> SEQUENCE: 45

Phe Val Tyr Lys Leu Ile Pro Thr Asn Met Asn Thr Pro Ala Gly Leu
1               5                   10                  15

Leu Lys Ile Gly Lys Ala Asn Leu Leu His Pro Phe Thr Asp Ala Val
            20                  25                  30

Phe Ser Ala Met Arg Val Asn Ala Glu Gln Ile Ala Tyr Ile Leu Leu
        35                  40                  45
```

Val Thr Asn Tyr Ile Gly Val Leu Phe Ala Arg Ser Leu His Tyr Gln
 50                  55                  60

Phe Leu Ser Trp Tyr His Trp Thr Leu Pro Val Leu Leu Asn Trp Ala
 65                  70                  75                  80

Asn Val Pro Tyr Pro Leu Cys Val Leu Trp Tyr Leu Thr His Glu Trp
                 85                  90                  95

Cys Trp Asn Ser Tyr Pro Pro Asn Ala Thr Ala Ser Thr Leu Leu His
                100                 105                 110

Ala Cys Asn Thr Tyr Cys Tyr Trp Leu Tyr Ser Glu Asp Pro Gln Thr
                115                 120                 125

Arg Lys Val Val Ile Thr Lys Gln His Thr Arg Lys Leu
130                 135                 140

<210> SEQ ID NO 46
<211> LENGTH: 118
<212> TYPE: PRT
<213> ORGANISM: Kluyveromyces lactis

<400> SEQUENCE: 46

Ala Asn Leu Leu His Pro Phe Thr Asp Ala Val Phe Ser Ala Met Arg
 1               5                  10                  15

Val Asn Ala Glu Gln Ile Ala Tyr Ile Leu Val Thr Asn Tyr Ile
             20                  25                  30

Gly Val Leu Phe Ala Arg Ser Leu His Tyr Gln Phe Leu Ser Trp Tyr
             35                  40                  45

His Trp Thr Leu Pro Val Leu Leu Asn Trp Ala Asn Val Pro Tyr Pro
 50                  55                  60

Leu Cys Val Leu Trp Tyr Leu Thr His Glu Trp Cys Trp Asn Ser Tyr
 65                  70                  75                  80

Pro Pro Asn Ala Thr Ala Ser Thr Leu Leu His Ala Cys Asn Thr Tyr
                 85                  90                  95

Cys Tyr Trp Leu Tyr Ser Glu Asp Pro Gln Thr Arg Lys Val Val Ile
                100                 105                 110

Thr Lys Gln His Thr Arg
            115

<210> SEQ ID NO 47
<211> LENGTH: 117
<212> TYPE: PRT
<213> ORGANISM: Saccharomyces cerevisiae

<400> SEQUENCE: 47

Ser Ser Leu Cys His Pro Leu Arg Lys Asn Ala Val Leu Asn Ala Asn
 1               5                  10                  15

Pro Ala Lys Thr Ile Pro Phe Val Leu Ile Ala Ser Asn Phe Ile Gly
             20                  25                  30

Val Leu Phe Ser Arg Ser Leu His Tyr Gln Phe Leu Ser Trp Tyr His
             35                  40                  45

Trp Thr Leu Pro Ile Leu Ile Phe Trp Ser Gly Met Pro Phe Phe Val
 50                  55                  60

Gly Pro Ile Trp Tyr Val Leu His Glu Trp Cys Trp Asn Ser Tyr Pro
 65                  70                  75                  80

Pro Asn Ser Gln Ala Ser Thr Leu Leu Ala Leu Asn Thr Val Leu
                 85                  90                  95

Leu Leu Leu Leu Ala Leu Thr Gly Leu Ser Gly Ser Val Ala Leu Ala
                100                 105                 110

Lys Ser His Leu Arg
        115

<210> SEQ ID NO 48
<211> LENGTH: 113
<212> TYPE: PRT
<213> ORGANISM: Kluyveromyces lactis

<400> SEQUENCE: 48

Phe Thr Asp Ala Val Phe Ser Ala Met Arg Val Asn Ala Glu Gln Ile
1               5                   10                  15

Ala Tyr Ile Leu Leu Val Thr Asn Tyr Ile Gly Val Leu Phe Ala Arg
            20                  25                  30

Ser Leu His Tyr Gln Phe Leu Ser Trp Tyr His Trp Thr Leu Pro Val
        35                  40                  45

Leu Leu Asn Trp Ala Asn Val Pro Tyr Pro Leu Cys Val Leu Trp Tyr
    50                  55                  60

Leu Thr His Glu Trp Cys Trp Asn Ser Tyr Pro Pro Asn Ala Thr Ala
65                  70                  75                  80

Ser Thr Leu Leu His Ala Cys Asn Thr Tyr Cys Tyr Trp Leu Tyr Ser
                85                  90                  95

Glu Asp Pro Gln Thr Arg Lys Val Val Ile Thr Lys Gln His Thr Arg
            100                 105                 110

Lys

<210> SEQ ID NO 49
<211> LENGTH: 106
<212> TYPE: PRT
<213> ORGANISM: Arabidopsis thaliana

<400> SEQUENCE: 49

Phe Ser Asp Val Ser Ala Ser Arg Ile Ile Thr Lys Glu His Val Val
1               5                   10                  15

Thr Ala Met Phe Val Gly Asn Phe Ile Gly Ile Val Phe Ala Arg Ser
            20                  25                  30

Leu His Tyr Gln Phe Tyr Ser Trp Tyr Phe Tyr Ser Leu Pro Tyr Leu
        35                  40                  45

Leu Trp Arg Thr Pro Phe Pro Thr Trp Leu Arg Leu Ile Met Phe Leu
    50                  55                  60

Gly Ile Glu Leu Cys Trp Asn Val Tyr Pro Ser Thr Pro Ser Ser Ser
65                  70                  75                  80

Gly Leu Leu Leu Cys Leu His Leu Ile Ile Leu Val Gly Leu Trp Leu
                85                  90                  95

Ala Pro Ser Val Asp Pro Tyr Gln Leu Lys
            100                 105

<210> SEQ ID NO 50
<211> LENGTH: 1668
<212> TYPE: DNA
<213> ORGANISM: Saccharomyces cerevisiae

<400> SEQUENCE: 50
atgaattgca aggcggtaac cattagttta ttactgttgt tatttttaac aagagtatat     60
attcagccga cattctcgtt aatttcagat tgcgatgaaa cttttaatta ttgggaacca    120 ttaaattat tggtacgtgg atttggtaaa caaacctggg aatattcacc cgagtattct    180
attagatcat gggctttctt attacctttt tactgtattc tttatccagt aaacaaattt    240

```
actgacctag aaagtcattg gaactttttc atcacaagag catgcttagg cttttttagt    300
tttatcatgg aatttaaact acatcgtgaa attgcaggca gcttggcatt gcaaatcgca    360
aatatttgga ttattttcca attgtttaat ccgggctggt ccatgcatc tgtggaatta    420
ttgccttctg ccgttgccat gttgttgtat gtaggtgcca ccagacactc tctacgctat    480
ctgtccactg ggtctacttc taactttacg aaaagtttag cgtacaattt cctggctagt    540
atactaggct ggccatttgt tttaatttta agcttgccat tatgtttaca ttaccttttc    600
aaccatagaa ttatttctac catcagaacc gcattcgact gctgtttgat atttcattg    660
actgcatttg ctgtgattgt cactgacagt atattttacg ggaagcttgc tcctgtatca    720
tggaacatct tattttacaa tgtcattaat gcaagtgagg aatctggccc aaatattttc    780
ggggttgagc catggtacta ctatccacta aatttgttac tgaatttccc actgcctgtg    840
ctagttttag ctattttggg aattttccat ttgagattat ggccattatg ggcatcatta    900
ttcacatgga ttgccgtttt cactcaacaa cctcacaaag aggaaagatt tctctatcca    960
atttacgggt aataaacttt gagtgcaagt atcgcctttt acaaagtgtt gaatctattc   1020
aatagaaagc cgattcttaa aaaaggtata aagttgtcag ttttattaat tgttgcaggc   1080
caggcaatgt cacggatagt ggctttggtg aacaattaca cagctcctat agccgtctac   1140
gagcaatttt cttcactaaa tcaaggtggt gtgaaggcac cggtagtgaa tgtatgtacg   1200
ggacgtgaat ggtatcactt cccaagttct ttcctgctgc cagataatca taggctaaaa   1260
tttgttaaat ctggatttga tggtcttctt ccaggtgatt ttccagagag tggttctatt   1320
ttcaaaaaga ttagaacttt acctaaggga atgaataaca agaatatata tgataccggt   1380
aaagagtggc cgatcactag atgtgattat tttattgaca tcgtcgcccc aataaattta   1440
acaaaagacg ttttcaaccc tctacatctg atggataact ggataagct ggcatgtgct   1500
gcattcatcg acggtgaaaa ttctaagatt ttgggtagag cattttacgt accggagcca   1560
atcaaccgaa tcatgcaaat agttttacca aaacaatgga atcaagtgta cggtgttcgt   1620
tacattgatt actgtttgtt tgaaaaacca actgagacta ctaattga               1668
```

<210> SEQ ID NO 51
<211> LENGTH: 555
<212> TYPE: PRT
<213> ORGANISM: Saccharomyces cerevisiae

<400> SEQUENCE: 51

```
Met Asn Cys Lys Ala Val Thr Ile Ser Leu Leu Leu Leu Phe Leu
 1               5                  10                  15

Thr Arg Val Tyr Ile Gln Pro Thr Phe Ser Leu Ile Ser Asp Cys Asp
            20                  25                  30

Glu Thr Phe Asn Tyr Trp Glu Pro Leu Asn Leu Leu Val Arg Gly Phe
        35                  40                  45

Gly Lys Gln Thr Trp Glu Tyr Ser Pro Glu Tyr Ser Ile Arg Ser Trp
    50                  55                  60

Ala Phe Leu Leu Pro Phe Tyr Cys Ile Leu Tyr Pro Val Asn Lys Phe
65                  70                  75                  80

Thr Asp Leu Glu Ser His Trp Asn Phe Phe Ile Thr Arg Ala Cys Leu
                85                  90                  95

Gly Phe Phe Ser Phe Ile Met Glu Phe Lys Leu His Arg Glu Ile Ala
            100                 105                 110

Gly Ser Leu Ala Leu Gln Ile Ala Asn Ile Trp Ile Ile Phe Gln Leu
        115                 120                 125
```

-continued

```
Phe Asn Pro Gly Trp Phe His Ala Ser Val Glu Leu Leu Pro Ser Ala
    130                 135                 140

Val Ala Met Leu Leu Tyr Val Gly Ala Thr Arg His Ser Leu Arg Tyr
145                 150                 155                 160

Leu Ser Thr Gly Ser Thr Ser Asn Phe Thr Lys Ser Leu Ala Tyr Asn
                165                 170                 175

Phe Leu Ala Ser Ile Leu Gly Trp Pro Phe Val Leu Ile Leu Ser Leu
                180                 185                 190

Pro Leu Cys Leu His Tyr Leu Phe Asn His Arg Ile Ile Ser Thr Ile
                195                 200                 205

Arg Thr Ala Phe Asp Cys Cys Leu Ile Phe Ser Leu Thr Ala Phe Ala
    210                 215                 220

Val Ile Val Thr Asp Ser Ile Phe Tyr Gly Lys Leu Ala Pro Val Ser
225                 230                 235                 240

Trp Asn Ile Leu Phe Tyr Asn Val Ile Asn Ala Ser Glu Glu Ser Gly
                245                 250                 255

Pro Asn Ile Phe Gly Val Glu Pro Trp Tyr Tyr Pro Leu Asn Leu
                260                 265                 270

Leu Leu Asn Phe Pro Leu Pro Val Leu Val Leu Ala Ile Leu Gly Ile
                275                 280                 285

Phe His Leu Arg Leu Trp Pro Leu Trp Ala Ser Leu Phe Thr Trp Ile
    290                 295                 300

Ala Val Phe Thr Gln Gln Pro His Lys Glu Glu Arg Phe Leu Tyr Pro
305                 310                 315                 320

Ile Tyr Gly Leu Ile Thr Leu Ser Ala Ser Ile Ala Phe Tyr Lys Val
                325                 330                 335

Leu Asn Leu Phe Asn Arg Lys Pro Ile Leu Lys Lys Gly Ile Lys Leu
                340                 345                 350

Ser Val Leu Leu Ile Val Ala Gly Gln Ala Met Ser Arg Ile Val Ala
    355                 360                 365

Leu Val Asn Asn Tyr Thr Ala Pro Ile Ala Val Tyr Glu Gln Phe Ser
370                 375                 380

Ser Leu Asn Gln Gly Gly Val Lys Ala Pro Val Asn Val Cys Thr
385                 390                 395                 400

Gly Arg Glu Trp Tyr His Phe Pro Ser Ser Phe Leu Leu Pro Asp Asn
                405                 410                 415

His Arg Leu Lys Phe Val Lys Ser Gly Phe Asp Gly Leu Leu Pro Gly
                420                 425                 430

Asp Phe Pro Glu Ser Gly Ser Ile Phe Lys Lys Ile Arg Thr Leu Pro
    435                 440                 445

Lys Gly Met Asn Asn Lys Asn Ile Tyr Asp Thr Gly Lys Glu Trp Pro
450                 455                 460

Ile Thr Arg Cys Asp Tyr Phe Ile Asp Ile Val Ala Pro Ile Asn Leu
465                 470                 475                 480

Thr Lys Asp Val Phe Asn Pro Leu His Leu Met Asp Asn Trp Asn Lys
                485                 490                 495

Leu Ala Cys Ala Ala Phe Ile Asp Gly Glu Asn Ser Lys Ile Leu Gly
                500                 505                 510

Arg Ala Phe Tyr Val Pro Glu Pro Ile Asn Arg Ile Met Gln Ile Val
    515                 520                 525

Leu Pro Lys Gln Trp Asn Gln Val Tyr Gly Val Arg Tyr Ile Asp Tyr
530                 535                 540
```

Cys Leu Phe Glu Lys Pro Thr Glu Thr Thr Asn
545                 550                 555

<210> SEQ ID NO 52
<211> LENGTH: 600
<212> TYPE: DNA
<213> ORGANISM: Pichia pastoris

<400> SEQUENCE: 52
tggccttcct gtctgctcga tacttccttt tacagtaacc aacatacatg ttctccaaca    60
tgctcttgta tgtattggcc tattctatct tgagacttga tatcaacctt ctatggtatt   120
atttcagact gtgatgaagt gttcaactac tgggagccac tcaacttcat cttagaggg    180 tttggaaaac agacttggga gtattctcca gagtatgcca tccgatcttg gtcctatcta   240
gtgccacttt ggatagcagg ctatccacca ttgttcctgg atatcccttc ttactacttt   300
ttctactttt tcagactact gctggttatt ttttcattgg ttgcagaagt caagttgtac   360
catagtttga agaaaaatgt cagcagtaag atcagtttct ggtaccttct atttacaacc   420
gttgctccag gaatgtctca tagcacgata gccttattac catcctcttt tgctatggtt   480
tgtcacactt ttgccattag atacgtcatt gattacctac aattaccaac attaatgcgc   540
acaatcagag agactgctgc catctcacca gctcacaaac aacaactagc caactctctc   600

<210> SEQ ID NO 53
<211> LENGTH: 199
<212> TYPE: PRT
<213> ORGANISM: Pichia pastoris

<400> SEQUENCE: 53

Trp Pro Ser Cys Leu Leu Asp Thr Ser Phe Tyr Ser Asn Gln His Thr
1               5                   10                  15

Cys Ser Pro Thr Cys Ser Cys Met Tyr Trp Pro Ile Leu Ser Asp Leu
            20                  25                  30

Ile Ser Thr Phe Tyr Gly Ile Ile Ser Asp Cys Asp Glu Val Phe Asn
        35                  40                  45

Tyr Trp Glu Pro Leu Asn Phe Met Leu Arg Gly Phe Gly Lys Gln Thr
50                  55                  60

Trp Glu Tyr Ser Pro Glu Tyr Ala Ile Arg Ser Trp Ser Tyr Leu Val
65                  70                  75                  80

Pro Leu Trp Ile Ala Gly Tyr Pro Pro Leu Phe Leu Asp Ile Pro Ser
                85                  90                  95

Tyr Tyr Phe Phe Tyr Phe Phe Arg Leu Leu Leu Val Ile Phe Ser Leu
            100                 105                 110

Val Ala Glu Val Lys Leu Tyr His Ser Leu Lys Lys Asn Val Ser Ser
        115                 120                 125

Lys Ile Ser Phe Trp Tyr Leu Leu Phe Thr Thr Val Ala Pro Gly Met
130                 135                 140

Ser His Ser Thr Ile Ala Leu Leu Pro Ser Ser Phe Ala Met Val Cys
145                 150                 155                 160

His Thr Phe Ala Ile Arg Tyr Val Ile Asp Tyr Leu Gln Leu Pro Thr
                165                 170                 175

Leu Met Arg Thr Ile Arg Glu Thr Ala Ala Ile Ser Pro Ala His Lys
            180                 185                 190

Gln Gln Leu Ala Asn Ser Leu
        195

-continued

```
<210> SEQ ID NO 54
<211> LENGTH: 140
<212> TYPE: PRT
<213> ORGANISM: Pichia pastoris
<220> FEATURE:
<221> NAME/KEY: MOD_RES
<222> LOCATION: (65)...(71)
<223> OTHER INFORMATION: Xaa is a variable amino acid

<400> SEQUENCE: 54

Ile Ser Thr Phe Tyr Gly Ile Ile Ser Asp Cys Asp Glu Val Phe Asn
  1               5                  10                  15

Tyr Trp Glu Pro Leu Asn Phe Met Leu Arg Gly Phe Gly Lys Gln Thr
             20                  25                  30

Trp Glu Tyr Ser Pro Glu Tyr Ala Ile Arg Ser Trp Ser Tyr Leu Val
         35                  40                  45

Pro Leu Trp Ile Ala Gly Tyr Pro Pro Leu Phe Leu Asp Ile Pro Ser
 50                  55                  60

Xaa Xaa Xaa Xaa Xaa Xaa Xaa Arg Leu Leu Leu Val Ile Phe Ser Leu
 65                  70                  75                  80

Val Ala Glu Val Lys Leu Tyr His Ser Leu Lys Lys Asn Val Ser Ser
                 85                  90                  95

Lys Ile Ser Phe Trp Tyr Leu Leu Phe Thr Thr Val Ala Pro Gly Met
            100                 105                 110

Ser His Ser Thr Ile Ala Leu Leu Pro Ser Ser Phe Ala Met Val Cys
            115                 120                 125

His Thr Phe Ala Ile Arg Tyr Val Ile Asp Tyr Leu
            130                 135                 140

<210> SEQ ID NO 55
<211> LENGTH: 141
<212> TYPE: PRT
<213> ORGANISM: Saccharomyces cerevisiae

<400> SEQUENCE: 55

Ile Gln Pro Thr Phe Ser Leu Ile Ser Asp Cys Asp Glu Thr Phe Asn
  1               5                  10                  15

Tyr Trp Glu Pro Leu Asn Leu Leu Val Arg Gly Phe Gly Lys Gln Thr
             20                  25                  30

Trp Glu Tyr Ser Pro Glu Tyr Ser Ile Arg Ser Trp Ala Phe Leu Leu
         35                  40                  45

Pro Phe Tyr Cys Ile Leu Tyr Pro Val Asn Lys Phe Thr Asp Leu Glu
 50                  55                  60

Ser His Trp Asn Phe Phe Ile Thr Arg Ala Cys Leu Gly Phe Phe Ser
 65                  70                  75                  80

Phe Ile Met Glu Phe Lys Leu His Arg Glu Ile Ala Gly Ser Leu Ala
                 85                  90                  95

Leu Gln Ile Ala Asn Ile Trp Ile Ile Phe Gln Leu Phe Asn Pro Gly
            100                 105                 110

Trp Phe His Ala Ser Val Glu Leu Pro Ser Ala Val Ala Met Leu
            115                 120                 125

Leu Tyr Val Gly Ala Thr Arg His Ser Leu Arg Tyr Leu
            130                 135                 140

<210> SEQ ID NO 56
<211> LENGTH: 127
<212> TYPE: PRT
<213> ORGANISM: Pichia pastoris
<220> FEATURE:
```

```
<221> NAME/KEY: MOD_RES
<222> LOCATION: (66)...(72)
<223> OTHER INFORMATION: Xaa is a variable amino acid

<400> SEQUENCE: 56

Leu Ile Ser Thr Phe Tyr Gly Ile Ile Ser Asp Cys Asp Glu Val Phe
1               5                   10                  15

Asn Tyr Trp Glu Pro Leu Asn Phe Met Leu Arg Gly Phe Gly Lys Gln
            20                  25                  30

Thr Trp Glu Tyr Ser Pro Glu Tyr Ala Ile Arg Ser Trp Ser Tyr Leu
        35                  40                  45

Val Pro Leu Trp Ile Ala Gly Tyr Pro Pro Leu Phe Leu Asp Ile Pro
50                  55                  60

Ser Xaa Xaa Xaa Xaa Xaa Xaa Arg Leu Leu Leu Val Ile Phe Ser
65                  70                  75                  80

Leu Val Ala Glu Val Lys Leu Tyr His Ser Leu Lys Lys Asn Val Ser
                85                  90                  95

Ser Lys Ile Ser Phe Trp Tyr Leu Leu Phe Thr Thr Val Ala Pro Gly
            100                 105                 110

Met Ser His Ser Thr Ile Ala Leu Leu Pro Ser Ser Phe Ala Met
        115                 120                 125

<210> SEQ ID NO 57
<211> LENGTH: 127
<212> TYPE: PRT
<213> ORGANISM: Anopheles gambiae

<400> SEQUENCE: 57

Leu Gln Ser Ala Leu Tyr Ser Ile Ile Ser Asp Cys Asp Glu Thr Tyr
1               5                   10                  15

Asn Tyr Trp Glu Pro Leu His Tyr Leu Leu Lys Gly Lys Gly Phe Gln
            20                  25                  30

Thr Trp Glu Tyr Ser Pro Glu Phe Ala Leu Arg Ser Tyr Ser Tyr Leu
        35                  40                  45

Trp Leu His Gly Leu Pro Ala Lys Val Leu Gln Leu Met Thr Asp Asn
50                  55                  60

Gly Val Leu Ile Phe Tyr Phe Val Arg Cys Leu Leu Ala Val Thr Cys
65                  70                  75                  80

Ala Leu Leu Glu Tyr Arg Leu Tyr Arg Ile Leu Gly Arg Lys Cys Gly
                85                  90                  95

Gly Gly Val Ala Ser Leu Trp Leu Leu Phe Gln Leu Thr Ser Ala Gly
            100                 105                 110

Met Phe Ile Ser Ser Ala Ala Leu Leu Pro Ser Ser Phe Ser Met
        115                 120                 125

<210> SEQ ID NO 58
<211> LENGTH: 157
<212> TYPE: PRT
<213> ORGANISM: Pichia pastoris
<220> FEATURE:
<221> NAME/KEY: MOD_RES
<222> LOCATION: (66)...(72)
<223> OTHER INFORMATION: Xaa is a variable amino acid

<400> SEQUENCE: 58

Leu Ile Ser Thr Phe Tyr Gly Ile Ile Ser Asp Cys Asp Glu Val Phe
1               5                   10                  15

Asn Tyr Trp Glu Pro Leu Asn Phe Met Leu Arg Gly Phe Gly Lys Gln
            20                  25                  30
```

Thr Trp Glu Tyr Ser Pro Glu Tyr Ala Ile Arg Ser Trp Ser Tyr Leu
            35                  40                  45

Val Pro Leu Trp Ile Ala Gly Tyr Pro Pro Leu Phe Leu Asp Ile Pro
 50                  55                  60

Ser Xaa Xaa Xaa Xaa Xaa Xaa Arg Leu Leu Leu Val Ile Phe Ser
 65                  70                  75                  80

Leu Val Ala Glu Val Lys Leu Tyr His Ser Leu Lys Lys Asn Val Ser
                 85                  90                  95

Ser Lys Ile Ser Phe Trp Tyr Leu Leu Phe Thr Thr Val Ala Pro Gly
                100                 105                 110

Met Ser His Ser Thr Ile Ala Leu Leu Pro Ser Ser Phe Ala Met Val
            115                 120                 125

Cys His Thr Phe Ala Ile Arg Tyr Val Ile Asp Tyr Leu Gln Leu Pro
            130                 135                 140

Thr Leu Met Arg Thr Ile Arg Glu Thr Ala Ala Ile Ser
145                 150                 155

<210> SEQ ID NO 59
<211> LENGTH: 154
<212> TYPE: PRT
<213> ORGANISM: Schizosaccharomyces pombe

<400> SEQUENCE: 59

Leu Thr Ser Ala Ser Phe Arg Val Ile Asp Asp Cys Asp Glu Val Tyr
 1               5                  10                  15

Asn Tyr Trp Glu Pro Leu His Tyr Leu Leu Tyr Gly Tyr Gly Leu Gln
             20                  25                  30

Thr Trp Glu Tyr Ser Pro Glu Tyr Ala Ile Arg Ser Trp Phe Tyr Ile
            35                  40                  45

Ala Leu His Ala Val Pro Gly Phe Leu Ala Arg Gly Leu Gly Leu Ser
 50                  55                  60

Arg Leu His Val Phe Tyr Phe Ile Arg Gly Val Leu Ala Cys Phe Ser
 65                  70                  75                  80

Ala Phe Cys Glu Thr Asn Leu Ile Leu Ala Val Ala Arg Asn Phe Asn
                 85                  90                  95

Arg Ala Val Ala Leu His Leu Thr Ser Val Leu Phe Val Asn Ser Gly
                100                 105                 110

Met Trp Ser Ala Ser Thr Ser Phe Leu Pro Ser Ser Phe Ala Met Asn
            115                 120                 125

Met Val Thr Leu Ala Leu Ser Ala Gln Leu Ser Pro Pro Ser Thr Lys
            130                 135                 140

Arg Thr Val Lys Val Val Ser Phe Ile Thr
145                 150

<210> SEQ ID NO 60
<211> LENGTH: 141
<212> TYPE: PRT
<213> ORGANISM: Pichia pastoris
<220> FEATURE:
<221> NAME/KEY: MOD_RES
<222> LOCATION: (80)...(86)
<223> OTHER INFORMATION: Xaa is a variable amino acid

<400> SEQUENCE: 60

Ser Pro Thr Cys Ser Cys Met Tyr Trp Pro Ile Leu Ser Asp Leu Ile
 1               5                  10                  15

Ser Thr Phe Tyr Gly Ile Ile Ser Asp Cys Asp Glu Val Phe Asn Tyr

```
            20                  25                  30

Trp Glu Pro Leu Asn Phe Met Leu Arg Gly Phe Gly Lys Gln Thr Trp
                35                  40                  45

Glu Tyr Ser Pro Glu Tyr Ala Ile Arg Ser Trp Ser Tyr Leu Val Pro
         50                  55                  60

Leu Trp Ile Ala Gly Tyr Pro Pro Leu Phe Leu Asp Ile Pro Ser Xaa
 65                  70                  75                  80

Xaa Xaa Xaa Xaa Xaa Arg Leu Leu Val Ile Phe Ser Leu Val
                 85                  90                  95

Ala Glu Val Lys Leu Tyr His Ser Leu Lys Lys Asn Val Ser Ser Lys
                100                 105                 110

Ile Ser Phe Trp Tyr Leu Leu Phe Thr Thr Val Ala Pro Gly Met Ser
                115                 120                 125

His Ser Thr Ile Ala Leu Leu Pro Ser Ser Phe Ala Met
            130                 135                 140

<210> SEQ ID NO 61
<211> LENGTH: 143
<212> TYPE: PRT
<213> ORGANISM: Mus musculus

<400> SEQUENCE: 61

Ala Pro Glu Gly Ser Thr Ala Phe Lys Cys Leu Leu Ser Ala Arg Leu
 1               5                  10                  15

Cys Ala Ala Leu Leu Ser Asn Ile Ser Asp Cys Asp Glu Thr Phe Asn
                20                  25                  30

Tyr Trp Glu Pro Thr His Tyr Leu Ile Tyr Gly Lys Gly Phe Gln Thr
                35                  40                  45

Trp Glu Tyr Ser Pro Val Tyr Ala Ile Arg Ser Tyr Ala Tyr Leu Leu
         50                  55                  60

Leu His Ala Trp Pro Ala Ala Phe His Ala Arg Ile Leu Gln Thr Asn
 65                  70                  75                  80

Lys Ile Leu Val Phe Tyr Phe Leu Arg Cys Leu Leu Ala Phe Val Ser
                85                  90                  95

Cys Val Cys Glu Leu Tyr Phe Tyr Lys Ala Val Cys Lys Lys Phe Gly
                100                 105                 110

Leu His Val Ser Arg Met Met Leu Ala Phe Leu Val Leu Ser Thr Gly
                115                 120                 125

Met Phe Cys Ser Ser Ser Ala Phe Leu Pro Ser Ser Phe Cys Met
            130                 135                 140

<210> SEQ ID NO 62
<211> LENGTH: 141
<212> TYPE: PRT
<213> ORGANISM: Pichia pastoris
<220> FEATURE:
<221> NAME/KEY: MOD_RES
<222> LOCATION: (80)...(86)
<223> OTHER INFORMATION: Xaa is a variable amino acid

<400> SEQUENCE: 62

Ser Pro Thr Cys Ser Cys Met Tyr Trp Pro Ile Leu Ser Asp Leu Ile
 1               5                  10                  15

Ser Thr Phe Tyr Gly Ile Ile Ser Asp Cys Asp Glu Val Phe Asn Tyr
                20                  25                  30

Trp Glu Pro Leu Asn Phe Met Leu Arg Gly Phe Gly Lys Gln Thr Trp
                35                  40                  45
```

```
Glu Tyr Ser Pro Glu Tyr Ala Ile Arg Ser Trp Ser Tyr Leu Val Pro
 50                  55                  60

Leu Trp Ile Ala Gly Tyr Pro Pro Leu Phe Leu Asp Ile Pro Ser Xaa
 65                  70                  75                  80

Xaa Xaa Xaa Xaa Xaa Arg Leu Leu Leu Val Ile Phe Ser Leu Val
             85                  90                  95

Ala Glu Val Lys Leu Tyr His Ser Leu Lys Lys Asn Val Ser Ser Lys
            100                 105                 110

Ile Ser Phe Trp Tyr Leu Leu Phe Thr Thr Val Ala Pro Gly Met Ser
            115                 120                 125

His Ser Thr Ile Ala Leu Leu Pro Ser Ser Phe Ala Met
            130                 135                 140
```

<210> SEQ ID NO 63
<211> LENGTH: 143
<212> TYPE: PRT
<213> ORGANISM: Homo sapiens

<400> SEQUENCE: 63

```
Ala Pro Glu Gly Ser Thr Ala Phe Lys Cys Leu Leu Ser Ala Arg Leu
  1               5                  10                  15

Cys Ala Ala Leu Leu Ser Asn Ile Ser Asp Cys Asp Glu Thr Phe Asn
             20                  25                  30

Tyr Trp Glu Pro Thr His Tyr Leu Ile Tyr Gly Glu Gly Phe Gln Thr
         35                  40                  45

Trp Glu Tyr Ser Pro Ala Tyr Ala Ile Arg Ser Tyr Ala Tyr Leu Leu
 50                  55                  60

Leu His Ala Trp Pro Ala Ala Phe His Ala Arg Ile Leu Gln Thr Asn
 65                  70                  75                  80

Lys Ile Leu Val Phe Tyr Phe Leu Arg Cys Leu Ala Phe Val Ser
             85                  90                  95

Cys Ile Cys Glu Leu Tyr Phe Tyr Lys Ala Val Cys Lys Lys Phe Gly
            100                 105                 110

Leu His Val Ser Arg Met Met Leu Ala Phe Leu Val Leu Ser Thr Gly
            115                 120                 125

Met Phe Cys Ser Ser Ser Ala Phe Leu Pro Ser Ser Phe Cys Met
            130                 135                 140
```

<210> SEQ ID NO 64
<211> LENGTH: 1656
<212> TYPE: DNA
<213> ORGANISM: Saccharomyces cerevisiae

<400> SEQUENCE: 64

```
atgcgttggt ctgtccttga tacagtgcta ttgaccgtga tttcctttca tctaatccaa      60
gctccattca ccaaggtgga agagagtttt aatattcaag ccattcatga tattttaacc     120
tacagcgtat ttgatatctc caatatgac cacttgaaat tcctggagt agtccctaga      180 acattcgttg gtgctgtgat tattgcaatg ctttcgagac cttatcttta cttgagttct     240
ttgatccaaa cttccaggcc tacgtctata gatgttcaat tggtcgttag ggggattgtt     300
ggcctcacca atgggctttc ttttatctat ttaaagaatt gtttgcaaga tatgtttgat     360
gaaatcactg aaaagaaaaa ggaagaaaat gaagacaagg atatatacat ttacgatagc     420
gctggtacat ggtttctttt atttttaatt ggcagtttcc acctcatgtt ctacagcact     480
aggactctgc ctaattttgt catgactctg cctctaacca acgtcgcatt ggggtgggtt     540
```

-continued

```
ttattgggtc gttataatgc agctatattc ctatctgcgc tcgtggcaat tgtatttaga    600
ctggaagtgt cagctctcag tgctggtatt gctctattta gcgtcatctt caagaagatt    660
tctttattcg atgctatcaa attcggtatc tttggcttgg acttggttc cgccatcagt    720
atcaccgttg attcatattt ctggcaagaa tggtgtctac ctgaggtaga tggtttcttg    780
ttcaacgtgg ttgcgggtta cgcttccaag tggggtgtgg agccagttac tgcttatttc    840
acgcattact tgagaatgat gtttatgcca ccaactgttt tactattgaa ttacttcggc    900
tataaattag cacctgcaaa attaaaaatt gtctcactag catctctttt ccacattatc    960
gtcttatcct ttcaacctca caagaatgg agattcatca tctacgctgt ccatctatc    1020
atgttgctag gtgccacagg agcagcacat ctatgggaga atatgaaagt aaaaaagatt    1080
accaatgttt tatgtttggc tatattgccc ttatctataa tgacctcctt tttcatttca    1140
atggcgttct tgtatatatc aagaatgaat tatccaggcg gcgaggcttt aacttctttt    1200
aatgacatga ttgtgaaaaa aatattaca aacgctacag ttcatatcag catacctcct    1260
tgcatgacag gtgtcacttt atttggtgaa ttgaactacg gtgtgtacgg catcaattac    1320
gataagactg aaaatacgac tttactgcag gaaatgtggc cctcctttga tttcttgatc    1380
acccacgagc caaccgcctc tcaattgcca ttcgagaata agactaccaa ccattgggag    1440
ctagttaaca caacaaagat gtttactgga tttgacccaa cctacattaa gaactttgtt    1500
ttccaagaga gagtgaatgt tttgtctcta ctcaaacaga tcattttcga caagacccct    1560
accgtttttt tgaaagaatt gacggccaat tcgattgtta aaagcgatgt cttcttcacc    1620
tataagagaa tcaaacaaga tgaaaaaact gattga                              1656
```

<210> SEQ ID NO 65
<211> LENGTH: 551
<212> TYPE: PRT
<213> ORGANISM: Saccharomyces cerevisiae

<400> SEQUENCE: 65

```
Met Arg Trp Ser Val Leu Asp Thr Val Leu Leu Thr Val Ile Ser Phe
 1               5                  10                  15

His Leu Ile Gln Ala Pro Phe Thr Lys Val Glu Glu Ser Phe Asn Ile
             20                  25                  30

Gln Ala Ile His Asp Ile Leu Thr Tyr Ser Val Phe Asp Ile Ser Gln
         35                  40                  45

Tyr Asp His Leu Lys Phe Pro Gly Val Val Pro Arg Thr Phe Val Gly
     50                  55                  60

Ala Val Ile Ile Ala Met Leu Ser Arg Pro Tyr Leu Tyr Leu Ser Ser
 65                  70                  75                  80

Leu Ile Gln Thr Ser Arg Pro Thr Ser Ile Asp Val Gln Leu Val Val
                 85                  90                  95

Arg Gly Ile Val Gly Leu Thr Asn Gly Leu Ser Phe Ile Tyr Leu Lys
            100                 105                 110

Asn Cys Leu Gln Asp Met Phe Asp Glu Ile Thr Glu Lys Lys Lys Glu
        115                 120                 125

Glu Asn Glu Asp Lys Asp Ile Tyr Ile Tyr Asp Ser Ala Gly Thr Trp
    130                 135                 140

Phe Leu Leu Phe Leu Ile Gly Ser Phe His Leu Met Phe Tyr Ser Thr
145                 150                 155                 160

Arg Thr Leu Pro Asn Phe Val Met Thr Leu Pro Leu Thr Asn Val Ala
                165                 170                 175
```

Leu Gly Trp Val Leu Gly Arg Tyr Asn Ala Ala Ile Phe Leu Ser
                180                 185                 190

Ala Leu Val Ala Ile Val Phe Arg Leu Glu Val Ser Ala Leu Ser Ala
            195                 200                 205

Gly Ile Ala Leu Phe Ser Val Ile Phe Lys Lys Ile Ser Leu Phe Asp
210                 215                 220

Ala Ile Lys Phe Gly Ile Phe Gly Leu Gly Leu Gly Ser Ala Ile Ser
225                 230                 235                 240

Ile Thr Val Asp Ser Tyr Phe Trp Gln Glu Trp Cys Leu Pro Glu Val
                245                 250                 255

Asp Gly Phe Leu Phe Asn Val Val Ala Gly Tyr Ala Ser Lys Trp Gly
            260                 265                 270

Val Glu Pro Val Thr Ala Tyr Phe Thr His Tyr Leu Arg Met Met Phe
        275                 280                 285

Met Pro Pro Thr Val Leu Leu Leu Asn Tyr Phe Gly Tyr Lys Leu Ala
        290                 295                 300

Pro Ala Lys Leu Lys Ile Val Ser Leu Ala Ser Leu Phe His Ile Ile
305                 310                 315                 320

Val Leu Ser Phe Gln Pro His Lys Glu Trp Arg Phe Ile Ile Tyr Ala
                325                 330                 335

Val Pro Ser Ile Met Leu Leu Gly Ala Thr Gly Ala Ala His Leu Trp
            340                 345                 350

Glu Asn Met Lys Val Lys Lys Ile Thr Asn Val Leu Cys Leu Ala Ile
        355                 360                 365

Leu Pro Leu Ser Ile Met Thr Ser Phe Phe Ile Ser Met Ala Phe Leu
370                 375                 380

Tyr Ile Ser Arg Met Asn Tyr Pro Gly Gly Glu Ala Leu Thr Ser Phe
385                 390                 395                 400

Asn Asp Met Ile Val Glu Lys Asn Ile Thr Asn Ala Thr Val His Ile
                405                 410                 415

Ser Ile Pro Pro Cys Met Thr Gly Val Thr Leu Phe Gly Glu Leu Asn
            420                 425                 430

Tyr Gly Val Tyr Gly Ile Asn Tyr Asp Lys Thr Glu Asn Thr Thr Leu
        435                 440                 445

Leu Gln Glu Met Trp Pro Ser Phe Asp Phe Leu Ile Thr His Glu Pro
        450                 455                 460

Thr Ala Ser Gln Leu Pro Phe Glu Asn Lys Thr Thr Asn His Trp Glu
465                 470                 475                 480

Leu Val Asn Thr Thr Lys Met Phe Thr Gly Phe Asp Pro Thr Tyr Ile
                485                 490                 495

Lys Asn Phe Val Phe Gln Glu Arg Val Asn Val Leu Ser Leu Leu Lys
            500                 505                 510

Gln Ile Ile Phe Asp Lys Thr Pro Thr Val Phe Leu Lys Glu Leu Thr
        515                 520                 525

Ala Asn Ser Ile Val Lys Ser Asp Val Phe Phe Thr Tyr Lys Arg Ile
        530                 535                 540

Lys Gln Asp Glu Lys Thr Asp
545                 550

<210> SEQ ID NO 66
<211> LENGTH: 840
<212> TYPE: DNA
<213> ORGANISM: Pichia pastoris

<400> SEQUENCE: 66

```
tcggtcgaga atgataactg aagaactcaa aatctctcac actttcatcg ttactgtact    60
ggcaatcatt gcatttcagc ctcataaaga atggagattt atagtttaca ttgttccacc   120
acttgtcatc accatatcta cagtacttgc acaactaccc aggagattca caatcgtcaa   180
agttgctgtt tttctcctaa gtttcggctc tttgctcata tccctgtcgt ttcttttcat   240
ctcatcgtat aactaccctg ggggtgaagc tttacagcat tgaacgaga aactccttct   300 actggaccaa agttccctac ctgttgatat taaggttcat atggatgtcc ctgcatgcat   360
gactggggtg actttatttg gttacttgga taactcaaaa ttgaacaatt taagaattgt   420
ctatgataaa acagaagacg agtcgctgga cacaatctgg gattctttca attatgtcat   480
ctccgaaatt gacttggatt cttcgactgc tcccaaatgg gaggggatt ggctgaagat   540 tgatgttgtc caaggctaca acggcatcaa taaacaatct atcaaaaata caattttcaa   600
ttatggaata cttaaacgga tgataagaga cgcaaccaaa cttgatgttg gatttattcg   660
tacggtcttt cgatccttca taaaatttga tgataaatta ttcatttatg agaggagcag   720
tcaaacctga aaatatatac ctcatttgtt caatttggtg taaagagtgt ggcggataga   780
cttcttgtaa atcaggaaag ctacaattcc aattgctgca aaaaatacca atgcccataa   840
```

<210> SEQ ID NO 67
<211> LENGTH: 239
<212> TYPE: PRT
<213> ORGANISM: Pichia pastoris

<400> SEQUENCE: 67

```
Arg Met Ile Thr Glu Glu Leu Lys Ile Ser His Thr Phe Ile Val Thr
  1               5                  10                  15

Val Leu Ala Ile Ile Ala Phe Gln Pro His Lys Glu Trp Arg Phe Ile
             20                  25                  30

Val Tyr Ile Val Pro Pro Leu Val Ile Thr Ile Ser Thr Val Leu Ala
         35                  40                  45

Gln Leu Pro Arg Arg Phe Thr Ile Val Lys Val Ala Val Phe Leu Leu
     50                  55                  60

Ser Phe Gly Ser Leu Leu Ile Ser Leu Ser Phe Leu Phe Ile Ser Ser
 65                  70                  75                  80

Tyr Asn Tyr Pro Gly Gly Glu Ala Leu Gln His Leu Asn Glu Lys Leu
                 85                  90                  95

Leu Leu Leu Asp Gln Ser Ser Leu Pro Val Asp Ile Lys Val His Met
            100                 105                 110

Asp Val Pro Ala Cys Met Thr Gly Val Thr Leu Phe Gly Tyr Leu Asp
        115                 120                 125

Asn Ser Lys Leu Asn Asn Leu Arg Ile Val Tyr Asp Lys Thr Glu Asp
    130                 135                 140

Glu Ser Leu Asp Thr Ile Trp Asp Ser Phe Asn Tyr Val Ile Ser Glu
145                 150                 155                 160

Ile Asp Leu Asp Ser Ser Thr Ala Pro Lys Trp Glu Gly Asp Trp Leu
                165                 170                 175

Lys Ile Asp Val Val Gln Gly Tyr Asn Gly Ile Asn Lys Gln Ser Ile
            180                 185                 190

Lys Asn Thr Ile Phe Asn Tyr Gly Ile Leu Lys Arg Met Ile Arg Asp
        195                 200                 205

Ala Thr Lys Leu Asp Val Gly Phe Ile Arg Thr Val Phe Arg Ser Phe
    210                 215                 220
```

```
Ile Lys Phe Asp Asp Lys Leu Phe Ile Tyr Glu Arg Ser Ser Gln
225                 230                 235
```

<210> SEQ ID NO 68
<211> LENGTH: 239
<212> TYPE: PRT
<213> ORGANISM: Pichia pastoris
<220> FEATURE:
<221> NAME/KEY: MOD_RES
<222> LOCATION: (62)...(80)
<223> OTHER INFORMATION: Xaa is a variable amino acid

<400> SEQUENCE: 68

```
Arg Met Ile Thr Glu Glu Leu Lys Ile Ser His Thr Phe Ile Val Thr
1               5                   10                  15

Val Leu Ala Ile Ile Ala Phe Gln Pro His Lys Glu Trp Arg Phe Ile
            20                  25                  30

Val Tyr Ile Val Pro Pro Leu Val Ile Thr Ile Ser Thr Val Leu Ala
        35                  40                  45

Gln Leu Pro Arg Arg Phe Thr Ile Val Lys Val Ala Val Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Tyr Asn Tyr Pro Gly Gly Glu Ala Leu Gln His Leu Asn Glu Lys Leu
            85                  90                  95

Leu Leu Leu Asp Gln Ser Ser Leu Pro Val Asp Ile Lys Val His Met
            100                 105                 110

Asp Val Pro Ala Cys Met Thr Gly Val Thr Leu Phe Gly Tyr Leu Asp
        115                 120                 125

Asn Ser Lys Leu Asn Asn Leu Arg Ile Val Tyr Asp Lys Thr Glu Asp
130                 135                 140

Glu Ser Leu Asp Thr Ile Trp Asp Ser Phe Asn Tyr Val Ile Ser Glu
145                 150                 155                 160

Ile Asp Leu Asp Ser Ser Thr Ala Pro Lys Trp Glu Gly Asp Trp Leu
                165                 170                 175

Lys Ile Asp Val Val Gln Gly Tyr Asn Gly Ile Asn Lys Gln Ser Ile
            180                 185                 190

Lys Asn Thr Ile Phe Asn Tyr Gly Ile Leu Lys Arg Met Ile Arg Asp
        195                 200                 205

Ala Thr Lys Leu Asp Val Gly Phe Ile Arg Thr Val Phe Arg Ser Phe
210                 215                 220

Ile Lys Phe Asp Asp Lys Leu Phe Ile Tyr Glu Arg Ser Ser Gln
225                 230                 235
```

<210> SEQ ID NO 69
<211> LENGTH: 245
<212> TYPE: PRT
<213> ORGANISM: Saccharomyces cerevisiae

<400> SEQUENCE: 69

```
Lys Leu Ala Pro Ala Lys Leu Lys Ile Val Ser Leu Ala Ser Leu Phe
1               5                   10                  15

His Ile Ile Val Leu Ser Phe Gln Pro His Lys Glu Trp Arg Phe Ile
            20                  25                  30

Ile Tyr Ala Val Pro Ser Ile Met Leu Leu Gly Ala Thr Gly Ala Ala
        35                  40                  45

His Leu Trp Glu Asn Met Lys Val Lys Lys Ile Thr Asn Val Leu Cys
50                  55                  60
```

```
Leu Ala Ile Leu Pro Leu Ser Ile Met Thr Ser Phe Phe Ile Ser Met
 65                  70                  75                  80

Ala Phe Leu Tyr Ile Ser Arg Met Asn Tyr Pro Gly Gly Glu Ala Leu
                 85                  90                  95

Thr Ser Phe Asn Asp Met Ile Val Glu Lys Asn Ile Thr Asn Ala Thr
            100                 105                 110

Val His Ile Ser Ile Pro Pro Cys Met Thr Gly Val Thr Leu Phe Gly
        115                 120                 125

Glu Leu Asn Tyr Gly Val Tyr Gly Ile Asn Tyr Asp Lys Thr Glu Asn
    130                 135                 140

Thr Thr Leu Leu Gln Glu Met Trp Pro Ser Phe Asp Phe Leu Ile Thr
145                 150                 155                 160

His Glu Pro Thr Ala Ser Gln Leu Pro Phe Glu Asn Lys Thr Thr Asn
                165                 170                 175

His Trp Glu Leu Val Asn Thr Thr Lys Met Phe Thr Gly Phe Asp Pro
            180                 185                 190

Thr Tyr Ile Lys Asn Phe Val Phe Gln Glu Arg Val Asn Val Leu Ser
        195                 200                 205

Leu Leu Lys Gln Ile Ile Phe Asp Lys Thr Pro Thr Val Phe Leu Lys
    210                 215                 220

Glu Leu Thr Ala Asn Ser Ile Val Lys Ser Asp Val Phe Phe Thr Tyr
225                 230                 235                 240

Lys Arg Ile Lys Gln
                245

<210> SEQ ID NO 70
<211> LENGTH: 141
<212> TYPE: PRT
<213> ORGANISM: Pichia pastoris
<220> FEATURE:
<221> NAME/KEY: MOD_RES
<222> LOCATION: (43)...(61)
<223> OTHER INFORMATION: Xaa is a variable amino acid

<400> SEQUENCE: 70

Ile Ile Ala Phe Gln Pro His Lys Glu Trp Arg Phe Ile Val Tyr Ile
  1               5                  10                  15

Val Pro Pro Leu Val Ile Thr Ile Ser Thr Val Leu Ala Gln Leu Pro
             20                  25                  30

Arg Arg Phe Thr Ile Val Lys Val Ala Val Xaa Xaa Xaa Xaa Xaa
         35                  40                  45

Xaa Xaa Xaa Xaa Xaa Xaa Xaa Xaa Xaa Xaa Xaa Tyr Asn Tyr
    50                  55                  60

Pro Gly Gly Glu Ala Leu Gln His Leu Asn Glu Lys Leu Leu Leu Leu
 65                  70                  75                  80

Asp Gln Ser Ser Leu Pro Val Asp Ile Lys Val His Met Asp Val Pro
                 85                  90                  95

Ala Cys Met Thr Gly Val Thr Leu Phe Gly Tyr Leu Asp Asn Ser Lys
            100                 105                 110

Leu Asn Asn Leu Arg Ile Val Tyr Asp Lys Thr Glu Asp Glu Ser Leu
        115                 120                 125

Asp Thr Ile Trp Asp Ser Phe Asn Tyr Val Ile Ser Glu
    130                 135                 140

<210> SEQ ID NO 71
<211> LENGTH: 137
```

```
<212> TYPE: PRT
<213> ORGANISM: Schizosaccharomyces pombe

<400> SEQUENCE: 71

Val Tyr Ser Phe Leu Gly His Lys Glu Trp Arg Phe Ile Ile Tyr Ser
 1               5                  10                  15

Ile Pro Trp Phe Asn Ala Ala Ser Ala Ile Gly Ala Ser Leu Cys Phe
                20                  25                  30

Asn Ala Ser Lys Phe Gly Lys Lys Ile Phe Glu Ile Leu Arg Leu Met
            35                  40                  45

Phe Phe Ser Gly Ile Ile Phe Gly Phe Ile Gly Ser Ser Phe Leu Leu
        50                  55                  60

Tyr Val Phe Gln Tyr Ala Tyr Pro Gly Gly Leu Ala Leu Thr Arg Leu
65                  70                  75                  80

Tyr Glu Ile Glu Asn His Pro Gln Val Ser Val His Met Asp Val Tyr
                85                  90                  95

Pro Cys Met Thr Gly Ile Thr Arg Phe Ser Gln Leu Pro Ser Trp Tyr
                100                 105                 110

Tyr Asp Lys Thr Glu Asp Pro Lys Met Leu Ser Asn Ser Leu Phe Ile
            115                 120                 125

Ser Gln Phe Asp Tyr Leu Ile Thr Glu
        130                 135

<210> SEQ ID NO 72
<211> LENGTH: 143
<212> TYPE: PRT
<213> ORGANISM: Pichia pastoris
<220> FEATURE:
<221> NAME/KEY: MOD_RES
<222> LOCATION: (45)...(63)
<223> OTHER INFORMATION: Xaa is a variable amino acid

<400> SEQUENCE: 72

Leu Ala Ile Ile Ala Phe Gln Pro His Lys Glu Trp Arg Phe Ile Val
 1               5                  10                  15

Tyr Ile Val Pro Pro Leu Val Ile Thr Ile Ser Thr Val Leu Ala Gln
                20                  25                  30

Leu Pro Arg Arg Phe Thr Ile Val Lys Val Ala Val Xaa Xaa Xaa Xaa
            35                  40                  45

Xaa Xaa Xaa Xaa Xaa Xaa Xaa Xaa Xaa Xaa Xaa Xaa Xaa Xaa Xaa Tyr
        50                  55                  60

Asn Tyr Pro Gly Gly Glu Ala Leu Gln His Leu Asn Glu Lys Leu Leu
65                  70                  75                  80

Leu Leu Asp Gln Ser Ser Leu Pro Val Asp Ile Lys Val His Met Asp
                85                  90                  95

Val Pro Ala Cys Met Thr Gly Val Thr Leu Phe Gly Tyr Leu Asp Asn
                100                 105                 110

Ser Lys Leu Asn Asn Leu Arg Ile Val Tyr Asp Lys Thr Glu Asp Glu
            115                 120                 125

Ser Leu Asp Thr Ile Trp Asp Ser Phe Asn Tyr Val Ile Ser Glu
        130                 135                 140

<210> SEQ ID NO 73
<211> LENGTH: 137
<212> TYPE: PRT
<213> ORGANISM: Homo sapiens

<400> SEQUENCE: 73
```

Met Ala Leu Tyr Ser Leu Leu Pro His Lys Glu Leu Arg Phe Ile Ile
1               5                   10                  15

Tyr Ala Phe Pro Met Leu Asn Ile Thr Ala Ala Arg Gly Cys Ser Tyr
                20                  25                  30

Leu Leu Asn Asn Tyr Lys Lys Ser Trp Leu Tyr Lys Ala Gly Ser Leu
            35                  40                  45

Leu Val Ile Gly His Leu Val Val Asn Ala Ala Tyr Ser Ala Thr Ala
        50                  55                  60

Leu Tyr Val Ser His Phe Asn Tyr Pro Gly Val Ala Met Gln Arg
65                  70                  75                  80

Leu His Gln Leu Val Pro Pro Gln Thr Asp Val Leu His Ile Asp
                85                  90                  95

Val Ala Ala Ala Gln Thr Gly Val Ser Arg Phe Leu Gln Val Asn Ser
                100                 105                 110

Ala Trp Arg Tyr Asp Lys Arg Glu Asp Val Gln Pro Gly Thr Gly Met
            115                 120                 125

Leu Ala Tyr Thr His Ile Leu Met Glu
        130                 135

<210> SEQ ID NO 74
<211> LENGTH: 1635
<212> TYPE: DNA
<213> ORGANISM: Saccharomyces cerevisiae

<400> SEQUENCE: 74
atggccattg gcaaaaggtt actggtgaac aaaccagcag aagaatcatt ttatgcttct        60
ccaatgtatg attttttgta ccgtttagg ccagtgggga accaatggct gccagaatat       120
attatctttg tatgtgctgt aatactgagg tgcacaattg gacttggtcc atattctggg       180
aaaggcagtc caccgctgta cggcgatttt gaggctcaga gacattggat ggaaattacg       240
caacatttac cgcttttctaa gtggtactgg tatgatttgc aatactgggg attggactat       300
ccaccattaa cagcatttca ttcgtacctt ctgggcctaa ttggatcttt tttcaatcca       360
tcttggtttg cactagaaaa gtcacgtggc tttgaatccc ccgataatgg cctgaaaaca       420
tatatgcgtt ctactgtcat cattagcgac atattgtttt actttcctgc agtaatatac       480
tttactaagt ggcttggtag atatcgaaac cagtcgccca taggacaatc tattgcggca       540
tcagcgattt tgttccaacc ttcattaatg ctcattgacc atgggcactt caatataat       600 tcagtcatgc ttggccttac tgcttatgcc ataaataact tattagatga gtattatgct       660
atggcggccg tttgttttgt cctatccatt tgttttaaac aaatggcatt gtattatgca       720 ccgattttt ttgcttatct attaagtcga tcattgctgt cccccaaatt taacatagct       780
agattgacgg ttattgcgtt tgcaacactc gcaacttttg ctataatatt tgcgccatta       840
tatttcttgg gaggaggatt aaagaatatt caccaatgta ttcacaggat attcccttt        900 gccaggggca tcttcgaaga caaggttgct aacttctggt gcgttacgaa cgtgtttgta       960
aaatacaagg aaagattcac tatacaacaa ctccagctat attcattgat tgccaccgtg      1020 attggttct accagccat gataatgaca ttacttcatc ccaaaaagca tcttctccca      1080
tacgtgttaa tcgcatgttc gatgtccttt tttctttta gctttcaagt acatgagaaa      1140
actatcctca tcccactttt gcctattaca ctactctact cctctactga ttggaatgtt      1200
ctatctcttg taagttggat aaacaatgtg gctttgttta cgctatggcc tttgttgaaa      1260
aaggacggtc ttcatttaca gtatgccgta tctttcttac taagcaattg gctgattgga      1320

-continued

```
aatttcagtt ttattacacc aaggttcttg ccaaaatctt taactcctgg cccttctatc    1380
agcagcatca atagcgacta tagaagaaga agcttactgc catataatgt ggtttggaaa    1440
agttttatca taggaacgta tattgctatg ggcttttatc atttcttaga tcaatttgta    1500
gcacctccat cgaaatatcc agacttgtgg gtgttgttga actgtgctgt tgggttcatt    1560
tgctttagca tattttggct atggtcttat tacaagatat tcacttccgg tagcaaatcc    1620
atgaaggact tgtag                                                    1635
```

<210> SEQ ID NO 75
<211> LENGTH: 544
<212> TYPE: PRT
<213> ORGANISM: Saccharomyces cerevisiae

<400> SEQUENCE: 75

```
Met Ala Ile Gly Lys Arg Leu Leu Val Asn Lys Pro Ala Glu Glu Ser
 1               5                  10                  15

Phe Tyr Ala Ser Pro Met Tyr Asp Phe Leu Tyr Pro Phe Arg Pro Val
             20                  25                  30

Gly Asn Gln Trp Leu Pro Glu Tyr Ile Ile Phe Val Cys Ala Val Ile
         35                  40                  45

Leu Arg Cys Thr Ile Gly Leu Gly Pro Tyr Ser Gly Lys Gly Ser Pro
     50                  55                  60

Pro Leu Tyr Gly Asp Phe Glu Ala Gln Arg His Trp Met Glu Ile Thr
 65                  70                  75                  80

Gln His Leu Pro Leu Ser Lys Trp Tyr Trp Tyr Asp Leu Gln Tyr Trp
                 85                  90                  95

Gly Leu Asp Tyr Pro Pro Leu Thr Ala Phe His Ser Tyr Leu Leu Gly
            100                 105                 110

Leu Ile Gly Ser Phe Phe Asn Pro Ser Trp Phe Ala Leu Glu Lys Ser
        115                 120                 125

Arg Gly Phe Glu Ser Pro Asp Asn Gly Leu Lys Thr Tyr Met Arg Ser
    130                 135                 140

Thr Val Ile Ile Ser Asp Ile Leu Phe Tyr Phe Pro Ala Val Ile Tyr
145                 150                 155                 160

Phe Thr Lys Trp Leu Gly Arg Tyr Arg Asn Gln Ser Pro Ile Gly Gln
                165                 170                 175

Ser Ile Ala Ala Ser Ala Ile Leu Phe Gln Pro Ser Leu Met Leu Ile
            180                 185                 190

Asp His Gly His Phe Gln Tyr Asn Ser Val Met Leu Gly Leu Thr Ala
        195                 200                 205

Tyr Ala Ile Asn Asn Leu Leu Asp Glu Tyr Tyr Ala Met Ala Ala Val
    210                 215                 220

Cys Phe Val Leu Ser Ile Cys Phe Lys Gln Met Ala Leu Tyr Tyr Ala
225                 230                 235                 240

Pro Ile Phe Phe Ala Tyr Leu Leu Ser Arg Ser Leu Leu Phe Pro Lys
                245                 250                 255

Phe Asn Ile Ala Arg Leu Thr Val Ile Ala Phe Ala Thr Leu Ala Thr
            260                 265                 270

Phe Ala Ile Ile Phe Ala Pro Leu Tyr Phe Leu Gly Gly Gly Leu Lys
        275                 280                 285

Asn Ile His Gln Cys Ile His Arg Ile Phe Pro Phe Ala Arg Gly Ile
    290                 295                 300

Phe Glu Asp Lys Val Ala Asn Phe Trp Cys Val Thr Asn Val Phe Val
305                 310                 315                 320
```

Lys Tyr Lys Glu Arg Phe Thr Ile Gln Gln Leu Gln Leu Tyr Ser Leu
            325                 330                 335

Ile Ala Thr Val Ile Gly Phe Leu Pro Ala Met Ile Met Thr Leu Leu
            340                 345                 350

His Pro Lys Lys His Leu Leu Pro Tyr Val Leu Ile Ala Cys Ser Met
            355                 360                 365

Ser Phe Phe Leu Phe Ser Phe Gln Val His Glu Lys Thr Ile Leu Ile
        370                 375                 380

Pro Leu Leu Pro Ile Thr Leu Tyr Ser Ser Thr Asp Trp Asn Val
385                 390                 395                 400

Leu Ser Leu Val Ser Trp Ile Asn Asn Val Ala Leu Phe Thr Leu Trp
            405                 410                 415

Pro Leu Leu Lys Lys Asp Gly Leu His Leu Gln Tyr Ala Val Ser Phe
            420                 425                 430

Leu Leu Ser Asn Trp Leu Ile Gly Asn Phe Ser Phe Ile Thr Pro Arg
            435                 440                 445

Phe Leu Pro Lys Ser Leu Thr Pro Gly Pro Ser Ile Ser Ser Ile Asn
        450                 455                 460

Ser Asp Tyr Arg Arg Ser Leu Leu Pro Tyr Asn Val Val Trp Lys
465                 470                 475                 480

Ser Phe Ile Ile Gly Thr Tyr Ile Ala Met Gly Phe Tyr His Phe Leu
            485                 490                 495

Asp Gln Phe Val Ala Pro Pro Ser Lys Tyr Pro Asp Leu Trp Val Leu
            500                 505                 510

Leu Asn Cys Ala Val Gly Phe Ile Cys Phe Ser Ile Phe Trp Leu Trp
            515                 520                 525

Ser Tyr Tyr Lys Ile Phe Thr Ser Gly Ser Lys Ser Met Lys Asp Leu
            530                 535                 540

<210> SEQ ID NO 76
<211> LENGTH: 1644
<212> TYPE: DNA
<213> ORGANISM: Pichia pastoris

<400> SEQUENCE: 76

```
atgccacata aaagaacgcc ctctagcagt ctgctgtatg caagaattcc agggatctct      60
tttgaaaact ctccggtgtt tgattttttg tctccttttg acccgctcc taatcaatgg     120 gtagcacgat acatcatcat catctttgca attctcatca gattggcagt tgggctgggc    180
tcctattccg gcttcaacac ccctccaatg tatggggatt ttgaagctca gaggcattgg    240
atggaaatta ctcagcattt atccatagaa aaatggtact tctacgactt gcaatattgg    300
gggcttgact atcctcccct tgacagcctt tcattcatact ctctttggcaa attaggcagc    360 ttcatcaatc cagcatggtt tgctttagac gtctccagag ggtttgaatc agtggatcta    420
aaatcgtaca tgagggcgac cgcaattctc agtgagctgt tatgtttttat tccagctgtc    480 atttggtatt gtcgttggat gggacttaac tacttcaatc aaaacgccat tgagcaaact    540
ataatagcgt ctgctattct tttcaatcca tctttaatta tcatagatca tggccacttc    600
cagtacaact cagttatgct aggttttgct ttattatcca tataaatct gttgtacgat    660 aattttgcat tagcggctat ttttttttcgtt ctttcaataa gctttaagca aatggctctc    720
tattatagcc ccatcatgtt ttttttacatg ctgagtgtga ttgttggcc tttgaaaaac    780 ttcaacttgt tgagattggc tactatcagt attgcagtac tcttgacttt tgcaactcta    840
```

```
ttactgcctt tgtattagt agatgggatg tcacaaattg gccaaatatt attcagagtt    900
ttcccgtttt caagaggctt gtttgaggat aaggtggcca acttttggtg tacaacgaat    960
atactggtaa agtacaaaca gttattcact gacaaaaccc ttactaggat atcgctagta   1020
gcaactttga ttgcaattag tccgtcttgc ttcatcattt ttactcaccc aaagaaggtt   1080
ttactaccgt gggcttttgc tgcttgctct tgggcgttct atcttttctc tttccaagtc   1140
cacgagaaat cagttttagt tccattgatg cctaccactc tattactggt agaaaaagac   1200
ttggacatca tctcaatggt ctgctggatt tctaatattg ccttcttcag catgtggcct   1260
ctattaaaaa gagacgggct ggctttggaa tattttgtct tgggaatatt gagtaattgg   1320
ctgattggaa acctcaattg gattagtaaa tggcttgtcc ccagtttcct gattccaggg   1380
cctactctct ccaaaaaagt tcctaaaaga gatactaaaa cagttgttca tactcactgg   1440
ttttgggggt cagtaacatt cgtttcatac ctcggagcta cagttatcca gttcgtagat   1500
tggctgtacc ttccacctgc caagtatcca gatttgtggg ttattttgaa cactacattg   1560
tcgtttgctt gtttcgggtt gttttggcta tggattaact acaatctgta cattttgcgt   1620
gattttaagc ttaaagatgc ttag                                          1644
```

<210> SEQ ID NO 77
<211> LENGTH: 547
<212> TYPE: PRT
<213> ORGANISM: Pichia pastoris

<400> SEQUENCE: 77

```
Met Pro His Lys Arg Thr Pro Ser Ser Ser Leu Leu Tyr Ala Arg Ile
 1               5                  10                  15

Pro Gly Ile Ser Phe Glu Asn Ser Pro Val Phe Asp Phe Leu Ser Pro
            20                  25                  30

Phe Gly Pro Ala Pro Asn Gln Trp Val Ala Arg Tyr Ile Ile Ile
        35                  40                  45

Phe Ala Ile Leu Ile Arg Leu Ala Val Gly Leu Gly Ser Tyr Ser Gly
    50                  55                  60

Phe Asn Thr Pro Pro Met Tyr Gly Asp Phe Glu Ala Gln Arg His Trp
65                  70                  75                  80

Met Glu Ile Thr Gln His Leu Ser Ile Glu Lys Trp Tyr Phe Tyr Asp
                85                  90                  95

Leu Gln Tyr Trp Gly Leu Asp Tyr Pro Pro Leu Thr Ala Phe His Ser
            100                 105                 110

Tyr Phe Phe Gly Lys Leu Gly Ser Phe Ile Asn Pro Ala Trp Phe Ala
        115                 120                 125

Leu Asp Val Ser Arg Gly Phe Glu Ser Val Asp Leu Lys Ser Tyr Met
    130                 135                 140

Arg Ala Thr Ala Ile Leu Ser Glu Leu Leu Cys Phe Ile Pro Ala Val
145                 150                 155                 160

Ile Trp Tyr Cys Arg Trp Met Gly Leu Asn Tyr Phe Asn Gln Asn Ala
                165                 170                 175

Ile Glu Gln Thr Ile Ile Ala Ser Ala Ile Leu Phe Asn Pro Ser Leu
            180                 185                 190

Ile Ile Ile Asp His Gly His Phe Gln Tyr Asn Ser Val Met Leu Gly
        195                 200                 205

Phe Ala Leu Leu Ser Ile Leu Asn Leu Tyr Asp Asn Phe Ala Leu
    210                 215                 220

Ala Ala Ile Phe Phe Val Leu Ser Ile Ser Phe Lys Gln Met Ala Leu
```

```
                    225                 230                 235                 240
Tyr Tyr Ser Pro Ile Met Phe Phe Tyr Met Leu Ser Val Ser Cys Trp
                245                 250                 255

Pro Leu Lys Asn Phe Asn Leu Leu Arg Leu Ala Thr Ile Ser Ile Ala
                260                 265                 270

Val Leu Leu Thr Phe Ala Thr Leu Leu Leu Pro Phe Val Leu Val Asp
                275                 280                 285

Gly Met Ser Gln Ile Gly Gln Ile Leu Phe Arg Val Phe Pro Phe Ser
                290                 295                 300

Arg Gly Leu Phe Glu Asp Lys Val Ala Asn Phe Trp Cys Thr Thr Asn
305                 310                 315                 320

Ile Leu Val Lys Tyr Lys Gln Leu Phe Thr Asp Lys Thr Leu Thr Arg
                325                 330                 335

Ile Ser Leu Val Ala Thr Leu Ile Ala Ile Ser Pro Ser Cys Phe Ile
                340                 345                 350

Ile Phe Thr His Pro Lys Lys Val Leu Leu Pro Trp Ala Phe Ala Ala
                355                 360                 365

Cys Ser Trp Ala Phe Tyr Leu Phe Ser Phe Gln Val His Glu Lys Ser
                370                 375                 380

Val Leu Val Pro Leu Met Pro Thr Thr Leu Leu Val Glu Lys Asp
385                 390                 395                 400

Leu Asp Ile Ile Ser Met Val Cys Trp Ile Ser Asn Ile Ala Phe Phe
                405                 410                 415

Ser Met Trp Pro Leu Leu Lys Arg Asp Gly Leu Ala Leu Glu Tyr Phe
                420                 425                 430

Val Leu Gly Ile Leu Ser Asn Trp Leu Ile Gly Asn Leu Asn Trp Ile
                435                 440                 445

Ser Lys Trp Leu Val Pro Ser Phe Leu Ile Pro Gly Pro Thr Leu Ser
                450                 455                 460

Lys Lys Val Pro Lys Arg Asp Thr Lys Thr Val Val His Thr His Trp
465                 470                 475                 480

Phe Trp Gly Ser Val Thr Phe Val Ser Tyr Leu Gly Ala Thr Val Ile
                485                 490                 495

Gln Phe Val Asp Trp Leu Tyr Leu Pro Pro Ala Lys Tyr Pro Asp Leu
                500                 505                 510

Trp Val Ile Leu Asn Thr Thr Leu Ser Phe Ala Cys Phe Gly Leu Phe
                515                 520                 525

Trp Leu Trp Ile Asn Tyr Asn Leu Tyr Ile Leu Arg Asp Phe Lys Leu
                530                 535                 540

Lys Asp Ala
545

<210> SEQ ID NO 78
<211> LENGTH: 527
<212> TYPE: PRT
<213> ORGANISM: Pichia pastoris
<220> FEATURE:
<221> NAME/KEY: MOD_RES
<222> LOCATION: (23)...(37)
<223> OTHER INFORMATION: Xaa is a variable amino acid
<220> FEATURE:
<221> NAME/KEY: MOD_RES
<222> LOCATION: (366)...(378)
<223> OTHER INFORMATION: Xaa is a variable amino acid

<400> SEQUENCE: 78

Ser Phe Glu Asn Ser Pro Val Phe Asp Phe Leu Ser Pro Phe Gly Pro
```

```
               1               5                  10                 15
            Ala Pro Asn Gln Trp Val Xaa Xaa Xaa Xaa Xaa Xaa Xaa Xaa
                            20                 25                 30

Xaa Xaa Xaa Xaa Xaa Val Gly Leu Gly Ser Tyr Ser Gly Phe Asn Thr
                        35                 40                 45

Pro Pro Met Tyr Gly Asp Phe Glu Ala Gln Arg His Trp Met Glu Ile
            50                  55                 60

Thr Gln His Leu Ser Ile Glu Lys Trp Tyr Phe Tyr Asp Leu Gln Tyr
            65                  70                 75                 80

Trp Gly Leu Asp Tyr Pro Pro Leu Thr Ala Phe His Ser Tyr Phe Phe
                            85                 90                 95

Gly Lys Leu Gly Ser Phe Ile Asn Pro Ala Trp Phe Ala Leu Asp Val
                            100                105                110

Ser Arg Gly Phe Glu Ser Val Asp Leu Lys Ser Tyr Met Arg Ala Thr
                            115                120                125

Ala Ile Leu Ser Glu Leu Leu Cys Phe Ile Pro Ala Val Ile Trp Tyr
                        130                135                140

Cys Arg Trp Met Gly Leu Asn Tyr Phe Asn Gln Asn Ala Ile Glu Gln
            145                 150                155                160

Thr Ile Ile Ala Ser Ala Ile Leu Phe Asn Pro Ser Leu Ile Ile Ile
                        165                170                175

Asp His Gly His Phe Gln Tyr Asn Ser Val Met Leu Gly Phe Ala Leu
                        180                185                190

Leu Ser Ile Leu Asn Leu Leu Tyr Asp Asn Phe Ala Leu Ala Ala Ile
                        195                200                205

Phe Phe Val Leu Ser Ile Ser Phe Lys Gln Met Ala Leu Tyr Tyr Ser
                    210                215                220

Pro Ile Met Phe Phe Tyr Met Leu Ser Val Ser Cys Trp Pro Leu Lys
            225                 230                235                240

Asn Phe Asn Leu Leu Arg Leu Ala Thr Ile Ser Ile Ala Val Leu Leu
                        245                250                255

Thr Phe Ala Thr Leu Leu Leu Pro Phe Val Leu Val Asp Gly Met Ser
                        260                265                270

Gln Ile Gly Gln Ile Leu Phe Arg Val Phe Pro Phe Ser Arg Gly Leu
                    275                280                285

Phe Glu Asp Lys Val Ala Asn Phe Trp Cys Thr Thr Asn Ile Leu Val
                    290                295                300

Lys Tyr Lys Gln Leu Phe Thr Asp Lys Thr Leu Thr Arg Ile Ser Leu
            305                 310                315                320

Val Ala Thr Leu Ile Ala Ile Ser Pro Ser Cys Phe Ile Ile Phe Thr
                        325                330                335

His Pro Lys Lys Val Leu Leu Pro Trp Ala Phe Ala Ala Cys Ser Trp
                        340                345                350

Ala Phe Tyr Leu Phe Ser Phe Gln Val His Glu Lys Ser Xaa Xaa Xaa
                        355                360                365

Xaa Xaa Xaa Xaa Xaa Xaa Xaa Xaa Xaa Glu Lys Asp Leu Asp Ile
                        370                375                380

Ile Ser Met Val Cys Trp Ile Ser Asn Ile Ala Phe Phe Ser Met Trp
            385                 390                395                400

Pro Leu Leu Lys Arg Asp Gly Leu Ala Leu Glu Tyr Phe Val Leu Gly
                        405                410                415

Ile Leu Ser Asn Trp Leu Ile Gly Asn Leu Asn Trp Ile Ser Lys Trp
                        420                425                430
```

```
Leu Val Pro Ser Phe Leu Ile Pro Gly Pro Thr Leu Ser Lys Lys Val
        435                 440                 445

Pro Lys Arg Asp Thr Lys Thr Val Val His Thr His Trp Phe Trp Gly
    450                 455                 460

Ser Val Thr Phe Val Ser Tyr Leu Gly Ala Thr Val Ile Gln Phe Val
465                 470                 475                 480

Asp Trp Leu Tyr Leu Pro Pro Ala Lys Tyr Pro Asp Leu Trp Val Ile
                485                 490                 495

Leu Asn Thr Thr Leu Ser Phe Ala Cys Phe Gly Leu Phe Trp Leu Trp
                500                 505                 510

Ile Asn Tyr Asn Leu Tyr Ile Leu Arg Asp Phe Lys Leu Lys Asp
                515                 520                 525

<210> SEQ ID NO 79
<211> LENGTH: 528
<212> TYPE: PRT
<213> ORGANISM: Saccharomyces cerevisiae

<400> SEQUENCE: 79

Ser Phe Tyr Ala Ser Pro Met Tyr Asp Phe Leu Tyr Pro Phe Arg Pro
1               5                   10                  15

Val Gly Asn Gln Trp Leu Pro Glu Tyr Ile Ile Phe Val Cys Ala Val
            20                  25                  30

Ile Leu Arg Cys Thr Ile Gly Leu Gly Pro Tyr Ser Lys Gly Ser
        35                  40                  45

Pro Pro Leu Tyr Gly Asp Phe Glu Ala Gln Arg His Trp Met Glu Ile
    50                  55                  60

Thr Gln His Leu Pro Leu Ser Lys Trp Tyr Trp Tyr Asp Leu Gln Tyr
65                  70                  75                  80

Trp Gly Leu Asp Tyr Pro Pro Leu Thr Ala Phe His Ser Tyr Leu Leu
                85                  90                  95

Gly Leu Ile Gly Ser Phe Phe Asn Pro Ser Trp Phe Ala Leu Glu Lys
            100                 105                 110

Ser Arg Gly Phe Glu Ser Pro Asp Asn Gly Leu Lys Thr Tyr Met Arg
        115                 120                 125

Ser Thr Val Ile Ile Ser Asp Ile Leu Phe Tyr Phe Pro Ala Val Ile
    130                 135                 140

Tyr Phe Thr Lys Trp Leu Gly Arg Tyr Arg Asn Gln Ser Pro Ile Gly
145                 150                 155                 160

Gln Ser Ile Ala Ala Ser Ala Ile Leu Phe Gln Pro Ser Leu Met Leu
                165                 170                 175

Ile Asp His Gly His Phe Gln Tyr Asn Ser Val Met Leu Gly Leu Thr
            180                 185                 190

Ala Tyr Ala Ile Asn Asn Leu Leu Asp Glu Tyr Tyr Ala Met Ala Ala
        195                 200                 205

Val Cys Phe Val Leu Ser Ile Cys Phe Lys Met Ala Leu Tyr Tyr
    210                 215                 220

Ala Pro Ile Phe Phe Ala Tyr Leu Leu Ser Arg Ser Leu Leu Phe Pro
225                 230                 235                 240

Lys Phe Asn Ile Ala Arg Leu Thr Val Ile Ala Phe Ala Thr Leu Ala
                245                 250                 255

Thr Phe Ala Ile Ile Phe Ala Pro Leu Tyr Phe Leu Gly Gly Gly Leu
            260                 265                 270

Lys Asn Ile His Gln Cys Ile His Arg Ile Phe Pro Phe Ala Arg Gly
```

```
                        275                 280                 285
Ile Phe Glu Asp Lys Val Ala Asn Phe Trp Cys Val Thr Asn Val Phe
            290                 295                 300
Val Lys Tyr Lys Glu Arg Phe Thr Ile Gln Gln Leu Gln Leu Tyr Ser
305                 310                 315                 320
Leu Ile Ala Thr Val Ile Gly Phe Leu Pro Ala Met Ile Met Thr Leu
                325                 330                 335
Leu His Pro Lys Lys His Leu Leu Pro Tyr Val Leu Ile Ala Cys Ser
            340                 345                 350
Met Ser Phe Phe Leu Phe Ser Phe Gln Val His Glu Lys Thr Ile Leu
                355                 360                 365
Ile Pro Leu Leu Pro Ile Thr Leu Leu Tyr Ser Ser Thr Asp Trp Asn
            370                 375                 380
Val Leu Ser Leu Val Ser Trp Ile Asn Asn Val Ala Leu Phe Thr Leu
385                 390                 395                 400
Trp Pro Leu Leu Lys Lys Asp Gly Leu His Leu Gln Tyr Ala Val Ser
                405                 410                 415
Phe Leu Leu Ser Asn Trp Leu Ile Gly Asn Phe Ser Phe Ile Thr Pro
            420                 425                 430
Arg Phe Leu Pro Lys Ser Leu Thr Pro Gly Pro Ser Ile Ser Ser Ile
                435                 440                 445
Asn Ser Asp Tyr Arg Arg Ser Leu Leu Pro Tyr Asn Val Val Trp
            450                 455                 460
Lys Ser Phe Ile Ile Gly Thr Tyr Ile Ala Met Gly Phe Tyr His Phe
465                 470                 475                 480
Leu Asp Gln Phe Val Ala Pro Pro Ser Lys Tyr Pro Asp Leu Trp Val
                485                 490                 495
Leu Leu Asn Cys Ala Val Gly Phe Ile Cys Phe Ser Ile Phe Trp Leu
            500                 505                 510
Trp Ser Tyr Tyr Lys Ile Phe Thr Ser Gly Ser Lys Ser Met Lys Asp
                515                 520                 525

<210> SEQ ID NO 80
<211> LENGTH: 511
<212> TYPE: PRT
<213> ORGANISM: Pichia pastoris
<220> FEATURE:
<221> NAME/KEY: MOD_RES
<222> LOCATION: (22)...(36)
<223> OTHER INFORMATION: Xaa is a variable amino acid
<220> FEATURE:
<221> NAME/KEY: MOD_RES
<222> LOCATION: (365)...(377)
<223> OTHER INFORMATION: Xaa is a variable amino acid

<400> SEQUENCE: 80

Phe Glu Asn Ser Pro Val Phe Asp Phe Leu Ser Pro Phe Gly Pro Ala
1               5                   10                  15
Pro Asn Gln Trp Val Xaa Xaa Xaa Xaa Xaa Xaa Xaa Xaa Xaa
            20                  25                  30
Xaa Xaa Xaa Xaa Val Gly Leu Gly Ser Tyr Ser Gly Phe Asn Thr Pro
                35                  40                  45
Pro Met Tyr Gly Asp Phe Glu Ala Gln Arg His Trp Met Glu Ile Thr
            50                  55                  60
Gln His Leu Ser Ile Glu Lys Trp Tyr Phe Tyr Asp Leu Gln Tyr Trp
65                  70                  75                  80
Gly Leu Asp Tyr Pro Pro Leu Thr Ala Phe His Ser Tyr Phe Phe Gly
```

```
                    85                  90                  95
Lys Leu Gly Ser Phe Ile Asn Pro Ala Trp Phe Ala Leu Asp Val Ser
                100                 105                 110

Arg Gly Phe Glu Ser Val Asp Leu Lys Ser Tyr Met Arg Ala Thr Ala
            115                 120                 125

Ile Leu Ser Glu Leu Leu Cys Phe Ile Pro Ala Val Ile Trp Tyr Cys
        130                 135                 140

Arg Trp Met Gly Leu Asn Tyr Phe Asn Gln Asn Ala Ile Glu Gln Thr
145                 150                 155                 160

Ile Ile Ala Ser Ala Ile Leu Phe Asn Pro Ser Leu Ile Ile Ile Asp
                165                 170                 175

His Gly His Phe Gln Tyr Asn Ser Val Met Leu Gly Phe Ala Leu Leu
            180                 185                 190

Ser Ile Leu Asn Leu Leu Tyr Asp Asn Phe Ala Leu Ala Ala Ile Phe
        195                 200                 205

Phe Val Leu Ser Ile Ser Phe Lys Gln Met Ala Leu Tyr Tyr Ser Pro
    210                 215                 220

Ile Met Phe Phe Tyr Met Leu Ser Val Ser Cys Trp Pro Leu Lys Asn
225                 230                 235                 240

Phe Asn Leu Leu Arg Leu Ala Thr Ile Ser Ile Ala Val Leu Leu Thr
                245                 250                 255

Phe Ala Thr Leu Leu Leu Pro Phe Val Leu Val Asp Gly Met Ser Gln
            260                 265                 270

Ile Gly Gln Ile Leu Phe Arg Val Phe Pro Phe Ser Arg Gly Leu Phe
        275                 280                 285

Glu Asp Lys Val Ala Asn Phe Trp Cys Thr Thr Asn Ile Leu Val Lys
    290                 295                 300

Tyr Lys Gln Leu Phe Thr Asp Lys Thr Leu Thr Arg Ile Ser Leu Val
305                 310                 315                 320

Ala Thr Leu Ile Ala Ile Ser Pro Ser Cys Phe Ile Ile Phe Thr His
                325                 330                 335

Pro Lys Lys Val Leu Leu Pro Trp Ala Phe Ala Ala Cys Ser Trp Ala
            340                 345                 350

Phe Tyr Leu Phe Ser Phe Gln Val His Glu Lys Ser Xaa Xaa Xaa Xaa
        355                 360                 365

Xaa Xaa Xaa Xaa Xaa Xaa Xaa Xaa Glu Lys Asp Leu Asp Ile Ile
    370                 375                 380

Ser Met Val Cys Trp Ile Ser Asn Ile Ala Phe Phe Ser Met Trp Pro
385                 390                 395                 400

Leu Leu Lys Arg Asp Gly Leu Ala Leu Glu Tyr Phe Val Leu Gly Ile
                405                 410                 415

Leu Ser Asn Trp Leu Ile Gly Asn Leu Asn Trp Ile Ser Lys Trp Leu
            420                 425                 430

Val Pro Ser Phe Leu Ile Pro Gly Pro Thr Leu Ser Lys Lys Val Pro
        435                 440                 445

Lys Arg Asp Thr Lys Thr Val Val His Thr His Trp Phe Trp Gly Ser
    450                 455                 460

Val Thr Phe Val Ser Tyr Leu Gly Ala Thr Val Ile Gln Phe Val Asp
465                 470                 475                 480

Trp Leu Tyr Leu Pro Pro Ala Lys Tyr Pro Asp Leu Trp Val Ile Leu
                485                 490                 495

Asn Thr Thr Leu Ser Phe Ala Cys Phe Gly Leu Phe Trp Leu Trp
            500                 505                 510
```

<210> SEQ ID NO 81
<211> LENGTH: 480
<212> TYPE: PRT
<213> ORGANISM: Schizosaccharomyces pombe

<400> SEQUENCE: 81

```
Phe Glu Asn Gly Ala Pro Val Gln Gln Phe Val Ser Arg Phe Arg Ser
  1               5                  10                  15

Tyr Ser Ser Lys Phe Leu Phe Pro Cys Leu Ile Met Ser Leu Val
             20                  25                  30

Phe Met Gln Trp Leu Ile Ser Ile Gly Pro Tyr Ser Gly Tyr Asn Thr
         35                  40                  45

Pro Pro Met Tyr Gly Asp Phe Glu Ala Gln Arg His Trp Met Glu Leu
     50                  55                  60

Thr Leu His Thr Pro Val Ser Gln Trp Tyr Phe Arg Asp Leu Gln Trp
 65                  70                  75                  80

Trp Gly Leu Asp Tyr Pro Pro Leu Thr Ala Tyr Val Ser Trp Phe Phe
                 85                  90                  95

Gly Ile Ile Gly His Tyr Phe Asn Pro Glu Trp Phe Ala Asp Val
            100                 105                 110

Thr Ser Arg Gly Phe Glu Ser Leu Glu Leu Lys Leu Phe Met Arg Ser
            115                 120                 125

Thr Val Ile Ala Ser His Leu Leu Ile Leu Val Pro Pro Leu Met Phe
    130                 135                 140

Tyr Ser Lys Trp Trp Ser Arg Arg Ile Pro Asn Phe Val Asp Arg Asn
145                 150                 155                 160

Ala Ser Leu Ile Met Val Leu Phe Gln Pro Ala Leu Leu Leu Ile Asp
                165                 170                 175

His Gly His Phe Gln Tyr Asn Cys Val Met Leu Gly Leu Val Met Tyr
            180                 185                 190

Ala Ile Ala Asn Leu Leu Lys Asn Gln Tyr Val Ala Ala Thr Phe Phe
        195                 200                 205

Phe Cys Leu Ala Leu Thr Phe Lys Gln Met Ala Leu Tyr Phe Ala Pro
    210                 215                 220

Pro Ile Phe Phe Tyr Leu Leu Gly Thr Cys Val Lys Pro Lys Ile Arg
225                 230                 235                 240

Phe Ser Arg Phe Ile Leu Leu Ser Val Thr Val Phe Thr Phe Ser
                245                 250                 255

Leu Ile Leu Phe Pro Trp Ile Tyr Met Asp Tyr Lys Thr Leu Leu Pro
            260                 265                 270

Gln Ile Leu His Arg Val Phe Pro Phe Ala Arg Gly Leu Trp Glu Asp
        275                 280                 285

Lys Val Ala Asn Phe Trp Cys Thr Leu Asn Thr Val Phe Lys Ile Arg
    290                 295                 300

Glu Val Phe Thr Leu His Gln Leu Gln Val Ile Ser Leu Ile Phe Thr
305                 310                 315                 320

Leu Ile Ser Ile Leu Pro Ser Cys Val Ile Leu Phe Leu Tyr Pro Arg
                325                 330                 335

Lys Arg Leu Leu Ala Leu Gly Phe Ala Ser Ala Ser Trp Gly Phe Phe
            340                 345                 350

Leu Phe Ser Phe Gln Val His Glu Lys Ser Val Leu Pro Leu Leu
        355                 360                 365

Pro Thr Ser Ile Leu Leu Cys His Gly Asn Ile Thr Thr Lys Pro Trp
```

-continued

```
                370                 375                 380

Ile Ala Leu Ala Asn Asn Leu Ala Val Phe Ser Leu Trp Pro Leu Leu
385                 390                 395                 400

Lys Lys Asp Gly Leu Gly Leu Gln Tyr Phe Thr Leu Val Leu Met Trp
                405                 410                 415

Asn Trp Ile Gly Asp Met Val Val Phe Ser Lys Asn Val Leu Phe Arg
                420                 425                 430

Phe Ile Gln Leu Ser Phe Tyr Val Gly Met Ile Val Ile Leu Gly Ile
                435                 440                 445

Asp Leu Phe Ile Pro Pro Ser Arg Tyr Pro Asp Leu Trp Val Ile
        450                 455                 460

Leu Asn Val Thr Leu Ser Phe Ala Gly Phe Phe Thr Ile Tyr Leu Trp
465                 470                 475                 480

<210> SEQ ID NO 82
<211> LENGTH: 477
<212> TYPE: PRT
<213> ORGANISM: Pichia pastoris
<220> FEATURE:
<221> NAME/KEY: MOD_RES
<222> LOCATION: (329)...(341)
<223> OTHER INFORMATION: Xaa is a variable amino acid

<400> SEQUENCE: 82

Val Gly Leu Gly Ser Tyr Ser Gly Phe Asn Thr Pro Pro Met Tyr Gly
1               5                   10                  15

Asp Phe Glu Ala Gln Arg His Trp Met Glu Ile Thr Gln His Leu Ser
                20                  25                  30

Ile Glu Lys Trp Tyr Phe Tyr Asp Leu Gln Tyr Trp Gly Leu Asp Tyr
            35                  40                  45

Pro Pro Leu Thr Ala Phe His Ser Tyr Phe Phe Gly Lys Leu Gly Ser
    50                  55                  60

Phe Ile Asn Pro Ala Trp Phe Ala Leu Asp Val Ser Arg Gly Phe Glu
65                  70                  75                  80

Ser Val Asp Leu Lys Ser Tyr Met Arg Ala Thr Ala Ile Leu Ser Glu
                85                  90                  95

Leu Leu Cys Phe Ile Pro Ala Val Ile Trp Tyr Cys Arg Trp Met Gly
                100                 105                 110

Leu Asn Tyr Phe Asn Gln Asn Ala Ile Glu Gln Thr Ile Ile Ala Ser
            115                 120                 125

Ala Ile Leu Phe Asn Pro Ser Leu Ile Ile Ile Asp His Gly His Phe
    130                 135                 140

Gln Tyr Asn Ser Val Met Leu Gly Phe Ala Leu Leu Ser Ile Leu Asn
145                 150                 155                 160

Leu Leu Tyr Asp Asn Phe Ala Leu Ala Ala Ile Phe Phe Val Leu Ser
                165                 170                 175

Ile Ser Phe Lys Gln Met Ala Leu Tyr Tyr Ser Pro Ile Met Phe Phe
            180                 185                 190

Tyr Met Leu Ser Val Ser Cys Trp Pro Leu Lys Asn Phe Asn Leu Leu
    195                 200                 205

Arg Leu Ala Thr Ile Ser Ile Ala Val Leu Leu Thr Phe Ala Thr Leu
210                 215                 220

Leu Leu Pro Phe Val Leu Val Asp Gly Met Ser Gln Ile Gly Gln Ile
225                 230                 235                 240

Leu Phe Arg Val Phe Pro Phe Ser Arg Gly Leu Phe Glu Asp Lys Val
                245                 250                 255
```

```
Ala Asn Phe Trp Cys Thr Thr Asn Ile Leu Val Lys Tyr Lys Gln Leu
            260                 265                 270

Phe Thr Asp Lys Thr Leu Thr Arg Ile Ser Leu Val Ala Thr Leu Ile
        275                 280                 285

Ala Ile Ser Pro Ser Cys Phe Ile Ile Phe Thr His Pro Lys Lys Val
    290                 295                 300

Leu Leu Pro Trp Ala Phe Ala Ala Cys Ser Trp Ala Phe Tyr Leu Phe
305                 310                 315                 320

Ser Phe Gln Val His Glu Lys Ser Xaa Xaa Xaa Xaa Xaa Xaa Xaa
                325                 330                 335

Xaa Xaa Xaa Xaa Glu Lys Asp Leu Asp Ile Ser Met Val Cys
        340                 345                 350

Trp Ile Ser Asn Ile Ala Phe Phe Ser Met Trp Pro Leu Leu Lys Arg
        355                 360                 365

Asp Gly Leu Ala Leu Glu Tyr Phe Val Leu Gly Ile Leu Ser Asn Trp
370                 375                 380

Leu Ile Gly Asn Leu Asn Trp Ile Ser Lys Trp Leu Val Pro Ser Phe
385                 390                 395                 400

Leu Ile Pro Gly Pro Thr Leu Ser Lys Lys Val Pro Lys Arg Asp Thr
                405                 410                 415

Lys Thr Val Val His Thr His Trp Phe Trp Gly Ser Val Thr Phe Val
            420                 425                 430

Ser Tyr Leu Gly Ala Thr Val Ile Gln Phe Val Asp Trp Leu Tyr Leu
        435                 440                 445

Pro Pro Ala Lys Tyr Pro Asp Leu Trp Val Ile Leu Asn Thr Thr Leu
    450                 455                 460

Ser Phe Ala Cys Phe Gly Leu Phe Trp Leu Trp Ile Asn
465                 470                 475

<210> SEQ ID NO 83
<211> LENGTH: 448
<212> TYPE: PRT
<213> ORGANISM: Drosophila melanogaster

<400> SEQUENCE: 83

Ile Ser Leu Tyr Ser Tyr Ser Gly Phe Asp Ser Pro Pro Met His Gly
1               5                   10                  15

Asp Tyr Glu Ala Gln Arg His Trp Gln Glu Ile Thr Val Asn Leu Ala
            20                  25                  30

Val Gly Glu Trp Tyr Thr Asn Ser Ser Asn Asn Asp Leu Gln Tyr Trp
        35                  40                  45

Gly Leu Asp Tyr Pro Pro Leu Thr Ala Tyr His Ser Tyr Leu Val Gly
    50                  55                  60

Arg Ile Gly Ala Ser Ile Asp Pro Arg Phe Val Glu Leu His Lys Ser
65                  70                  75                  80

Arg Gly Phe Glu Ser Lys Glu His Lys Arg Phe Met Arg Ala Thr Val
                85                  90                  95

Val Ser Ala Asp Val Leu Ile Tyr Leu Pro Ala Met Leu Leu Leu Ala
            100                 105                 110

Tyr Ser Leu Asp Lys Ala Phe Arg Ser Asp Asp Lys Leu Phe Leu Phe
        115                 120                 125

Thr Leu Val Ala Ala Tyr Pro Gly Gln Thr Leu Ile Asp Asn Gly His
    130                 135                 140

Phe Gln Tyr Asn Asn Ile Ser Leu Gly Phe Ala Ala Val Ala Ile Ala
```

```
            145                 150                 155                 160

Ala Ile Leu Arg Arg Arg Phe Tyr Ala Ala Ala Phe Phe Thr Leu
                    165                 170                 175

Ala Leu Asn Tyr Lys Gln Met Glu Leu Tyr His Ser Leu Pro Phe Phe
                    180                 185                 190

Ala Phe Leu Leu Gly Glu Cys Val Ser Gln Lys Ser Phe Ala Ser Phe
                    195                 200                 205

Ile Ala Glu Ile Ser Arg Ile Ala Ala Val Val Leu Gly Thr Phe Ala
    210                 215                 220

Ile Leu Trp Val Pro Trp Leu Gly Ser Leu Gln Ala Val Leu Gln Val
    225                 230                 235                 240

Leu His Arg Leu Phe Pro Val Ala Arg Gly Val Phe Glu Asp Lys Val
                    245                 250                 255

Ala Asn Val Trp Cys Ala Val Asn Val Val Trp Lys Leu Lys Lys His
                    260                 265                 270

Ile Ser Asn Asp Gln Met Ala Leu Val Cys Ile Ala Cys Thr Leu Ile
                    275                 280                 285

Ala Ser Leu Pro Thr Asn Val Leu Leu Phe Arg Arg Arg Thr Asn Val
    290                 295                 300

Gly Phe Leu Leu Ala Leu Phe Asn Thr Ser Leu Ala Phe Phe Leu Phe
    305                 310                 315                 320

Ser Phe Gln Val His Glu Lys Thr Ile Leu Leu Thr Ala Leu Pro Ala
                    325                 330                 335

Leu Phe Leu Leu Lys Cys Trp Pro Asp Glu Met Ile Leu Phe Leu Glu
                    340                 345                 350

Val Thr Val Phe Ser Met Leu Pro Leu Leu Ala Arg Asp Glu Leu Leu
                    355                 360                 365

Val Pro Ala Val Val Ala Thr Val Ala Phe His Leu Ile Phe Lys Cys
    370                 375                 380

Phe Asp Ser Lys Ser Lys Leu Ser Asn Glu Tyr Pro Leu Lys Tyr Ile
    385                 390                 395                 400

Ala Asn Ile Ser Gln Ile Leu Met Ile Ser Val Val Ala Ser Leu
                    405                 410                 415

Thr Val Pro Ala Pro Thr Lys Tyr Pro Asp Leu Trp Pro Leu Ile Ile
                    420                 425                 430

Ser Val Thr Ser Cys Gly His Phe Phe Leu Phe Phe Leu Trp Gly Asn
                    435                 440                 445

<210> SEQ ID NO 84
<211> LENGTH: 478
<212> TYPE: PRT
<213> ORGANISM: Pichia pastoris
<220> FEATURE:
<221> NAME/KEY: MOD_RES
<222> LOCATION: (324)...(336)
<223> OTHER INFORMATION: Xaa is a variable amino acid

<400> SEQUENCE: 84

Tyr Ser Gly Phe Asn Thr Pro Pro Met Tyr Gly Asp Phe Glu Ala Gln
    1               5                   10                  15

Arg His Trp Met Glu Ile Thr Gln His Leu Ser Ile Glu Lys Trp Tyr
                    20                  25                  30

Phe Tyr Asp Leu Gln Tyr Trp Gly Leu Asp Tyr Pro Pro Leu Thr Ala
                    35                  40                  45

Phe His Ser Tyr Phe Phe Gly Lys Leu Gly Ser Phe Ile Asn Pro Ala
                    50                  55                  60
```

-continued

```
Trp Phe Ala Leu Asp Val Ser Arg Gly Phe Glu Ser Val Asp Leu Lys
 65                  70                  75                  80

Ser Tyr Met Arg Ala Thr Ala Ile Leu Ser Glu Leu Leu Cys Phe Ile
                 85                  90                  95

Pro Ala Val Ile Trp Tyr Cys Arg Trp Met Gly Leu Asn Tyr Phe Asn
            100                 105                 110

Gln Asn Ala Ile Glu Gln Thr Ile Ile Ala Ser Ala Ile Leu Phe Asn
        115                 120                 125

Pro Ser Leu Ile Ile Ile Asp His Gly His Phe Gln Tyr Asn Ser Val
130                 135                 140

Met Leu Gly Phe Ala Leu Leu Ser Ile Leu Asn Leu Leu Tyr Asp Asn
145                 150                 155                 160

Phe Ala Leu Ala Ala Ile Phe Phe Val Leu Ser Ile Ser Phe Lys Gln
                165                 170                 175

Met Ala Leu Tyr Tyr Ser Pro Ile Met Phe Phe Tyr Met Leu Ser Val
            180                 185                 190

Ser Cys Trp Pro Leu Lys Asn Phe Asn Leu Leu Arg Leu Ala Thr Ile
        195                 200                 205

Ser Ile Ala Val Leu Leu Thr Phe Ala Thr Leu Leu Pro Phe Val
210                 215                 220

Leu Val Asp Gly Met Ser Gln Ile Gly Gln Ile Leu Phe Arg Val Phe
225                 230                 235                 240

Pro Phe Ser Arg Gly Leu Phe Glu Asp Lys Val Ala Asn Phe Trp Cys
                245                 250                 255

Thr Thr Asn Ile Leu Val Lys Tyr Lys Gln Leu Phe Thr Asp Lys Thr
            260                 265                 270

Leu Thr Arg Ile Ser Leu Val Ala Thr Leu Ile Ala Ile Ser Pro Ser
        275                 280                 285

Cys Phe Ile Ile Phe Thr His Pro Lys Lys Val Leu Leu Pro Trp Ala
290                 295                 300

Phe Ala Ala Cys Ser Trp Ala Phe Tyr Leu Phe Ser Phe Gln Val His
305                 310                 315                 320

Glu Lys Ser Xaa Xaa Xaa Xaa Xaa Xaa Xaa Xaa Xaa Xaa Xaa Xaa Xaa
                325                 330                 335

Glu Lys Asp Leu Asp Ile Ile Ser Met Val Cys Trp Ile Ser Asn Ile
            340                 345                 350

Ala Phe Phe Ser Met Trp Pro Leu Leu Lys Arg Asp Gly Leu Ala Leu
        355                 360                 365

Glu Tyr Phe Val Leu Gly Ile Leu Ser Asn Trp Leu Ile Gly Asn Leu
        370                 375                 380

Asn Trp Ile Ser Lys Trp Leu Val Pro Ser Phe Leu Ile Pro Gly Pro
385                 390                 395                 400

Thr Leu Ser Lys Lys Val Pro Lys Arg Asp Thr Lys Thr Val Val His
                405                 410                 415

Thr His Trp Phe Trp Gly Ser Val Thr Phe Val Ser Tyr Leu Gly Ala
            420                 425                 430

Thr Val Ile Gln Phe Val Asp Trp Leu Tyr Leu Pro Pro Ala Lys Tyr
        435                 440                 445

Pro Asp Leu Trp Val Ile Leu Asn Thr Thr Leu Ser Phe Ala Cys Phe
450                 455                 460

Gly Leu Phe Trp Leu Trp Ile Asn Tyr Asn Leu Tyr Ile Leu
465                 470                 475
```

-continued

```
<210> SEQ ID NO 85
<211> LENGTH: 459
<212> TYPE: PRT
<213> ORGANISM: Arabidopsis thaliana

<400> SEQUENCE: 85

Tyr Ser Gly Ala Gly Ile Pro Pro Lys Phe Gly Asp Phe Glu Ala Gln
  1               5                  10                  15

Arg His Trp Met Glu Ile Thr Thr Asn Leu Pro Val Ile Asp Trp Tyr
                 20                  25                  30

Arg Asn Gly Thr Tyr Asn Asp Leu Thr Tyr Trp Gly Leu Asp Tyr Pro
             35                  40                  45

Pro Leu Thr Ala Tyr Gln Ser Tyr Ile His Gly Ile Phe Leu Arg Phe
 50                  55                  60

Phe Asn Pro Glu Ser Val Ala Leu Leu Ser Ser Arg Gly His Glu Ser
 65                  70                  75                  80

Tyr Leu Gly Lys Leu Leu Met Arg Trp Thr Val Leu Ser Ser Asp Ala
                 85                  90                  95

Phe Ile Phe Phe Pro Ala Ala Leu Phe Phe Val Leu Val Tyr His Arg
            100                 105                 110

Asn Arg Thr Arg Gly Gly Lys Ser Glu Val Ala Trp His Ile Ala Met
            115                 120                 125

Ile Leu Leu Asn Pro Cys Leu Ile Leu Ile Asp His Gly His Phe Gln
130                 135                 140

Tyr Asn Cys Ile Ser Leu Gly Leu Thr Val Gly Ala Ile Ala Ala Val
145                 150                 155                 160

Leu Cys Glu Ser Glu Val Leu Thr Cys Val Leu Phe Ser Leu Ala Leu
                165                 170                 175

Ser His Lys Gln Met Ser Ala Tyr Phe Ala Pro Ala Phe Phe Ser His
            180                 185                 190

Leu Leu Gly Lys Cys Leu Arg Arg Lys Ser Pro Ile Leu Ser Val Ile
            195                 200                 205

Lys Leu Gly Ile Ala Val Ile Val Thr Phe Val Ile Phe Trp Trp Pro
210                 215                 220

Tyr Val His Ser Leu Asp Asp Phe Leu Met Val Leu Ser Arg Leu Ala
225                 230                 235                 240

Pro Phe Glu Arg Gly Ile Tyr Glu Asp Tyr Val Ala Asn Phe Trp Cys
                245                 250                 255

Thr Thr Ser Ile Leu Ile Lys Trp Lys Asn Leu Phe Thr Thr Gln Ser
            260                 265                 270

Leu Lys Ser Ile Ser Leu Ala Ala Thr Ile Leu Ala Ser Leu Pro Ser
            275                 280                 285

Met Val Gln Gln Ile Leu Ser Pro Ser Asn Glu Gly Phe Leu Tyr Gly
290                 295                 300

Leu Leu Asn Ser Ser Met Ala Phe Tyr Leu Phe Ser Phe Gln Val His
305                 310                 315                 320

Glu Lys Ser Ile Leu Met Pro Phe Leu Ser Ala Thr Leu Leu Ala Leu
                325                 330                 335

Lys Leu Pro Asp His Phe Ser Leu Thr Tyr Ala Leu Phe Ser
            340                 345                 350

Met Phe Pro Leu Leu Cys Arg Asp Lys Leu Leu Ile Pro Tyr Leu Thr
            355                 360                 365

Leu Ser Phe Leu Phe Thr Val Ile Tyr His Ser Pro Gly Asn His His
370                 375                 380
```

```
Ala Ile Gln Lys Thr Asp Val Ser Phe Phe Ser Phe Lys Asn Phe Pro
385                 390                 395                 400

Gly Tyr Val Phe Leu Leu Arg Thr His Phe Ile Ser Val Val Leu
            405                 410                 415

His Val Leu Tyr Leu Thr Ile Lys Pro Pro Gln Lys Tyr Pro Phe Leu
                420                 425                 430

Phe Glu Ala Leu Ile Met Ile Leu Cys Phe Ser Tyr Phe Ile Met Phe
            435                 440                 445

Ala Phe Tyr Thr Asn Tyr Thr Gln Trp Thr Leu
        450                 455
```

<210> SEQ ID NO 86
<211> LENGTH: 836
<212> TYPE: DNA
<213> ORGANISM: Kluyveromyces lactis

<400> SEQUENCE: 86

```
atctctgttt caacagctct tgcattcatt ggttctttcg gtccaatcta tatctttgga     60
ggatacaaga acttagtgca atcaatgcac aggatttttc catttgccag gggtatcttt    120
gaagataaag ttgcgaattt ttggtgcgtt tctaatattt tcatcaaata tagaaatcta    180
ttcactcaga aggatcttca attatactca ttactcgcaa cagttattgg gcttttacca    240
tcattcatta taacatttt ataccccgaag agacattac taccatatgc tttggccgca    300
tgttcgatgt cattcttctt attcagcttc caggttcatg aaaagacaat cttattacct    360
ttacttccta ttacactctt gtacacgtca agagattgga atgttctatc attggtttgt    420
tggattaaca acgtggcatt gtttacactc tggccattac tgaaaaagga caatctagta    480
ttgcaatatg gagtcatgtt catgtttagc aattggttga tcggtaactt cagtttcgtc    540
acaccacgct tcctcccaaa atttttgaca ccagggccat ccatcagtga tatagatgtt    600
gattatagac gggcaagttt actacccaag agcctaatat ggagattaat cattgttggc    660
tcatatattg caatgggat tattcatttt ctagactatt acgtctcccc gccatcaaaa    720
taccctgatt tatgggtgct tgccaattgt tccttgggct tctcatgttt tgtgacattt    780
tggatatgga acaattataa ttattcgaaa tgagaaacag cactttgcaa gattta        836
```

<210> SEQ ID NO 87
<211> LENGTH: 277
<212> TYPE: PRT
<213> ORGANISM: Kluyveromyces lactis

<400> SEQUENCE: 87

```
Ile Ser Val Ser Thr Ala Leu Ala Phe Ile Gly Ser Phe Gly Pro Ile
  1               5                  10                  15

Tyr Ile Phe Gly Gly Tyr Lys Asn Leu Val Gln Ser Met His Arg Ile
             20                  25                  30

Phe Pro Phe Ala Arg Gly Ile Phe Glu Asp Lys Val Ala Asn Phe Trp
         35                  40                  45

Cys Val Ser Asn Ile Phe Ile Lys Tyr Arg Asn Leu Phe Thr Gln Lys
 50                  55                  60

Asp Leu Gln Leu Tyr Ser Leu Leu Ala Thr Val Ile Gly Leu Leu Pro
 65                  70                  75                  80

Ser Phe Ile Ile Thr Phe Leu Tyr Pro Lys Arg His Leu Leu Pro Tyr
             85                  90                  95

Ala Leu Ala Ala Cys Ser Met Ser Phe Phe Leu Phe Ser Phe Gln Val
```

```
            100                 105                 110
His Glu Lys Thr Ile Leu Leu Pro Leu Leu Pro Ile Thr Leu Leu Tyr
            115                 120                 125
Thr Ser Arg Asp Trp Asn Val Leu Ser Leu Val Cys Trp Ile Asn Asn
        130                 135                 140
Val Ala Leu Phe Thr Leu Trp Pro Leu Leu Lys Lys Asp Asn Leu Val
145                 150                 155                 160
Leu Gln Tyr Gly Val Met Phe Met Phe Ser Asn Trp Leu Ile Gly Asn
                165                 170                 175
Phe Ser Phe Val Thr Pro Arg Phe Leu Pro Lys Phe Leu Thr Pro Gly
            180                 185                 190
Pro Ser Ile Ser Asp Ile Asp Val Asp Tyr Arg Arg Ala Ser Leu Leu
            195                 200                 205
Pro Lys Ser Leu Ile Trp Arg Leu Ile Ile Val Gly Ser Tyr Ile Ala
        210                 215                 220
Met Gly Ile Ile His Phe Leu Asp Tyr Tyr Val Ser Pro Pro Ser Lys
225                 230                 235                 240
Tyr Pro Asp Leu Trp Val Leu Ala Asn Cys Ser Leu Gly Phe Ser Cys
                245                 250                 255
Phe Val Thr Phe Trp Ile Trp Asn Asn Tyr Asn Tyr Ser Lys Glu Thr
            260                 265                 270
Ala Leu Cys Lys Ile
            275

<210> SEQ ID NO 88
<211> LENGTH: 284
<212> TYPE: PRT
<213> ORGANISM: Kluyveromyces lactis
<220> FEATURE:
<221> NAME/KEY: MOD_RES
<222> LOCATION: (116)...(127)
<223> OTHER INFORMATION: Xaa is a variable amino acid
<220> FEATURE:
<221> NAME/KEY: MOD_RES
<222> LOCATION: 271
<223> OTHER INFORMATION: Xaa is a variable amino acid

<400> SEQUENCE: 88

Ile Ser Val Ser Thr Ala Leu Ala Phe Ile Gly Ser Phe Gly Pro Ile
1               5                   10                  15
Tyr Ile Phe Gly Gly Tyr Lys Asn Leu Val Gln Ser Met His Arg Ile
                20                  25                  30
Phe Pro Phe Ala Arg Gly Ile Phe Glu Asp Lys Val Ala Asn Phe Trp
            35                  40                  45
Cys Val Ser Asn Ile Phe Ile Lys Tyr Arg Asn Leu Phe Thr Gln Lys
        50                  55                  60
Asp Leu Gln Leu Tyr Ser Leu Leu Ala Thr Val Ile Gly Leu Leu Pro
65                  70                  75                  80
Ser Phe Ile Ile Thr Phe Leu Tyr Pro Lys Arg His Leu Leu Pro Tyr
                85                  90                  95
Ala Leu Ala Ala Cys Ser Met Ser Phe Phe Leu Phe Ser Phe Gln Val
            100                 105                 110
His Glu Lys Xaa Xaa Xaa Xaa Xaa Xaa Xaa Xaa Xaa Xaa Xaa Xaa Tyr
            115                 120                 125
Thr Ser Arg Asp Trp Asn Val Leu Ser Leu Val Cys Trp Ile Asn Asn
        130                 135                 140
Val Ala Leu Phe Thr Leu Trp Pro Leu Leu Lys Lys Asp Asn Leu Val
```

```
                145                 150                 155                 160
Leu Gln Tyr Gly Val Met Phe Met Phe Ser Asn Trp Leu Ile Gly Asn
                    165                 170                 175

Phe Ser Phe Val Thr Pro Arg Phe Leu Pro Lys Phe Leu Thr Pro Gly
                180                 185                 190

Pro Ser Ile Ser Asp Ile Asp Val Asp Tyr Arg Arg Ala Ser Leu Leu
            195                 200                 205

Pro Lys Ser Leu Ile Trp Arg Leu Ile Val Gly Ser Tyr Ile Ala
        210                 215                 220

Met Gly Ile Ile His Phe Leu Asp Tyr Tyr Val Ser Pro Pro Ser Gln
225                 230                 235                 240

Glu Arg Tyr Lys Tyr Pro Asp Leu Trp Val Leu Ala Asn Cys Ser Leu
                    245                 250                 255

Gly Phe Ser Cys Phe Val Thr Phe Trp Ile Trp Asn Asn Tyr Xaa Leu
                260                 265                 270

Phe Glu Arg Met Arg Asn Ser Thr Leu Gln Asp Leu
            275                 280

<210> SEQ ID NO 89
<211> LENGTH: 280
<212> TYPE: PRT
<213> ORGANISM: Saccharomyces cerevisiae

<400> SEQUENCE: 89

Ile Ala Phe Ala Thr Leu Ala Thr Phe Ala Ile Ile Phe Ala Pro Leu
1               5                   10                  15

Tyr Phe Leu Gly Gly Gly Leu Lys Asn Ile His Gln Cys Ile His Arg
                20                  25                  30

Ile Phe Pro Phe Ala Arg Gly Ile Phe Glu Asp Lys Val Ala Asn Phe
            35                  40                  45

Trp Cys Val Thr Asn Val Phe Val Lys Tyr Lys Glu Arg Phe Thr Ile
        50                  55                  60

Gln Gln Leu Gln Leu Tyr Ser Leu Ile Ala Thr Val Ile Gly Phe Leu
65                  70                  75                  80

Pro Ala Met Ile Met Thr Leu Leu His Pro Lys Lys His Leu Leu Pro
                85                  90                  95

Tyr Val Leu Ile Ala Cys Ser Met Ser Phe Phe Leu Phe Ser Phe Gln
                100                 105                 110

Val His Glu Lys Thr Ile Leu Ile Pro Leu Leu Pro Ile Thr Leu Leu
            115                 120                 125

Tyr Ser Ser Thr Asp Trp Asn Val Leu Ser Leu Val Ser Trp Ile Asn
        130                 135                 140

Asn Val Ala Leu Phe Thr Leu Trp Pro Leu Leu Lys Lys Asp Gly Leu
145                 150                 155                 160

His Leu Gln Tyr Ala Val Ser Phe Leu Leu Ser Asn Trp Leu Ile Gly
                    165                 170                 175

Asn Phe Ser Phe Ile Thr Pro Arg Phe Leu Pro Lys Ser Leu Thr Pro
                180                 185                 190

Gly Pro Ser Ile Ser Ser Ile Asn Ser Asp Tyr Arg Arg Arg Ser Leu
            195                 200                 205

Leu Pro Tyr Asn Val Val Trp Lys Ser Phe Ile Ile Gly Thr Tyr Ile
        210                 215                 220

Ala Met Gly Phe Tyr His Phe Leu Asp Gln Phe Val Ala Pro Pro Ser
225                 230                 235                 240
```

```
Lys Tyr Pro Asp Leu Trp Val Leu Leu Asn Cys Ala Val Gly Phe Ile
            245                 250                 255

Cys Phe Ser Ile Phe Trp Leu Trp Ser Tyr Tyr Lys Ile Phe Thr Ser
        260                 265                 270

Gly Ser Lys Ser Met Lys Asp Leu
        275                 280

<210> SEQ ID NO 90
<211> LENGTH: 284
<212> TYPE: PRT
<213> ORGANISM: Kluyveromyces lactis
<220> FEATURE:
<221> NAME/KEY: MOD_RES
<222> LOCATION: (116)...(127)
<223> OTHER INFORMATION: Xaa is a variable amino acid
<220> FEATURE:
<221> NAME/KEY: MOD_RES
<222> LOCATION: 271
<223> OTHER INFORMATION: Xaa is a variable amino acid

<400> SEQUENCE: 90

Ile Ser Val Ser Thr Ala Leu Ala Phe Ile Gly Ser Phe Gly Pro Ile
1               5                   10                  15

Tyr Ile Phe Gly Gly Tyr Lys Asn Leu Val Gln Ser Met His Arg Ile
            20                  25                  30

Phe Pro Phe Ala Arg Gly Ile Phe Glu Asp Lys Val Ala Asn Phe Trp
        35                  40                  45

Cys Val Ser Asn Ile Phe Ile Lys Tyr Arg Asn Leu Phe Thr Gln Lys
    50                  55                  60

Asp Leu Gln Leu Tyr Ser Leu Leu Ala Thr Val Ile Gly Leu Leu Pro
65                  70                  75                  80

Ser Phe Ile Ile Thr Phe Leu Tyr Pro Lys Arg His Leu Leu Pro Tyr
                85                  90                  95

Ala Leu Ala Ala Cys Ser Met Ser Phe Phe Leu Phe Ser Phe Gln Val
            100                 105                 110

His Glu Lys Xaa Xaa Xaa Xaa Xaa Xaa Xaa Xaa Xaa Xaa Xaa Xaa Tyr
        115                 120                 125

Thr Ser Arg Asp Trp Asn Val Leu Ser Leu Val Cys Trp Ile Asn Asn
    130                 135                 140

Val Ala Leu Phe Thr Leu Trp Pro Leu Leu Lys Lys Asp Asn Leu Val
145                 150                 155                 160

Leu Gln Tyr Gly Val Met Phe Met Phe Ser Asn Trp Leu Ile Gly Asn
                165                 170                 175

Phe Ser Phe Val Thr Pro Arg Phe Leu Pro Lys Phe Leu Thr Pro Gly
            180                 185                 190

Pro Ser Ile Ser Asp Ile Asp Val Asp Tyr Arg Arg Ala Ser Leu Leu
        195                 200                 205

Pro Lys Ser Leu Ile Trp Arg Leu Ile Ile Val Gly Ser Tyr Ile Ala
    210                 215                 220

Met Gly Ile Ile His Phe Leu Asp Tyr Tyr Val Ser Pro Pro Ser Gln
225                 230                 235                 240

Glu Arg Tyr Lys Tyr Pro Asp Leu Trp Val Leu Ala Asn Cys Ser Leu
                245                 250                 255

Gly Phe Ser Cys Phe Val Thr Phe Trp Ile Trp Asn Asn Tyr Xaa Leu
            260                 265                 270

Phe Glu Arg Met Arg Asn Ser Thr Leu Gln Asp Leu
        275                 280
```

```
<210> SEQ ID NO 91
<211> LENGTH: 250
<212> TYPE: PRT
<213> ORGANISM: Schizosaccharomyces pombe

<400> SEQUENCE: 91

Leu Ser Val Thr Val Phe Thr Phe Ser Leu Ile Leu Phe Pro Trp
1               5                   10                  15

Ile Tyr Met Asp Tyr Lys Thr Leu Leu Pro Gln Ile Leu His Arg Val
            20                  25                  30

Phe Pro Phe Ala Arg Gly Leu Trp Glu Asp Lys Val Ala Asn Phe Trp
            35                  40                  45

Cys Thr Leu Asn Thr Val Phe Lys Ile Arg Glu Val Phe Thr Leu His
50                  55                  60

Gln Leu Gln Val Ile Ser Leu Ile Phe Thr Leu Ile Ser Ile Leu Pro
65                  70                  75                  80

Ser Cys Val Ile Leu Phe Leu Tyr Pro Arg Lys Arg Leu Leu Ala Leu
                85                  90                  95

Gly Phe Ala Ser Ala Ser Trp Gly Phe Phe Leu Phe Ser Phe Gln Val
            100                 105                 110

His Glu Lys Ser Val Leu Leu Pro Leu Leu Pro Thr Ser Ile Leu Leu
        115                 120                 125

Cys His Gly Asn Ile Thr Thr Lys Pro Trp Ile Ala Leu Ala Asn Asn
130                 135                 140

Leu Ala Val Phe Ser Leu Trp Pro Leu Leu Lys Lys Asp Gly Leu Gly
145                 150                 155                 160

Leu Gln Tyr Phe Thr Leu Val Leu Met Trp Asn Trp Ile Gly Asp Met
                165                 170                 175

Val Val Phe Ser Lys Asn Val Leu Phe Arg Phe Ile Gln Leu Ser Phe
            180                 185                 190

Tyr Val Gly Met Ile Val Ile Leu Gly Ile Asp Leu Phe Ile Pro Pro
        195                 200                 205

Pro Ser Arg Tyr Pro Asp Leu Trp Val Ile Leu Asn Val Thr Leu Ser
210                 215                 220

Phe Ala Gly Phe Phe Thr Ile Tyr Leu Trp Thr Leu Gly Arg Leu Leu
225                 230                 235                 240

His Ile Ser Ser Lys Leu Ser Thr Asp Leu
                245                 250

<210> SEQ ID NO 92
<211> LENGTH: 238
<212> TYPE: PRT
<213> ORGANISM: Kluyveromyces lactis
<220> FEATURE:
<221> NAME/KEY: MOD_RES
<222> LOCATION: (88)...(99)
<223> OTHER INFORMATION: Xaa is a variable amino acid

<400> SEQUENCE: 92

Met His Arg Ile Phe Pro Phe Ala Arg Gly Ile Phe Glu Asp Lys Val
1               5                   10                  15

Ala Asn Phe Trp Cys Val Ser Asn Ile Phe Ile Lys Tyr Arg Asn Leu
            20                  25                  30

Phe Thr Gln Lys Asp Leu Gln Leu Tyr Ser Leu Leu Ala Thr Val Ile
        35                  40                  45

Gly Leu Leu Pro Ser Phe Ile Ile Thr Phe Leu Tyr Pro Lys Arg His
    50                  55                  60
```

```
Leu Leu Pro Tyr Ala Leu Ala Ala Cys Ser Met Ser Phe Phe Leu Phe
 65                  70                  75                  80

Ser Phe Gln Val His Glu Lys Xaa Xaa Xaa Xaa Xaa Xaa Xaa Xaa Xaa
                 85                  90                  95

Xaa Xaa Xaa Tyr Thr Ser Arg Asp Trp Asn Val Leu Ser Leu Val Cys
            100                 105                 110

Trp Ile Asn Asn Val Ala Leu Phe Thr Leu Trp Pro Leu Leu Lys Lys
            115                 120                 125

Asp Asn Leu Val Leu Gln Tyr Gly Val Met Phe Met Phe Ser Asn Trp
        130                 135                 140

Leu Ile Gly Asn Phe Ser Phe Val Thr Pro Arg Phe Leu Pro Lys Phe
145                 150                 155                 160

Leu Thr Pro Gly Pro Ser Ile Ser Asp Ile Asp Val Asp Tyr Arg Arg
                165                 170                 175

Ala Ser Leu Leu Pro Lys Ser Leu Ile Trp Arg Leu Ile Ile Val Gly
            180                 185                 190

Ser Tyr Ile Ala Met Gly Ile Ile His Phe Leu Asp Tyr Tyr Val Ser
        195                 200                 205

Pro Pro Ser Lys Tyr Pro Asp Leu Trp Val Leu Ala Asn Cys Ser Leu
210                 215                 220

Gly Phe Ser Cys Phe Val Thr Phe Trp Ile Trp Asn Asn Tyr
225                 230                 235

<210> SEQ ID NO 93
<211> LENGTH: 219
<212> TYPE: PRT
<213> ORGANISM: Arabidopsis thaliana

<400> SEQUENCE: 93

Leu Ser Arg Leu Ala Pro Phe Glu Arg Gly Ile Tyr Glu Asp Tyr Val
 1               5                  10                  15

Ala Asn Phe Trp Cys Thr Thr Ser Ile Leu Ile Lys Trp Lys Asn Leu
            20                  25                  30

Phe Thr Thr Gln Ser Leu Lys Ser Ile Ser Leu Ala Ala Thr Ile Leu
        35                  40                  45

Ala Ser Leu Pro Ser Met Val Gln Gln Ile Leu Ser Pro Ser Asn Glu
 50                  55                  60

Gly Phe Leu Tyr Gly Leu Leu Asn Ser Ser Met Ala Phe Tyr Leu Phe
 65                  70                  75                  80

Ser Phe Gln Val His Glu Lys Ser Ile Leu Met Pro Phe Leu Ser Ala
                 85                  90                  95

Thr Leu Leu Ala Leu Lys Leu Pro Asp His Phe Ser His Leu Thr Tyr
            100                 105                 110

Tyr Ala Leu Phe Ser Met Phe Pro Leu Leu Cys Arg Asp Lys Leu Leu
            115                 120                 125

Ile Pro Tyr Leu Thr Leu Ser Phe Leu Phe Thr Val Ile Tyr His Ser
        130                 135                 140

Pro Gly Asn His His Ala Ile Gln Lys Thr Asp Val Ser Phe Phe Ser
145                 150                 155                 160

Phe Lys Asn Phe Pro Gly Tyr Val Phe Leu Arg Thr His Phe Phe
                165                 170                 175

Ile Ser Val Val Leu His Val Leu Tyr Leu Thr Ile Lys Pro Pro Gln
            180                 185                 190

Lys Tyr Pro Phe Leu Phe Glu Ala Leu Ile Met Ile Leu Cys Phe Ser
```

Tyr Phe Ile Met Phe Ala Phe Tyr Thr Asn Tyr
    210                 215

<210> SEQ ID NO 94
<211> LENGTH: 252
<212> TYPE: PRT
<213> ORGANISM: Kluyveromyces lactis
<220> FEATURE:
<221> NAME/KEY: MOD_RES
<222> LOCATION: (114)...(125)
<223> OTHER INFORMATION: Xaa is a variable amino acid

<400> SEQUENCE: 94

Val Ser Thr Ala Leu Ala Phe Ile Gly Ser Phe Gly Pro Ile Tyr Ile
1               5                   10                  15

Phe Gly Gly Tyr Lys Asn Leu Val Gln Ser Met His Arg Ile Phe Pro
            20                  25                  30

Phe Ala Arg Gly Ile Phe Glu Asp Lys Val Ala Asn Phe Trp Cys Val
        35                  40                  45

Ser Asn Ile Phe Ile Lys Tyr Arg Asn Leu Phe Thr Gln Lys Asp Leu
    50                  55                  60

Gln Leu Tyr Ser Leu Leu Ala Thr Val Ile Gly Leu Leu Pro Ser Phe
65                  70                  75                  80

Ile Ile Thr Phe Leu Tyr Pro Lys Arg His Leu Leu Pro Tyr Ala Leu
                85                  90                  95

Ala Ala Cys Ser Met Ser Phe Phe Leu Phe Ser Phe Gln Val His Glu
            100                 105                 110

Lys Xaa Xaa Xaa Xaa Xaa Xaa Xaa Xaa Xaa Xaa Tyr Thr Ser
        115                 120                 125

Arg Asp Trp Asn Val Leu Ser Leu Val Cys Trp Ile Asn Asn Val Ala
    130                 135                 140

Leu Phe Thr Leu Trp Pro Leu Leu Lys Lys Asp Asn Leu Val Leu Gln
145                 150                 155                 160

Tyr Gly Val Met Phe Met Val Thr Pro Arg Phe Leu Pro Lys Phe Leu
                165                 170                 175

Thr Pro Gly Pro Ser Ile Ser Asp Ile Asp Val Asp Tyr Arg Arg Ala
            180                 185                 190

Ser Leu Leu Pro Lys Ser Leu Ile Trp Arg Leu Ile Ile Val Gly Ser
        195                 200                 205

Tyr Ile Ala Met Gly Ile Ile His Phe Leu Asp Tyr Tyr Val Ser Pro
    210                 215                 220

Pro Ser Lys Tyr Pro Asp Leu Trp Val Leu Ala Asn Cys Ser Leu Gly
225                 230                 235                 240

Phe Ser Cys Phe Val Thr Phe Trp Ile Trp Asn Asn
                245                 250

<210> SEQ ID NO 95
<211> LENGTH: 259
<212> TYPE: PRT
<213> ORGANISM: Homo sapiens

<400> SEQUENCE: 95

Val Lys Leu Ala Cys Ile Val Val Ala Ser Phe Val Leu Cys Trp Leu
1               5                   10                  15

Pro Phe Phe Thr Glu Arg Glu Gln Thr Leu Gln Val Leu Arg Arg Leu
            20                  25                  30

```
Phe Pro Val Asp Arg Gly Leu Phe Glu Asp Lys Val Ala Asn Ile Trp
        35                  40                  45
Cys Ser Phe Asn Val Phe Leu Lys Ile Lys Asp Ile Leu Pro Arg His
 50                  55                  60
Ile Gln Leu Ile Met Ser Phe Cys Phe Thr Phe Leu Ser Leu Leu Pro
 65                  70                  75                  80
Ala Cys Ile Lys Leu Ile Leu Gln Pro Ser Ser Lys Gly Phe Lys Phe
                 85                  90                  95
Thr Leu Val Ser Cys Ala Leu Ser Phe Phe Leu Phe Ser Phe Gln Val
            100                 105                 110
His Glu Lys Ser Ile Leu Leu Val Ser Leu Pro Val Cys Leu Val Leu
        115                 120                 125
Ser Glu Ile Pro Phe Met Ser Thr Trp Phe Leu Leu Val Ser Thr Phe
130                 135                 140
Ser Met Leu Pro Leu Leu Leu Lys Asp Glu Leu Leu Met Pro Ser Val
145                 150                 155                 160
Val Thr Thr Met Ala Phe Phe Ile Ala Cys Val Thr Ser Phe Ser Ile
                165                 170                 175
Phe Glu Lys Thr Ser Glu Glu Leu Gln Leu Lys Ser Phe Ser Ile
            180                 185                 190
Ser Val Arg Lys Tyr Leu Pro Cys Phe Thr Phe Leu Ser Arg Ile Ile
        195                 200                 205
Gln Tyr Leu Phe Leu Ile Ser Val Ile Thr Met Val Leu Leu Thr Leu
210                 215                 220
Met Thr Val Thr Leu Asp Pro Pro Gln Lys Leu Pro Asp Leu Phe Ser
225                 230                 235                 240
Val Leu Val Cys Phe Val Ser Cys Leu Asn Phe Leu Phe Leu Val
                245                 250                 255
Tyr Phe Asn

<210> SEQ ID NO 96
<211> LENGTH: 1617
<212> TYPE: DNA
<213> ORGANISM: Mus musculus

<400> SEQUENCE: 96
atgaagatga  dacgctacaa  gctctttctc  atgttctgta  tggctggcct  gtgcctcata     60
tccttcctgc  acttctttaa  gaccttatcc  tatgtcacct  tcccgagaga  actggcctcc    120
ctcagcccta  acctcgtatc  cagcttcttc  tggaacaatg  ccctgtcac   tccccaggcc    180
agtccggagc  cgggtggccc  cgacctattg  cggacacccc  tctactccca  ctctcccctg    240
ctccagccac  tgtccccgag  caaggccaca  gaggaactgc  accgggtgga  cttcgtgttg    300
ccggaggaca  ccacggagta  ttttgtgcgc  accaaagctg  gtggtgtgtg  cttcaaacca    360
ggtaccagga  tgctggagaa  accttcgcca  gggcggacag  aggagaagcc  cgaagtgtct    420
gagggctcct  cagcccgggg  acctgctcgg  aggcccatga  ggcacgtgtt  gagtacgcgg    480
gagcgcctgg  gcagccgggg  cactaggcgc  aagtgggttg  agtgtgtgtg  cctgccaggc    540
tggcacgggc  ccagttgcgg  ggtgccacg   gtggtgcagt  attccaacct  gcccaccaag    600
gaacgcctgg  tacccaggga  ggtaccgagg  cgggttatca  cgccatcaa   catcaaccac    660
gagttcgacc  tgctggatgt  gcgcttccat  gagctgggag  atgttgtgga  cgccttcgtg    720
gtctgtgaat  ctaatttcac  cgcctacggg  gagcctcggc  cgctcaagtt  ccgagagatg    780
ctgaccaatg  gcaccttcga  gtacatccgc  cacaaggtgc  tctatgtctt  cctggaccat    840
```

```
ttcccacctg gtggccgtca ggacggctgg attgcggatg actacctgcg caccttcctc    900
acccaggatg gcgtctcccg cctgcgcaac ctgcggcccg atgacgtctt tatcatcgac    960
gatgcggacg agatccctgc gcgtgatggt gtgctgttcc tcaaactcta cgatggctgg   1020
acagagccct tcgccttcca catgcggaag tccctgtatg gtttcttctg gaagcagccg   1080
ggcacactgg aggtggtgtc aggctgcacc atggacatgc tgcaggccgt gtatgggctg   1140
gatggcatcc gcctgcgccg ccgccagtac tacaccatgc ccaacttccg gcagtatgag   1200
aaccgcaccg gccacatcct agtgcagtgg tctctcggca gcccctgca cttcgcgggc   1260
tggcattgct cctggtgctt cacacccgag ggcatctact ttaaactcgt gtcagcccag   1320
aatggcgact tccccgctg gggtgactat gaggacaaga gggacctcaa ttacatccgc   1380
agcttgatcc gcactggggg atggttcgac ggaacgcagc aggagtaccc tcctgcggac   1440
cccagtgagc acatgtatgc tcctaaatac ctgctcaaga actatgacca gttccgctac   1500
ttgctggaaa atccctaccg ggagcccaag agcactgtag agggtgggcg ccagaaccag   1560
ggctcagatg gaaggccatc tgctgtcagg ggcaagttgg atacagtgga gggctag     1617
```

<210> SEQ ID NO 97
<211> LENGTH: 536
<212> TYPE: PRT
<213> ORGANISM: Mus musculus

<400> SEQUENCE: 97

```
Met Arg Arg Tyr Lys Leu Phe Leu Met Phe Cys Met Ala Gly Leu Cys
  1               5                  10                  15

Leu Ile Ser Phe Leu His Phe Lys Thr Leu Ser Tyr Val Thr Phe
             20                  25                  30

Pro Arg Glu Leu Ala Ser Leu Ser Pro Asn Leu Ile Ser Ser Phe Phe
         35                  40                  45

Trp Asn Asn Ala Pro Val Thr Pro Gln Ala Ser Pro Glu Pro Gly Asp
 50                  55                  60

Pro Asp Leu Leu Arg Thr Pro Leu Tyr Ser His Ser Pro Leu Leu Gln
 65                  70                  75                  80

Pro Leu Ser Pro Ser Lys Ala Thr Glu Glu Leu His Arg Val Asp Phe
                 85                  90                  95

Val Leu Pro Glu Asp Thr Thr Glu Tyr Phe Val Arg Thr Lys Ala Gly
            100                 105                 110

Gly Val Cys Phe Lys Pro Gly Thr Arg Met Leu Glu Lys Pro Ser Pro
        115                 120                 125

Gly Arg Thr Glu Glu Lys Thr Glu Val Ser Glu Gly Ser Ser Ala Arg
    130                 135                 140

Gly Pro Ala Arg Arg Pro Met Arg His Val Leu Ser Ser Arg Glu Arg
145                 150                 155                 160

Leu Gly Ser Arg Gly Thr Arg Arg Lys Trp Val Glu Cys Val Cys Leu
                165                 170                 175

Pro Gly Trp His Gly Pro Ser Cys Gly Val Pro Thr Val Val Gln Tyr
            180                 185                 190

Ser Asn Leu Pro Thr Lys Glu Arg Leu Val Pro Arg Glu Val Pro Arg
        195                 200                 205

Arg Val Ile Asn Ala Ile Asn Ile Asn His Glu Phe Asp Leu Leu Asp
    210                 215                 220

Val Arg Phe His Glu Leu Gly Asp Val Val Asp Ala Phe Val Val Cys
225                 230                 235                 240
```

```
Asp Ser Asn Phe Thr Ala Tyr Gly Glu Pro Arg Pro Leu Lys Phe Arg
            245                 250                 255

Glu Met Leu Thr Asn Gly Thr Phe Glu Tyr Ile Arg His Lys Val Leu
            260                 265                 270

Tyr Val Phe Leu Asp His Phe Pro Pro Gly Gly Arg Gln Asp Gly Trp
            275                 280             285

Ile Ala Asp Asp Tyr Leu Arg Thr Phe Leu Thr Gln Asp Gly Val Ser
            290                 295                 300

Arg Leu Arg Asn Leu Arg Pro Asp Asp Val Phe Ile Ile Asp Asp Ala
305                 310                 315                 320

Asp Glu Ile Pro Ala Arg Asp Gly Val Leu Phe Leu Lys Leu Tyr Asp
            325                 330                 335

Gly Trp Thr Glu Pro Phe Ala Phe His Met Arg Lys Ser Leu Tyr Gly
            340                 345                 350

Phe Phe Trp Lys Gln Pro Gly Thr Leu Glu Val Val Ser Gly Cys Thr
            355                 360                 365

Met Asp Met Leu Gln Ala Val Tyr Gly Leu Asp Gly Ile Arg Leu Arg
            370                 375             380

Arg Arg Gln Tyr Tyr Thr Met Pro Asn Phe Arg Gln Tyr Glu Asn Arg
385                 390                 395                 400

Thr Gly His Ile Leu Val Gln Trp Ser Leu Gly Ser Pro Leu His Phe
            405                 410                 415

Ala Gly Trp His Cys Ser Trp Cys Phe Thr Pro Glu Gly Ile Tyr Phe
            420                 425             430

Lys Leu Val Ser Ala Gln Asn Gly Asp Phe Pro Arg Trp Gly Asp Tyr
            435                 440                 445

Glu Asp Lys Arg Asp Leu Asn Tyr Ile Arg Ser Leu Ile Arg Thr Gly
            450                 455                 460

Gly Trp Phe Asp Gly Thr Gln Gln Glu Tyr Pro Pro Ala Asp Pro Ser
465                 470                 475                 480

Glu His Met Tyr Ala Pro Lys Tyr Leu Leu Lys Asn Tyr Asp Gln Phe
            485                 490                 495

Arg Tyr Leu Leu Glu Asn Pro Tyr Arg Glu Pro Lys Ser Thr Val Glu
            500                 505                 510

Gly Gly Arg Gln Asn Gln Gly Ser Asp Gly Arg Ser Ser Ala Val Arg
            515                 520                 525

Gly Lys Leu Asp Thr Ala Glu Gly
530                 535

<210> SEQ ID NO 98
<211> LENGTH: 2115
<212> TYPE: DNA
<213> ORGANISM: Homo sapiens

<400> SEQUENCE: 98
gaaatgaacc tctcttattg attttattg gcctagagcc aggagtactg cattcagttg      60
actttcaggg taaaagaaa acagtcctgg ttgttgtcat cataaacata tggaccagtg    120
tgatggtgaa atgagatgag gctccgcaat ggaactgtag ccactgcttt agcatttatc    180
acttccttcc ttactttgtc ttggtatact acatggcaaa atgggaaaga aaaactgatt    240
gcttatcaac gagaattcct tgctttgaaa gaacgtcttc gaatagctga acacagaatc    300
tcacagcgct cttctgaatt aaatacgatt gtgcaacagt tcaagcgtgt aggagcagaa    360
acaaatggaa gtaaggatgc gttgaataag ttttcagata ataccctaaa gctgttaaag    420
```

```
gagttaacaa gcaaaaaatc tcttcaagtg ccaagtattt attatcattt gcctcattta    480
ttgaaaaatg aaggaagtct tcaacctgct gtacagattg gcaacggaag aacaggagtt    540
tcaatagtca tgggcattcc cacagtgaag agagaagtta aatcttacct catagaaact    600
cttcattccc ttattgataa cctgtatcct gaagagaagt tggactgtgt tatagtagtc    660
ttcataggag agacagatat tgattatgta catggtgttg tagccaacct ggagaaagaa    720
ttttctaaag aaatcagttc tggcttggtg gaagtcatat caccccctga agctattat    780 cctgacttga caaacctaaa ggagacattt ggagactcca agaaagagt aagatggaga    840 acaaagcaaa acctagatta ctgttttcta atgatgtatg ctcaagaaaa gggcatatat    900
tacattcagc ttgaagatga tattattgtc aaacaaaatt atttttaatac cataaaaaat    960 tttgcacttc aactttcttc tgaggaatgg atgattctag agtttcccca gctgggcttc   1020
attggtaaaa tgtttcaagc gccggatctt actctgattg tagaattcat attcatgttt   1080
tacaaggaga aacccattga ttggctcctg gaccatattc tctgggtgaa agtctgcaac   1140
cctgaaaaag atgcaaaaca ttgtgataga cagaaagcaa atctgcgaat tcgcttcaga   1200
ccttcccttt tccaacatgt tggtctgcac tcatcactat caggaaaaat ccaaaaactc   1260
acggataaag attatatgaa accattactt cttaaaatcc atgtaaaccc acctgcggag   1320
gtatctactt ccttgaaggt ctaccaaggg catacgctgg agaaaactta catgggagag   1380
gatttcttct gggctatcac accgatagct ggagactaca tcttgtttaa atttgataaa   1440
ccagtcaatg tagaaagtta tttgttccat agcggcaacc aagaacatcc tggagatatt   1500
ctgctaaaca caactgtgga agttttgcct tttaagagtg aaggtttgga aataagcaaa   1560
gaaaccaaag acaaacgatt agaagatggc tatttcagaa taggaaaatt tgagaatggt   1620
gttgcagaag aatggtgga tccaagtctc aatcccattt cagcctttcg actttcagtt   1680
attcagaatt ctgctgtttg ggccattctt aatgagattc atattaaaaa agccaccaac   1740
tgatcatctg agaaaccaac acattttttc ctgtgaattt gttaattaaa gatagttaag   1800
catgtatctt tttttatttt ctacttgaac actacctctt gtgaagtcta ctgtagataa   1860
gacgattgtc atttccactt ggaaagtgaa tctcccataa taattgtatt tgtttgaaac   1920
taagctgtcc tcagatttta acttgactca aacatttttc aattatgaca gcctgttaat   1980
atgacttgta ctattttggt attatactaa tacataagag ttgtacatat tgttacattc   2040
tttaaatttg agaaaaacta atgttacata catttttatga aggggtacta tttgaggttc   2100
acttatttta ctatt                                                     2115
```

<210> SEQ ID NO 99
<211> LENGTH: 535
<212> TYPE: PRT
<213> ORGANISM: Homo sapiens

<400> SEQUENCE: 99

Met Arg Leu Arg Asn Gly Thr Val Ala Thr Ala Leu Ala Phe Ile Thr
1               5                   10                  15

Ser Phe Leu Thr Leu Ser Trp Tyr Thr Thr Trp Gln Asn Gly Lys Glu
            20                  25                  30

Lys Leu Ile Ala Tyr Gln Arg Glu Phe Leu Ala Leu Lys Glu Arg Leu
        35                  40                  45

Arg Ile Ala Glu His Arg Ile Ser Gln Arg Ser Ser Glu Leu Asn Thr
    50                  55                  60

-continued

```
Ile Val Gln Gln Phe Lys Arg Val Gly Ala Glu Thr Asn Gly Ser Lys
 65                  70                  75                  80

Asp Ala Leu Asn Lys Phe Ser Asp Asn Thr Leu Lys Leu Leu Lys Glu
                 85                  90                  95

Leu Thr Ser Lys Lys Ser Leu Gln Val Pro Ser Ile Tyr Tyr His Leu
            100                 105                 110

Pro His Leu Leu Lys Asn Glu Gly Ser Leu Gln Pro Ala Val Gln Ile
        115                 120                 125

Gly Asn Gly Arg Thr Gly Val Ser Ile Val Met Gly Ile Pro Thr Val
    130                 135                 140

Lys Arg Glu Val Lys Ser Tyr Leu Ile Glu Thr Leu His Ser Leu Ile
145                 150                 155                 160

Asp Asn Leu Tyr Pro Glu Glu Lys Leu Asp Cys Val Ile Val Val Phe
                165                 170                 175

Ile Gly Glu Thr Asp Ile Asp Tyr Val His Gly Val Val Ala Asn Leu
            180                 185                 190

Glu Lys Glu Phe Ser Lys Glu Ile Ser Ser Gly Leu Val Glu Val Ile
        195                 200                 205

Ser Pro Pro Glu Ser Tyr Tyr Pro Asp Leu Thr Asn Leu Lys Glu Thr
    210                 215                 220

Phe Gly Asp Ser Lys Glu Arg Val Arg Trp Arg Thr Lys Gln Asn Leu
225                 230                 235                 240

Asp Tyr Cys Phe Leu Met Met Tyr Ala Gln Glu Lys Gly Ile Tyr Tyr
                245                 250                 255

Ile Gln Leu Glu Asp Asp Ile Ile Val Lys Gln Asn Tyr Phe Asn Thr
            260                 265                 270

Ile Lys Asn Phe Ala Leu Gln Leu Ser Ser Glu Glu Trp Met Ile Leu
        275                 280                 285

Glu Phe Ser Gln Leu Gly Phe Ile Gly Lys Met Phe Gln Ala Pro Asp
    290                 295                 300

Leu Thr Leu Ile Val Glu Phe Ile Phe Met Phe Tyr Lys Glu Lys Pro
305                 310                 315                 320

Ile Asp Trp Leu Leu Asp His Ile Leu Trp Val Lys Val Cys Asn Pro
                325                 330                 335

Glu Lys Asp Ala Lys His Cys Asp Arg Gln Lys Ala Asn Leu Arg Ile
            340                 345                 350

Arg Phe Arg Pro Ser Leu Phe Gln His Val Gly Leu His Ser Ser Leu
        355                 360                 365

Ser Gly Lys Ile Gln Lys Leu Thr Asp Lys Asp Tyr Met Lys Pro Leu
    370                 375                 380

Leu Leu Lys Ile His Val Asn Pro Pro Ala Glu Val Ser Thr Ser Leu
385                 390                 395                 400

Lys Val Tyr Gln Gly His Thr Leu Glu Lys Thr Tyr Met Gly Glu Asp
                405                 410                 415

Phe Phe Trp Ala Ile Thr Pro Ile Ala Gly Asp Tyr Ile Leu Phe Lys
            420                 425                 430

Phe Asp Lys Pro Val Asn Val Glu Ser Tyr Leu Phe His Ser Gly Asn
        435                 440                 445

Gln Glu His Pro Gly Asp Ile Leu Leu Asn Thr Thr Val Glu Val Leu
    450                 455                 460

Pro Phe Lys Ser Glu Gly Leu Glu Ile Ser Lys Glu Thr Lys Asp Lys
465                 470                 475                 480

Arg Leu Glu Asp Gly Tyr Phe Arg Ile Gly Lys Phe Glu Asn Gly Val
```

|  |  | 485 |  |  |  | 490 |  |  |  | 495 |  |
| --- | --- | --- | --- | --- | --- | --- | --- | --- | --- | --- | --- |

Ala Glu Gly Met Val Asp Pro Ser Leu Asn Pro Ile Ser Ala Phe Arg
           500               505               510

Leu Ser Val Ile Gln Asn Ser Ala Val Trp Ala Ile Leu Asn Glu Ile
     515               520               525

His Ile Lys Lys Ala Thr Asn
     530               535

```
<210> SEQ ID NO 100
<211> LENGTH: 3226
<212> TYPE: DNA
<213> ORGANISM: Mus musculus

<400> SEQUENCE: 100
attgctagag agagatggct ttcttttctc cctggaagtt gtcctctcag aagctgggct      60
ttttcctggt gactttcggc ttcatctggg gcatgatgct tctgcacttc accatccagc     120
agcggactca gcccgagagc agctccatgt tacgggagca gatccttgac ctcagcaaga     180
ggtacattaa ggcactggca gaggagaaca gggacgtggt ggatggcccc tacgctggtg     240
tcatgacagc ctatgatctg aagaaaacgc tcgccgtctt gctggataac atcctgcagc     300
gcattggcaa gctcgagtca aaggtggaca atctggtcaa cggcacagga gcgaactcca     360
ccaactccac cacggctgtc cccagcttgg tgtcgcttga aaaattaat gtggcagata     420 tcattaatgg agttcaggaa aaatgtgtat tgcctcctat ggatggctac ccccactgcg     480
aggggaaaat caagtggatg aaggacatgt ggcgctcgga ccctgctac gcagactatg     540 gagtggacgg gacctcctgc tcctttttta tttacctcag tgaggttgaa aattggtgtc     600
ctcgtttacc ttggagagca aaaaatccct atgaagaagc tgatcataac tcattggcgg     660
aaatccgtac ggatttaac attctctacg gcatgatgaa gaagcacgag gagttccgtt     720
ggatgaggct tcggatccgg cgaatggctg acgcgtggat ccaagctatc aagtctctgg     780
cggagaaaca aaaccttgag aagaggaaac ggaagaaaat ccttgttcac ctggggctcc     840
tgaccaagga atcgggcttc aagattgcgg agacagcatt cagcggtggc cctctgggtg     900
aactcgttca gtggagtgac ttaatcacat ctctgtacct gctgggccat gacatccgga     960
tctcggcctc actggctgag ctcaaggaga taatgaagaa ggttgttgga aaccggtctg    1020
gctgtccaac tgtaggagac agaatcgttg agctgattta tatcgatatt gtgggacttg    1080
ctcaatttaa gaaaacacta gggccatcct gggttcatta ccagtgcatg ctccgggtgc    1140
tagactcctt tggaacagaa cctgagttca atcatgcgag ctatgcccag tcaaaaggcc    1200
acaagacccc ctggggaaag tggaatctga acccgcagca gttttacacc atgttccctc    1260
ataccccaga caacagcttt ctgggcttcg tggtggagca gcacctgaac tccagcgaca    1320
ttcaccacat caacgagatc aaaaggcaga accagtccct tgtgtatggc aaagtggata    1380
gtttctggaa gaataagaaa atctacctgg atatcattca cacgtacatg gaagtgcacg    1440 ccactgtttta tggctccagt accaagaaca ttcccagtta cgtgaaaaac catggcattc    1500
tcagtggacg tgacctgcag ttttcttctcc gggaaaccaa gctgttcgtt gggctcggat    1560
tcccttatga aggcccagct cccctggagg ccatcgcgaa tggatgtgct ttcctgaacc    1620
ccaagttcaa ccctcccaaa agcagcaaaa acacagactt cttcattggc aagccaacac    1680
tgagagagct gacatcccag catccttacg cagaagtctt catcggccgg ccacacgtct    1740
ggactgtgga tctcaataac cgagaggaag tagaagatgc agtaaaagcc atcttaaacc    1800
```

```
agaagattga gccgtatatg ccatatgagt tcacatgtga aggcatgctg cagagaatca   1860
acgctttcat tgaaaaacag gacttctgcc atggccaagt gatgtggccg ccccctcagcg   1920 ccctgcaggt taagctggct gagccagggc agtcctgcaa acaggtgtgc caggagagcc   1980
agctcatctg cgagccatcc ttctttcaac acctcaacaa ggaaaaggac ctgctgaagt   2040
ataaggtgac ctgccaaagc tcagaactgt acaaggacat cctggtgccc tccttctacc   2100
ccaagagcaa gcactgtgtg ttccaagggg acctcctgct cttcagttgt gccggagccc   2160
atcccacaca ccagcggatc tgcccctgcc gggacttcat caagggccaa gtggccctct   2220
gcaaagactg cctatagcat cgctgccctg aattaactca gacgggaaag acgtggctcc   2280
actgggcagg gccaagggc acaaagacat tcagggactc tgaccagagc ctgagatctt   2340
tggtccaggg cttgagttta gtaccgctcc agccacagcc agtgcatccc agtttacacc   2400
aaaaccacaa gggaacaggt tagaacagga acctgggttc tcctcagtgt aaggaatgtc   2460
ctctctgtct gggagatcga gcgactgtag ggaaaggatc caggcagttg ctcccgggaa   2520
tttttttttt tttttttttt aaagaaggga taaaagtccg gagactcatt caaactgaaa   2580
acaaaacagg aagagggaat tgagccaatt gggaaggact ttggggccga tcctaaacca   2640
attaatttat ttatttggga ggatggggc gggctcggga ggaggagag gggttgaaca   2700 gtttcctttt gttcctcact gttaattcgc ccaccttcgg gcccttcttg ttctgcagcg   2760
ccaagcaggt gcagagggg ctgtggcttg cttgaggggc cactgtgggg cttcactcct   2820
ggtcacaggt ggcagcagag aaaagagatg tctataagca gggggatgta gctcagtttg   2880
tagaatgctt gcatagcata aatgaagtcc tgggttccat ccccagcacc acataaatgc   2940
aggtaagaaa cagagtcagg aggaccaagc attctccttg gctacataac aaaagcaagg   3000
cctttgtccc catgtcttgg ctacaagaga ccctatctca gaaaattgtg gggggagg   3060 gggggaaat ggccttgaaa acacagccag tcactgtcac tgcattgcca gaactggtgg   3120
atcccaggtg tgcttggcag ataacagcta aaaggcacat aaccttggtg gggaaataaa   3180
tgcctgtggt gtcctgaggg ccccaccaag ttccaaaaaa aaaaaa   3226
```

<210> SEQ ID NO 101
<211> LENGTH: 740
<212> TYPE: PRT
<213> ORGANISM: Mus musculus

<400> SEQUENCE: 101

```
Met Ala Phe Phe Ser Pro Trp Lys Leu Ser Gln Lys Leu Gly Phe
  1               5                  10                  15

Phe Leu Val Thr Phe Gly Phe Ile Trp Gly Met Met Leu Leu His Phe
                 20                  25                  30

Thr Ile Gln Gln Arg Thr Gln Pro Glu Ser Ser Met Leu Arg Glu
                 35                  40                  45

Gln Ile Leu Asp Leu Ser Lys Arg Tyr Ile Lys Ala Leu Ala Glu Glu
         50                  55                  60

Asn Arg Asp Val Val Asp Gly Pro Tyr Ala Gly Val Met Thr Ala Tyr
 65                  70                  75                  80

Asp Leu Lys Lys Thr Leu Ala Val Leu Leu Asp Asn Ile Leu Gln Arg
                 85                  90                  95

Ile Gly Lys Leu Glu Ser Lys Val Asp Asn Leu Val Asn Gly Thr Gly
                100                 105                 110

Ala Asn Ser Thr Asn Ser Thr Thr Ala Val Pro Ser Leu Val Ser Leu
            115                 120                 125
```

```
Glu Lys Ile Asn Val Ala Asp Ile Ile Asn Gly Val Gln Glu Lys Cys
    130                 135                 140
Val Leu Pro Pro Met Asp Gly Tyr Pro His Cys Glu Gly Lys Ile Lys
145                 150                 155                 160
Trp Met Lys Asp Met Trp Arg Ser Asp Pro Cys Tyr Ala Asp Tyr Gly
                165                 170                 175
Val Asp Gly Thr Ser Cys Ser Phe Phe Ile Tyr Leu Ser Glu Val Glu
                180                 185                 190
Asn Trp Cys Pro Arg Leu Pro Trp Arg Ala Lys Asn Pro Tyr Glu Glu
            195                 200                 205
Ala Asp His Asn Ser Leu Ala Glu Ile Arg Thr Asp Phe Asn Ile Leu
    210                 215                 220
Tyr Gly Met Met Lys Lys His Glu Glu Phe Arg Trp Met Arg Leu Arg
225                 230                 235                 240
Ile Arg Arg Met Ala Asp Ala Trp Ile Gln Ala Ile Lys Ser Leu Ala
                245                 250                 255
Glu Lys Gln Asn Leu Glu Lys Arg Lys Arg Lys Lys Ile Leu Val His
            260                 265                 270
Leu Gly Leu Leu Thr Lys Glu Ser Gly Phe Lys Ile Ala Glu Thr Ala
    275                 280                 285
Phe Ser Gly Gly Pro Leu Gly Glu Leu Val Gln Trp Ser Asp Leu Ile
290                 295                 300
Thr Ser Leu Tyr Leu Leu Gly His Asp Ile Arg Ile Ser Ala Ser Leu
305                 310                 315                 320
Ala Glu Leu Lys Glu Ile Met Lys Lys Val Val Gly Asn Arg Ser Gly
                325                 330                 335
Cys Pro Thr Val Gly Asp Arg Ile Val Glu Leu Ile Tyr Ile Asp Ile
                340                 345                 350
Val Gly Leu Ala Gln Phe Lys Lys Thr Leu Gly Pro Ser Trp Val His
            355                 360                 365
Tyr Gln Cys Met Leu Arg Val Leu Asp Ser Phe Gly Thr Glu Pro Glu
    370                 375                 380
Phe Asn His Ala Ser Tyr Ala Gln Ser Lys Gly His Lys Thr Pro Trp
385                 390                 395                 400
Gly Lys Trp Asn Leu Asn Pro Gln Gln Phe Tyr Thr Met Phe Pro His
                405                 410                 415
Thr Pro Asp Asn Ser Phe Leu Gly Phe Val Val Glu Gln His Leu Asn
                420                 425                 430
Ser Ser Asp Ile His His Ile Asn Glu Ile Lys Arg Gln Asn Gln Ser
            435                 440                 445
Leu Val Tyr Gly Lys Val Asp Ser Phe Trp Lys Asn Lys Lys Ile Tyr
    450                 455                 460
Leu Asp Ile Ile His Thr Tyr Met Glu Val His Ala Thr Val Tyr Gly
465                 470                 475                 480
Ser Ser Thr Lys Asn Ile Pro Ser Tyr Val Lys Asn His Gly Ile Leu
                485                 490                 495
Ser Gly Arg Asp Leu Gln Phe Leu Leu Arg Glu Thr Lys Leu Phe Val
                500                 505                 510
Gly Leu Gly Phe Pro Tyr Glu Gly Pro Ala Pro Leu Glu Ala Ile Ala
            515                 520                 525
Asn Gly Cys Ala Phe Leu Asn Pro Lys Phe Asn Pro Pro Lys Ser Ser
    530                 535                 540
```

Lys Asn Thr Asp Phe Phe Ile Gly Lys Pro Thr Leu Arg Glu Leu Thr
545                 550                 555                 560

Ser Gln His Pro Tyr Ala Glu Val Phe Ile Gly Arg Pro His Val Trp
            565                 570                 575

Thr Val Asp Leu Asn Asn Arg Glu Glu Val Glu Asp Ala Val Lys Ala
        580                 585                 590

Ile Leu Asn Gln Lys Ile Glu Pro Tyr Met Pro Tyr Glu Phe Thr Cys
            595                 600                 605

Glu Gly Met Leu Gln Arg Ile Asn Ala Phe Ile Glu Lys Gln Asp Phe
610                 615                 620

Cys His Gly Gln Val Met Trp Pro Pro Leu Ser Ala Leu Gln Val Lys
625                 630                 635                 640

Leu Ala Glu Pro Gly Gln Ser Cys Lys Gln Val Cys Gln Glu Ser Gln
            645                 650                 655

Leu Ile Cys Glu Pro Ser Phe Phe Gln His Leu Asn Lys Glu Lys Asp
            660                 665                 670

Leu Leu Lys Tyr Lys Val Thr Cys Gln Ser Ser Glu Leu Tyr Lys Asp
            675                 680                 685

Ile Leu Val Pro Ser Phe Tyr Pro Lys Ser Lys His Cys Val Phe Gln
        690                 695                 700

Gly Asp Leu Leu Phe Ser Cys Ala Gly Ala His Pro Thr His Gln
705                 710                 715                 720

Arg Ile Cys Pro Cys Arg Asp Phe Ile Lys Gly Gln Val Ala Leu Cys
                725                 730                 735

Lys Asp Cys Leu
            740

<210> SEQ ID NO 102
<211> LENGTH: 4
<212> TYPE: PRT
<213> ORGANISM: Artificial Sequence
<220> FEATURE:
<223> OTHER INFORMATION: Illustrative retention signal peptide

<400> SEQUENCE: 102

Lys Asp Glu Leu
 1

<210> SEQ ID NO 103
<211> LENGTH: 60
<212> TYPE: PRT
<213> ORGANISM: Saccharomyces cerevisiae

<400> SEQUENCE: 103

Ile Pro Phe Val Leu Ile Ala Ser Asn Phe Ile Gly Val Leu Phe Ser
 1               5                  10                  15

Arg Ser Leu His Tyr Gln Phe Leu Ser Trp Tyr His Trp Thr Leu Pro
            20                  25                  30

Ile Leu Ile Phe Trp Ser Gly Met Pro Phe Phe Val Gly Pro Ile Trp
        35                  40                  45

Tyr Val Leu His Glu Trp Cys Trp Asn Ser Tyr Pro
    50                  55                  60

<210> SEQ ID NO 104
<211> LENGTH: 58
<212> TYPE: PRT
<213> ORGANISM: Drosophila virilis

<400> SEQUENCE: 104

```
Leu Pro Phe Phe Leu Cys Asn Phe Ile Gly Val Ala Cys Ala Arg Ser
1               5                   10                  15

Leu His Tyr Gln Phe Tyr Ile Trp Tyr Phe His Ser Leu Pro Tyr Leu
                20                  25                  30

Val Trp Ser Thr Pro Tyr Ser Leu Gly Val Arg Tyr Leu Ile Leu Gly
            35                  40                  45

Ile Ile Glu Tyr Cys Trp Asn Thr Tyr Pro
        50                  55

<210> SEQ ID NO 105
<211> LENGTH: 60
<212> TYPE: PRT
<213> ORGANISM: Saccharomyces cerevisiae

<400> SEQUENCE: 105

Ile Pro Phe Val Leu Ile Ala Ser Asn Phe Ile Gly Val Leu Phe Ser
1               5                   10                  15

Arg Ser Leu His Tyr Gln Phe Leu Ser Trp Tyr His Trp Thr Leu Pro
                20                  25                  30

Ile Leu Ile Phe Trp Ser Gly Met Pro Phe Phe Val Gly Pro Ile Trp
            35                  40                  45

Tyr Val Leu His Glu Trp Cys Trp Asn Ser Tyr Pro
        50                  55                  60

<210> SEQ ID NO 106
<211> LENGTH: 59
<212> TYPE: PRT
<213> ORGANISM: Drosophila melanogaster

<400> SEQUENCE: 106

Leu Pro Phe Phe Leu Cys Asn Leu Val Gly Val Ala Cys Ala Ser Arg
1               5                   10                  15

Ser Leu His Tyr Gln Phe Tyr Val Trp Tyr Phe His Ser Leu Pro Tyr
                20                  25                  30

Leu Ala Trp Ser Thr Pro Tyr Ser Leu Gly Val Arg Cys Leu Ile Leu
            35                  40                  45

Gly Leu Ile Glu Tyr Cys Trp Asn Thr Tyr Pro
        50                  55
```

METHOD TO ENGINEER MAMMALIAN-TYPE CARBOHYDRATE STRUCTURES

CROSS-REFERENCE TO RELATED APPLICATIONS

This application claims priority to U.S. provisional application Ser. No. 60/344,169, Dec. 27, 2001, which is incorporated by reference herein in its entirety.

FIELD OF THE INVENTION

The present invention generally relates to modifying the glycosylation structures of recombinant proteins expressed in fungi or other lower eukaryotes, to more closely resemble the glycosylation of proteins of higher mammals, in particular humans.

BACKGROUND OF THE INVENTION

After DNA is transcribed and translated into a protein, further post translational processing involves the attachment of sugar residues, a process known as glycosylation. Different organisms produce different glycosylation enzymes (glycosyltransferases and glycosidases), and have different substrates (nucleotide sugars) available, so that the glycosylation patterns as well as composition of the individual oligosaccharides, even of one and the same protein, will be different depending on the host system in which the particular protein is being expressed. Bacteria typically do not glycosylate proteins, and if so only in a very unspecific manner (Moens, 1997). Lower eukaryotes such as filamentous fungi and yeast add primarily mannose and mannosylphosphate sugars, whereas insect cells such as Sf9 cells glycosylate proteins in yet another way. See for example (Bretthauer, 1999; Martinet, 1998; Weikert, 1999; Malissard, 2000; Jarvis, 1998; and Takeuchi, 1997).

Synthesis of a mammalian-type oligosaccharide structure consists of a series of reactions in the course of which sugar-residues are added and removed while the protein moves along the secretory pathway in the host organism. The enzymes which reside along the glycosylation pathway of the host organism or cell determine what the resulting glycosylation patterns of secreted proteins. Unfortunately, the resulting glycosylation pattern of proteins expressed in lower eukaryotic host cells differs substantially from the glycosylation found in higher eukaryotes such as humans and other mammals (Bretthauer, 1999). Moreover, the vastly different glycosylation pattern has, in some cases, been shown to increase the immunogenicity of these proteins in humans and reduce their half-life (Takeuchi, 1997). It would be desirable to produce human-like glycoproteins in non-human host cells, especially lower eukaryotic cells.

The early steps of human glycosylation can be divided into at least two different phases: (i) lipid-linked Glc$_3$Man$_9$GlcNAc$_2$ oligosaccharides are assembled by a sequential set of reactions at the membrane of the endoplasmic reticulum (ER) and (ii) the transfer of this oligosaccharide from the lipid anchor dolichyl pyrophosphate onto de novo synthesized protein. The site of the specific transfer is defined by an asparagine (Asn) residue in the sequence Asn-Xaa-Ser/Thr (see FIG. 1), where Xaa can be any amino acid except proline (Gavel, 1990). Further processing by glucosidases and mannosidases occurs in the ER before the nascent glycoprotein is transferred to the early Golgi apparatus, where additional mannose residues are removed by Golgi specific alpha ($\alpha$)-1,2-mannosidases. Processing continues as the protein proceeds through the Golgi. In the medial Golgi, a number of modifying enzymes, including N-acetylglucosaminyltransferases (GnT I, GnT II, GnT III, GnT IV GnT V GnT VI), mannosidase II and fucosyltransferases, add and remove specific sugar residues (see, e.g., FIGS. 2 and 3). Finally, in the trans-Golgi, galactosyltranferases and sialyltransferases produce a glycoprotein structure that is released from the Golgi. It is this structure, characterized by bi-, tri- and tetra-antennary structures, containing galactose, fucose, N-acetylglucosamine and a high degree of terminal sialic acid, that gives glycoproteins their human characteristics.

In nearly all eukaryotes, glycoproteins are derived from the common core oligosaccharide precursor Glc$_3$Man$_9$GlcNAc$_2$-PP-Dol, where PP-Dol stands for dolichol-pyrophosphate (FIG. 1). Within the endoplasmic reticulum, synthesis and processing of dolichol pyrophosphate bound oligosaccharides are identical between all known eukaryotes. However, further processing of the core oligosaccharide by yeast, once it has been transferred to a peptide leaving the ER and entering the Golgi, differs significantly from humans as it moves along the secretory pathway and involves the addition of several mannose sugars.

In yeast, these steps are catalyzed by Golgi residing mannosyltransferases, like Och1p, Mnt1p and Mnn1p, which sequentially add mannose sugars to the core oligosaccharide. The resulting structure is undesirable for the production of humanoid proteins and it is thus desirable to reduce or eliminate mannosyltransferase activity. Mutants of S. cerevisiae, deficient in mannosyltransferase activity (for example och1 or mnn9 mutants) have been shown to be non-lethal and display a reduced mannose content in the oligosachride of yeast glycoproteins. Other oligosacharide processing enzymes, such as mannosylphophate transferase may also have to be eliminated depending on the host's particular endogenous glycosylation pattern.

Lipid-Linked Oligosaccharide Precursors

Of particular interest for this invention are the early steps of N-glycosylation (FIGS. 1 and 2). The study of alg (asparagine-linked glycosylation) mutants defective in the biosynthesis of the Glc$_3$Man$_9$GlcNAc$_2$-PP-Dol has helped to elucidate the initial steps of N-glycosylation.

The ALG3 gene of S. cerevisiae has been successfully cloned and knocked out by deletion (Aebi, 1996). ALG3 has been shown to encode the enzyme Dol-P-Man:Man$_5$GlcNAc$_2$-PP-Dol Mannosyltransferase, which is involved in the first Dol-P-Man dependent mannosylation step from Man$_5$GlcNAc$_2$-PP-Dol to Man$_6$GlcNAc$_2$-PP-Dol at the luminal side of the ER (Sharma, 2001) (FIGS. 1 and 2). S. cerevisiae cells harboring a leaky alg3-1 mutation accumulate Man$_5$GlcNAc$_2$-PP-Dol (structure I) (Huffaker, 1983).

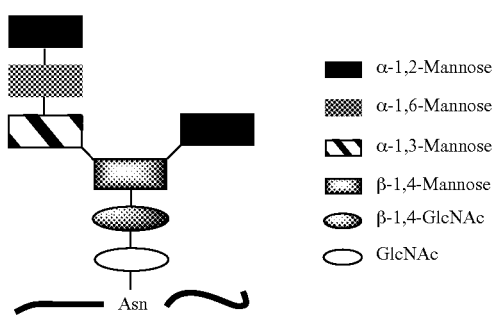

Structure I: Man$_5$GlcNAc$_2$

Man$_5$GlcNAc$_2$ (Structure I) and Man$_8$GlcNAc$_2$ accumulate in total cell mannoprotein of an och1 mnn1 alg3 mutant (Nakanishi-Shindo, 1993). This *S. cerevisiae* och1, mnn1, alg3 mutant was shown to be viable, but temperature-sensitive, and to lack α-1,6 polymannose outer chains.

In another study, secretory proteins expressed in a strain deleted for alg 3 (Δalg3 background) were studied for their resistance to Endo-β-N-acetylglucosaminidase H (Endo H) (Aebi, 1996). Previous observations have indicated that only those oligosaccharides larger than Man$_5$GlcNAc$_2$ are susceptible to cleavage by Endo H (Hubbard, 1980). In the alg3-1 phenotype, some glycoforms were sensitive to Endo H cleavage, confirming its leakiness, whereas in the Δalg3 mutant all glycoforms appeared to be resistant and of the Man$_5$-type (Aebi, 1996), suggesting a tight phenotype and transfer of Man$_5$GlcNAc$_2$ oligosaccharide structures onto the nascent polypeptide chain. No obvious phenotype was connected with the inactivation of the ALG3 gene (Aebi, 1996). Secreted exogluconase produced in a *Saccharomyces cerevisiae* alg3 mutant was found to contain between 35-44% underglycosylated and unglycosylated forms and only about 50% of the transferred oligosaccharides remained resistant to Endo H treatment (Cueva, 1996). Exoglucanase (Exg), an enzyme that contains two potential N-glycosylation sites at Asn$_{165}$ and Asn$_{325}$, was analyzed in more detail. For Exg molecules that received two oligosaccharides it was shown that the first N-glycosylation site (Asn$_{165}$) was enriched in truncated residues, whereas the second (Asn$_{325}$) was enriched in regular oligosaccharides. 35-44% of secreted exoglucanase was non- or underglycosylated and about 73-78% of all available N-glycosylation sites were occupied with either truncated or regular oligosaccharides (Cueva, 1996).

Transfer of Glucosylated Lipid-Linked Oligosaccharides

Evidence suggests that, in mammalian cells, only glucosylated lipid-linked oligosaccharides are transferred to nascent proteins (Turco, 1977), while in yeast alg5, alg6 and dpg1 mutants, nonglucosylated oligosaccharideds can be transferred (Ballou, 1986; Runge, 1984). In a *Saccharomyces cerevisiae* alg8 mutant, underglucosylated GlcMan$_9$GlcNAc$_2$ is transferred (Runge, 1986). Verostek and co-workers studied an alg3, sec18, gls1 mutant and proposed that glucosylation of a Man$_5$GlcNAc$_2$ structure (Structure I, above) is relatively slow in comparison to glucosylation of a lipid-linked Man$_9$ structure. In addition, the transfer of this Man$_5$GlcNAc$_2$ structure to protein appears to be about 5-fold more efficient than the glucosylation to Glc$_3$Man$_5$GlcNAc$_2$. The decreased rate of Man$_5$GlcNAc$_2$ glucosylation in combination with the comparatively faster rate of Man$_5$ structure transfer onto nascent protein is believed to be the cause of the observed accumulation of nonglucosylated Man$_5$ structures in alg3 mutant yeast (Verostek-a, 1993; Verostek-b, 1993).

Studies preceding the above work did not reveal any lipid-linked glucosylated oligosaccharides (Orlean, 1990; Huffaker, 1983) allowing the conclusion that glucosylated oligosaccharides are transferred at a much higher rate than their nonglucosylated counterparts and thus are much harder to isolate. Recent work has allowed the creation and study of yeast strains with un- and hypoglucosylated oligosaccharides and has further confirmed the importance of the addition of glucose to the antenna of lipid-linked oligosaccharides for substrate recognition by the oligosaccharyltransferase complex (Reiss, 1996; Stagljar, 1994; Burda, 1998). The decreased degree of glucosylation of the lipid-linked Man$_5$-oligosaccharides in an alg3 mutant negatively impacts the kinetics of the transfer of lipid-linked oligosaccharides onto nascent protein and is believed to be the cause for the strong underglycosylation of secreted proteins in an alg3 knock-out strain (Aebi, 1996).

The assembly of the lipid-linked core oligosaccharide Man$_9$GlcNAc$_2$ occurs, as described above, at the membrane of the endoplasmatic reticulum. The additions of three glucose units to the α-1,3-antenna of the lipid-linked oligosaccharides are the final reactions in the oligosaccharide assembly. First an α-1,3 glucose residue is added followed by another α-1,3 glucose residue and a terminal α-1,2 glucose residue. Mutants accumulating dolichol-linked Man$_9$GlcNAc$_2$ have been shown to be defective in the ALG6 locus, and Alg6p has similarities to Alg8p, the α-1,3-glucosyltransferase catalyzing the addition of the second α-1,3-linked glucose (Reiss, 1996). Cells with a defective ALG8 locus accumulate dolichol-linked Glc$_1$Man$_9$GlcNAc$_2$ (Runge, 1986; Stagljar, 1994). The ALG10 locus encodes the α-1,2 glucosyltransferase responsible for the addition of a single terminal glucose to Glc$_2$Man$_9$GlcNAc$_2$-PP-Dol (Burda, 1998).

Sequential Processing of N-Glycans by Localized Enzyme Activities

Sugar transferases and mannosidases line the inner (luminal) surface of the ER and Golgi apparatus and thereby provide a "catalytic" surface that allows for the sequential processing of glycoproteins as they proceed through the ER and Golgi network. In fact the multiple compartments of the cis, medial, and trans Golgi and the trans-Golgi Network (TGN), provide the different localities in which the ordered sequence of glycosylation reactions can take place. As a glycoprotein proceeds from synthesis in the ER to full maturation in the late Golgi or TGN, it is sequentially exposed to different glycosidases, mannosidases and glycosyltransferases such that a specific carbohydrate structure may synthesized. Much work has been dedicated to revealing the exact mechanism by which these enzymes are retained and anchored to their respective organelle. The evolving picture is complex but evidence suggests that, stem region, membrane spanning region and cytoplasmic tail individually or in concert direct enzymes to the membrane of individual organelles and thereby localize the associated catalytic domain to that locus.

In some cases these specific interactions were found to function across species. For example the membrane spanning domain of α2,6-ST from rats, an enzyme known to localize in the trans-Golgi of the animal, was shown to also localize a reporter gene (invertase) in the yeast Golgi (Schwientek, 1995). However, the very same membrane spanning domain as part of a full-length α2,6 ST was retained in the ER and not further transported to the Golgi of yeast (Krezdorn, 1994). A full length Gal-Tr from humans was not even synthesized in yeast, despite demonstrably high transcription levels. On the other hand the transmembrane region of human the same GalT fused to an invertase reporter was able to direct localization to the yeast Golgi, albeit it at low production levels. Schwientek and co-workers have shown that fusing 28 amino acids of a yeast mannosyltransferase (Mnt1), a region containing a cytoplamic tail, a transmembrane region and eight amino acids of the stem region, to the catalytic domain of human GalT are sufficient for Golgi localization of an active GalT. Other galactosyltransferases appear to rely on interactions with enzymes resident in particular organelles since after removal of their transmembrane region they are still able to localize properly. To date there exists no reliable way of predicting whether a particular heterologously expressed glycosyltransferase or mannosidase in a lower eukaryote will be (1), sufficiently translated (2), catalytically active or (3) located to the proper organelle within the secretory pathway.

Since all three of these are necessary to effect glycosylation patterns in lower eukaryotes, a systematic scheme to achieve the desired catalytic function and proper retention of enzymes in the absence of predictive tools, which are currently not available, has been designed.

Production of Therapeutic Glycoproteins

A significant number of proteins isolated from humans or animals are post-translationally modified, with glycosylation being one of the most significant modifications. An estimated 70% of all therapeutic proteins are glycosylated and thus currently rely on a production system (i.e., host cell) that is able to glycosylate in a manner similar to humans. To date, most glycoproteins are made in a mammalian host system. Several studies have shown that glycosylation plays an important role in determining the (1) immunogenicity, (2) pharmacokinetic properties, (3) trafficking, and (4) efficacy of therapeutic proteins. It is thus not surprising that substantial efforts by the pharmaceutical industry have been directed at developing processes to obtain glycoproteins that are as "humanoid" or "human-like" as possible. This may involve the genetic engineering of such mammalian cells to enhance the degree of sialylation (i.e., terminal addition of sialic acid) of proteins expressed by the cells, which is known to improve pharmacokinetic properties of such proteins. Alternatively one may improve the degree of sialylation by in vitro addition of such sugars using known glycosyltransferases and their respective nucleotide sugars (e.g., 2,3 sialyltransferase and CMP-Sialic acid).

Future research may reveal the biological and therapeutic significance of specific glycoforms, thereby rendering the ability to produce such specific glycoforms desirable. To date, efforts have concentrated on making proteins with fairly well characterized glycosylation patterns, and expressing a cDNA encoding such a protein in one of the following higher eukaryotic protein expression systems:
1. Higher eukaryotes such as Chinese hamster ovary cells (CHO), mouse fibroblast cells and mouse myeloma cells (Werner, 1998);
2. Transgenic animals such as goats, sheep, mice and others (Dente, 1988); (Cole, 1994); (McGarvey, 1995); (Bardor, 1999);
3. Plants (*Arabidopsis thaliana*, tobacco etc.) (Staub, 2000); (McGarvey, 1995); (Bardor, 1999);
4. Insect cells (*Spodoptera frugiperda* Sf9, Sf21, *Trichoplusia ni*, etc., in combination with recombinant baculoviruses such as *Autographa californica* multiple nuclear polyhedrosis virus which infects lepidopteran cells (Altmann, 1999).

While most higher eukaryotes carry out glycosylation reactions that are similar to those found in humans, recombinant human proteins expressed in the above mentioned host systems invariably differ from their "natural" human counterpart (Raju, 2000). Extensive development work has thus been directed at finding ways to improving the "human character" of proteins made in these expression systems. This includes the optimization of fermentation conditions and the genetic modification of protein expression hosts by introducing genes encoding enzymes involved in the formation of human like glycoforms (Werner, 1998); (Weikert, 1999); (Andersen, 1994); (Yang, 2000). Inherent problems associated with all mammalian expression systems have not been solved.

Fermentation processes based on mammalian cell culture (e.g., CHO, murine, or human cells), for example, tend to be very slow (fermentation times in excess of one week are not uncommon), often yield low product titers, require expensive nutrients and cofactors (e.g., bovine fetal serum), are limited by programmed cell death (apoptosis), and often do not enable expression of particular therapeutically valuable proteins. More importantly, mammalian cells are susceptible to viruses that have the potential to be human pathogens and stringent quality controls are required to assure product safety. This is of particular concern since many such processes require the addition of complex and temperature sensitive media components that are derived from animals (e.g., bovine calf serum), which may carry agents pathogenic to humans such as bovine spongiform encephalopathy (BSE) prions or viruses. Moreover, the production of therapeutic compounds is preferably carried out in a well-controlled sterile environment. An animal farm, no matter how cleanly kept, does not constitute such an environment, thus constituting an additional problem in the use of transgenic animals for manufacturing high volume therapeutic proteins.

Most, if not all, currently produced therapeutic glycoproteins are therefore expressed in mammalian cells and much effort has been directed at improving (i.e., "humanizing") the glycosylation pattern of these recombinant proteins. Changes in medium composition as well as the co-expression of genes encoding enzymes involved in human glycosylation have been successfully employed (see, for example, Weikert, 1999).

While recombinant proteins similar to their human counterparts can be made in mammalian expression systems, it is currently not possible to make proteins with a human-like glycosylation pattern in lower eukaryotes (fungi and yeast). Although the core oligosaccharide structure transferred to a protein in the endoplasmic reticulum is basically identical in mammals and lower eukaryotes, substantial differences have been found in the subsequent processing reactions which occur in in the Golgi apparatus of fungi and mammals. In fact, even amongst different lower eukaryotes there exist a great variety of glycosylation structures. This has prevented the use of lower eukaryotes as hosts for the production of recombinant human glycoproteins despite otherwise notable advantages over mammalian expression systems, such as: (1) generally higher product titers, (2) shorter fermentation times, (3) having an alternative for proteins that are poorly expressed in mammalian cells, (4) the ability to grow in a chemically defined protein free medium and thus not requiring complex animal derived media components, (5) and the absence of viral, especially retroviral infections of such hosts.

Various methylotrophic yeasts such as *Pichia pastoris*, *Pichia methanolica*, and *Hansenula polymorpha*, have played particularly important roles as eukaryotic expression systems because they are able to grow to high cell densities and secrete large quantities of recombinant protein. However, as noted above, lower eukaryotes such as yeast do not glycosylate proteins like higher mammals. See for example, Martinet et al. (1998) Biotechnol Let. Vol. 20. No. 12, which discloses the expression of a heterologous mannosidase in the endoplasmic reticulum (ER).

Chiba et al. (1998) have shown that *S. cerevisiae* can be engineered to provide structures ranging from $Man_8GlcNAc_2$ to $Man_5GlcNAc_2$ structures, by eliminating 1,6 mannosyltransferase (OCH1), 1,3 mannosyltransferase (MNN1) and a regulator of mannosylphosphatetransferase (MNN4) and by targeting the catalytic domain of α-1,2-mannosidase I from *Aspergillus saitoi* into the ER of *S. cerevisiae* using an ER retrieval sequence (Chiba, 1998). However, this attempt resulted in little or no production of the desired $Man_5GlcNAc_2$, e.g., one that was made in vivo and which could function as a substrate for GnT1 (the next step in making human-like glycan structures). Chiba et al. (1998)

showed that *P. pastoris* is not inherently able to produce useful quantities (greater than 5%) of GlcNAcTransferase I accepting carbohydrate.

Maras and co-workers assert that in *T. reesei* "sufficient concentrations of acceptor substrate (i.e. Man$_5$GlcNAc$_2$) are present", however when trying to convert this acceptor substrate to GlcNAcMan$_5$GlcNAc$_2$ in vitro less than 2% were converted thereby demonstrating the presence of Man$_5$GlcNAc$_2$ structures that are not suitable precursors for complex N-glycan formation (Maras, 1997; Maras, 1999). To date no enabling disclosure exists, that allows for the production of commercially relevant quantities of GlcNAcMan$_5$GlcNAc$_2$ in lower eukaryotes.

It is therefore an object of the present invention to provide a system and methods for humanizing glycosylation of recombinant glycoproteins expressed in non-human host cells.

SUMMARY OF THE INVENTION

The present invention relates to host cells such as fungal strains having modified lipid-linked oligosaccharides which may be modified further by heterologous expression of a set of glycosyltransferases, sugar transporters and mannosidases to become host-strains for the production of mammalian, e.g., human therapeutic glycoproteins. A protein production method has been developed using (1) a lower eukaryotic host such as a unicellular or filamentous fungus, or (2) any non-human eukaryotic organism that has a different glycosylation pattern from humans, to modify the glycosylation composition and structures of the proteins made in a host organism ("host cell") so that they resemble more closely carbohydrate structures found in human proteins. The process allows one to obtain an engineered host cell which can be used to express and target any desirable gene(s) involved in glycosylation by methods that are well established in the scientific literature and generally known to the artisan in the field of protein expression. As described herein, host cells with modified lipid-linked oligosaccharides are created or selected. N-glycans made in the engineered host cells have a GlcNAcMan$_3$GlcNAc$_2$ core structure which may then be modified further by heterologous expression of one or more enzymes, e.g., glycosyl-transferases, sugar transporters and mannosidases, to yield human-like glycoproteins. For the production of therapeutic proteins, this method may be adapted to engineer cell lines in which any desired glycosylation structure may be obtained.

BRIEF DESCRIPTION OF THE DRAWINGS

FIGS. 4A-4F
SEQ ID NO:24 *S. Cerevisiae* (Query 1)
SEQ ID NO:25 *S. Cerevisiae* (Subject 1)
SEQ ID NO:26 *S. Cerevisiae* (Query)
SEQ ID NO:27 *H. sapiens* (Subject)
SEQ ID NO:28 *S. Cerevisiae* (Query 1)
SEQ ID NO:29 *Drosophilia virilis* (Subject)
SEQ ID NO:30 *S. Cerevisiae* (Query)
SEQ ID NO:31 *Drosophila melanogaster* (Subject)

FIG. 5
SEQ ID NO:32 DNA sequence
SEQ ID NO:33 amino acid sequence
FIG. 6
SEQ ID NO:34 DNA sequence
SEQ ID NO:35 amino acid sequence
FIGS. 7A-7D
SEQ ID NO:36 *Pichia Pastoris* (Query)
SEQ ID NO:37 *S. Cerevisiae* (Subject)
SEQ ID NO:38 (Query)
SEQ ID NO:39 *Neurospora Crassa* (Subject)
SEQ ID NO:40 *Pichia Patoris* (Query)
SEQ ID NO:41 *Schizosaccharomyces pombe* (Subject)
SEQ ID NO:42 *Pichia Pastoris*
SEQ ID NO:43 *Arabidopsis thaliana*
FIG. 8
SEQ ID NO:44 DNA sequence
SEQ ID NO:45 amino acid sequence
FIG. 9
SEQ ID NO:46 *K. lactis*
SEQ ID NO:47 *S. Cerevisiae*
SEQ ID NO:48 *K. lactis*
SEQ ID NO:49 *Arabidopsis thaliana*
FIG. 10
SEQ ID NO:50 *S. Cerevisiae* Alg 9 DNA
SEQ ID NO:51 *S. Cerevisiae* amino acid
FIG. 11
SEQ ID NO:52 *Pichia Pastoris* Alg 9 DNA
SEQ ID NO:53 *Pichia Pastoris* amino acid
FIGS. 12A-12C
SEQ ID NO:54 *Pichia Pastoris* (Query)
SEQ ID NO:55 *S. Cerevisiae* (Subject)
SEQ ID NO:56 *Pichia Pastoris* (Query)
SEQ ID NO:57 *Anopheles gambiae* (Subject)
SEQ ID NO:58 *Pichia Pastoris* (Query)
SEQ ID NO:59 *S. pombe* (Subject)
SEQ ID NO:60 *Pichia Pastoris* (Query)
SEQ ID NO:61 *M. Musculus* (Subject)
SEQ ID NO:62 *Pichia Pastoris* (Query)
SEQ ID NO:63 *H. Sapiens* (Subject)
FIG. 13
SEQ ID NO:64 *S. Cerevisiae* Alg 12 DNA
SEQ ID NO:65 *S. Cerevisiae* Alg 12 amino acid
FIG. 14
SEQ ID NO:66 *Pichia Pastoris* Alg 12 DNA
SEQ ID NO:67 *S. Cerevisiae* Alg 12 amino acid
FIGS. 15A-15B
SEQ ID NO:68 *Pichia Pastoris* (Query)
SEQ ID NO:69 *S. Cerevisiae* (Subject)
SEQ ID NO:70 *Pichia Pastoris* (Query)
SEQ ID NO:71 *S. pombe* (Subject)
SEQ ID NO:72 *Pichia Pastoris* (Query)
SEQ ID NO:73 *S. pombe* (Subject)

FIGS. 25A-25B
SEQ ID NO:74 *S. Cerevisiae* DNA Alg 6
SEQ ID NO:75 *S. Cerevisiae* amino acid
SEQ ID NO:76 *Pichia Pastoris* DNA Alg 6
SEQ ID NO:77 *Pichia Pastoris* amino acid Alg 6
FIGS. 26A-26B
SEQ ID NO:78 *Pichia Pastoris* (Query)
SEQ ID NO:79 *S. Cerevisiae* (Subject)
SEQ ID NO:80 *Pichia Pastoris* (Query)
SEQ ID NO:81 *S. pombe* (Subject)
SEQ ID NO:82 *Pichia Pastoris* (Query)
SEQ ID NO:83 *D. melanogaster* (Subject)
SEQ ID NO:84 *Pichia Pastoris* (Query)
SEQ ID NO:85 *A. thaliana* (Subject)
FIGS. 27A-27E show *P. pastoris* Alg 6 Sequence Comparisons (Blast)
FIG. 28
SEQ ID NO:86 *K. lactis* Alg 6 DNA
SEQ ID NO:87 *K. lactis* Alg 6 amino acid
FIGS. 29A-29C
SEQ ID NO:88 *K. lactis* Alg 6 DNA
SEQ ID NO:89 *S. Cerevisiae* (Subject)
SEQ ID NO:90 *K. lactis* (Query)
SEQ ID NO:91 *S. pombe* (Subject)
SEQ ID NO:92 *K. lactis* (Query)
SEQ ID NO:93 *A. thaliana* (Subject)
SEQ ID NO:94 *K. lactis* (Query)
SEQ ID NO:95 *H. Sapiens* (Subject)
FIG. 30 Model of an IgG immunoglobulin. Heavy chain and light chain can be, based on similar secondary and tertiary structure, subdivided into domains. The two heavy chains (domains $V_H$, $C_H1$, $C_H2$ and $C_H3$) are linked through three disulfide bridges. The light chains (domains $V_L$ and $C_L$) are linked by another disulfide bridge to the $C_H1$ portion of the heavy chain and, together with the $C_H1$ and $V_H$ fragments, make up the Fab region. Antigens bind to the terminal portion of the Fab region. Effector-functions, such as Fc-gamma-Receptor binding have been localized to the $C_H2$ domain, just downstream of the hinge region and are influenced by N-glycosylation of asparagine 297 in the heavy chain.

FIG. 32
SEQ ID NO:96 *M. musculus* DNA GnTIII
SEQ ID NO:97 *M. musculus* amino acid GnTIII
FIGS. 33A-33B
SEQ ID NO:98 *H. Sapiens* DNA GnTIV
SEQ ID NO:99 *H. Sapiens* aa Gn TIV
FIGS. 34A-34B
SEQ ID NO:100 *M. musculus* DNA GnTV
SEQ ID NO:101 *M. musculus* aa GnTV

DETAILED DESCRIPTION OF THE INVENTION

Figure 1:
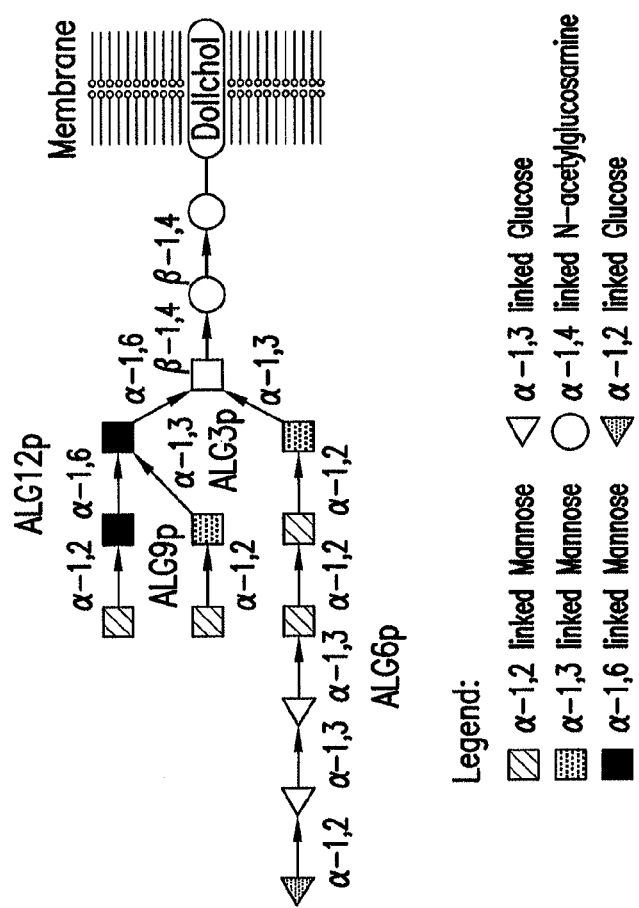
FIG. 1 is a schematic of the structure of the dolichyl pyrophosphate-linked oligosaccharide.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present invention are generally performed according to conventional methods well known in the art. Generally, nomenclatures used in connection with, and techniques of biochemistry, enzymology, molecular and cellular biology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane Antibodies: A Laboratory Manual Cold Spring Harbor Laboratory Press, Cold Spring Harbor, N.Y. (1990); Introduction to Glycobiology, Maureen E. Taylor, Kurt Drickamer, Oxford Univ. Press (2003); Worthington Enzyme Manual, Worthington Biochemical Corp. Freehold, N.J.; Handbook of Biochemistry: Section A Proteins Vol I 1976 CRC Press; Handbook of Biochemistry: Section A Proteins Vol II 1976 CRC Press; Essentials of Glycobiology, Cold Spring Harbor Laboratory Press (1999). The nomenclatures used in connection with, and the laboratory procedures and techniques of, biochemistry and molecular biology described herein are those well known and commonly used in the art.

All publications, patents and other references mentioned herein are incorporated by reference.

The following terms, unless otherwise indicated, shall be understood to have the following meanings:

As used herein, the term "N-glycan" refers to an N-linked oligosaccharide, e.g., one that is attached by an asparagine-N-acetylglucosamine linkage to an asparagine residue of a polypeptide. N-glycans have a common pentasaccharide core of Man₃GlcNAc₂ ("Man" refers to mannose; "Glc" refers to glucose; and "NAc" refers to N-acetyl; GlcNAc refers to N-acetylglucosamine). N-glycans differ with respect to the number of branches (antennae) comprising peripheral sugars (e.g., fucose and sialic acid) that are added to the Man₃GlcNAc₂ ("Man3") core structure. N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. The "trimannose core" is the pentasaccharide core having a Man3 structure. Complex N-glycans may also have galactose ("Gal") residues that are optionally modified with sialic acid or derivatives ("NeuAc", where "Neu" refers to neuraminic acid and "Ac" refers to acetyl). Complex N-glycans may also have intrachain substitutions comprising "bisecting" GlcNAc and core fucose ("Fuc"). A "hybrid" N-glycan has at least one GlcNAc on the terminal of the 1,3 mannose arm of the trimannose core and zero or more mannoses on the 1,6 mannose arm of the trimannose core.

Abbreviations used herein are of common usage in the art, see, e.g., abbreviations of sugars, above. Other common abbreviations include "PNGase", which refers to peptide N-glycosidase F (EC 3.2.2.18); "GlcNAc Tr (I-III)", which refers to one of three N-acetylglucosaminyltransferase enzymes; "NANA" refers to N-acetylneuraminic acid.

As used herein, the term "secretion pathway" refers to the assembly line of various glycosylation enzymes to which a lipid-linked oligosaccharide precursor and an N-glycan substrate are sequentially exposed, following the molecular flow of a nascent polypeptide chain from the cytoplasm to the endoplasmic reticulum (ER) and the compartments of the Golgi apparatus. Enzymes are said to be localized along this pathway. An enzyme X that acts on a lipid-linked glycan or an N-glycan before enzyme Y is said to be or to act "upstream" to enzyme Y; similarly, enzyme Y is or acts "downstream" from enzyme X.

As used herein, the term "alg X activity" refers to the enzymatic activity encoded by the "alg X" gene, and to an enzyme having that enzymatic activity encoded by a homologous gene or gene product (see below) or by an unrelated gene or gene product.

As used herein, the term "antibody" refers to a full antibody (consisting of two heavy chains and two light chains) or a fragment thereof. Such fragments include, but are not limited to, those produced by digestion with various proteases, those produced by chemical cleavage and/or chemical dissociation, and those produced recombinantly, so long as the fragment remains capable of specific binding to an antigen. Among these fragments are Fab, Fab', F(ab')2, and single chain Fv (scFv) fragments. Within the scope of the term "antibody" are also antibodies that have been modified in sequence, but remain capable of specific binding to an antigen. Example of modified antibodies are interspecies chimeric and humanized antibodies; antibody fusions; and heteromeric antibody complexes, such as diabodies (bispecific antibodies), single-chain diabodies, and intrabodies (see, e.g., Marasco (ed.), Intracellular Antibodies: Research and Disease Applications, Springer-Verlag New York, Inc. (1998) (ISBN: 3540641513), the disclosure of which is incorporated herein by reference in its entirety).

As used herein, the term "mutation" refers to any change in the nucleic acid or amino acid sequence of a gene product, e.g., of a glycosylation-related enzyme.

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. The term includes single and double stranded forms of DNA.

Unless otherwise indicated, a "nucleic acid comprising SEQ ID NO:X" refers to a nucleic acid, at least a portion of which has either (i) the sequence of SEQ ID NO:X, or (ii) a sequence complementary to SEQ ID NO:X. The choice between the two is dictated by the context. For instance, if the nucleic acid is used as a probe, the choice between the two is dictated by the requirement that the probe be complementary to the desired target.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosoines, polymerases, and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems.

However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence (i.e., a sequence that is not naturally adjacent to this endogenous nucleic acid sequence) is placed adjacent to the endogenous nucleic acid sequence, such that the expression of this endogenous nucleic acid sequence is altered. By way of example, a non-native promoter sequence can be substituted (e.g., by homologous recombination) for the native promoter of a gene in the genome of a human cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g., by human intervention. An "isolated nucleic acid" also includes a nucleic acid integrated into a host cell chromosome at a heterologous site, a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences (Pearson, 1990, (herein incorporated by reference). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., supra, page 9.51, hereby incorporated by reference. For purposes herein, "high stringency conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product. See, e.g., Leung, D. W., et al., *Technique*, 1, pp. 11-15 (1989) and Caldwell, R. C. & Joyce G. F., *PCR Methods Applic.*, 2, pp. 28-33 (1992)); and "oligonucleotide-directed mutagenesis" (a process which enables the generation of site-specific mutations in any cloned DNA segment of interest. See, e.g., Reidhaar-Olson, J. F. & Sauer, R. T., et al., *Science*, 241, pp. 53-57 (1988)).

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

"Operatively linked" expression control-sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences.

Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) when it exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{125}$I, $^{32}$P, $^{35}$S, and $^{3}$H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See Ausubel et al., 1992, hereby incorporated by reference.

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

The term "non-peptide analog" refers to a compound with properties that are analogous to those of a reference polypeptide. A non-peptide compound may also be termed a "peptide mimetic" or a "peptidomimetic". See, e.g., Jones, (1992) Amino Acid and Peptide Synthesis, Oxford University Press; Jung, (1997) Combinatorial Peptide and Nonpeptide Libraries: A Handbook John Wiley; Bodanszky et al., (1993) Peptide Chemistry—A Practical Textbook, Springer Verlag; "Synthetic Peptides: A Users Guide", G. A. Grant, Ed, W. H. Freeman and Co., 1992; Evans et al. *J. Med. Chem.* 30:1229 (1987); Fauchere, *J. Adv. Drug Res.* 15:29 (1986); Veber and Freidinger *TINS* p. 392 (1985); and references sited in each of the above, which are incorporated herein by reference. Such compounds are often developed with the aid of computerized molecular modeling. Peptide mimetics that are structurally similar to useful peptides of the invention may be used to produce an equivalent effect and are therefore envisioned to be part of the invention.

A "polypeptide mutant" or "mutein" refers to a polypeptide whose sequence contains an insertion, duplication, deletion, rearrangement or substitution of one or more amino acids compared to the amino acid sequence of a native or wild type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein. For instance, a mutein may have an increased or decreased neuron or NgR binding activity. In a preferred embodiment of the present invention, a MAG derivative that is a mutein (e.g., in MAG Ig-like domain 5) has decreased neuronal growth inhibitory activity compared to endogenous or soluble wild-type MAG.

A mutein has at least 70% overall sequence homology to its wild-type counterpart. Even more preferred are muteins having 80%, 85% or 90% overall sequence homology to the wild-type protein. In an even more preferred embodiment, a mutein exhibits 95% sequence identity, even more preferably 97%, even more preferably 98% and even more preferably 99% overall sequence identity. Sequence homology may be measured by any common sequence analysis algorithm, such as Gap or Bestfit.

Preferred amino acid substitutions are those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* (2$^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, s-N-methylarginine, and other similar amino acids and imino acids (e.g., 4-hydroxyproline). In the polypeptide notation used herein, the left-hand direction is the amino terminal direction and the right hand direction is the carboxy-terminal direction, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences). In a preferred embodiment, a homologous protein is one that exhibits 60% sequence homology to the wild type protein, more preferred is 70% sequence homology. Even more preferred are homologous proteins that exhibit 80%, 85% or 90% sequence homology to the wild type protein. In a yet more preferred embodiment, a homologous protein exhibits 95%, 97%, 98% or 99% sequence identity. As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, herein incorporated by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A preferred algorithm when comparing a inhibitory molecule sequence to a database containing a large number of sequences from different organisms is the computer program BLAST (Altschul, S. F. et al. (1990) *J. Mol. Biol.* 215:403-410; Gish and States (1993) *Nature Genet.* 3:266-272; Madden, T. L. et al. (1996) *Meth. Enzymol.* 266:131-141; Altschul, S. F. et al. (1997) *Nucleic Acids Res.* 25:3389-3402; Zhang, J. and Madden, T. L. (1997) *Genome Res.* 7:649-656), especially blastp or tblastn (Altschul et al., 1997). Preferred parameters for BLASTp are:

| | |
|---|---|
| Expectation value: | 10 (default) |
| Filter: | seg (default) |
| Cost to open a gap: | 11 (default) |
| Cost to extend a gap: | 1 (default |
| Max. alignments: | 100 (default) |
| Word size: | 11 (default) |
| No. of descriptions: | 100 (default) |
| Penalty Matrix: | BLOWSUM62 |

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, herein incorporated by reference). For example, percent sequence identity between amino acid sequences can be determined using FASTA with its default parameters (a word size of 2 and the PAM250 scoring matrix), as provided in GCG Version 6.1, herein incorporated by reference.

"Specific binding" refers to the ability of two molecules to bind to each other in preference to binding to other molecules in the environment. Typically, "specific binding" discriminates over adventitious binding in a reaction by at least two-fold, more typically by at least 10-fold, often at least 100-fold. Typically, the affinity or avidity of a specific binding reaction is at least about 10-7 M (e.g., at least about $10^{-8}$ M or $10^{-9}$ M).

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain.

As used herein, the term "molecule" means any compound, including, but not limited to, a small molecule, peptide, protein, sugar, nucleotide, nucleic acid, lipid, etc., and such a compound can be natural or synthetic.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Throughout this specification and claims, the word "comprise" or variations such as "comprises" or "comprising", will be understood to imply the inclusion of a stated integer or group of integers but not the exclusion of any other integer or group of integers.

Engineering or Selecting Hosts with Modified Lipid-Linked Oligosaccharides for the Generation of Human-Like N-Glycans The invention provides a method for producing a human-like glycoprotein in a non-human eukaryotic host cell. The method involves making or using a non-human eukaryotic host cell diminished or depleted in an alg gene activity (i.e., alg activities, including equivalent enzymatic activities in non-fungal host cells) and introducing into the host cell at least one glycosidase activity. In a preferred embodiment, the glycosidase activity is introduced by causing expression of one or more mannosidase activities within the host cell, for example, by activation of a mannosidase activity, or by expression from a nucleic acid molecule of a mannosidase activity, in the host cell.

In another embodiment, the method involves making or using a host cell diminished or depleted in the activity of one or more enzymes that transfer a sugar residue to the 1,6 arm of lipid-linked oligosaccharide precursors (FIG. 1). A host cell of the invention is selected for or is engineered by introducing a mutation in one or more of the genes encoding an enzyme that transfers a sugar residue (e.g., mannosylates) the 1,6 arm of a lipid-linked oligosaccharide precursor. The sugar residue is more preferably mannose, is preferably a glucose, GlcNAc, galactose, sialic acid, fucose or GlcNAc phosphate residue. In a preferred embodiment, the activity of one or more enzymes that mannosylate the 1,6 arm of lipid-linked oligosaccharide precursors is diminished or depleted. The method may further comprise the step of introducing into the host cell at least one glycosidase activity (see below).

In yet another embodiment, the invention provides a method for producing a human-like glycoprotein in a non-human host, wherein the glycoprotein comprises an N-glycan having at least two GlcNAcs attached to a trimannose core structure.

Figure 2A:
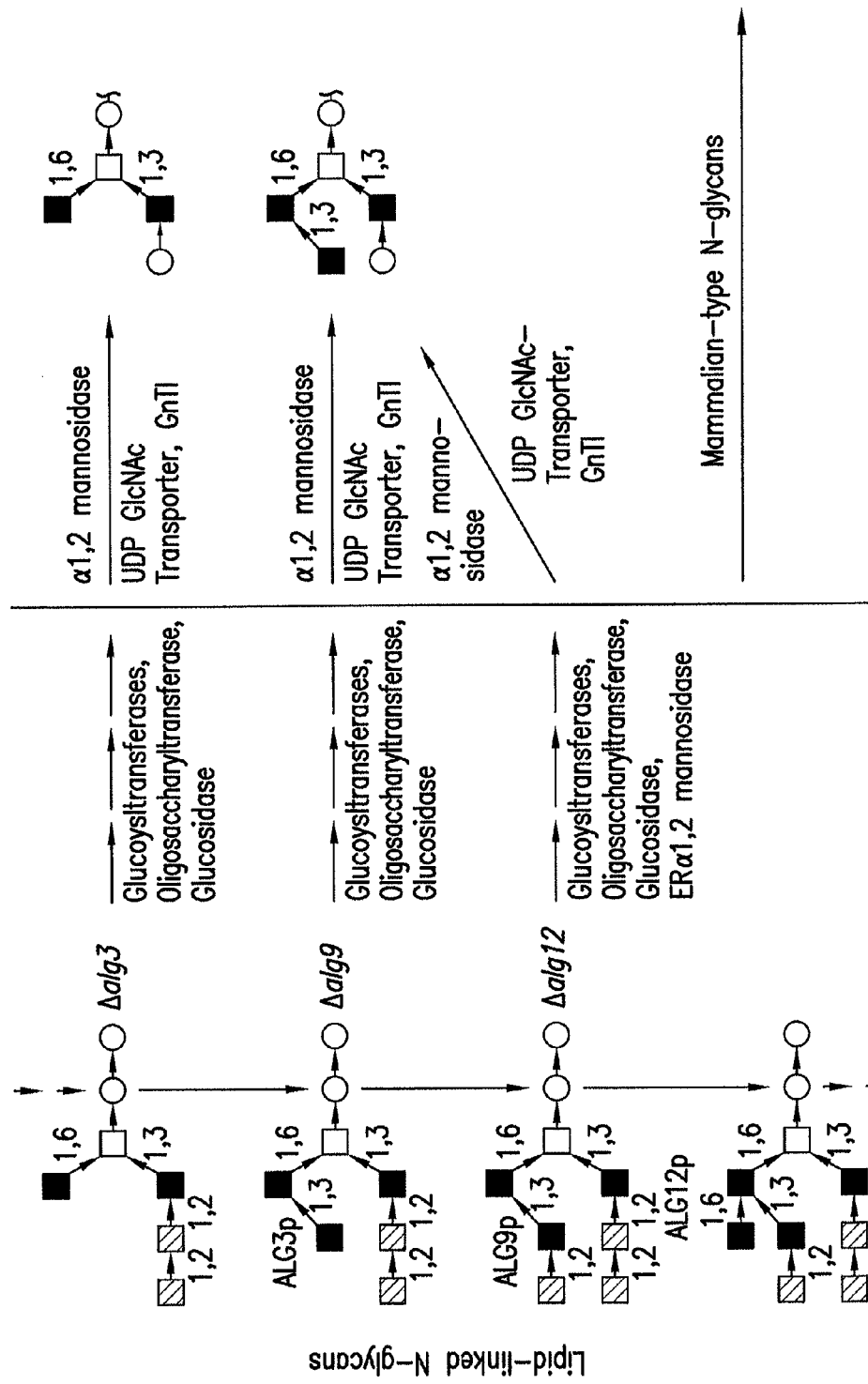
FIGS. 2A-2B show a schematic of the generation of GlcNAc$_2$Man$_3$GlcNAc$_2$ N-glycans from fungal host cells which are deficient in alg3, alg9 or alg 12 activities.
Figure 2B:
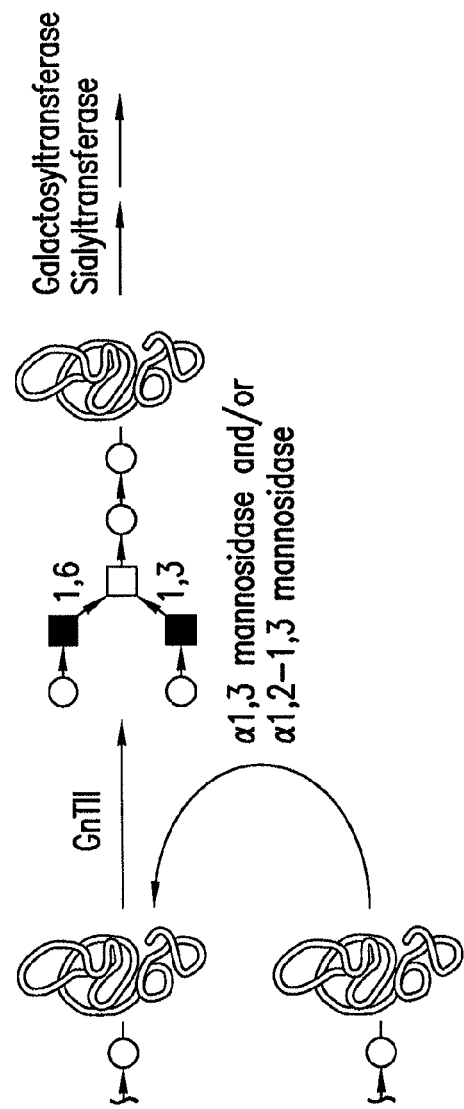
Figure 3:
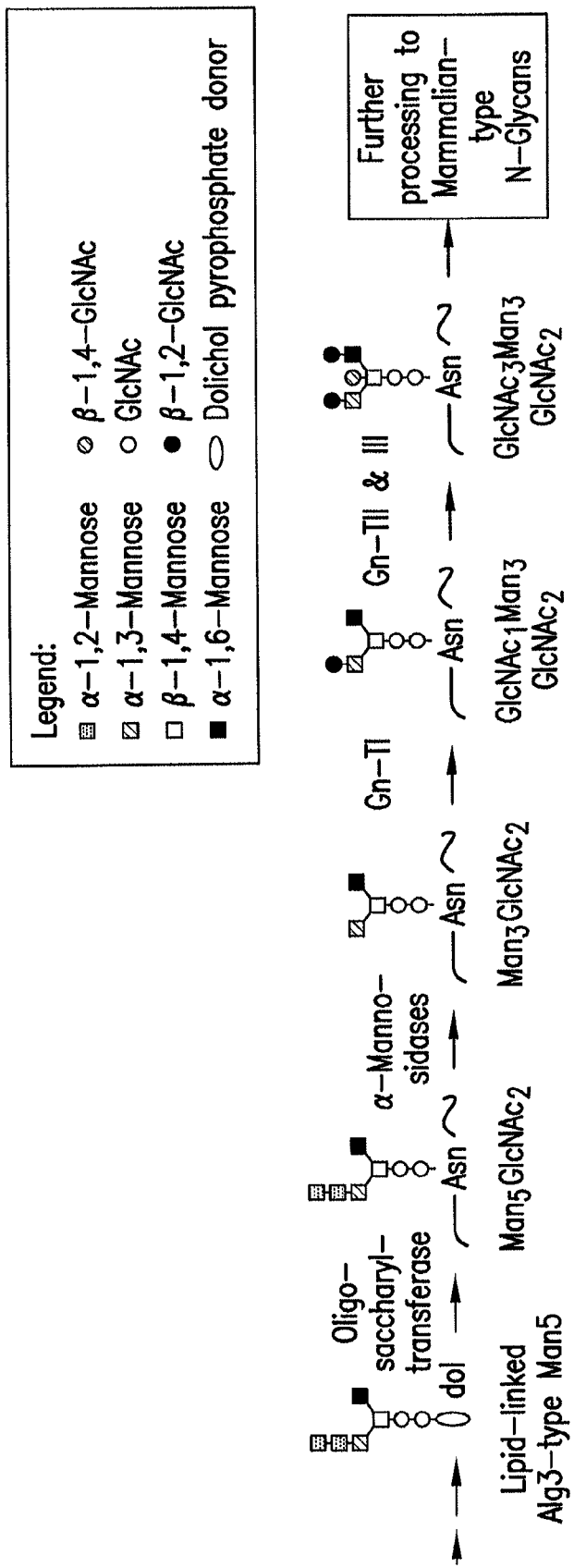
FIG. 3 is a schematic of processing reactions required to produce mammalian-type oligosaccharide structures in a fungal host cell with an alg3, och1 genotype.

In each above embodiment, the method is directed to making a host cell in which the lipid-linked oligosaccharide precursors are enriched in $Man_xGlcNAc_2$ structures, where X is 3, 4 or 5 (FIG. 2). These structures are transferred in the ER of the host cell onto nascent polypeptide chains by an oligosaccharyl-transferase and may then be processed by treatment with glycosidases (e.g., α-mannosidases) and glycosyltransferases (e.g., GnT1) to produce N-glycans having GlcNAc-$Man_xGlcNAc_2$ core structures, wherein X is 3, 4 or 5, and is preferably 3 (FIGS. 2 and 3). As shown in FIG. 2, N-glycans having a $GlcNAcMan_xGlcNAc_2$ core structure where X is greater than 3 may be converted to $GlcNAcMan_3GlcNAc_2$, e.g., by treatment with an α-1,3 and/or α-1,2-1,3 mannosidase activity, where applicable.

Additional processing of $GlcNAcMan_3GlcNAc_2$ by treatment with glycosyltransferases (e.g., GnTII) produces $GlcNAc_2Man_3GlcNAc_2$ core structures which may then be modified, as desired, e.g., by ex vivo treatment or by heterologous expression in the host cell of a set of glycosylation enzymes, including glycosyltransferases, sugar transporters and mannosidases (see below), to become human-like N-glycans. Preferred human-like glycoproteins which may be produced according to the invention include those which comprise N-glycans having seven or fewer, or three or fewer, mannose residues; comprise one or more sugars selected from the group consisting of galactose, GlcNAc, sialic acid, and fucose; and comprise at least one oligosaccharide branch comprising the structure NeuNAc-Gal-GlcNAc-Man.

In one embodiment, the host cell has diminished or depleted Dol-P-Man:$Man_5GlcNAc_2$-PP-Dol Mannosyltransferase activity, which is an activity involved in the first mannosylation step from $Man_5GlcNAc_2$-PP-Dol to $Man_6GlcNAc_2$-PP-Dol at the luminal side of the ER (e.g., ALG3 FIG. 1; FIG. 2). In S. cerevisiae, this enzyme is encoded by the ALG3 gene. As described above, S. cerevisiae cells harboring a leaky alg3-1 mutation accumulate $Man_5GlcNAc_2$-PP-Dol and cells having a deletion in alg3 appear to transfer $Man_5GlcNAc_2$ structures onto nascent polypeptide chains within the ER. Accordingly, in this embodiment, host cells will accumulate N-glycans enriched in $Man_5GlcNAc_2$ structures which can then be converted to $GlcNAc_2Man_3GlcNAc_2$ by treatment with glycosidases (e.g., with α-1,2 mannosidase, α-1,3 mannosidase or α-1,2-1,3 mannosidase activities (FIG. 2).

As described in Example 1, degenerate primers were designed based on an alignment of Alg3 protein sequences from S. cerevisiae, D. melanogaster and humans (H. sapiens) (FIGS. 4 and 5), and were used to amplify a product from P. pastoris genomic DNA. The resulting PCR product was used as a probe to identify and isolate a P. pastoris genomic clone comprising an open reading frame (ORF) that encodes a protein having 35% overall sequence identity and 53% sequence similarity to the S. cerevisiae ALG3 gene (FIGS. 6 and 7). This P. pastoris gene is referred to herein as "PpALG3". The ALG3 gene was similarly identified and isolated from *K. lactis* (Example 1; FIGS. 8 and 9).

Thus, in another embodiment, the invention provides an isolated nucleic acid molecule having a nucleic acid sequence comprising or consisting of at least forty-five, preferably at least 50, more preferably at least 60 and most preferably 75 or more nucleotide residues of the *P. pastoris* ALG 3gene (FIG. 6) and the *K. lactis* ALG 3gene (FIG. 8), and homologs, variants and derivatives thereof. The invention also provides nucleic acid molecules that hybridize under stringent conditions to the above-described nucleic acid molecules. Similarly, isolated polypeptides (including muteins, allelic variants, fragments, derivatives, and analogs) encoded by the nucleic acid molecules of the invention are provided (*P. pastoris* and *K. lactis* ALG 3gene products are shown in FIGS. 6 and 8). In addition, also provided are vectors, including expression vectors, which comprise a nucleic acid molecule of the invention, as described further herein.

Using gene-specific primers, a construct was made to delete the PpALG3 gene from the genome of *P. pastoris* (Example 1). This strain was used to generate a host cell depleted in Dol-P-Man:Man$_5$GlcNAc$_2$-PP-Dol Mannosyltransferase activity and produce lipid-linked Man$_5$GlcNAc$_2$-PP-Dol precursors which are transferred onto nascent polypeptide chains to produce N-glycans having a Man$_5$GlcNAc$_2$ carbohydrate structure.

As described in Example 2, such a host cell may be engineered by expression of appropriate mannosidases to produce N-glycans having the desired Man$_3$GlcNAc$_2$ core carbohydrate structure. Expression of GnTs in the host cell (e.g., by targeting a nucleic acid molecule or a library of nucleic acid molecules as described below) enables the modified host cell to produce N-glycans having one or two GlcNAc structures attached to each arm of the Man3 core structure (i.e., GlcNAc$_1$Man$_3$GlcNAc$_2$ or GlcNAc$_2$Man$_3$GlcNAc$_2$; see FIG. 3). These structures may be processed further using the methods of the invention to produce human-like N-glycans on proteins which enter the secretion pathway of the host cell.

In another embodiment, the host cell has diminished or depleted dolichyl-P-Man:Man$_6$GlcNAc2-PP-dolichyl α-1,2 mannosyltransferase activity, which is an α-1,2 mannosyltransferase activity involved in the mannosylation step converting Man$_6$GlcNAc$_2$-PP-Dol to Man$_7$GlcNAc$_2$-PP-Dol at the luminal side of the ER (see above and FIGS. 1 and 2). In *S. cerevisiae*, this enzyme is encoded by the ALG9 gene. Cells harboring an alg9 mutation accumulate Man$_6$GlcNAc$_2$-PP-Dol (FIG. 2) and transfer Man$_6$GlcNAc$_2$ structures onto nascent polypeptide chains within the ER. Accordingly, in this embodiment, host cells will accumulate N-glycans enriched in Man$_6$GlcNAc$_2$ structures which can then be processed down to core Man3 structures by treatment with α-1,2 and α-1,3 mannosidases (see FIG. 3 and Examples 3 and 4).

A host cell in which the alg9 gene (or gene encoding an equivalent activity) has been deleted is constructed (see, e.g., Example 3). Deletion of ALG9 (or ALG12; see below) creates a host cell which produces N-glycans with one or two additional mannoses, respectively, on the 1,6 arm (FIG. 2). In order to make the 1,6 core-mannose accessible to N-acetylglucosaminyltransferase II (GnTII) these mannoses have to be removed by glycosidase(s). ER mannosidase typically will remove the terminal 1,2 mannose on the 1,6 arm and subsequently Mannosidase II (alpha 1-3,6 mannosidase) or other mannosidases such as alpha 1,2, alpha1,3 or alpha 1-2,3 mannosidases (e.g., from *Xanthomonas manihotis*; see Example 4) can act upon the 1,6 arm and subsequently GnTII can transfer an N-acetylglucosamine, resulting in GlcNAc$_2$Man$_3$ (FIG. 2).

The resulting host cell, which is depleted for alg9p activity, is engineered to express α-1,2 and α-1,3 mannosidase activity (from one or more enzymes, and preferably, by expression from a nucleic acid molecule introduced into the host cell and which expresses an enzyme targeted to a preferred subcellular compartment (see below). Example 4 describes the cloning and expression of one such enzyme from *Xanthomonas manihotis*.

In another embodiment, the host cell has diminished or depleted dolichyl-P-Man:Man7GlcNAc2-PP-dolichyl α-1,6 mannosyltransferase activity, which is an α-1,6 mannosyltransferase activity involved in the mannosylation step converting Man$_7$GlcNAc$_2$-PP-Dol to Man$_8$GlcNAc$_2$-PP-Dol (which mannosylates the α-1,6 mannose on the 1,6 arm of the core mannose structure) at the luminal side of the ER (see above and FIGS. 1 and 2). In *S. cerevisiae*, this enzyme is encoded by the ALG12 gene. Cells harboring an alg12 mutation accumulate Man$_7$GlcNAc$_2$-PP-Dol (FIG. 2) and transfer Man$_7$GlcNAc$_2$ structures onto nascent polypeptide chains within the ER. Accordingly, in this embodiment, host cells will accumulate N-glycans enriched in Man$_7$GlcNAc$_2$ structures which can then be processed down to core Man3 structures by treatment with α-1,2 and α-1,3 mannosidases (see FIG. 3 and Examples 3 and 4).

As described above for alg9 mutant hosts, the resulting host cell, which is depleted for alg12p activity, is engineered to express α-1,2 and α-1,3 mannosidase activity (e.g., from one or more enzymes, and preferably, by expression from one or more nucleic acid molecules introduced into the host cell and which express an enzyme activity which is targeted to a preferred subcellular compartment (see below).

Engineering or Selecting Hosts Optionally Having Decreased Initiating α-1,6 Mannosyltransferase Activity In a preferred embodiment, the method of the invention involves making or using a host cell which is both (a) diminished or depleted in the activity of an alg gene or in one or more activities that mannosylate N-glycans on the α-1,6 arm of the Man$_3$GlcNAc$_2$ ("Man3") core carbohydrate structure; and (b) diminished or depleted in the activity of an initiating α-1,6-mannosyltransferase, i.e., an initiation specific enzyme that initiates outer chain mannosylation (on the α-1,3 arm of the Man3 cores structure). In *S. cerevisiae*, this enzyme is encoded by the OCH1 gene. Disruption of the och1 gene in *S. cerevisiae* results in a phenotype in which N-linked sugars completely lack the poly-mannose outer chain. Previous approaches for obtaining mammalian-type glycosylation in fungal strains have required inactivation of OCH1 (see, e.g., Chiba, 1998). Disruption of the initiating α-1,6-mannosyltransferase activity in a host cell of the invention is optional, however (depending on the selected host cell), as the Och1p enzyme requires an intact Man$_8$GlcNAc for efficient mannose outer chain initiation. Thus, the host cells selected or produced according to this invention, which accumulate lipid-linked oligosaccharides having seven or fewer mannose residues will, after transfer, produce hypoglycosylated N-glycans that will likely be poor substrates for Och1p (see, e.g., Nakayama, 1997).

Engineering or Selecting Hosts Having Increased Glucosyltransferase Activity

As discussed above, glucosylated oligosaccharides are thought to be transferred to nascent polypeptide chains at a much higher rate than their nonglucosylated counterparts. It appears that substrate recognition by the oligosaccharyltransferase complex is enhanced by addition of glucose to the antennae of lipid-linked oligosaccharides. It is thus desirable to create or select host cells capable of optimal glucosylation of the lipid-linked oligosaccharides. In such host cells, underglycosylation will be substantially decreased or even abolished, due to a faster and more efficient transfer of glucosylated $Man_5$ structures onto the nascent polypeptide chain.

Accordingly, in another embodiment of the invention, the method is directed to making a host cell in which the lipid-linked N-glycan precursors are transferred efficiently to the nascent polypeptide chain in the ER. In a preferred embodiment, transfer is augmented by increasing the level of glucosylation on the branches of lipid-linked oligosaccharides which, in turn, will make them better substrates for oligosaccharyltransferase.

In one preferred embodiment, the invention provides a method for making a human-like glycoprotein which uses a host cell in which one or more enzymes responsible for glucosylation of lipid-linked oligosaccharides in the ER has increased activity. One way to enhance the degree of glucosylation of the lipid-linked oligosaccharides is to overexpress one or more enzymes responsible for the transfer of glucose residues onto the antennae of the lipid-linked oligosaccharide. In particular, increasing $\alpha$-1,3 glucosyltransferase activity will increase the amount of glucosylated lipid-linked $Man_5$ structures and will reduce or eliminate the underglycosylation of secreted proteins. In S. cerevisiae, this enzyme is encoded by the ALG6 gene.

Saccharomyces cerevisiae ALG6 and its human counterpart have been cloned (Imbach, 1999; Reiss, 1996). Due to the evolutionary conservation of the early steps of glycosylation, ALG6 loci are expected to be homologous between species and may be cloned based on sequence similarities by anyone skilled in the art. (The same holds true for cloning and identification of ALG8 and ALG10 loci from different species.) In addition, different glucosyltransferases from different species can then be tested to identify the ones with optimal activities.

The introduction of additional copies of an ALG6 gene and/or the expression of ALG6 under the control of a strong promoter, such as the GAPDH promoter, is one of several ways to increase the degree of glucosylated lipid-linked oligosaccharides. The ALG6 gene from P. pastoris is cloned and expressed (Example 5). ALG6 nucleic acid and amino acid sequences are show in FIG. 25 (S. cerevisiae) and FIG. 26 (P. pastoris). These sequences are compared to other eukaryotic ALG6 sequences in FIG. 27.

Accordingly, another embodiment of the invention provides a method to enhance the degree of glucosylation of lipid-linked oligosaccharides comprising the step of increasing alpha-1,3 glucosyltransferase activity in a host cell. The increase in activity may be achieved by overexpression of nucleic acid sequences encoding the activity, e.g., by operatively linking the nucleic acid encoding the activity with one or more heterologous expression control sequences. Preferred expression control sequences include transcription initiation, termination, promoter and enhancer sequences; RNA splice donor and polyadenylation signals; mRNA stabilizing sequences; ribosome binding sites; protein stabilizing sequences; and protein secretion sequences.

In another embodiment, the increase in alpha-1,3 glucosyltransferase activity is achieved by introducing a nucleic acid molecule encoding the activity on a multi-copy plasmid, using techniques well known to the skilled worker. In yet another embodiment, the degree of glucosylation of lipid-linked oligosaccharides comprising decreasing the substrate specificity of oligosaccharyl transferase activity in a host cell. This is achieved by, for example, subjecting at least one nucleic acid encoding the activity to a technique such as gene shuffling, in vitro mutagenesis, and error-prone polymerase chain reaction, all of which are well-known to one of skill in the art. Naturally, ALG8 and ALG10 can be overexpressed in a host cell and tested in a similar fashion.

Accordingly, in a preferred embodiment, the invention provides a method for making a human-like glycoprotein using a host cell which is engineered or selected so that one or more enzymes responsible for glucosylation of lipid-linked oligosaccharides in the ER has increased activity. In a more preferred embodiment, the invention uses a host cell having both (a) diminished or depleted in the activity of one or more alg gene activities or activities that mannosylate N-glycans on the $\alpha$-1,6 arm of the $Man_3GlcNAc_2$ ("Man3") core carbohydrate structure and (b) engineered or selected so that one or more enzymes responsible for glucosylation of lipid-linked oligosaccharides in the ER has increased activity. The lipid-linked $Man_5$ structure found in an alg3 mutant background, however, is not a preferred substrate for Alg6p. Accordingly, the skilled worker may identify Alg6p, Alg8p and Alg10p with an increased substrate specificity (Gibbs, 2001) e.g., by subjecting nucleic acids encoding such enzymes to one or more rounds of gene shuffling, error prone PCR, or in vitro mutagenesis approaches and selecting for increased substrate specificity in a host cell of interest, using molecular biology and genetic selection techniques well known to those of skill in the art. It will be appreciated by the skilled worker that such techniques for improving enzyme substrate specificities in a selected host strain are not limited to this particular embodiment of the invention but rather, may be used in any embodiment to optimize further the production of human-like N-glycans in a non-human host cell.

As described, once $Man_5$ is transferred onto the nascent polypeptide chain, expression of suitable $\alpha$-1,2-mannosidase(s), as provided by the present invention, will further trim $Man_5GlcNAc_2$ structures to yield the desired core $Man_3GlcNAc_2$ structures. $\alpha$-1,2-mannosidases remove only terminal $\alpha$-1,2-linked mannose residues and are expected to recognize the $Man_5GlcNAc_2$-$Man_7GlcNAc_2$ specific structures made in alg3, 9 and 12 mutant host cells and in host cells in which homologs to these genes are mutated.

As schematically presented in FIG. 3, co-expression of appropriate UDP-sugar-transporter(s) and -transferase(s) will cap the terminal $\alpha$-1,6 and $\alpha$-1,3 residues with GlcNAc, resulting in the necessary precursor for mammalian-type complex and hybrid N-glycosylation: $GlcNAc_2Man_5GlcNAc_2$. The peptide-bound N-linked oligosaccharide chain $GlcNAc_2Man_3GlcNAc_2$ (FIG. 3) then serves as a precursor for further modification to a mammalian-type oligosaccharide structure. Subsequent expression of galactosyl-tranferases and genetically engineering the capacity to transfer sialylic acid will produce a mammalian-type (e.g., human-like) N-glycan structure.

A desired host cell according to the invention can be engineered one enzyme or more than one enzyme at a time. In addition, a library of genes encoding potentially useful enzymes can be created, and a strain having one or more enzymes with optimal activities or producing the most "human-like" glycoproteins, selected by transforming target host cells with one or more members of the library. Lower eukaryotes that are able to produce glycoproteins having the core N-glycan $Man_3GlcNAc_2$ are particularly useful because of the ease of performing genetic manipulations, and safety and efficiency features. In a preferred embodiment, at least one further glycosylation reaction is performed, ex vivo or in vivo, to produce a human-like N-glycan. In a more preferred embodiment, active forms of glycosylating enzymes are expressed in the endoplasmic reticulum and/or Golgi apparatus of the host cell to produce the desired human-like glycoprotein.

Host Cells

A preferred non-human host cell of the invention is a lower eukaryotic cell, e.g., a unicellular or filamentous fungus, which is diminished or depleted in the activity of one or more alg gene activities (including an enzymatic activity which is a homolog or equivalent to an alg activity). Another preferred host cell of the invention is diminished or depleted in the activity of one or more enzymes (other than alg activities) that mannosylate the α-1,6 arm of a lipid-linked oligosaccharide structure.

While lower eukaryotic host cells are preferred, a wide variety of host cells having the aforementioned properties are envisioned as being useful in the methods of the invention. Plant cells, for instance, may be engineered to express a human-like glycoprotein according to the invention. Likewise, a variety of non-human, mammalian host cells may be altered to express more human-like glycoproteins using the methods of the invention. An appropriate host cell can be engineered, or one of the many such mutants already described in yeasts may be used. A preferred host cell of the invention, as exemplified herein, is a hypermannosylation-minus (OCH1) mutant in Pichia pastoris which has further been modified to delete the alg3 gene. Other preferred hosts are Pichia pastoris mutants having och1 and alg 9 or alg12 mutations.

Formation of Complex N-Glycans

The sequential addition of sugars to the modified, nascent N-glycan structure involves the successful targeting of glucosyltransferases into the Golgi apparatus and their successful expression. This process requires the functional expression, e.g., of GnT I, in the early or medial Golgi apparatus as well as ensuring a sufficient supply of UDP-GlcNAc (e.g., by expression of a UDP-GlcNAc transporter).

To characterize the glycoproteins and to confirm the desired glycosylation, the glycoproteins were purified, the N-glycans were PNGase-F released and then analyzed by MALDI-TOF-MS (Example 2). Kringle 3 domain of human plasminogen was used as the reporter protein. This soluble glycoprotein was produced in P. pastoris in an alg3, och1 knockout background (Example 2).

Figure 16:
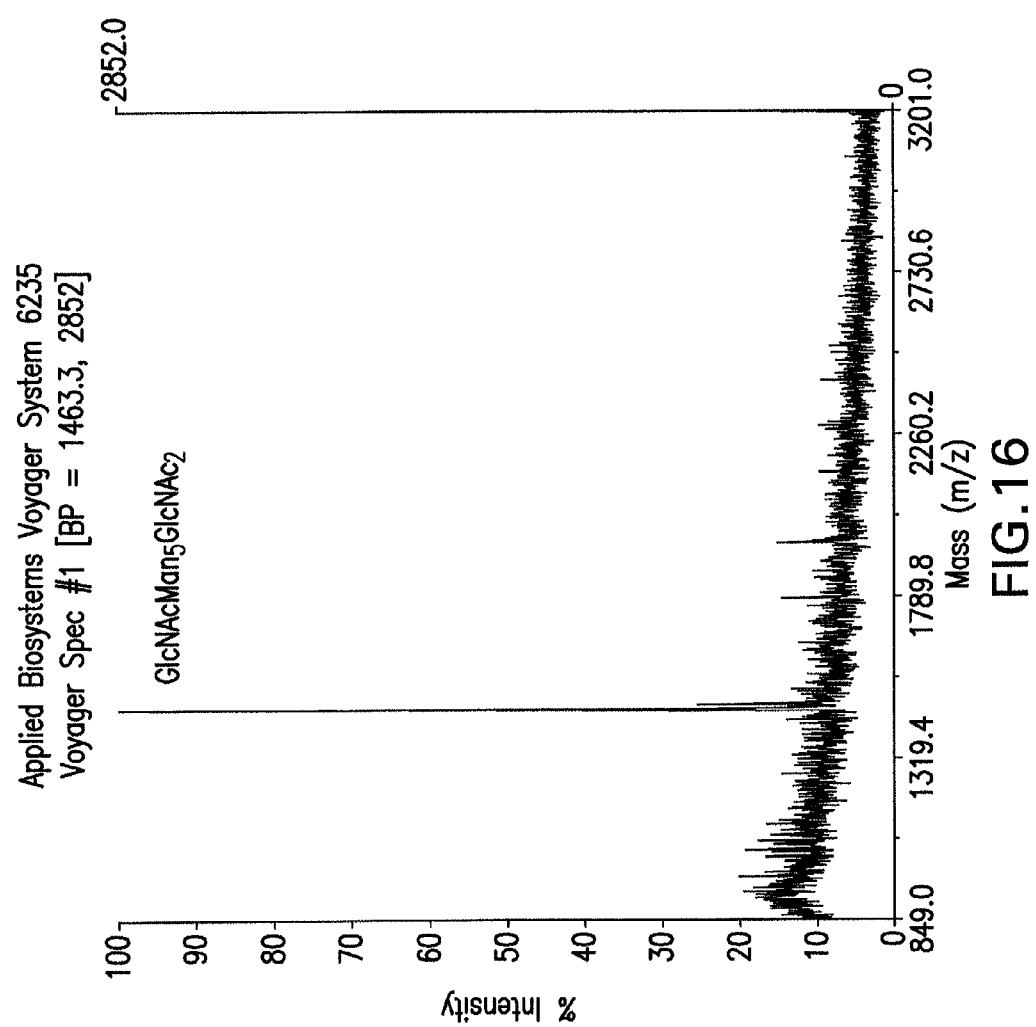
FIG. 16 is a MALDI-TOF-MS analysis of N-glycans isolated from a kringle 3 glycoprotein produced in a *P. pastoris* showing that the predominant N-glycan is GlcNAcMan$_5$GlcNAc$_2$.
Figure 17:
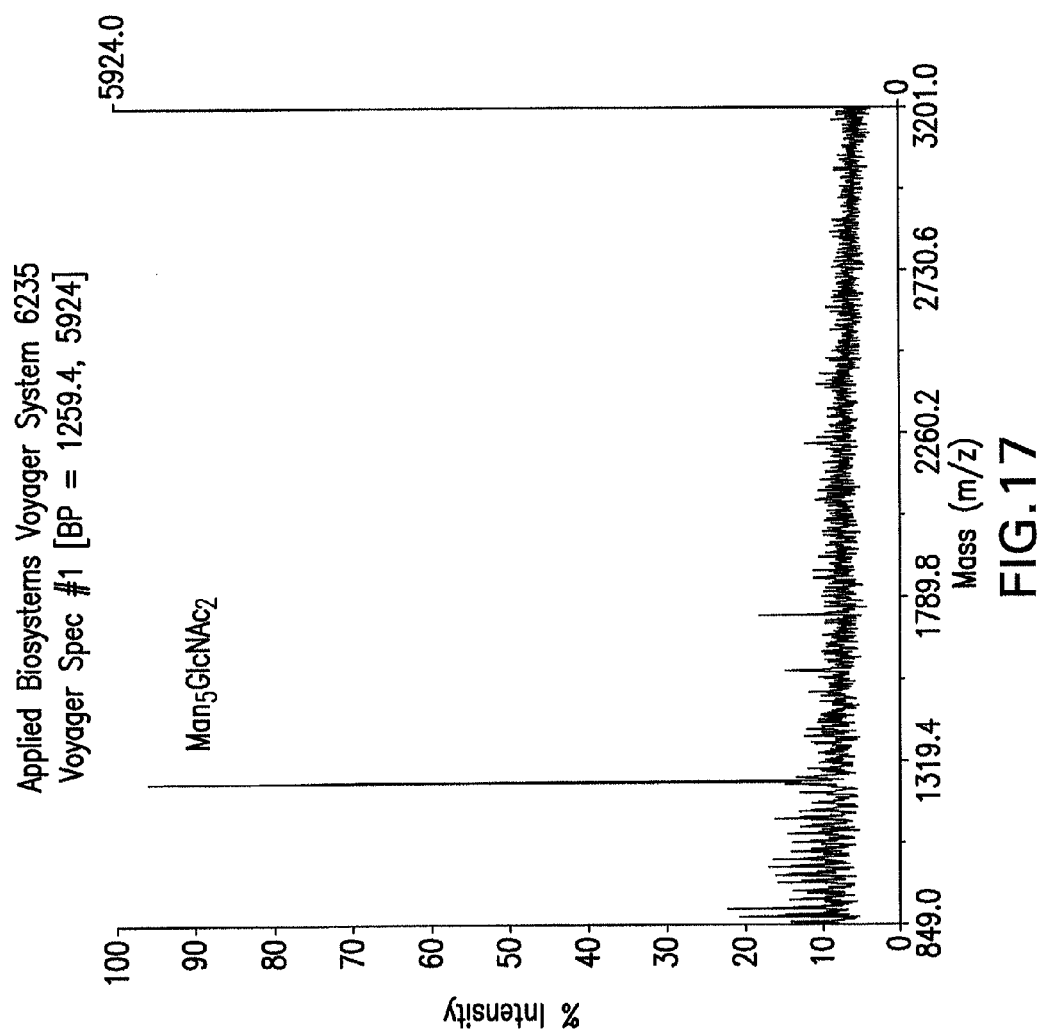
FIG. 17 is a MALDI-TOF-MS analysis of N-glycans isolated from a kringle 3 glycoprotein produced in a *P. pastoris* (FIG. 16) treated with β-N-hexosaminidase (peak corresponding to Man$_5$GlcNAc$_2$) to confirm that the predominant N-glycan of FIG. 16 is GlcNAcMan$_5$GlcNAc$_2$.

GlcNAcMan$_5$GlcNAc$_2$ was produced as the predominant N-glycan after addition of human GnT I, and K. lactis UDP-GlcNAc transporter in FIG. 16 (Example 2). The mass of this N-glycan is consistent with the mass of GlcNAcMan$_5$GlcNAc$_2$ at 1463 (m/z). To confirm the addition of the GlcNAc onto Man$_5$GlcNAc$_2$, a β-N-hexosaminidase digest was performed, which revealed a peak at 1260 (m/z), consistent with the mass of Man$_5$GlcNAc$_2$ (FIG. 17).

Figure 18:
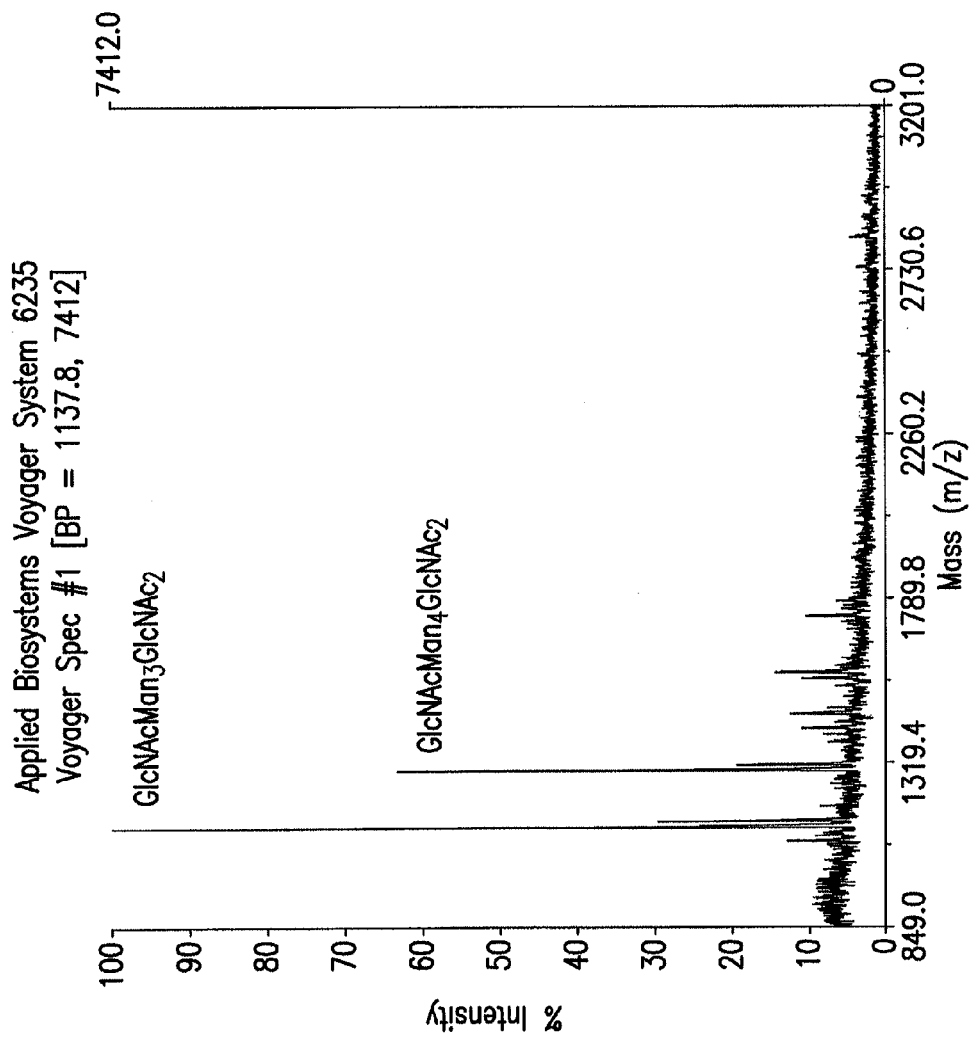
FIG. 18 is a MALDI-TOF-MS analysis of N-glycans isolated from a kringle 3 glycoprotein produced in a *P. pastoris* alg3 deletion mutant showing that the predominant N-glycans are GlcNAcMan$_3$GlcNAc$_2$ and GlcNAcMan$_4$GlcNAc$_2$.
Figure 19:
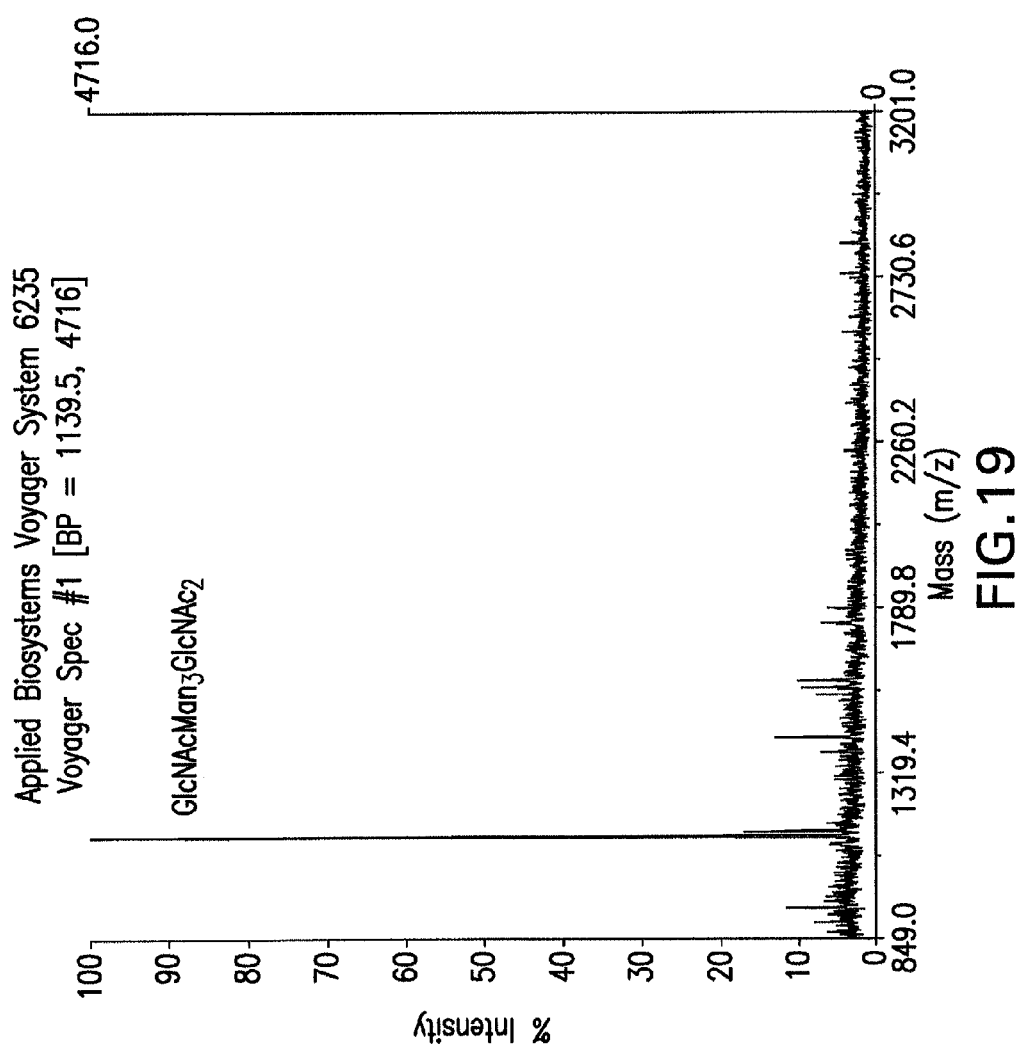
FIG. 19 is a MALDI-TOF-MS analysis of N-glycans isolated from a kringle 3 glycoprotein produced in a *P. pastoris* alg3 deletion mutant treated with α1,2 marmosidase, showing that the GlcNAcMan₄GlcNAc₂ of FIG. 18 is converted to GlcNAcMan₃GlcNAc₂.
Figure 20:
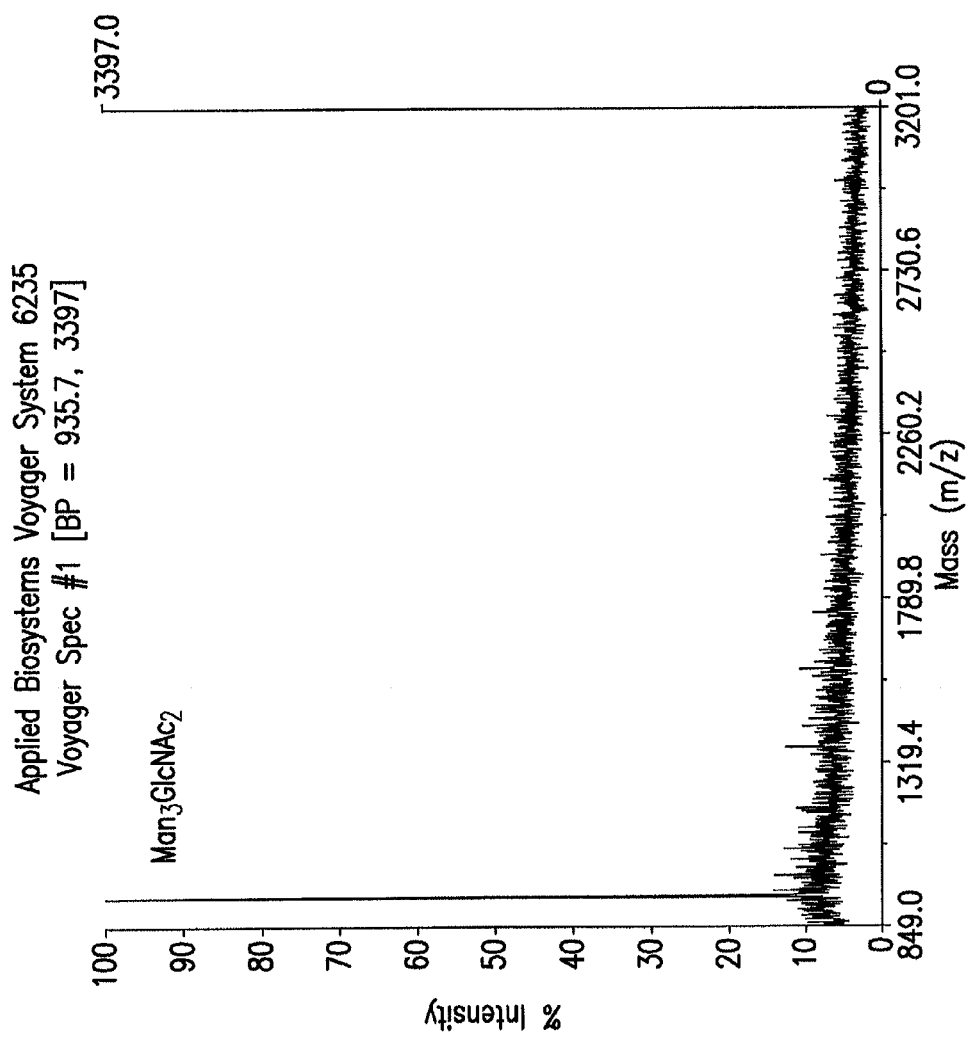
FIG. 20 is a MALDI-TOF-MS analysis of N-glycans of FIG. 19 treated with β-N-hexosaminidase (peak corresponding to Man₃GlcNAc₂) to confirm that the N-glycan of FIG. 19 is GlcNAcMan₃GlcNAc₂.

The N-glycans from the alg3 och1 deletion in one strain PBP3 (Example 2) provided two distinct peaks at 1138 (m/z) and 1300 (m/z), which is consistent with structures GlcNAcMan$_3$GlcNAc$_2$ and GlcNAcMan$_4$GlcNAc$_2$ (FIG. 18). After an in vitro α1,2-mannosidase digestion for redundant mannoses, a peak eluted at 1138 (m/z), which is consistent with GlcNAcMan$_3$GlcNAc$_2$ (FIG. 19). To confirm the addition of the GlcNAc onto the Man$_3$GlcNAc$_2$ structure, a β-N-hexosaminidase digest was performed, which revealed a peak at 934 (m/z), consistent with the mass of Man$_3$GlcNAc$_2$ (FIG. 20).

Figure 21:
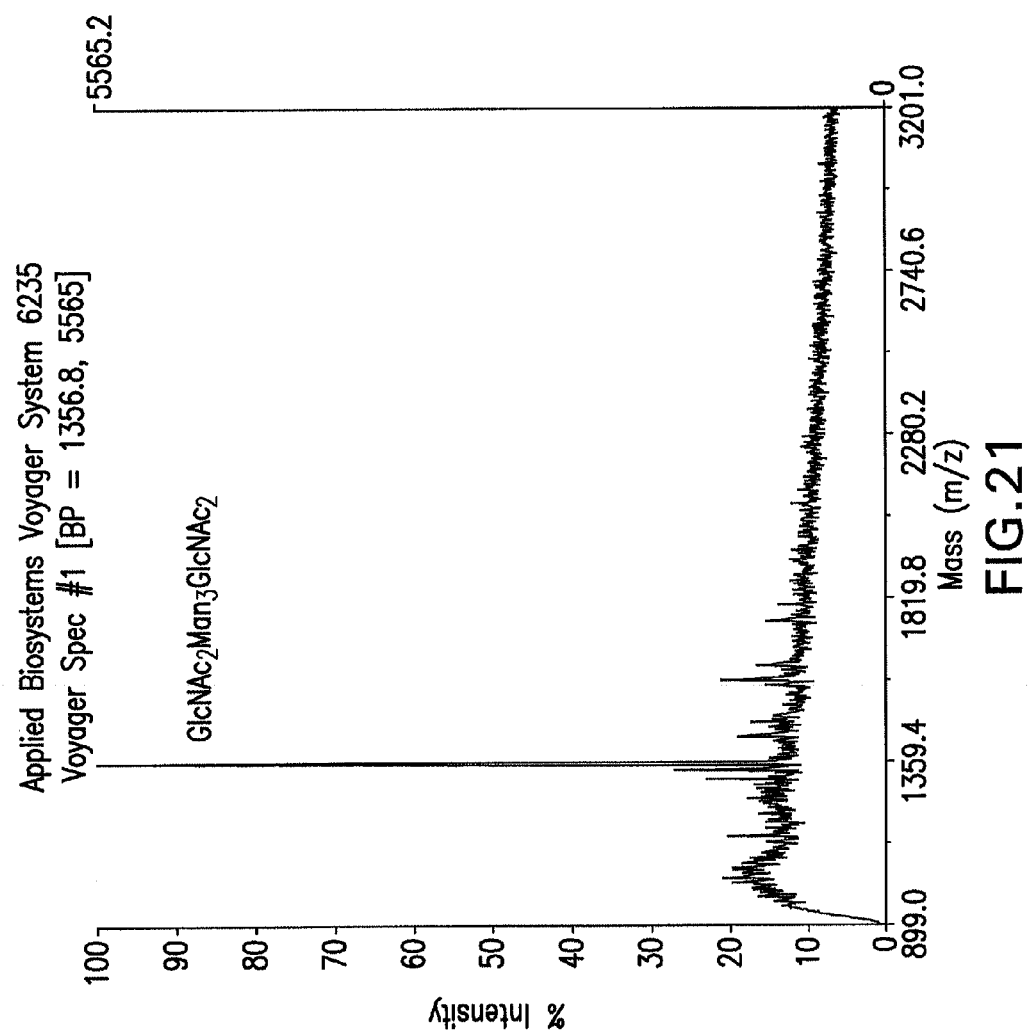
FIG. 21 is a MALDI-TOF-MS analysis of N-glycans isolated from a kringle 3 glycoprotein produced in a *P. pastoris* alg3 deletion mutant treated with α1,2 mannosidase and GnTII, showing that the GlcNAcMan₃GlcNAc₂ of FIG. 19 is converted to GlcNAc₂Man₃GlcNAc₂.
Figure 22:
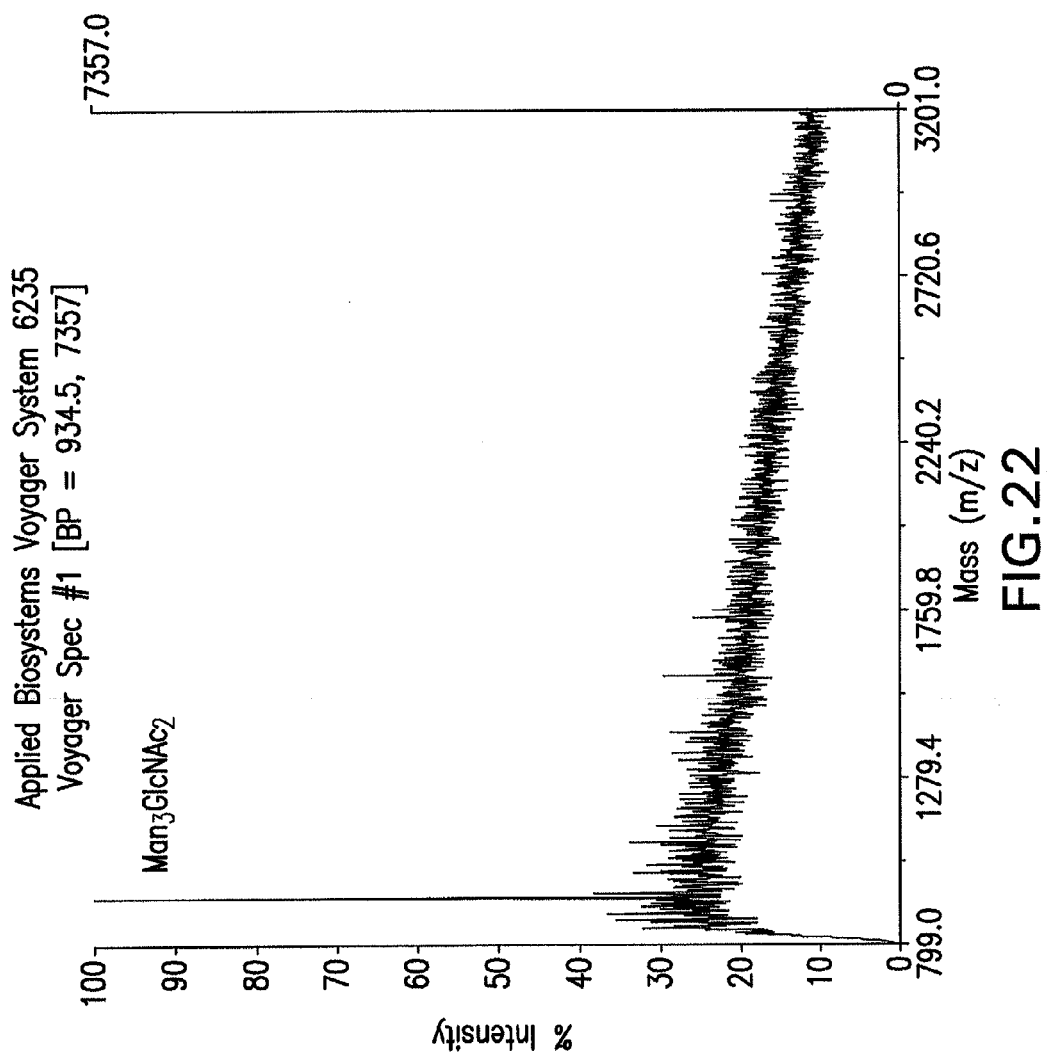
FIG. 22 is a MALDI-TOF-MS analysis of N-glycans of FIG. 21 treated with β-N-hexosaminidase (peak corresponding to Man₃GlcNAc₂) to confirm that the N-glycan of FIG. 21 is GlcNAc₂Man₃GlcNAc₂.

The addition of the second GlcNAc onto GlcNAcMan$_3$GlcNAc$_2$ is shown in FIG. 21. The peak at 1357 (m/z) corresponds to GlcNAc$_2$Man$_3$GlcNAc$_2$. To confirm the addition of the two GlcNAcs onto the core mannose structure Man$_3$GlcNAc$_2$, another β-N-hexosaminidase digest was performed, which revealed a peak at 934 (m/z), consistent with the mass of Man$_3$GlcNAc$_2$ (FIG. 22). This is conclusive data displaying a complex-type glycoprotein made in yeast cells.

Figure 23:
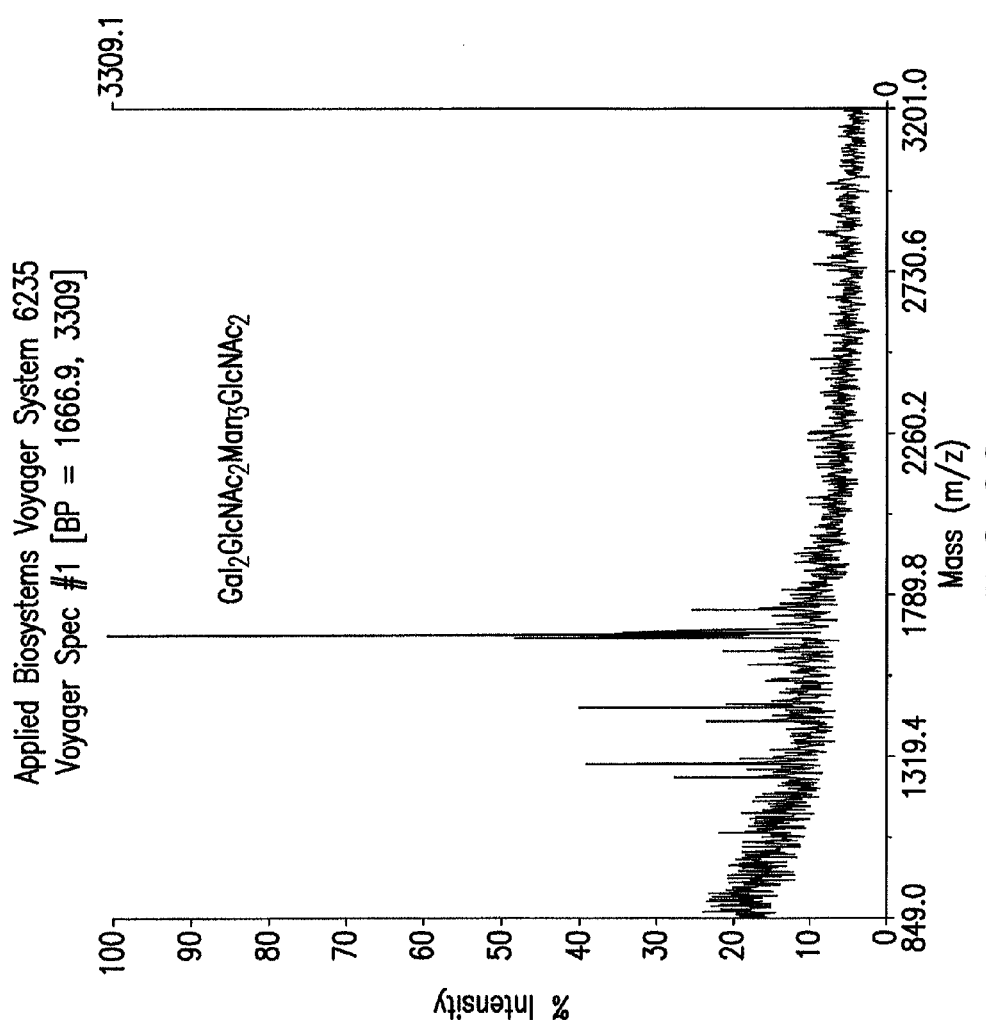
FIG. 23 is a MALDI-TOF-MS analysis of N-glycans isolated from a kringle 3 glycoprotein produced in a *P. pastoris* alg3 deletion mutant treated with α1,2 mannosidase and GnTII in the presence of UDP-galactose and β1,4-galactosyltransferase, showing that the GlcNAc₂Man₃GlcNAc₂ of FIG. 21 is converted to Gal₂GlcNAc₂Man₃GlcNAc₂.
Figure 24:
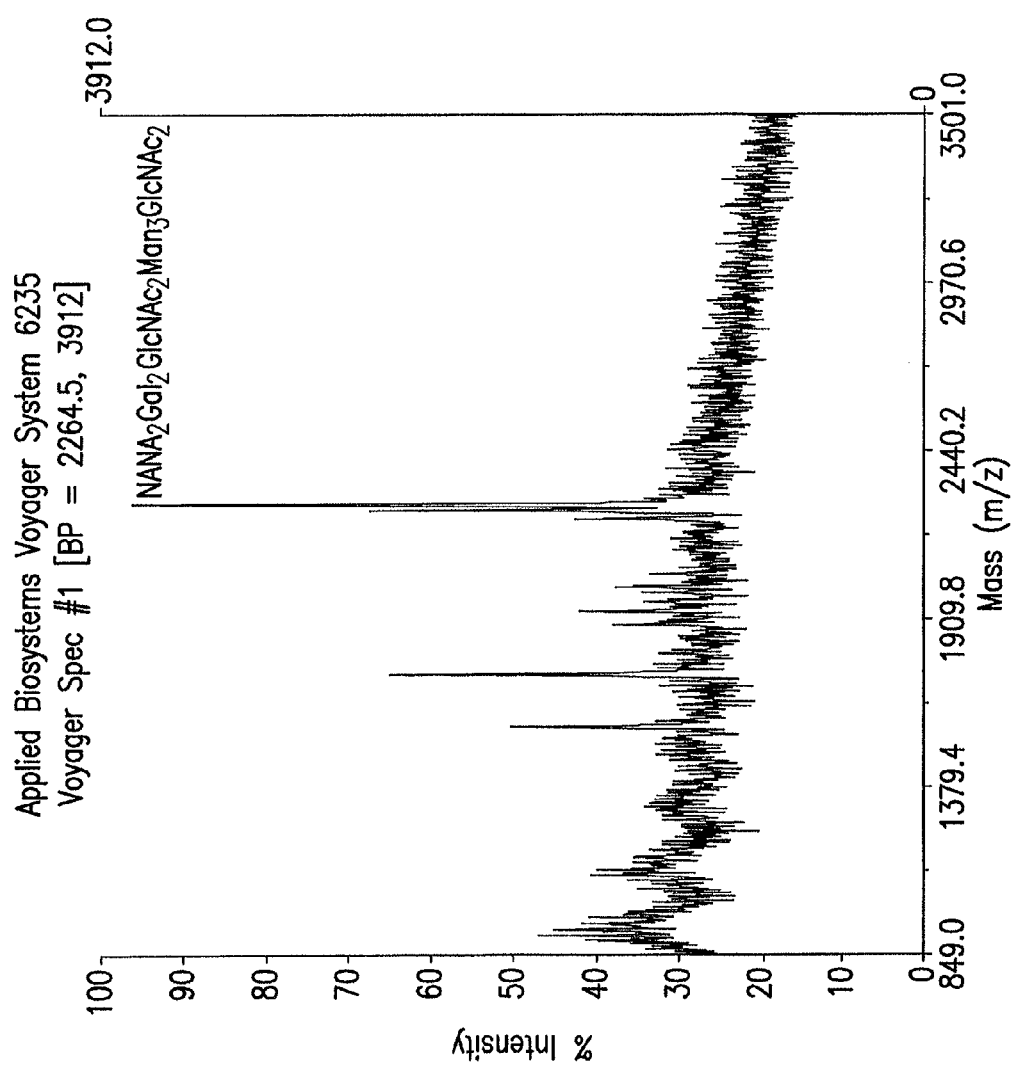
FIG. 24 is a MALDI-TOF-MS analysis of N-glycans isolated from a kringle 3 glycoprotein produced in a *P. pastoris* alg3 deletion mutant treated with α1,2 mannosidase and GnTII in the presence of UDP-galactose and β1,4-galactosyltransferase, and further treated with CMP-N-acetyl-neuraminic acid and sialyltransferase, showing that the Gal₂GlcNAc₂Man₃GlcNAc₂ is converted to NANA₂Gal₂GlcNAc₂Man₃GlcNAc₂.

The in vitro addition of UDP-galactose and β1,4-galactosyltransferase onto the GlcNAc$_2$Man$_3$GlcNAc$_2$ resulted in a peak at 1664 (m/z), which is consistent with the mass of Gal$_2$GlcNAc$_2$Man$_3$GlcNAc$_2$ (FIG. 23) Finally, the in vitro addition of CMP-N-acetylneuraminic acid and sialyltransferase resulted in a peak at 2248 (m/z), which is consistent with the mass of NANA$_2$Gal$_2$GlcNAc$_2$Man$_3$GlcNAC$_2$ (FIG. 24). The above data supports the use of non-mammalian host cells, which are capable of producing complex human-like glycoproteins.

Targeting of Glycosyl- and Galactosyl-Transferases to Specific Organelles.

Much work has been dedicated to revealing the exact mechanism by which these enzymes are retained and anchored to their respective organelle. Although complex, evidence suggests that, stem region, membrane spanning region and cytoplasmic tail individually or in concert direct enzymes to the membrane of individual organelles and thereby localize the associated catalytic domain to that locus.

The method by which active glycosyltransferases can be expressed and directed to the appropriate organelle such that a sequential order of reactions may occur, that leads to complex N-glycan formation, is as follows:

(A) Establish a DNA library of regions that are known to encode proteins/peptides that mediate localization to a particular location in the secretory pathway (ER, Golgi and trans Golgi network). A limited selection of such enzymes and their respective location is shown in Table 1. These sequences may be selected from the host to be engineered as well as other related or unrelated organism. Generally such sequences fall into three categories: (1) N-terminal sequences encoding a cytosolic tail (ct), a transmembrane domain (tmd) and part of a somewhat more ambiguously defined stem region (sr), which together or individually anchor proteins to the inner (lumenal) membrane of the Golgi, (2) retrieval signals which are generally found at the C-terminus such as the HDEL or KDEL tetrapeptide, and (3) membrane spanning nucleotide sugar transporters, which are known to locate in the Golgi. In the first case, where the localization region consists of various elements (ct, tmd and sr) the library is designed such that the ct, the tmd and various parts of the stem region are represented. This may be accomplished by using PCR primers that bind to the 5' end of the DNA encoding the cytosolic region and employing a series of opposing primers that bind to various parts of the stem region. In addition one would create fusion protein constructs that encode sugar nucleotide transporters and known retrieval signals.

(B) A second step involves the creation of a series of fusion protein constructs, that encode the above mentioned localization sequences and the catalytic domain of a particular glycosyltransferase cloned in frame to such localization sequence (e.g. GnT I, GalT, Fucosyltransferase or ST). In the case of a sugar nucleotide transporter fused to a catalytic domain one may design such constructs such that the catalytic domain (e.g. GnT I) is either at the N- or the C-terminus of the resulting polypeptide. The catalytic domain, like the localization sequence, may be derived from various different sources. The choice of such a catalytic domains may be guided by the knowledge of the particular environment in which the catalytic domain is to be active. For example, if a particular glycosyltransferase is to be active in the late Golgi, and all known enzymes of the host organism in the late Golgi have a pH optimum of 7.0, or the late Golgi is known to have a particular pH, one would try to select a catalytic domain that has maximum activity at that pH. Existing in vivo data on the activity of such enzymes, in particular hosts, may also be of use. For example, Schwientek and coworkers showed that GalT activity can be engineered into the Golgi of *S. cerevisiae* and showed that such activity was present by demonstrating the transfer of some Gal to existing $GlcNAc_2$ in an alg mutant of *S. cerevisiae*. In addition, one may perform several rounds of gene shuffling or error prone PCR to obtain a larger diversity within the pool of fusion constructs, since it has been shown that single amino mutations may drastically alter the activity of glycoprotein processing enzymes (Romero et al., 2000). Full length sequences of glycosyltransferases and their endogenous anchoring sequence may also be used. In a preferred embodiment, such localization/catalytic domain libraries are designed to incorporate existing information on the sequential nature of glycosylation reactions in higher eukaryotes. In other words, reactions known to occur early in the course of glycoprotein processing require the targeting of enzymes that catalyze such reactions to an early part of the Golgi or the ER. For example, the trimming of $Man_8GlcNAc_2$ to $Man_5GlcNAc_2$ is an early step in complex N-glycan formation. Since protein processing is initiated in the ER and then proceeds through the early, medial and late Golgi, it is desirable to have this reaction occur in the ER or early Golgi. When designing a library for mannosidase I localization, one thus attempts to match ER and early Golgi targeting signals with the catalytic domain of mannosidase I.

Upon transformation of the host strain with the fusion construct library a selection process is used to identify which particular combination of localization sequence and catalytic domain in fact have the maximum effect on the carbohydrate structure found in such host strain. Such selection can be based on any number of assays or detection methods. They may be carried out manually or may be automated through the use of high throughput screening equipment.

In another example, GnT I activity is required for the maturation of complex N-glycans, because only after addition of GlcNAc to the terminal α1,3 mannose residue may further trimming of such a structure to the subsequent intermediate $GlcNAcMan_3GlcNAc_2$ structure occur. Mannosidase II is most likely not capable of removing the terminal α1,3- and α1,6-mannose residues in the absence of a terminal β1,2-GlcNAc and thus the formation of complex N-glycans will not proceed in the absence of GnT I activity (Schachter, 1991). Alternatively, one may first engineer or select a strain that makes sufficient quantities of $Man_5GlcNAc_2$ as described in this invention by engineering or selecting a strain deficient in Alg3P activity. In the presence of sufficient UDP-GlcNAc transporter activity, as may be achieved by engineering or selecting a strain that has such UDP-GlcNAc transporter activity, GlcNAc can be added to the terminal α-1,3 residue by GnTI as in vitro a $Man_3$ structure is recognized by by rat liver GnTI (Moller, 1992).

In another approach, one may incorporate the expression of a UDP-GlcNAc transporter into the library mentioned above such that the desired construct will contain: (1) a region by which the transformed construct is maintained in the cell (e.g. origin of replication or a region that mediates chromosomal integration), (2) a marker gene that allows for the selection of cells that have been transformed, including counterselectable and recyclable markers such as ura3 or T-urf13 (Soderholm, 2001) or other well characterized selection-markers (e.g. his4, bla, Sh ble etc.), (3) a gene encoding a UDP-GlcNAc transporter (e.g. from *K. lactis*, (Abeijon, 1996), or from *H. sapiens* (Ishida, 1996), and (4) a promotor activating the expression of the above mentioned localization/catalytic domain fusion construct library.

After transformation of the host with the library of fusion constructs described above, one may screen for those cells that have the highest concentration of terminal GlcNAc on the cell surface, or secrete the protein with the highest terminal GlcNAc content. Such a screen may be based on a visual method, like a staining procedure, the ability to bind specific terminal GlcNAc binding antibodies or lectins conjugated to a marker (such lectins are available from E.Y. Laboratories Inc., San Mateo, Calif.), the reduced ability of specific lectins to bind to terminal mannose residues, the ability to incorporate a radioactively labeled sugar in vitro, altered binding to dyes or charged surfaces, or may be accomplished by using a Fluorescence Assisted Cell Sorting (FACS) device in conjunction with a fluorophore labeled lectin or antibody (Guillen, 1998). It may be advantageous to enrich particular phenotypes within the transformed population with cytotoxic lectins. U.S. Pat. No. 5,595,900 teaches several methods by which cells with a desired extra-cellular carbohydrate structures may be identified. Repeatedly carrying out this strategy allows for the sequential engineering of more and more complex glycans in lower eukaryotes.

After transformation, one may select for transformants that allow for the most efficient transfer of GlcNAc by GlcNAc Transferase II from UDP-GlcNAc in an in vitro assay. This screen may be carried out by growing cells harboring the transformed library under selective pressure on an agar plate and transferring individual colonies into a 96-well microtiter plate. After growing the cells, the cells are centrifuged, the cells resuspended in buffer, and after addition of UDP-GlcNAc and GnT V, the release of UDP is determined either by HPLC or an enzyme linked assay for UDP. Alternatively, one may use radioactively labeled UDP-GlcNAc and GnT V, wash the cells and then look for the release of radioactive GlcNAc by N-actylglucosaminidase. All this may be carried out manually or automated through the use of high throughput screening equipment.

Transformants that release more UDP, in the first assay, or more radioactively labeled GlcNAc in the second assay, are expected to have a higher degree of $GlcNAcMan_3GlcNAc_2$ (FIG. 3) on their surface and thus constitute the desired phenotype. Alternatively, one may any use any other suitable screen such as a lectin binding assay that is able to reveal altered glycosylation patterns on the surface of transformed cells. In this case the reduced binding of lectins specific to terminal mannoses may be a suitable selection tool. *Galantus nivalis* lectin binds specifically to terminal a-1,3 mannose, which is expected to be reduced if sufficient mannsosidase II activity is present in the Golgi. One may also enrich for desired transformants by carrying out a chromatographic separation step that allows for the removal of cells containing a high terminal mannose content. This separation step would be carried out with a lectin column that specifically binds cells with a high terminal mannose content (e.g *Galantus nivalis* lectin bound to agarose, SIGMA®, St. Louis, Mo.) over those that have a low terminal mannose content. In addition, one may directly create such fusion protein constructs, as additional information on the localization of active carbohydrate modifying enzymes in different lower eukaryotic hosts becomes available in the scientific literature. For example, the prior art teaches us that human beta 1,4-GalTr can be fused to the membrane domain of MNT, a mannosyltransferase from *S. cerevisiae*, and localized to the Golgi apparatus while retaining its catalytic activity (Schwientek et al., 1995), If *S. cerevisiae* or a related organism is the host to be engineered one may directly incorporate such findings into the overall strategy to obtain complex N-glycans from such a host. Several such gene fragments in *P. pastoris* have been identified that are related to glycosyltransferases in *S. cerevisiae* and thus could be used for that purpose.

TABLE 1

| Gene or sequence | Organism | Function | Location of gene product |
|---|---|---|---|
| MnsI | S. cerevisiae | mannosidase | ER |
| Och1 | S. cerevisiae | 1,6-mannosyltransferase | Golgi (cis) |
| Mnn2 | S. cerevisiae | 1,2-mannosyltransferase | Golgi (medial) |
| Mnn1 | S. cerevisiae | 1,3-mannosyltransferase | Golgi (trans) |
| Och1 | P. pastoris | 1,6-mannosyltransferase | Golgi (cis) |
| 2,6 ST | H. sapiens S. frugiperda | 2,6-sialyltransferase | trans-Golgi network |
| β1,4 Gal T | bovine milk | UDP-Gal transporter | Golgi |
| Mnt1 | S. cerevisiae | 1,2-mannosyltransferase | Golgi (cis) |
| HDEL at C-terminus | S. cerevisiae | retrieval signal | ER |

Integration Sites

As one ultimate goal of this genetic engineering effort is a robust protein production strain that is able to perform well in an industrial fermentation process, the integration of multiple genes into the host (e.g., fungal) chromosome involves careful planning. The engineered strain will most likely have to be transformed with a range of different genes, and these genes will have to be transformed in a stable fashion to ensure that the desired activity is maintained throughout the fermentation process. Any combination of the following enzyme activities will have to be engineered into the fungal protein expression host: sialyltransferases, mannosidases, fucosyltransferases, galactosyltransferases, glucosyltransferases, GlcNAc transferases, ER and Golgi specific transporters (e.g. syn and antiport transporters for UDP-galactose and other precursors), other enzymes involved in the processing of oligosaccharides, and enzymes involved in the synthesis of activated oligosaccharide precursors such as UDP-galactose, CMP-N-acetylneuraminic acid. At the same time, a number of genes which encode enzymes known to be characteristic of non-human glycosylation reactions, will have to be deleted. Such genes and their corresponding proteins have been extensively characterized in a number of lower eukaryotes (e.g. S. cerevisiae, T. reesei, A. nidulans etc.), thereby providing a list of known glycosyltransferases in lower eukaryotes, their activities and their respective genetic sequence. These genes are likely to be selected from the group of mannosyltransferases e.g. 1,3 mannosyltransferases (e.g. MNN1 in S. cerevisiae) (Graham, 1991), 1,2 mannosyltransferases (e.g. KTR/KRE family from S. cerevisiae), 1,6 mannosyltransferases (OCH1 from S. cerevisiae), mannosylphosphate transferases (MNN4 and MNN6 from S. cerevisiae) and additional enzymes that are involved in aberrant i.e. non human glycosylation reactions. Many of these genes have in fact been deleted individually giving rise to viable phenotypes with altered glycosylation profiles. Examples are shown in Table 2:

prehensive scheme will attempt to coordinate both requirements. Genes that encode enzymes that are undesirable serve as potential integration sites for genes that are desirable. For example, 1,6 mannosyltransferase activity is a hallmark of glycosylation in many known lower eukaryotes. The gene encoding alpha-1,6 mannosyltransferase (OCH1) has been cloned from S. cerevisiae and mutations in the gene give raise to a viable phenotype with reduced mannosylation. The gene locus encoding alpha-1,6 mannosyltransferase activity therefor is a prime target for the integration of genes encoding glycosyltransferase activity. In a similar manner, one can choose a range of other chromosomal integration sites that, based on a gene disruption event in that locus, are expected to: (1) improve the cells ability to glycosylate in a more human like fashion, (2) improve the cells ability to secrete proteins, (3) reduce proteolysis of foreign proteins and (4) improve other characteristics of the process that facilitate purification or the fermentation process itself.

Providing Sugar Nucleotide Precursors

A hallmark of higher eukaryotic glycosylation is the presence of galactose, fucose, and a high degree of terminal sialic acid on glycoproteins. These sugars are not generally found on glycoproteins produced in yeast and filamentous fungi and the method discussed above allows for the engineering of strains that localize glycosyltransferase in the desired organelle. Formation of complex N-glycan synthesis is a sequential process by which specific sugar residues are removed and attached to the core oligosaccharide structure. In higher eukaryotes, this is achieved by having the substrate sequentially exposed to various processing enzymes. These enzymes carry out specific reactions depending on their particular location within the entire processing cascade. This "assembly line" consists of ER, early, medial and late Golgi, and the trans Golgi network all with their specific processing environment. To recreate the processing of human glycoproteins in the Golgi and ER of lower eukaryotes, numerous enzymes (e.g. glycosyltransferases, glycosidases, phosphatases and transporters) have to be expressed and specifically targeted to these organelles, and preferably, in a location so that they function most efficiently in relation to their environment as well as to other enzymes in the pathway.

Several individual glycosyltransferases have been cloned and expressed in S. cerevisiae (GalT, GnT I), Aspergillus nidulans (GnT I) and other fungi, without however demonstrating the desired outcome of "humanization" on the glycosylation pattern of the organisms (Yoshida, 1995; Schwientek, 1995; Kalsner, 1995). It was speculated that the carbohydrate structure required to accept sugars by the action of such glycosyltransferases was not present in sufficient amounts. While this most likely contributed to the lack of

TABLE 2

| Strain | Mutant | Structure wild type | Structure mutant | Authors |
|---|---|---|---|---|
| Schizosaccharomyces pombe | OCH1 | Mannan (i.e. Man$_{>9}$GlcNAc$_2$) | Man$_8$GlcNAc$_2$ | Yoko-o et al., 2001 |
| S. cerevisiae | OCH1, MNN1 | Mannan (i.e. Man$_{>9}$GlcNAc$_2$) | Man$_8$GlcNAc$_2$ | Nakanishi-Shindo et al,. 1993 |
| S. cerevisiae | OCH1, MNN1, MNN4 | Mannan (i.e. Man$_{>9}$GlcNAc$_2$) | Man$_8$GlcNAc$_2$ | Chiba et al., 1998 |

As any strategy to engineer the formation of complex N-glycans into a lower eukaryote involves both the elimination as well as the addition of glycosyltransferase activities, a comprehensive complex N-glycan formation, there are currently no reports of a fungus supplying a Man$_5$GlcNAc$_2$ structure, having GnT I activity and having UDP-Gn transporter activity engineered into the fungus. It is the combination of these three biochemical events that are required for hybrid and complex N-glycan formation.

In humans, the full range of nucleotide sugar precursors (e.g. UDP-N-acetylglucosamine, UDP-N-acetylgalactosamine, CMP-N-acetylneuraminic acid, UDP-galactose, etc.) are generally synthesized in the cytosol and transported into the Golgi, where they are attached to the core oligosaccharide by glycosyltransferases. To replicate this process in lower eukaryotes, sugar nucleoside specific transporters have to be expressed in the Golgi to ensure adequate levels of nucleoside sugar precursors (Sommers, 1981; Sommers, 1982; Perez, 1987). A side product of this reaction is either a nucleoside diphosphate or monophosphate. While monophosphates can be directly exported in exchange for nucleoside triphosphate sugars by an antiport mechanism, diphospho nucleosides (e.g. GDP) have to be cleaved by phosphatases (e.g. GDPase) to yield nucleoside monophosphates and inorganic phosphate prior to being exported. This reaction appears to be important for efficient glycosylation, as GDPase from S. cerevisiae has been found to be necessary for mannosylation. However, the enzyme only has 10% of the activity towards UDP (Berninsone, 1994). Lower eukaryotes often do not have UDP specific diphosphatase activity in the Golgi since they do not utilize UDP-sugar precursors for glycoprotein synthesis in the Golgi.

Schizosaccharomyces pombe, a yeast found to add galactose residues to cell wall polysaccharides (from UDP-galactose) was found to have specific UDPase activity further suggesting the requirement for such an enzyme (Berninsone et al., 1994). UDP is known to be a potent inhibitor of glycosyltransferases and the removal of this glycosylation side product is important in order to prevent glycosyltransferase inhibition in the lumen of the Golgi (Khatara et al., 1974). Thus, one may need to provide for the removal of UDP, which is expected to accumulate in the Golgi of such an engineered strains (Beminsone, 1995; Beaudet, 1998).

In another example, 2,3 sialyltransferase and 2,6 sialyltransferase cap galactose residues with sialic acid in the trans-Golgi and TGN of humans leading to a mature form of the glycoprotein. To reengineer this processing step into a metabolically engineered yeast or fungus will require (1) 2,3-sialyltransferase activity and (2) a sufficient supply of CMP-N-acetyl neuraminic acid, in the late Golgi of yeast. To obtain sufficient 2,3-sialyltransferase activity in the late Golgi, the catalytic domain of a known sialyltransferase (e.g. from humans) has to be directed to the late Golgi in fungi (see above). Likewise, transporters have to be engineered to that allow the transport of CMP-N-acetyl neuraminic acid into the late Golgi. There is currently no indication that fungi synthesize sufficient amounts of CMP-N-acetyl neuraminic acid, not to mention the transport of such a sugar-nucleotide into the Golgi. Consequently, to ensure the adequate supply of substrate for the corresponding glycosyltransferases, one has to metabolically engineer the production of CMP-sialic acid into the fungus.

Methods for Providing Sugar Nucleotide Precursors to the Golgi Apparatus:

UDP-N-acetyl-glucosamine

The cDNA of human UDP-N-acetylglucosamine transporter, which was recognized through a homology search in the expressed sequence tags database (dbEST) was cloned by Ishida and coworkers (Ishida, 1999). Guillen and coworkers have cloned the mammalian Golgi membrane transporter for UDP-N-acetylglucosamine by phenotypic correction with cDNA from canine kidney cells (MDCK) of a recently characterized Kluyveromyces lactis mutant deficient in Golgi transport of the above nucleotide sugar (Guillen, 1998). Their results demonstrate that the mammalian Golgi UDP-GlcNAc transporter gene has all of the necessary information for the protein to be expressed and targeted functionally to the Golgi apparatus of yeast and that two proteins with very different amino acid sequences may transport the same solute within the same Golgi membrane (Guillen, 1998).

GDP-Fucose

The rat liver Golgi membrane GDP-fucose transporter has been identified and purified by Puglielli, L. and C. B. Hirschberg (Puglielli, 1999). The corresponding gene has not been identified however N-terminal sequencing can be used for the design of oligonucleotide probes specific for the corresponding gene. These oligonucleotides can be used as probes to clone the gene encoding for GDP-fucose transporter.

UDP-Galactose

Two heterologous genes, gma12(+) encoding alpha 1,2-galactosyltransferase (alpha 1,2 GalT) from Schizosaccharomyces pombe and (hUGT2) encoding human UDP-galactose (UDP-Gal) transporter, have been functionally expressed in S. cerevisiae to examine the intracellular conditions required for galactosylation. Correlation between protein galactosylation and UDP-galactose transport activity indicated that an exogenous supply of UDP-Gal transporter, rather than alpha 1,2 GalT played a key role for efficient galactosylation in S. cerevisiae (Kainuma, 1999). Likewise a UDP-galactose transporter from S. pombe was cloned (Aoki, 1999; Segawa, 1999).

CMP-N-acetylneuraminic acid (CMP-Sialic Acid)

Human CMP-sialic acid transporter (hCST) has been cloned and expressed in Lec 8 CHO cells (Aoki, 1999; Eckhardt, 1997). The functional expression of the murine CMP-sialic acid transporter was achieved in Saccharomyces cerevisiae (Beminsone, 1997). Sialic acid has been found in some fungi, however it is not clear whether the chosen host system will be able to supply sufficient levels of CMP-Sialic acid. Sialic acid can be either supplied in the medium or alternatively fungal pathways involved in sialic acid synthesis can also be integrated into the host genome.

Diphosphatases

When sugars are transferred onto a glycoprotein, either a nucleoside diphosphate or monophosphate, is released from the sugar nucleotide precursors. While monophosphates can be directly exported in exchange for nucleoside triphosphate sugars by an antiport mechanism, diphospho nucleosides (e.g. GDP) have to be cleaved by phosphatases (e.g. GDPase) to yield nucleoside monophosphates and inorganic phosphate prior to being exported. This reaction appears to be important for efficient glycosylation, as GDPase from S. cerevisiae has been found to be necessary for mannosylation. However, the enzyme only has 10% of the activity towards UDP (Berninsone, 1994). Lower eukayotes often do not have UDP specific diphosphatase activity in the Golgi since they do not utilize UDP-sugar precursors for glycoprotein synthesis in the Golgi. Schizosaccharomyces pombe, a yeast found to add galactose residues to cell wall polysaccharides (from UDP-galactose) was found to have specific UDPase activity further suggesting the requirement for such an enzyme (Berninsone, 1994). UDP is known to be a potent inhibitor of glycosyltransferases and the removal of this glycosylation side product is important in order to prevent glycosyltransferase inhibition in the lumen of the Golgi (Khatara et al. 1974).

Expression of GnTs to Produce Complex N-glycans

Expression of GnT-III to Boost Antibody Functionality

The addition of an N-acetylglucosamine to the $GlcNAc_1Man_3GlcNAc_2$ structure by N-acetylglucosaminyltransferases II and III yields a so-called bisected N-glycan GlcNAc$_3$Man$_3$GlcNAc$_2$ (FIG. 3). This structure has been implicated in greater antibody-dependent cellular cytotoxicity (ADCC) (Umana et al. 1999). Re-engineering glycoforms of immunoglobulins expressed by mammalian cells is a tedious and cumbersome task. Especially in the case of GnTIII, where over-expression of this enzyme has been implicated in growth inhibition, methods involving regulated (inducible) gene expression had to be employed to produce immunoglobulins with bisected N-glycans (Umana et al 1999a, 1999b).

Accordingly, in another embodiment, the invention provides systems and methods for producing human-like N-glycans having bisecting N-acetylglucosamine (GlcNAcs) on the core mannose structure. In a preferred embodiment, the invention provides a system and method for producing immunoglobulins having bisected N-glycans. The systems and methods described herein will not suffer from previous problems, e.g., cytotoxicity associated with overexpression of GnTIII or ADCC, as the host cells of the invention are engineered and selected to be viable and preferably robust cells which produce N-glycans having substantially modified human-type glycoforms such as GlcNAc$_2$Man$_3$GlcNAc$_2$. Thus, addition of a bisecting N-acetylglucosamine in a host cell of the invention will have a negligible effect on the growth-phenotype or viability of those host cells.

In addition, previous work (Umana) has shown that there is no linear correlation between GnTIII expression levels and the degree of ADCC. Finding the optimal expression level in mammalian cells and maintaining it throughout an FDA approved fermentation process seems to be a challenge. However, in cells of the invention, such as fungal cells, finding a promoter of appropriate strength to establish a robust, reliable and optimal GnTIII expression level is a comparatively easy task for one of skill in the art.

A host cell such as a yeast strain capable of producing glycoproteins with bisecting N-glycans is engineered according to the invention, by introducing into the host cell a GnTIII activity (Example 6). Preferably, the host cell is transformed with a nucleic acid that encodes GnTIII (see, e.g., FIG. 32) or a domain thereof having enzymatic activity, optionally fused to a heterologous cell signal targeting peptide (e.g., using the libraries and associated methods of the invention.) Host cells engineered to express GnTIII will produce higher antibody titers than mammalian cells are capable of. They will also produce antibodies with higher potency with respect to ADCC.

Antibodies produced by mammalian cell lines transfected with GnTIII have been shown to be as effective as antibodies produced by non-transfected cell-lines, but at a 10-20 fold lower concentration (Davies et al. 2001). An increase of productivity of the production vehicle of the invention over mammalian systems by a factor of twenty, and a ten-fold increase of potency will result in a net-productivity improvement of two hundred. The invention thus provides a system and method for producing high titers of an antibody having high potency (e.g., up to several orders of magnitude more potent than what can currently be produced). The system and method is safe and provides high potency antibodies at low cost in short periods of time. Host cells engineered to express GnT III according to the invention produce immunoglobulins having bisected N-glycans at rates of at least 50 mg/liter/day to at least 500 mg/liter/day. In addition, each immunoglobulin (Ig) molecule (comprising bisecting GlcNAcs) is more potent than the same Ig molecule produced without bisecting GlcNAcs.

Cloning and Expression of GnT-IV and GnT-V

All branching structures in complex N-glycans are synthesized on a common core-pentasaccharide (Man$_3$GlcNAc$_2$ or Man alpha1-6(Man alpha1-3)Man beta1-4 GlcNAc beta1-4 GlcNAc beta1-4 or Man$_3$GlcNAc$_2$) by N-acetylglucosamine transferases (GnTs) -I to -VI (Schachter H et al. (1989) *Methods Enzymo;* 179:351-97). Current understanding of the biosynthesis of more highly branched N-glycans suggests that after the action of GnTII (generation of GlcNAc$_2$Man$_3$GlcNAc$_2$ structures) GnTIV transfers GlcNAc from UDP-GlcNAc in beta1,4 linkage to the Man alpha1,3 Man beta1,4 arm of GlcNAc$_2$Man$_3$GlcNAc$_2$ N-glycans (Allen S D et al. (1984) *J Biol Chem*. June 10; 259(11): 6984-90; and Gleeson P A and Schachter H. J (1983); *J. Biol Chem* 25; 258(10):6162-73) resulting in a triantennary agalacto sugar chain. This N-glycan (GlcNAc beta1-2 Man alpha1-6(GlcNAc beta1-2 Man alpha1-3) Man beta1-4 GlcNAc beta 1-4 GlcNAc beta1,4 Asn) is a common substrate for GnT-III and -V, leading to the synthesis of bisected, tri- and tetra-antennary structures. Where the action of GnTIII results in a bisected N-glycan and where GnTV catalyzes the addition of beta 1-6GlcNAc to the alpha 1-6 mannosyl core, creating the beta 1-6 branch. Addition of galactose and sialic acid to these branches leads to the generation of a fully sialylated complex N-glycan.

Branched complex N-glycans have been implicated in the physiological activity of therapeutic proteins, such as human erythropoietin (hEPO). Human EPO having bi-antennary structures has been shown to have a low activity, whereas hEPO having tetra-antennary structures resulted in slower clearance from the bloodstream and thus in higher activity (Misaizu T et al. (1995) *Blood* December 1; 86(11):4097-104).

With DNA sequence information, the skilled worker can clone DNA molecules encoding GnT IV and/or V activities (Example 6; FIGS. 33 and 34). Using standard techniques well-known to those of skill in the art, nucleic acid molecules encoding GnT IV or V (or encoding catalytically active fragments thereof) may be inserted into appropriate expression vectors under the transcriptional control of promoters and other expression control sequences capable of driving transcription in a selected host cell of the invention, e.g., a fungal host such as *Pichia* sp., *Kluyveromyces* sp. and *Aspergillus* sp., as described herein, such that one or more of these mammalian GnT enzymes may be actively expressed in a host cell of choice for production of a human-like complex glycoprotein.

The following are examples which illustrate the compositions and methods of this invention. These examples should not be construed as limiting: the examples are included for the purposes of illustration only.

EXAMPLE 1

Identification, Cloning and Deletion of the ALG3 Gene in *P. pastoris* and *K. lactis*

Degenerate primers were generated based on an alignment of Alg3 protein sequences from *S. cerevisiae, H. sapiens*, and *D. melanogaster* and were used to amplify an 83 bp product from *P. pastoris* genomic DNA: 5'-GGT-GTTTTGTTTTCTAGATCTTTGCAYTAYCARTT-3' (SEQ ID NO. 1) and 5'-AGAATTTGGTGGGTAAGAATTCCA-RCACCAYTCRTG-3' (SEQ ID NO. 2). The resulting PCR product was cloned into the pCR2.1 vector (Invitrogen, Carlsbad, Calif.) and sequence analysis revealed homology to known ALG3/RHK1/NOT56 homologs (Genbank NC.sub.—001134.2, AF309689, NC.sub.—003424.1). Subsequently, 1929 bp upstream and 2738 bp downstream of the initial PCR product were amplified from a *P. pastoris* genomic DNA library (Boehm, T. Yeast May 1999; 15(7): 563-72) using the internal oligonucleotides 5'-CCTAAGCTGGTATGCGTTCTCTTTGCCATATC-3' (SEQ ID NO. 3) and 5'-GCGGCATAAACAATAATAGAT-GCTATAAAG-3' (SEQ ID NO. 4) along with T3 (5'-AAT-TAACCCTCACTAAAGGG-3') (SEQ ID NO. 5) and T7 (5'-GTAA TACGACTCACTATAGGGC-3') (SEQ ID NO. 6) (Integrated DNA Technologies, Coralville, Iowa) in the backbone of the library bearing plasmid lambda ZAP II (Stratagene, La Jolla, Calif.). The resulting fragments were cloned into the pCR2.1-TOPO vector (Invitrogen) and sequenced. From this sequence, a 1395 bp ORF was identified that encodes a protein with 35% identity and 53% similarity to the *S. cerevisiae* ALG3 gene (using BLAST programs). The gene was named PpALG3.

The sequence of PpALG3 was used to create a set of primers to generate a deletion construct of the PpALG3 gene by PCR overlap (Davidson et al, 2002 Microbiol. 148(Pt 8):2607-15). Primers below were used to amplify 1 kb regions 5' and 3' of the PpALG3 ORF and the KAN$^R$ gene, respectively:

```
RCD142
                                (SEQ ID NO. 7)
(5'-CCACATCATCCGTGCTACATATAG-3'),

RCD144
                                (SEQ ID NO. 8)
(5'-ACGAGGCAAGCTAAACAGATCTCGAAGTATCGAGGG
TTATCCAG-3'),

RCD145
                                (SEQ ID NO. 9)
(5'-CCATCCAGTGTCGAAAACGAGCCAATGGTTCATGTC
TATAAATC-3'),

RCD147
                                (SEQ ID NO. 10)
(5'-AGCCTCAGCGCCAACAAGCGATGG-3'),

RCD143
                                (SEQ ID NO. 11)
(5'-CTGGATAACCCTCGATACTTCGAGATCTGTTTAGCT
TGCCTCGT-3'), and RCD146
                                (SEQ ID NO. 12)
(5'-GATTTATAGACATGAACCATTGGCTCGTTTTCGACA
CTGGATGG-3').
```

Subsequently, primers RCD142 and RCD147 were used to overlap the three resulting PCR products into a single 3.6 kb alg3::KAN$^R$ deletion allele.
Identification, Cloning and Deletion of the ALG3 Gene in *K. lactis*.

The ALG3p sequences from *S. cerevisiae*, *Drosophila melanogaster*, *Homo sapiens* etc were aligned with *K. lactis* sequences (PENDANT EST database). Regions of high homology that were in common homologs but distinct in exact sequence from the homologs were used to create pairs of degenerate primers that were directed against genomic DNA from the *K. lactis* strain MG 1/2 (Bianchi et al, 1987). In the case of ALG3, PCR amplification with primers KAL-1 (5'-ATCCTTTACCGATGCTGTAT-3') (SEQ ID NO. 13) and KAL-2 (5'-ATAACAGTATGTGTTACACGCGTGTAG-3') (SEQ ID NO. 14) resulted in a product that was cloned and sequenced and the predicted translation was shown to have a high degree of homology to Alg3p proteins (>50% to *S. cerevisiae* Alg3p).

The PCR product was used to probe a Southern blot of genomic DNA from *K. lactis* strain (MG1/2) with high stringency (Sambrook et al, 1989). Hybridization was observed in a pattern consistent with a single gene. This Southern blot was used to map the genomic loci. Genomic fragments were cloned by digesting genomic DNA and ligating those fragments in the appropriate size-range into pUC19 to create a *K. lactis* subgenomic library. This subgenomic library was transformed into *E. coli* and several hundred clones were tested by colony PCR, using primers KAL-1 and KAL-2. The clones containing the predicted KlALG3 and KlALG61 genes were sequenced and open reading frames identified.

Primers for construction of an alg3::NAT$^R$ deletion allele, using a PCR overlap method (Davidson et al, 2002), were designed and the resulting deletion allele was transformed into two *K. lactis* strains and NAT-resistant colonies selected. These colonies were screened by PCR and transformants were obtained in which the ALG3 ORF was replaced with the och1::NAT$^R$ mutant allele.

EXAMPLE 2

Generation of an alg3/och1 Mutant Strain Expressing an α-1,2-Mannosidase, GnT1 and GnTII for Production of a Human-Like Glycoprotein The 1215 bp open reading frame of the *P. pastoris* OCH1 gene as well as 2685 bp upstream and 1175 bp downstream was amplified by PCR (B. K. Choi et al., submitted to *Proc. Natl. Acad. Sci. USA* 2002; see also WO 02/00879; each of which is incorporated herein by reference), cloned into the pCR2.1-TOPO vector (Invitrogen) and designated pBK9. To create an och1 knockout strain containing multiple auxotrophic markers, 100 μg of pJN329, a plasmid containing an och1::URA3 mutant allele flanked with SfiI restriction sites was digested with SfiI and used to transform *P. pastoris* strain JC308 (Cereghino et al. *Gene* 263 (2001) 159-169) by electroporation. Following incubation on defined medium lacking uracil for 10 days at room temperature, 1000 colonies were picked and re-streaked. URA$^+$ clones that were unable to grow at 37° C., but grew at room temperature, were subjected to colony PCR to test for the correct integration of the och1::URA3 mutant allele. One clone that exhibited the expected PCR pattern was designated YJN153. The Kringle 3 domain of human plasminogen (K3) was used as a model protein. A Neo$^R$ marked plasmid containing the K3 gene was transformed into strain YJN153 and a resulting strain, expressing K3, was named BK64-1 (B. K. Choi et al, submitted to *Proc. Natl. Acad. Sci. USA* 2002).

Plasmid pPB103, containing the *Kluyveromyces lactis* MNN2-2 gene, encoding a Golgi UDP-N-acetylglucosamine transporter was constructed by cloning a blunt BglII-HindIII fragment from vector pDL02 (Abeijon et al. (1996) *Proc. Natl. Acad. Sci. U.S.A.* 93:5963-5968) into BglII and BamHI digested and blunt ended pBLADE-SX containing the *P. pastoris* ADE1 gene (Cereghino et al. (2001) *Gene* 263:159-169). This plasmid was linearized with EcoNI and transformed into strain BK64-1 by electroporation and one strain confirmed to contain the MNN2-2 by PCR analysis was named PBP1.

A library of mannosidase constructs was generated, comprising in-frame fusions of the leader domains of several type I or type II membrane proteins from *S. cerevisiae* and *P. pastoris* fused with the catalytic domains of several α-1,2-mannosidase genes from human, mouse, fly, worm and yeast sources (see, e.g., WO02/00879, incorporated herein by reference). This library was created in a *P. pastoris* HIS4 integration vector and screened by linearizing with SalI, transforming by electroporation into strain PBP1, and analyzing the glycans released from the K3 reporter protein. One active construct chosen was a chimera of the 988-1296 nucleotides (C-terminus) of the yeast SEC12 gene fused with a N-terminal deletion of the mouse α-1,2-mannosidase IA (MmMannIA) gene, which was missing the 187 nucleotides. A *P. pastoris* strain expressing this construct was named PBP2.

A library of GnTI constructs was generated, comprising in-frame fusions of the same leader library with the catalytic domains of GnTI genes from human, worm, frog and fly sources (WO 02/00879). This library was created in a *P. pastoris* ARG4 integration vector and screened by linearizing with AatII, transforming by electroporation into strain PBP2, and analyzing the glycans released from K3. One active construct chosen was a chimera of the first 120 bp of the *S. cerevisiae* MNN9 gene fused to a deletion of the human GnTI gene, which was missing the first 154 bp. A *P. pastoris* strain expressing this construct was named PBP3.

Subsequently, a *P. pastoris* alg3::KAN$^R$ deletion construct was generated as described above. Approximately 5 μg of the resulting PCR product was transformed into strain PBP3 and colonies were selected on YPD medium containing 200 μg/ml G418. One strain out of 20 screened by PCR was confirmed to contain the correct integration of the alg3::KAN$^R$ mutant allele and lack the wild-type allele. This strain was named RDP27.

Finally, a library of GnTII constructs was generated, which was comprised of in-frame fusions of the leader library with the catalytic domains of GnTII genes from human and rat sources (WO 02/00879). This library was created in a *P. pastoris* integration vector containing the NST$^R$ gene conferring resistance to the drug nourseothricin. The library plasmids were linearized with EcoRI, transformed into strain RDP27 by electroporation, and the resulting strains were screened by analysis of the released glycans from purified K3.

Materials

MOPS, sodium cacodylate, manganese chloride, UDP-galactose and CMP-N-acetylneuraminic acid were from SIGMA®. TFA was from ALDRICH®. Recombinant rat a2,6-sialyltransferase from *Spodoptera frugiperda* and beta 1,4-galactosyltransferase from bovine milk were from CALBIOCHEM®. Protein N-glycosidase F, mannosidases, and oligosaccharides were from GLYKO® (San Rafael, Calif.). DEAE TOYOPEARL® resin was from TosoHaas. Metal chelating "HisBind" resin was from Novagen (Madison, Wis.). 96-well lysate-clearing plates were from Promega (Madison, Wis.). Protein-binding 96-well plates were from Millipore (Bedford, Mass.). Salts and buffering agents were from SIGMA® (St. Louis, Mo.). MALDI matrices were from ALDRICH® (Milwaukee, Wis.).

Protein Purification

Kringle 3 was purified using a 96-well format on a Beckman BioMek 2000 sample-handling robot (Beckman/Coulter Ranch Cucamonga, Calif.). Kringle 3 was purified from expression media using a C-terminal hexa-histidine tag. The robotic purification is an adaptation of the protocol provided by Novagen for their HisBind resin. Briefly, a 150 uL (μL) settled volume of resin is poured into the wells of a 96-well lysate-binding plate, washed with 3 volumes of water and charged with 5 volumes of 50 mM NiSO4 and washed with 3 volumes of binding buffer (5 mM imidazole, 0.5M NaCl, 20 mM Tris-HCL pH7.9). The protein expression media is diluted 3:2, media/PBS (60 mM PO4, 16 mM KCl, 822 mM NaCl pH7.4) and loaded onto the columns. After draining, the columns are washed with 10 volumes of binding buffer and 6 volumes of wash buffer (30 mM imidazole, 0.5M NaCl, 20 mM Tris-HCl pH7.9) and the protein is eluted with 6 volumes of elution buffer (1M imidazole, 0.5M NaCl, 20 mM Tris-HCl pH7.9). The eluted glycoproteins are evaporated to dryness by lyophilyzation.

Release of N-Linked Glycans

The glycans are released and separated from the glycoproteins by a modification of a previously reported method (Papac, et al. A. J. S. (1998) *Glycobiology* 8, 445-454). The wells of a 96-well Multi Screen IP (Immobilon-P membrane) plate (Millipore) are wetted with 100 uL of methanol, washed with 3×150 uL of water and 50 uL of RCM buffer (8M urea, 360 mM Tris, 3.2 mM EDTA pH8.6), draining with gentle vacuum after each addition. The dried protein samples are dissolved in 30 uL of RCM buffer and transferred to the wells containing 10 uL of RCM buffer. The wells are drained and washed twice with RCM buffer. The proteins are reduced by addition of 60 uL of 0.1M DTT in RCM buffer for 1 hr at 37° C. The wells are washed three times with 300 uL of water and carboxymethylated by addition of 60 uL of 0.1M iodoacetic acid for 30 min in the dark at room temperature. The wells are again washed three times with water and the membranes blocked by the addition of 100 uL of 1% PVP 360 in water for 1 hr at room temperature. The wells are drained and washed three times with 300 uL of water and deglycosylated by the addition of 30 uL of 10 mM NH4HCO3 pH 8.3 containing one milliunit of N-glycanase (Glyko). After 16 hours at 37° C., the solution containing the glycans was removed by centrifugation and evaporated to dryness.

Matrix Assisted Laser Desorption Ionization Time of Flight Mass Spectrometry

Molecular weights of the glycans were determined using a Voyager DE PRO linear MALDI-TOF (Applied Biosciences) mass spectrometer using delayed extraction. The dried glycans from each well were dissolved in 15 uL of water and 0.5 uL spotted on stainless steel sample plates and mixed with 0.5 uL of S-DHB matrix (9 mg/mL of dihydroxybehzoic acid, 1 mg/mL of 5-methoxysalicilic acid in 1:1 water/acetonitrile 0.1% TFA) and allowed to dry.

Ions were generated by irradiation with a pulsed nitrogen laser (337 nm) with a 4 ns pulse time. The instrument was operated in the delayed extraction mode with a 125 ns delay and an accelerating voltage of 20 kV. The grid voltage was 93.00%, guide wire voltage was 0.10%, the internal pressure was less than 5×10-7 torr, and the low mass gate was 875 Da. Spectra were generated from the sum of 100-200 laser pulses and acquired with a 2 GHz digitizer. Man5 oligosaccharide was used as an external molecular weight standard. All spectra were generated with the instrument in the positive ion mode. The estimated mass accuracy of the spectra was 0.5%.

Materials:

MOPS, sodium cacodylate, manganese chloride, UDP-galactose and CMP-N-acetylneuraminic acid were from SIGMA®, Saint Louis, Mo. Trifluroacetic acid (TFA) was from SIGMA/ALDRICH®., Saint Louis, Mo. Recombinant rat alpha-2,6-sialyltransferase from *Spodoptera frugiperda* and beta-1,4-galactosyltransferase from bovine milk were from CALBIOCHEM®, San Diego, Calif.

β-N-acetylhexosaminidase Digestion

The glycans were released and separated from the glycoproteins by a modification of a previously reported method (Papac, et al. A. J. S. (1998) *Glycobiology* 8, 445-454). After the proteins were reduced and carboxymethylated, and the membranes blocked, the wells were washed three time with water. The protein was deglycosylated by the addition of 30 μl of 10 mM NH$_4$HCO$_3$ pH 8.3 containing one milliunit of N-glycanase (Glyko, Novato, Calif.). After 16 hr at 37° C., the solution containing the glycans was removed by centrifugation and evaporated to dryness. The glycans were then dried in SC210A speed vac (Thermo Savant, Halbrook, N.Y.). The dried glycans were put in 50 mM NH$_4$Ac pH 5.0 at 37° C. overnight and 1 mU of hexos (Glyko, Novato, Calif.) was added.

Galactosyltransferase Reaction

Approximately 2 mg of protein (r-K3:hPg [PBP6-5]) was purified by nickel-affinity chromatography, extensively dialyzed against 0.1% TFA, and lyophilized to dryness. The protein was redissolved in 150 µL of 50 mM MOPS, 20 mM MnCl2, pH7.4. After addition of 32.5 µg (533 nmol) of UDP-galactose and 4 mU of β 1,4-galactosyltransferase, the sample was incubated at 37° C. for 18 hours. The samples were then dialyzed against 0.1% TFA for analysis by MALDI-TOF mass spectrometry.

The spectrum of the protein reacted with galactosyltransferase showed an increase in mass consistent with the addition of two galactose moieties when compared with the spectrum of a similar protein sample incubated without enzyme. Protein samples were next reduced, carboxymethylated and deglycosylated with PNGase F. The recovered N-glycans were analyzed by MALDI-TOF mass spectrometry. The mass of the predominant glycan from the galactosyltransferase reacted protein was greater than that of the control glycan by a mass consistent with the addition of two galactose moieties (325.4 Da).

Sialyltransferase Reaction

After resuspending the (galactosyltransferase reacted) proteins in 10 µL of 50 mM sodium cacodylate buffer pH6.0, 300 µg (488 nmol) of CMP-N-acetylneuraminic acid (CMP-NANA) dissolved in 15 µL of the same buffer, and 5 µL (2 mU) of recombinant α-2,6 sialyltransferase were added. After incubation at 37° C. for 15 hours, an additional 200 µg of CMP-NANA and 1 mU of sialyltransferase were added. The protein samples were incubated for an additional 8 hours and then dialyzed and analyzed by MALDI-TOF-MS as above.

The spectrum of the glycoprotein reacted with sialyltransferase showed an increase in mass when compared with that of the starting material (the protein after galactosyltransferase reaction). The N-glycans were released and analyzed as above. The increase in mass of the two ion-adducts of the predominant glycan was consistent with the addition of two sialic acid residues (580 and 583 Da).

EXAMPLE 3

Identification, Cloning and Deletion of the ALG9 and ALG 12 Genes in *P. pastoris*

Similar to Example 1, the ALG9p and ALG12 sequences, respectively from *S. cerevisiae, Drosophila melanogaster, Homo sapiens*, etc., is aligned and regions of high homology are used to design degenerate primers. These primers are employed in a PCR reaction on genomic DNA from the *P. pastoris*. The resulting initial PCR product is subcloned, sequenced and used to probe a Southern blot of genomic DNA from *P. pastoris* with high stringency (Sambrook et al., 1989). Hybridization is observed. This Southern blot is used to map the genomic loci. Genomic fragments are cloned by digesting genomic DNA and ligating those fragments in the appropriate size-range into pUC19 to create a *P. pastoris* subgenomic library. This subgenomic library is transformed into *E. coli* and several hundred clones tested by colony PCR, using primers designed based on the sequence of the initial PCR product. The clones containing the predicted genes are sequenced and open reading frames identified. Primers for construction of an alg9::NAT$^R$ deletion allele, using a PCR overlap method (Davidson et al., 2002), are designed. The resulting deletion allele is transformed into two *P. pastoris* strains and NAT resistant colonies are selected. These colonies are screened by PCR and transformants obtained in which the ALG9 ORF is replaced with the och1::NAT$^R$ mutant allele. See generally, Cipollo et al. *Glycobiology* 2002 (12)11:749-762; Chantret et al. *J. Biol. Chem.* Jul. 12, 2002 (277)28:25815-25822; Cipollo et al. J. Biol. Chem. Feb. 11, 2000 (275)6:4267-4277; Burda et al. *Proc. Natl. Acad. Sci. U.S.A.* July 1996 (93):7160-7165; Karaoglu et al. *Biochemistry* 2001, 40, 12193-12206; Grimme et al. *J. Biol. Chem.* Jul. 20, 2001 (276)29:27731-27739; Verostek et al. *J. Biol. Chem.* Jun. 5, 1993 (268)16:12095-12103; Huffaker et al. *Proc. Natl. Acad. Sci. U.S.A.* December 1983 (80):7466-7470.

EXAMPLE 4

Identification, Cloning and Expression of Alpha 1,2-3 Mannosidase from *Xanthomonas Manihotis*

The alpha 1,2-3 Mannosidase from *Xanthomonas Manihotis* has two activities: an alpha-1,2 and an alpha-1,3 mannosidase. The methods of the invention may also use two independent mannosidases having these activities, which may be similarly identified and cloned from a selected organism of interest.

As described by Landry et al., alpha-mannosidases can be purified from *Xanthomonas* sp., such as *Xanthomonas manihotis*. *X. manihotis* can be purchased from the American Type Culture Collection (ATCC catalog number 49764) (*Xanthomonas axonopodis* Starr and Garces pathovar *manihotis* deposited as *Xanthomonas manihotis* (Arthaud-Berthet) Starr). Enzymes are purified from crude cell-extracts as previously described (Wong-Madden, S. T. and Landry, D. (1995) Purification and characterization of novel glycosidases from the bacterial genus *Xanthomonas*; and Landry, D. U.S. Pat. No. 6,300,113 B1 Isolation and composition of novel Glycosidases). After purification of the mannosidase, one of several methods are used to obtain peptide sequence tags (see, e.g., W. Quadroni M et al. (2000). A method for the chemical generation of N-terminal peptide sequence tags for rapid protein identification. *Anal Chem* (2000) March 1; 72(5):1006-14; Wilkins M R et al. Rapid protein identification using N-terminal "sequence tag" and amino acid analysis. Biochem Biophys Res Commun. (1996) April 25; 221(3): 609-13; and Tsugita A. (1987) Developments in protein microsequencing. *Adv Biophys* (1987) 23:81-113).

Sequence tags generated using a method above are then used to generate sets of degenerate primers using methods well-known to the skilled worker. Degenerate primers are used to prime DNA amplification in polymerase chain reactions (e.g., using Taq polymerase kits according to manufacturers' instructions) to amplify DNA fragments. The amplified DNA fragments are used as probes to isolate DNA molecules comprising the gene encoding a desired mannosidase, e.g., using standard Southern DNA hybridization techniques to identify and isolate (clone) genomic pieces encoding the enzyme of interest. The genomic DNA molecules are sequenced and putative open reading frames and coding sequences are identified. A suitable expression construct encoding for the glycosidase of interest can then be generated using methods described herein and well-known in the art.

Nucleic acid fragments comprising sequences encoding alpha 1,2-3 mannosidase activity (or catalytically active fragments thereof) are cloned into appropriate expression vectors for expression, and preferably targeted expression, of these activities in an appropriate host cell according to the methods set forth herein.

EXAMPLE 5

Identification, Cloning and Expression of the ALG6 Gene in *P. pastoris*

Similar to Example 1, the ALG6p sequences from *S. cerevisiae, Drosophila melanogaster, Homo sapiens* etc., are aligned and regions of high homology are used to design degenerate primers. These primers are employed in a PCR reaction on genomic DNA from the *P. pastoris*. The resulting initial PCR product is subcloned, sequenced and used to probe a Southern blot of genomic DNA from *P. pastoris* with high stringency (Sambrook et al, 1989). Hybridization is observed. This Southern blot is used to map the genomic loci. Genomic fragments are cloned by digesting genomic DNA and ligating those fragments in the appropriate size-range into pUC19 to create a *P. pastoris* subgenomic library. This subgenomic library is transformed into *E. coli* and several hundred clones are tested by colony PCR, using primers designed based on the sequence of the initial PCR product. The clones containing the predicted genes are sequenced and open reading frames identified. Primers for construction of an alg6::NAT$^R$ deletion allele, using a PCR overlap method (Davidson et al, 2002), are designed and the resulting deletion allele is transformed into two *P. pastoris* strains and NAT resistant colonies selected. These colonies are screened by PCR and transformants are obtained in which the ALG6 ORF is replaced with the och1::NAT$^R$ mutant allele. See, e.g., Imbach et al. *Proc. Natl. Acad. Sci. U.S.A.* June 1999 (96) 6982-6987.

Nucleic acid fragments comprising sequences encoding Alg6p (or catalytically active fragments thereof) are cloned into appropriate expression vectors for expression, and preferably targeted expression, of these activities in an appropriate host cell according to the methods set forth herein. The cloned ALG6 gene can be brought under the control of any suitable promoter to achieve overexpression. Even expression of the gene under the control of its own promoter is possible. Expression from multicopy plasmids will generate high levels of expression ("overexpression").

EXAMPLE 6

Cloning and Expression of GnT III to Produce Bisecting GlcNAcs which Boost Antibody Functionality A. Background The addition of an N-acetylglucosamine to the GlcNAc$_2$Man$_3$GlcNAc$_2$ structure by N-acetylglucosaminyl-transferases III yields a so-called bisected N-glycan (see FIG. 3). This structure has been implicated in greater antibody-dependent cellular cytotoxicity (ADCC) (Umana et al. 1999).

A host cell such as a yeast strain capable of producing glycoproteins with bisected N-glycans is engineered according to the invention, by introducing into the host cell a GnTIII activity. Preferably, the host cell is transformed with a nucleic acid that encodes GnTIII (e.g., a mammalian such as the murine GnT III shown in FIG. 32) or a domain thereof having enzymatic activity, optionally fused to a heterologous cell signal targeting peptide (e.g., using the libraries and associated methods of the invention.)

Figure 30:
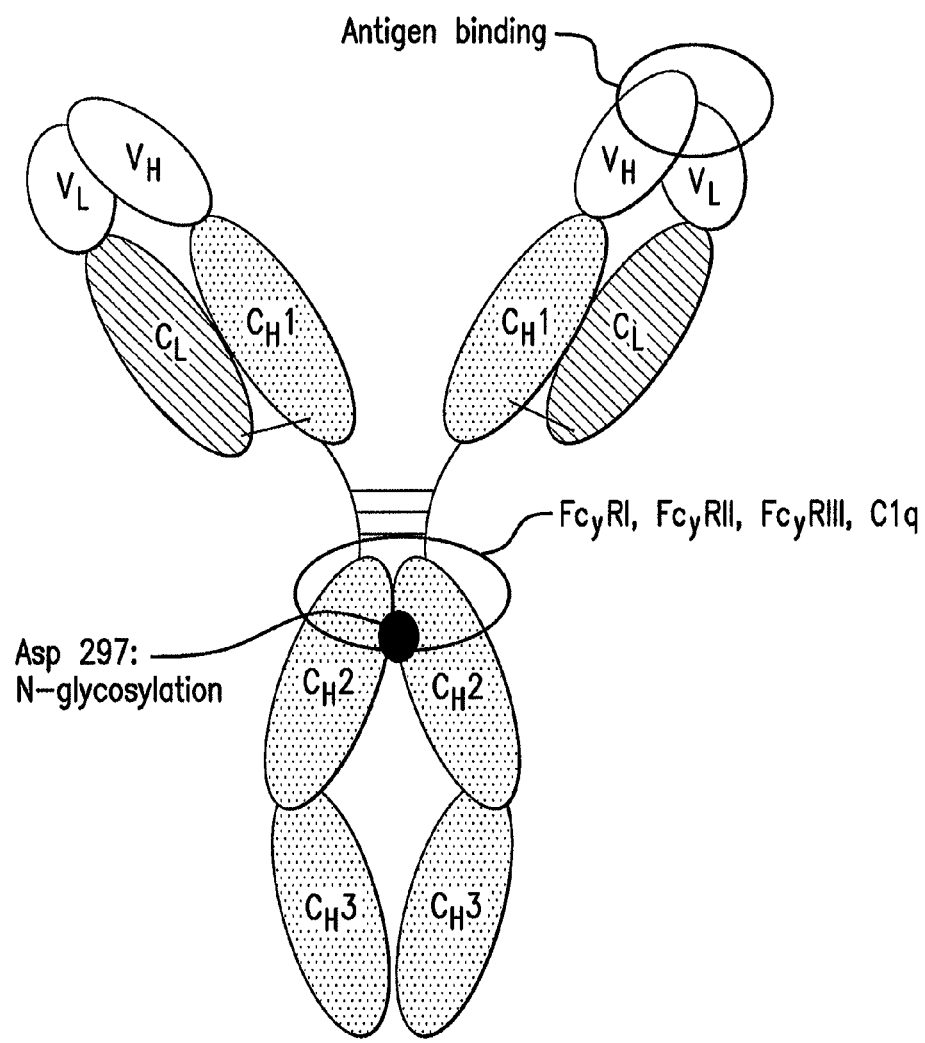

IgGs consist of two heavy-chains ($V_H$, $C_H1$, $C_H2$ and $C_H3$ in FIG. 30), interconnected in the hinge region through three disulfide bridges, and two light chains ($V_L$, $C_L$ in FIG. 30). The light chains (domains $V_L$ and $C_L$) are linked by another disulfide bridge to the $C_H1$ portion of the heavy chain and together with the $C_H1$ and $V_H$ fragment make up the so-called Fab region. Antigens bind to the terminal portion of the Fab region. The Fc region of IgGs consists of the $C_H3$, the $C_H^2$ and the hinge region and is responsible for the exertion of so-called effector functions (see below).

The primary function of antibodies is binding to an antigen. However, unless binding to the antigen directly inactivates the antigen (such as in the case of bacterial toxins), mere binding is meaningless unless so-called effector-functions are triggered. Antibodies of the IgG subclass exert two major effector-functions: the activation of the complement system and induction of phagocytosis. The complement system consists of a complex group of serum proteins involved in controlling inflammatory events, in the activation of phagocytes and in the lytical destruction of cell membranes. Complement activation starts with binding of the C1 complex to the Fc portion of two IgGs in close proximity. C1 consists of one molecule, C1q, and two molecules, C1r and C1s. Phagocytosis is initiated through an interaction between the IgG's Fc fragment and Fc-gamma-receptors (FcγRI, II and III in FIG. 30). Fc receptors are primarily expressed on the surface of effector cells of the immune system, in particular macrophages, monocytes, myeloid cells and dendritic cells.

The $C_H2$ portion harbors a conserved N-glycosylation site at asparagine 297 (Asp297). The Asp297 N-glycans are highly heterogeneous and are known to affect Fc receptor binding and complement activation. Only a minority (i.e., about 15-20%) of IgGs bears a disialylated, and 3-10% have a monosialylated N-glycan (reviewed in Jefferis, R., Glycosylation of human IgG Antibodies. BioPharm, 2001). Interestingly, the minimal N-glycan structure shown to be necessary for fully functional antibodies capable of complement activation and Fc receptor binding is a pentasacharide with terminal N-acetylglucosamine residues (GlcNAc.sub.2Man.sub.3) (reviewed in Jefferis, R., Glycosylation of human IgG Antibodies. BioPharm, 2001). Antibodies with less than a GlcNAc.sub.2Man.sub.3 N-glycan or no N-glycosylation at Asp297 might still be able to bind an antigen but most likely will not activate the crucial downstream events such as phagocytosis and complement activation. In addition, antibodies with fungal-type N-glycans attached to Asp297 will in all likelihood solicit an immune-response in a mammalian organism which will render that antibody useless as a therapeutic glycoprotein.

B. Cloning and Expression of GnTIII

The DNA fragment encoding part of the mouse GnTIII protein lacking the TM domain is PCR amplified from murine (or other mammalian) genomic DNA using forward 5'-TC-CTGGCGCGCCTTCCCGAGAGAACTGGCCTCCCTC-3' (SEQ ID NO. 15) and 5'-AATTAATTAACCCTAGCCCTC-CGCTGTATCCAACTTG-3' (SEQ ID NO. 16) reversed primers. Those primers include AscI and PacI restriction sites that will be used for cloning into the vector suitable for the fusion with leader library. The nucleic acid and amino acid sequence of murine GnTIII is shown in FIG. 32.

C. Cloning of Immunoglobulin Encoding Sequences

Protocols for the cloning of the variable regions of antibodies, including primer sequences, have been published previously. Sources of antibodies and encoding genes can be, among others, in vitro immunized human B cells (see, e.g., Borreback, C. A. et al. (1988) *Proc. Natl. Acad. Sci. USA* 85, 3995-3999), periphal blood lymphocytes or single human B cells (see, e.g., Lagerkvist, A. C. et al. (1995) *Biotechniques* 18, 862-869; and Terness, P. et al. (1997) *Hum. Immunol.* 56, 17-27) and transgenic mice containing human immunoglobulin loci, allowing the creation of hybridoma cell-lines.

Using standard recombinant DNA techniques, antibody-encoding nucleic acid sequences can be cloned. Sources for the genetic information encoding immunoglobulins of interest are typically total RNA preparations from cells of interest, such as blood lymphocytes or hybridoma cell lines. For example, by employing a PCR based protocol with specific primers, variable regions can be cloned via reverse transcription initiated from a sequence-specific primer hybridizing to the IgG $C_H1$ domain site and a second primer encoding amino acids 111-118 of the murine kappa constant region. The $V_H$ and $V_K$ encodingcDNAs will then be amplified as previously published (see, e.g., Graziano, R. F. et al. (1995) *J Immunol.* 155(10): p. 4996-5002; Welschof, M. et al. (1995) *J. Immunol. Methods* 179, 203-214; and Orlandi, R. et al. (1988) *Proc. Natl. Acad. Sci. USA* 86: 3833). Cloning procedures for whole immunoglobulins (heavy and light chains have also been published (see, e.g., Buckel, P. et al. (1987) *Gene* 51:13-19; Recinos A 3$^{rd}$ et al. (1994) *Gene* 149:385-386; (1995) *Gene* June 9; 158(2):311-2; and Recinos A 3$^{rd}$ et al. (1994) *Gene* November 18; 149(2):385-6). Additional protocols for the cloning and generation of antibody fragment and antibody expression constructs have been described in Antibody Engineering, R. Kontermann and S. Dübel (2001), Editors, Springer Verlag: Berlin Heidelberg N.Y.

Figure 31:
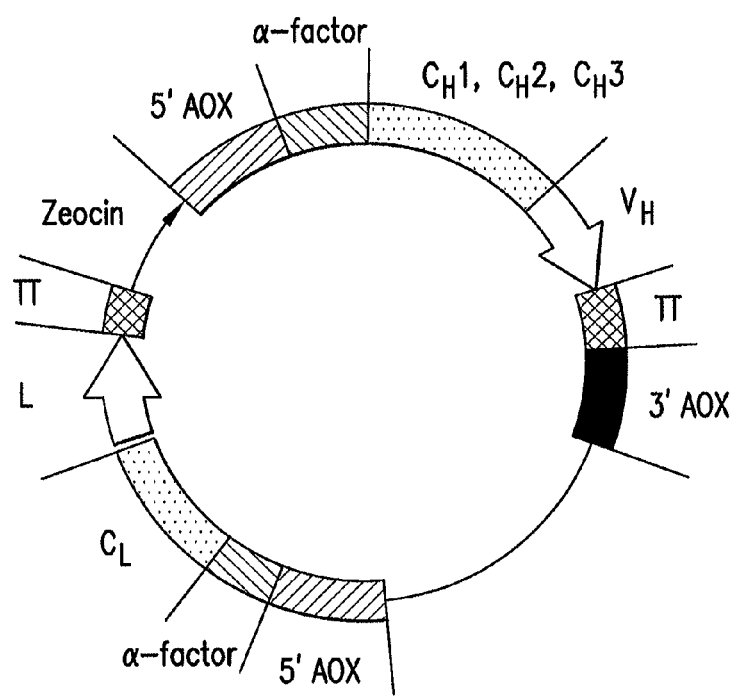
FIG. 31 Schematic overview of a modular IgG1 expression vector.

Fungal expression plasmids encoding heavy and light chain of immunoglobulins have been described (see, e.g., Abdel-Salam, H. A. et al. (2001) *Appl. Microbiol. Biotechnol.* 56: 157-164; and Ogunjimi, A. A. et al. (1999) *Biotechnology Letters* 21: 561-567). One can thus generate expression plasmids harboring the constant regions of immunoglobulins. To facilitate the cloning of variable regions into these expression vectors, suitable restriction sites can be placed in close proximity to the termini of the variable regions. The constant regions can be constructed in such a way that the variable regions can be easily in-frame fused to them by a simple restriction-digest/ligation experiment. FIG. 31 shows a schematic overview of such an expression construct, designed in a very modular way, allowing easy exchange of promoters, transcriptional terminators, integration targeting domains and even selection markers.

As shown in FIG. 31, $V_L$ as well as $V_H$ domains of choice can be easily cloned in-frame with $C_L$ and the $C_H$ regions, respectively. Initial integration is targeted to the *P. pastoris* AOX locus (or homologous locus in another fungal cell) and the methanol-inducible AOX promoter will drive expression. Alternatively, any other desired constitutive or inducible promoter cassette may be used. Thus, if desired, the 5'AOX and 3'AOX regions as well as transcriptional terminator (TT) fragments can be easily replaced with different TT, promoter and integration targeting domains to optimize expression. Initially the alpha-factor secretion signal with the standard KEX protease site is employed to facilitate secretion of heavy and light chains. The properties of the expression vector may be further refined using standard techniques.

An Ig expression vector such as the one described above is introduced into a host cell of the invention that expresses GnTIII, preferably in the Golgi apparatus of the host cell. The Ig molecules expressed in such a host cell comprise N-glycans having bisecting GlcNAcs.

EXAMPLE 7

Cloning and Expression of GnT-IV (UDP-GlcNAc: alpha-1,3-D-mannoside beta-1,4-N-Acetylglucosaminyltransferase IV) and GnT-V (beta 1-6-N-acetylglucosaminyltransferase)

GnTIV-encoding cDNAs were isolated from bovine and human cells (Minowa, M. T. et al. (1998) *J. Biol. Chem.* 273 (19), 11556-11562; and Yoshida, A. et al. (1999) *Glycobiology* 9 (3), 303-310. The DNA fragments encoding full length and a part of the human GnT-IV protein (FIG. 33) lacking the TM domain are PCR amplified from the cDNA library using forward 5'-AATGAGATGAGGCTCCGCAATGGAACTG-3' (SEQ ID NO. 17), 5'-CTGATTGCTTATCAACGAGAAT-TCCT-TG-3' (SEQ ID NO. 18), and reverse 5'-TGTTG-GTTTCTCAGATGATCAGTTGGTG-3' (SEQ ID NO. 19) primers, respectively. The resulting PCR products are cloned and sequenced.

Similarly, genes encoding GnT-V protein have been isolated from several mammalian species, including mouse. (See, e.g., Alverez, K. et al. *Glycobiology* 12 (7),389-394 (2002)). The DNA fragments encoding full length and a part of the mouse GnT-V protein (FIG. 34) lacking the TM domain are PCR amplified from the cDNA library using forward 5'-AGAGAGAGATGGCTTTCTTTTCTCCCTGG-3' (SEQ ID NO. 20), 5'-AAATCAAGTGGATGAAGGACAT-GTGGC-3' (SEQ ID NO. 21), and reverse 5'-AGCGATGC-TATAGGCAGTCTTTGCAGAG-3' (SEQ ID NO. 22) primers, respectively. The resulting PCR products are cloned and sequenced.

Nucleic acid fragments comprising sequences encoding GnT IV or V (or catalytically active fragments thereof) are cloned into appropriate expression vectors for expression, and preferably targeted expression, of these activities in an appropriate host cell according to the methods set forth herein.

REFERENCES

Aebi, M., J. Gassenhuber, et al. (1996). "Cloning and characterization of the ALG3 gene of *Saccharomyces cerevisiae*." *Glycobiology* 6(4): 439-444.

Altmann, F., E. Staudacher, et al. (1999). "Insect cells as hosts for the expression of recombinant glycoproteins." *Glycoconjugate Journal* 16(2): 109-123.

Andersen, D. C. and C. F. Goochee (1994). "The effect of cell-culture conditions on the oligosaccharide structures of secreted glycoproteins." *Current Opinion in Biotechnology* 5: 546-549.

Bardor, M., L. Faye, et al. (1999). "Analysis of the N-glycosylation of recombinant glycoproteins produced in transgenic plants." *Trends in Plant Science* 4(9): 376-380.

Bretthauer, R. K. and F. J. Castellino (1999). "Glycosylation of *Pichia pastoris*-derived proteins." *Biotechnology and Applied Biochemistry* 30: 193-200.

Burda, P. and M. Aebi (1999). "The dolichol pathway of N-linked glycosylation." *Biochimica Et Biophysica Acta-General Subjects* 1426(2): 239-257.

Chiba, Y., M. Suzuki, et al. (1998). "Production of human compatible high mannose-type (Man(5)GlcNAc(2)) sugar chains in *Saccharomyces cerevisiae*." *Journal of Biological Chemistry* 273(41): 26298-26304.

Cole, E. S., E. Higgins, et al. (1994). "Glycosylation Patterns of Human Proteins Expressed in Transgenic Goat Milk." *Journal of Cellular Biochemistry*: 265-265.

Davies et al. Biotechnol Bioeng. Aug. 20, 2001; 74(4):288-294. (Expression of GnTIII in a Recombinant Anti-CD20 CHO Production Cell Line: Expression of Antibodies with Altered Glycoforms Leads to an Increase in ADCC Through Higher Affinity for FcgRIII).

Dente, L., U. Ruther, et al. (1988). "Expression of Human Alpha-1-Acid Glycoprotein Genes in Cultured-Cells and in Transgenic Mice." *Genes & Development* 2(2): 259-266.

Huffaker, T. C. and P. W. Robbins (1983). "Yeast Mutants Deficient in Protein Glycosylation." *Proceedings of the National Academy of Sciences of the United States of America-Biological Sciences* 80(24): 7466-7470.

Jarvis, D. L., Z. S. Kawar, et al. (1998). "Engineering N-glycosylation pathways in the baculovirus-insect cell system." *Current Opinion in Biotechnology* 9(5): 528-533.

Kimura, T., N. Kitamoto, et al. (1997). "A novel yeast gene, RHK1, is involved in the synthesis of the cell wall receptor for the HM-1 killer toxin that inhibits beta-1,3-glucan synthesis." *Molecular & General Genetics* 254(2): 139-147.

Kimura, T., T. Komiyama, et al. (1999). "N-glycosylation is involved in the sensitivity of *Saccharomyces cerevisiae* to HM-1 killer toxin secreted from Hansenula mrakii IFO 0895." *Applied Microbiology and Biotechnology* 51(2): 176-184.

Malissard, M., S. Zeng, et al. (2000). "Expression of functional soluble forms of human beta-1,4-galactosyltransferase I, alpha-2,6-sialyltransferase, and alpha-1,3-fucosyltransferase VI in the methylotrophic yeast *Pichia pastoris.*" *Biochemical and Biophysical Research Communications* 267(1): 169-173.

Maras, M. and R. Contreras (1994). Methods of Modifying Carbohydrate Moieties. United States, Alko Group Ltd., Helsinki, Finland.

Maras, M., A. De Bruyn, et al. (1999). "In vivo synthesis of complex N-glycans by expression of human N-acetylglucosaminyltransferase I in the filamentous fungus *Trichoderma reesei.*" *Febs Letters* 452(3): 365-370.

Maras, M., X. Saelens, et al. (1997). "In vitro conversion of the carbohydrate moiety of fungal glycoproteins to mammalian-type oligosaccharides—Evidence for N-acetylglucosaminyltransferase-I-accepting glycans from *Trichoderma reesei.*" *European Journal of Biochemistry* 249(3): 701-707.

Martinet, W., M. Maras, et al. (1998). "Modification of the protein glycosylation pathway in the methylotrophic yeast *Pichia pastoris.*" *Biotechnology Letters* 20(12): 1171-1177.

McGarvey, P. B., J. Hammond, et al. (1995). "Expression of the Rabies Virus Glycoprotein in Transgenic Tomatoes." *Bio-Technology* 13(13): 1484-1487.

Moens, S. and J. Vanderleyden (1997). "Glycoproteins in prokaryotes." *Archives of Microbiology* 168(3): 169-175.

Nakanishishindo, Y., K. Nakayama, et al. (1993). "Structure of the N-Linked Oligosaccharides That Show the Complete Loss of Alpha-1,6-Polymannose Outer Chain From Och1, Och1 Mnn1, and Och1 Mnn1 Alg3 Mutants of *Saccharomyces-Cerevisiae.*" *Journal of Biological Chemistry* 268(35): 26338-26345.

Raju, T. S., J. B. Briggs, et al. (2000). "Species-specific variation in glycosylation of IgG: evidence for the species-specific sialylation and branch-specific galactosylation and importance for engineering recombinant glycoprotein therapeutics." *Glycobiology* 10(5): 477-486.

Sharma, C. B., R. Knauer, et al. (2001). "Biosynthesis of lipid-linked oligosaccharides in yeast: the ALG3 gene encodes the DoI-P-Man: Man(5)GlcNAc(2)-PP-DoI mannosyltransferase." *Biological Chemistry* 382(2): 321-328.

Staub, J. M., B. Garcia, et al. (2000). "High-yield production of a human therapeutic protein in tobacco chloroplasts." *Nature Biotechnology* 18(3): 333-338.

Takeuchi, M. (1997). "Trial for molecular breeding of yeast for the production of glycoprotein therapeutics." *Trends in Glycoscience and Glycotechnology* 9: S29-S35.

Umana et al., *Nat Biotechnol.* 1999a February (17)176-180. (Engineered glycoforms of an antineuroblastoma IgG1 with optimized antibodydependent cellular cytotoxic activity)

Umana et al., *Biotechnol Bioeng.* Dec. 5, 1999b; 65(5):542-549. (Regulated Overexpression of glycosyltransferase).

Verostek, M. F., P. H. Atkinson, et al. (1993). "Glycoprotein-Biosynthesis in the Alg3 *Saccharomyces-Cerevisiae* Mutant. 1. Role of Glucose in the Initial Glycosylation of Invertase in the Endoplasmic-Reticulum." *Journal of Biological Chemistry* 268(16): 12095-12103.

Verostek, M. F., P. H. Atkinson, et al. (1993). "Glycoprotein-Biosynthesis in the Alg3 *Saccharomyces-Cerevisiae* Mutant. 2. Structure of Novel Man6-10glcnac2 Processing Intermediates On Secreted Invertase." *Journal of Biological Chemistry* 268(16): 12104-12115.

Weikert, S., D. Papac, et al. (1999). "Engineering Chinese hamster ovary cells to maximize sialic acid content of recombinant glycoproteins." *Nature Biotechnology* 17(11): 1116-1121.

Werner, R. G., W. Noe, et al. (1998). "Appropriate mammalian expression systems for biopharmaceuticals." *Arzneimittel-Forschung-Drug Research* 48(8): 870-880.

Yang, M. and M. Butler (2000). "*Effects of ammonia on CHO cell growth, erythropoietin production and glycosylation.*" *Biotechnology and Bioengineering* 68(4): 370-380.Zufferey, R., R. Knauer, et al. (1995). "Stt3, a Highly Conserved Protein Required for Yeast Oligosaccharyl Transferase-Activity in-Vivo." *EMBO Journal* 14(20): 4949-4960.

What is claimed is:

1. A method for producing a recombinant glycoprotein in a *Pichia pastoris* host cell that lacks OCH1 activity, the method comprising the steps of diminishing or depleting the activity of one or more enzymes-selected from the group consisting of:
   (a) an enzyme having dolichyl-P-Man:Man$_5$GlcNAc$_2$-PP-dolichyl alpha-1,3 mannosyltransferase activity;
   (b) an enzyme having dolichyl-P-Man:Man$_6$GlcNAc$_2$-PP-dolichyl alpha-1,2 mannosyltransferase activity; and
   (c) an enzyme having dolichyl-P-Man:Man$_7$GlcNAc$_2$-PP-dolichyl alpha-1,6 mannosyltransferase activity,
   said host cell further expressing: (i) an α1,2-mannosidase catalytic domain fused to a targeting peptide that targets the endoplasmic reticulum (ER) or Golgi apparatus in the host cell, (ii) a GlcNAc transferase I (GnT I) catalytic domain fused to a targeting peptide that targets the ER or Golgi apparatus of the host cell, and (iii) the recombinant glycoprotein,
   wherein said method results in the production within the host cell of recombinant glycoproteins having N-glycans attached thereto comprising GlcNAc-Man$_x$GlcNAc$_2$ core structures, wherein X is 3 or 4.

2. The method of claim 1, wherein the host cell further includes a nucleic acid molecule encoding a mannosidase II catalytic domain fused to a targeting peptide that targets the ER or Golgi apparatus of the host cell and the method results in the production within the host cell of recombinant glycoproteins having N-glycans attached thereto comprising GlcNAcMan$_3$GlcNAc$_2$ core structures.

3. The method of claim 2, wherein the host cell further includes a nucleic acid molecule encoding a GnT II catalytic domain fused to a targeting peptide that targets the ER or Golgi apparatus of the host cell and the method results in the production within the host cell of recombinant glycoproteins having N-glycans attached thereto comprising GlcNAc$_2$Man$_3$GlcNAc$_2$ core structures.

4. The method of claim 1 wherein the host cell further includes a nucleic acid molecule encoding a GnT II catalytic domain fused to a targeting peptide that targets the ER or Golgi apparatus of the host cell and the method results in the production within the host cell of recombinant glycoproteins having N-glycans attached thereto comprising GlcNAc$_2$Man$_3$GlcNAc$_2$ core structures.

5. The method of claim 4, wherein the wherein the host cell further includes one or more nucleic acid molecules encoding one or more enzyme activities selected from galactosyltransferase, sialyltransferase, fucosyltransferase, and GlcNAc transferase III, IV, V, and VI.

6. The method of claim 1, wherein the diminished or depleted enzyme has dolichyl-P-Man:Man$_5$GlcNAc$_2$-PP-dolichyl alpha-1,3 mannosyltransferase activity.

7. The method of claim 1, wherein the enzyme is diminished or depleted by mutation of a host cell gene encoding the enzymatic activity.

8. The method of claim 7, wherein the mutation is a partial or total deletion of a host cell gene encoding the enzymatic activity.

9. The method of claim 1, wherein the attached N glycans have seven or fewer mannose residues.

10. The method of claim 1, wherein the glycoprotein comprises one or more sugars selected from the group consisting of galactose, GlcNAc, sialic acid, and fucose.

11. The method of claim 1, wherein the glycoprotein comprises at least one oligosaccharide branch comprising the structure NeuNAc-Gal-GlcNAc-Man.

12. A method for producing a human-like glycoprotein in a *Pichia pastoris* host cell that lacks OCH1 activity comprising the steps of diminishing or depleting from the host cell an alg gene activity selected from the group consisting of:
  (a) an enzyme having dolichyl-P-Man:Man$_5$GlcNAc$_2$-PP-dolichyl alpha-1,3 mannosyltransferase activity,
  (b) an enzyme having dolichyl-P-Man:Man$_6$GlcNAc$_2$-PP-dolichyl alpha-1,2 mannosyltransferase activity, and
  (c) an enzyme having dolichyl-P-Man:Man$_7$GlcNAc$_2$-PP-dolichyl alpha-1,6 mannosyltransferase activity;
  and introducing into the host cell at least one glycosidase activity.

13. A method for producing a recombinant glycoprotein in a *Pichia pastoris* host cell, the method comprising:
  (a) providing a *Pichia pastoris* host cell that lacks OCH1 activity and that has diminished or depleted activity of one or more enzymes selected from the group consisting of:
    (a) an enzyme having dolichyl-P-Man:Man$_5$GlcNAc$_2$-PP-dolichyl alpha-1,3 mannosyltransferase activity,
    (b) an enzyme having dolichyl-P-Man:Man$_6$GlcNAc$_2$-PP-dolichyl alpha-1,2 mannosyltransferase activity, and
    (c) an enzyme having dolichyl-P-Man:Man$_7$GlcNAc$_2$-PP-dolichyl alpha-1,6 mannosyltransferase activity,
    said host cell further expressing:
      (i) an α1,2-mannosidase catalytic domain fused to a targeting peptide that targets the endoplasmic reticulum (ER) or Golgi apparatus in the host cell,
      (ii) a GlcNAc transferase I (GnT I) catalytic domain fused to a targeting peptide that targets the ER or Golgi apparatus of the host cell, and
      (iii) a recombinant glycoprotein; and
  (b) growing the host cell under conditions to produce the recombinant glycoprotein, wherein the recombinant glycoprotein has N-glycans attached thereto comprising GlcNAcMan$_x$GlcNAc$_2$ core structures, wherein X is 3 or 4.

14. The method of claim 13, wherein the host cell further includes a nucleic acid molecule encoding a mannosidase II catalytic domain fused to a targeting peptide that targets the ER or Golgi apparatus of the host cell and wherein the recombinant glycoprotein that is produced has N-glycans attached thereto comprising GlcNAcMan$_3$GlcNAc$_2$ core structures.

15. The method of claim 14, wherein the host cell further includes a nucleic acid molecule encoding a GnT II catalytic domain fused to a targeting peptide that targets the ER or Golgi apparatus of the host cell and wherein the recombinant glycoprotein that is produced has N-glycans attached thereto comprising a GlcNAc$_2$Man$_3$GlcNAc$_2$ structure.

16. The method of claim 13, wherein the host cell further includes a nucleic acid molecule encoding a GnT II catalytic domain fused to a targeting peptide that targets the ER or Golgi apparatus of the host cell and wherein the recombinant glycoprotein that is produced has N-glycans attached thereto comprising a GlcNAc$_2$Man$_3$GlcNAc$_2$ structure.

17. The method of claim 13, wherein the host cell further includes one or more nucleic acid molecules encoding one or more sugar transporters selected from UDP-GlcNAc transporter, UDP-galactose transporter, GDP-fucose transporter, and CMP-sialic acid transporter.

18. The method of claim 13, wherein the host cell further includes one or more nucleic acid molecules encoding at least one enzyme activity selected from galactosyltransferase, sialyltransferase, fucosyltransferase, and GlcNAc transferase III, IV, V, and VI.

19. The method of claim 13, wherein the diminished or depleted enzyme has dolichyl-P-Man:Man$_5$GlcNAc$_2$-PP-dolichyl alpha-1,3 mannosyltransferase activity.

20. The method of claim 13, wherein the diminished or depleted enzyme activity is by mutation of a host cell gene encoding the enzymatic activity.

21. The method of claim 20, wherein the mutation is a partial or total deletion of a host cell gene encoding the enzymatic activity.

22. The method of claim 13, wherein the glycoprotein comprises one or more sugars selected from the group consisting of galactose, GlcNAc, sialic acid, and fucose.

23. The method of claim 13, wherein the glycoprotein comprises at least one oligosaccharide branch comprising the structure NeuNAc-Gal-GlcNAc-Man.

24. A method for producing a recombinant glycoprotein in a *Pichia pastoris* host cell, the method comprising
  (a) providing a *Pichia pastoris* host cell in which OCH1 activity and dolichyl-P-Man:Man$_5$GlcNAc$_2$-PP-dolichyl alpha-1,3 mannosyltransferase activity of the host cell have been diminished or depleted, and which comprises one or more nucleic acid molecules encoding
    (i) an α1,2-mannosidase catalytic domain fused to a targeting peptide that targets the endoplasmic reticulum (ER) or Golgi apparatus in the host cell,
    (ii) a GlcNAc transferase I (GnT I) catalytic domain fused to a targeting peptide that targets the ER or Golgi apparatus of the host cell, and
    (iii) a recombinant glycoprotein; and
  (b) growing the host cell under conditions to produce the recombinant glycoprotein, wherein the recombinant glycoprotein has N-glycans attached thereto comprising GlcNAcMan$_3$GlcNAc$_2$ core structures.

25. The method of claim 24, wherein the host cell further includes a nucleic acid molecule encoding a GnT II catalytic domain fused to a targeting peptide that targets the ER or Golgi apparatus of the host cell and wherein the recombinant glycoprotein that is produced has N-glycans attached thereto comprising a GlcNAc$_2$Man$_3$GlcNAc$_2$ structure.

26. The method of claim 24, wherein the host cell further includes one or more nucleic acid molecules encoding one or more sugar transporters selected from UDP-GlcNac transporter, UDP-galactose transporter, GDP-fucose transporter, and CMP-sialic acid transporter.

27. The method of claim 24, wherein the host cell further includes one or more nucleic acid molecules encoding at least one enzyme activity selected from galactosyltransferase, sialyltransferase, fucosyltransferase, and GlcNAc transferase III, IV, V, andr VI.

28. The method of claim 24, wherein the diminished or depleted enzyme activity is by mutation of a host cell gene encoding the enzymatic activity.

29. The method of claim 8, wherein the mutation is a partial or total deletion of a host cell gene encoding the enzymatic activity.

30. The method of claim 24, wherein the glycoprotein comprises one or more sugars selected from the group consisting of galactose, GlcNAc, sialic acid, and fucose.

31. The method of claim 24, wherein the glycoprotein comprises at least one oligosaccharide branch comprising the structure NeuNAc-Gal-GlcNAc-Man.

* * * * *